(12) United States Patent
Quijano Rubio et al.

(10) Patent No.: US 12,234,572 B2
(45) Date of Patent: Feb. 25, 2025

(54) SPLIT INTERLEUKIN MIMETICS AND THEIR USE

(71) Applicant: UNIVERSITY OF WASHINGTON, Seattle, WA (US)

(72) Inventors: Alfredo Quijano Rubio, Seattle, WA (US); Daniel Adriano Silva Manzano, Seattle, WA (US); David Baker, Seattle, WA (US); Umut Ulge, Seattle, WA (US); Marc Joseph Lajoie, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 775 days.

(21) Appl. No.: 17/294,807

(22) PCT Filed: Nov. 19, 2019

(86) PCT No.: PCT/US2019/062198
§ 371 (c)(1),
(2) Date: May 18, 2021

(87) PCT Pub. No.: WO2020/106708
PCT Pub. Date: May 28, 2020

(65) Prior Publication Data
US 2022/0017588 A1 Jan. 20, 2022

Related U.S. Application Data

(60) Provisional application No. 62/770,152, filed on Nov. 20, 2018.

(51) Int. Cl.
*C40B 40/10* (2006.01)
*A61K 38/20* (2006.01)
(Continued)

(52) U.S. Cl.
CPC .......... *C40B 40/10* (2013.01); *A61K 38/2013* (2013.01); *A61K 38/2026* (2013.01);
(Continued)

(58) Field of Classification Search
None
See application file for complete search history.

(56) References Cited

U.S. PATENT DOCUMENTS

| 1,015,080 A | 1/1912 | Rockwood |
| 5,229,109 A | 7/1993 | Grimm et al. |
| (Continued) | | |

FOREIGN PATENT DOCUMENTS

| CN | 101166823 | 4/2008 |
| CN | 101166823 A | 4/2008 |
| (Continued) | | |

OTHER PUBLICATIONS

Abraham et al., "GROMACS: High performance molecular simulations through multi-level parallelism from laptops to supercomputers", SoftwareX 1-2, 19-25 (2015).
(Continued)

*Primary Examiner* — Christian C Boesen
(74) *Attorney, Agent, or Firm* — MCDONNELL BOEHNEN HULBERT AND BERGHOFF LLP

(57) ABSTRACT

Conditionally active receptor agonists that, when activated, bind to IL-2 receptor $\beta V_c$ heterodimer (IL-2R$\beta V_c$), IL-4 receptor $\alpha V_c$ heterodimer (IL-4R$\alpha V_c$), or IL-13 receptor a subunit (IL-13 R$\alpha$) are disclosed, as are components of the conditionally active receptor agonists and methods for using the conditionally active receptor agonists.

16 Claims, 51 Drawing Sheets

Specification includes a Sequence Listing.

(51) Int. Cl.
*A61P 35/00* (2006.01)
*A61P 37/04* (2006.01)
*C07K 14/54* (2006.01)
*C07K 14/55* (2006.01)
*A61K 48/00* (2006.01)

(52) U.S. Cl.
CPC .......... *A61K 38/2086* (2013.01); *A61P 35/00* (2018.01); *A61P 37/04* (2018.01); *C07K 14/5406* (2013.01); *C07K 14/5443* (2013.01); *C07K 14/55* (2013.01); *A61K 48/00* (2013.01); *C07K 2319/30* (2013.01)

(56) References Cited

U.S. PATENT DOCUMENTS

| | | | |
|---|---|---|---|
| 7,101,965 | B2 | 9/2006 | Theze |
| 7,105,653 | B2 | 9/2006 | Shanafelt |
| 9,844,582 | B2 | 12/2017 | Wittrup et al. |
| 10,035,836 | B1 | 7/2018 | Greve |
| 10,703,791 | B2 | 7/2020 | Silva Manzano et al. |
| 10,844,105 | B2 | 11/2020 | Silva Manzano et al. |
| 11,117,944 | B2 | 9/2021 | Manzano et al. |
| 2017/0015722 | A1 | 1/2017 | Garcia |
| 2020/0347109 | A1 | 11/2020 | Silva Manzano et al. |

FOREIGN PATENT DOCUMENTS

| | | |
|---|---|---|
| CN | 106659757 A | 5/2017 |
| CN | 111040981 | 4/2020 |
| WO | 2002/012337 | 2/2002 |
| WO | 2002/101629 | 12/2002 |
| WO | 2008/138017 | 11/2008 |
| WO | WO 2015/164815 A1 | 10/2015 |
| WO | 2020/005819 | 1/2020 |
| WO | WO 2020/106708 | 5/2020 |
| WO | WO 2020/106843 | 5/2020 |
| WO | WO 2021/081193 | 4/2021 |
| WO | WO 2021/133476 | 7/2021 |
| WO | WO 2021/188374 | 9/2021 |

OTHER PUBLICATIONS

Adams et al., "PHENIX: a comprehensive Python-based system for macromolecular structure solution" Acta Crystallogr. D 66, 213-221 (2010).
Akdis et al., "Interleukins, from 1 to 37, and interferon-65 : receptors, functions, and roles in diseases", J. Allergy Clin. Immunol. 127, 701-21.e1-70 (2011).
Antonelli et al., "Neutralizing antibodies to interferon-alpha: relative frequency in patients treated with different interferon preparations", J. Infect. Dis. 163, 882-885 (1991).
Ardolino et al., "Cytokine treatment in cancer immunotherapy", Oncotarget vol. 6, (2015).
Arenas-Ramirez et al., "Improved cancer immunotherapy by a CD25-mimobody conferring selectivity to human interleukin-2", Sci Transl Med, vol. 8 Issue: 367 (Nov. 2016).
Basser et al., "Development of pancytopenia with neutralizing antibodies to thrombopoietin after multicycle chemotherapy supported by megakaryocyte growth and development factor", Blood 99, 2599-2602 (2002).
Behnel et al., Cython: the best of both worlds Comput. Sci. Eng. 13, 31-39 (2011).
Benatuil et al., "An improved yeast transformation method for the generation of very large human antibody libraries", Protein Eng. Des. Sel. 23, 155-159 (2010).
Berendsen et al., "Molecular dynamics with coupling to an external bath", J. Chem. Phys. 81, 3684-3690 (1984).
Berger et al., "Computationally designed high specifcity inhibitors delineate the roles of BCL2 family proteins in cancer", eLife 5, e20352 (2016).

Blattman et al., "Therapeutic use of IL-2 to enhance antiviral T-cell responses in vivo", Nat. Med. 9, 540-547 (2003).
Bouchaud et al., "The Exon-3-Encoded Domain of IL-15Rα Contributes to IL-15 High-Affinity Binding and Is Crucial for the IL-15 Antagonistic Effect of Soluble IL-15Rα", J. Mol. Biol. 382, 1-12 (2008).
Boyman et al., "The role of interleukin-2 during homeostasis and activation of the immune system", Nat. Rev. Immunol. 12, 180-190 (2012).
Bruhn et al., "Crystal structure of the Marburg virus VP35 oligomerization domain", J. Virol. 3, e01085-16 (2017).
Cancer Immunotherapy Market (Therapy Type—Monoclonal Antibodies, Immune Checkpoint Inhibitors (PD-1/PD-L1 and CTLA-4), Immune System Modulators, and Cancer Vaccines; Therapeutic Areas—Lung Cancer, Colorectal Cancer, Breast Cancer, Prostate Cancer, Mel. Transparency Market Research https://www.transparencymarketresearch.com/cancer-immunotherapy-market.html (published Dec. 2016) 4 pages.
Cancer Immunotherapy Market Analysis By Product (Monoclonal Antibodies, Immunomodulators, Oncolytic Viral Therapies, Cancer Vaccines), By Cancer Type, And Segment Forecasts, 2018-2025. Grand View Research. https://www.grandviewresearch.com/industry-analysis/cancer-immunotherapy-market (published Feb. 2019) 7 pages.
Cancer Immunotherapy Market by Technology (Monoclonal Antibodies, Cytokines & Immunomodulators, and Others), by Application (Lung Cancer, Breast Cancer, Colorectal Cancer, Melanoma, Prostate Cancer, Head & Neck Cancer, and Others) by End User (Hospitals). Allied Market Research https://www.alliedmarketresearch.com/cancer-immunotherapy-market (published May 2017) 4 pages.
Cancer Immunotherapy Market by Type (Monoclonal Antibodies, Cancer Vaccines, Check Point Inhibitors & Immunomodulators), Application (Lung, Breast, Colorectal, Melanoma, Prostate, Head & Neck), End User (Hospital and Clinics)—Global Forecast to 2021. Markets And Markets https://www.marketsandmarkets.com/Market-Reports/cancer-immunotherapy-market-197577894.html (published Sep. 2016) 7 pages.
Cao, "Regulatory T cells and immune tolerance to tumors", Immunol. Res. 46, 79-93 (2009).
Carmenate et al., "Human IL-2 mutein with higher antitumor efcacy than wild type IL-2" J. Immunol. 190, 6230-6238 (2013).
Chang et al., "A general method for facilitating heterodimeric pairing between two proteins: application to expression of alpha and beta T-cell receptor extracellular segments", Proc. Natl Acad. Sci. USA 91, 11408-11412 (1994).
Charych et al., "Modeling the receptor pharmacology, pharmacokinetics, and pharmacodynamics of NKTR-214, a kinetically-controlled interleukin-2 (IL2) receptor agonist for cancer immunotherapy", PLoS One 12, e0179431 (2017).
Chaudhury et al., "PyRosetta: a script-based interface for implementing molecular modeling algorithms using Rosetta", Bioinformatics 26, 689-691 (2010).
Chen et al., "Combination therapy of an IL-15 superagonist complex, ALT-803, and a tumor targeting monoclonal antibody promotes direct antitumor activity and protective vaccinal efect in a syngenic mouse melanoma model", J. Immunother. Cancer 3, 347 (2015).
Correia et al., "Proof of principle for epitope-focused vaccine design", Nature 507, 201-206 (2014).
Crooks et al., "WebLogo: a sequence logo generator", Genome Res. 14, 1188-1190 (2004).
D'Arcy et al., "Microseed matrix screening for optimization in protein crystallization: what have we learned?" Acta Crystallogr. F 70, 1117-1126 (2014).
De Groot et al., "Immunogenicity of protein therapeutics", Trends Immunol. 28, 482-490 (2007).
Dougan et al., "Immune Therapy for Cancer", Annu. Rev. Immunol. 27, 83-117 (2009).
Eckardt et al., "Pure red-cell aplasia due to anti-erythropoietin antibodies", Nephrol. Dial. Transplant 18, 865-869 (2003).
Emsley et al., "Features and development of Coot. Acta Crystallogr", D 66, 486-501 (2010).

(56) References Cited

OTHER PUBLICATIONS

Essmann et al., "A smooth particle mesh Ewald method", J. Chem. Phys. 103, 8577-8593 (1995).
Evans, "How good are my data and what is the resolution?", Acta Crystallogr. D 69, 1204-1214 (2013).
Evans, "Scaling and assessment of data quality", Acta Crystallogr. D 62, 72-82 (2006).
Fehniger et al., "Interleukin 15: biology and relevance to human disease", Blood 97, 14-32 (2001).
Fineberg et al., "Immunological responses to exogenous insulin", Endocr. Rev. 28, 625-652 (2007).
Fleishman et al., "Computational design of proteins targeting the conserved stem region of infuenza hemagglutinin", Science 332, 816-821 (2011).
Fleishman et al., "RosettaScripts: a scripting language interface to the Rosetta macromolecular modeling suite", PLoS One 6, e20161 (2011).
Foit et al., "Optimizing Protein Stability In Vivo", Mol. Cell 36, 861-871 (2009).
Fontenot et al., "A function for interleukin 2 in Foxp3-expressing regulatory T cells", Nat. Immunol. 6, 1142-1151 (2005).
Frokjaer, et al., "Protein drug stability: a formulation challenge" Nat. Rev. Drug Discov. 4, 298 (2005).
Giri et al., "Identification and cloning of a novel IL-15 binding protein that is structurally related to the alpha chain of the IL-2 receptor", EMBO J. 14, 3654-63 (1995).
Goldenzweig et al., "Principles of Protein Stability and Their Application in Computational Design", Annu. Rev. Biochem. (2018). doi:10.1146/annurev-biochem-062917-012102.
Goodson, et al., "Site-directed pegylation of recombinant interleukin-2 at its glycosylation site", Biotechnology 8, 343-346 (1990).
Hie et al., "NMR structures of two designed proteins with high sequence identity but different fold and function", Proc. Natl. Acad. Sci. U. S. A. 105, 14412-14417 (2008).
Hondowicz et al., "Interleukin-2-dependent allergen-specifc tissue-resident memory cells drive asthma", Immunity 44, 155-166 (2016).
Hunter, "Matplotlib: a 2D graphics environment" Comput. Sci. Eng. 9, 90-95 (2007).
Jacobs et al., "Design of structurally distinct proteins using strategies inspired by evolution" Science 352, 687-690 (2016).
Jiang, et al., "S. Role of IL-2 in cancer immunotherapy", OncoImmunology 5, (2016).
Kabsch, "XDS", Acta Crystallogr D 66, 125-132 (2010).
Kim et al., "The sequences of small proteins are not extensively optimized for rapid folding by natural selection" Proceedings of the National Academy of Sciences 95, 4982-4986 (1998).
Knipper et al., Interleukin-4 Receptor α Signaling in Myeloid Cells Controls Collagen Fibril Assembly in Skin Repair, Immunity 43, 803-816 (2015).
Krieg, et al,., "Improved IL-2 immunotherapy by selective stimulation of IL-2 receptors on lymphocytes and endothelial cells", Proc. Natl. Acad. Sci. 107, 11906-11911 (2010).
Kuziel et al., "Unexpected effects of the IL-2 receptor alpha subunit on high affinity IL-2 receptor assembly and function detected with a mutant IL-2 analog", J. Immunol. 150, 3357-3365 (1993).
Laporte et al., "De novo design of an IL-4 antagonist and its structure at 1.9 Å" PNAS, 182(6):1889-94 (Jan. 2005).
Leaver-Fay et al., "Chapter nineteen—Rosetta3: An Object-oriented Software Suite for the Simulation and Design of Macromolecules" in "Protein Engineering", Academic Press, Amsterdam, NL, vol. 487:545-74 (2010).
Liao, et al., "W. J. Interleukin-2 at the Crossroads of Effector Responses, Tolerance, and Immunotherapy", Immunity 38, 13-25 (2013).
Lin et al., "The role of shared receptor motifs and common Stat proteins in the generation of cytokine pleiotropy and redundancy by IL-2, IL-4, IL-7, IL-13, and IL-15", Immunity 2, 331-339 (1995).
Lindorf-Larsen et al., "Improved side-chain torsion potentials for the Amber f99SB protein force feld" Proteins 78, 1950-1958 (2010).

Liu et al., "Inclusion of Strep-Tag II in design of antigen receptors for T-cell immunotherapy", Nat. Biotechnol. 34, 430-434 (2016).
Lotze et al., "In vivo administration of purified human interleukin 2. II. Half life, immunologic effects, and expansion of peripheral lymphoid cells in vivo with recombinant IL 2", J. Immunol. 135, 2865-2875 (1985).
Ma et al., "The pleiotropic functions of interleukin 15: not so interleukin 2-like after all", J. Exp. Med. 191, 753-756 (2000).
Marcos et al., "Principles for designing proteins with cavities formed by curved β sheets", Science 355(6321):201-06 (Jan. 2017).
Marshall et al., "Rational design and engineering of therapeutic proteins" Drug Discov. Today 8, 212-221 (2003).
McCoy et al., "Phaser crystallographic software" J Appl. Crystallogr. 40, 658-674 (2007).
Minami et al., "MICAN: a protein structure alignment algorithm that can handle multiple-chains, inverse alignments, Cα only models, alternative alignments, and non-sequential alignments", BMC Bioinformatics 14, 24 (2013).
Moraga et al. Synthekines are surrogate cytokine and growth factor agonists that compel signaling through non-natural receptor dimers. Elife 6, (2017).
Morin et al., "Collaboration gets the most out of software", eLife 2, e01456 (2013).
Mott et al., "The solution structure of the F42A mutant of human interleukin 2", J. Mol. Biol. 247, 979-994 (1995).
Oliphant, "Python for scientifc computing", Comput. Sci. Eng. 9, 10-20 (2007).
Ozaki et al., "Cytokine and cytokine receptor pleiotropy and redundancy", J. Biol. Chem. 277, 29355-29358 (2002).
Pall et al., "A fexible algorithm for calculating pair interactions on SIMD architectures", Comput. Phys. Commun. 184, 2641-2650 (2013).
Parrinello et al., "Polymorphic transitions in single crystals: A new molecular dynamics method", J. Appl. Phys. 52, 7182-7190 (1981).
Perez et al., "IPython: a system for interactive scientifc computing", Comput. Sci. Eng. 9, 21-29 (2007).
Peyvandi et al., "A Randomized Trial of Factor VIII and Neutralizing Antibodies in Hemophilia A" N. Engl. J. Med. 374(21):2054-64 (May 2016).
Procko et al., "A computationally designed inhibitor of an Epstein-Barr viral Bcl-2 protein induces apoptosis in infected cells", Cell 157, 1644-1656 (2014).
Prümmer et al., "Treatment-induced antibodies to interleukin-2", Biotherapy 10, 15-24 (1997).
Ring et al., "Mechanistic and structural insight into the functional dichotomy between IL-2 and IL-15", Nat. Immunol. 13, 1187-1195 (2012).
Roberts et al., "J. M. Chemistry for peptide and protein PEGylation", Adv. Drug Deliv. Rev. 64, 116-127 (2012).
Robinson et al., "The potential and promise of IL-15 in immuno-oncogenic therapies", Immunol. Lett. 190, 159-168 (2017).
Sakaguchi, "Naturally arising Foxp3-expressing CD25+CD4+ regulatory T cells in immunological tolerance to self and non-self" Nat. Immunol. (2005). doi:10.1038/ni1178.
Salmon-Her et al., "Implication of interleukin-4 in wound healing", Lab. Invest. 80, 1337-1343 (2000).
Sarkar et al., "Rational cytokine design for increased lifetime and enhanced potency using pH-activated 'histidine switching'". Nat. Biotechnol. 20, 908-913 (2002).
Siegel et al., "Interleukin-2 toxicity", J. Clin. Oncol. 9, 694-704 (1991).
Silva et al., "Motif-Driven Design of Protein-Protein Interfaces", Methods Mol. Biol. 1414, 285-304 (2016).
Silva et al., "Structures and disulfide cross-linking of de novo designed therapeutic mini-proteins", FEBS J. (2018). doi:10.1111/febs.14394.
Smart et al., "Exploiting structure similarity in refnement: automated NCS and target-structure restraints in BUSTER", Acta Crystallogr. D 68, 368-380 (2012).
Smyth et al., "Cytokines in cancer immunity and immunotherapy" Immunol. Rev. 202, 275-293 (2004).
Spangler et al., "Insights into cytokine-receptor interactions from cytokine engineering. Annu. Rev.", Immunol. 33, 139-167 (2015).

(56) References Cited

OTHER PUBLICATIONS

Stockman et al., "Pure Red-Cell Aplasia and Epoetin Therapy", Yearbook of Pediatrics 2006, 54-55 (2006).
Stumpp et al., "DARPins: A new generation of protein therapeutics", Drug Discov. Today 13, 695-701 (2008).
Tagaya et al., "IL-15: a pleiotropic cytokine with diverse receptor/ signaling pathways whose expression is controlled at multiple levels", Immunity 4, 329-336 (1996).
Taverna et al., "Why are proteins marginally stable?" Proteins 46, 105-109 (2002).
Terwilliger et al., "Iterative model building, structure refnement and density modifcation with the PHENIX AutoBuild wizard" Acta Crystallogr. D 64, 61-69 (2008).
Thanos et al., "Hot-spot mimicry of a cytokine receptor by a small molecule", Proc. Natl. Acad. Sci. U. S. A. 103, 15422-15427 (2006).
Vazquez-Lombardi et al., "Potent antitumour activity of interleukin-2-Fc fusion proteins requires Fc-mediated depletion of regulatory T-cells", Nat. Commun. 8, 15373 (2017).
Vyas et al., "Clinical manufacturing of recombinant human interleukin 15. I. Production cell line development and protein expression in *E. coli* with stop codon optimization", Biotechnol. Prog. 28, 497-507 (2012).
Waldmann, "The Shared and Contrasting Roles of IL2 and IL15 in the Life and Death of Normal and Neoplastic Lymphocytes: Implications for Cancer Therapy", Cancer Immunol. Res. 3, 219-227 (2015).
Wang et al., "Structure of the quaternary complex of interleukin-2 with its alpha, beta, and gammac receptors", Science 310, 1159-1163 (2005).
Wieckowski et al., "Therapeutic efficacy of the F8-IL2 immunocytokine in a metastatic mouse model of lung adenocarcinoma", Lung Cancer vol. 88 Issue: 1, p. 9-15 (2015).
Winn et al., "Overview of the CCP4 suite and current developments" Acta Crystallogr. D 67, 235-242 (2011).
Yodoi et al., "TCGF (Il 2)-receptor inducing factor(s). I. Regulation of IL 2 receptor on a natural killer-like cell line (YT cells)", J. Immunol. 134, 1623-1630 (1985).
Zhu et al., "Synergistic innate and adaptive immune response to combination immunotherapy with anti-tumor antigen antibodies and extended serum half-life IL-2", Cancer Cell 27, 489-501 (2015).
Boyken, et al., "De novo design of protein homo-oligomers with modular hydrogen-bond network-mediated specificity," Science, vol. 352, No. 6286, May 6, 2016 (May 6, 2016), pp. 680-687.
Chevalier, et al., "Massively parallel de novo protein design for targeted therapeutics", Nature, vol. 550, No. 7674, Sep. 27, 2017 (Sep. 27, 2017), pp. 74-79.
Domingues, et al., "Rational Design of a GCN4-DERIVED Mimetic of Interleukin-4", Nature Structural Biology, vol. 6, No. 7, Jul. 1, 1999 (Jul. 1, 1999), pp. 652-656.
Eckenberg, et al., "IL-2R[beta] Agonist PI-30 Acts in Synergy with IL-2, IL-4, IL-9, and IL-15: Biological and Molecular Effects", The Journal of Immunology, vol. 165, No. 8, Oct. 15, 2000 (Oct. 15, 2000), pp. 4312-4318.
Kureshi, et al., "Reprogramming immune proteins as therapeutics using molecular engineering," Current Opinion in Chemical Engineering, vol. 19, Mar. 2018, pp. 27-34.
Mitra, et al., "Interleukin-2 Activity Can Be Fine Tuned with Engineered Receptor Signaling Clamps", Immunity, vol. 42, No. 5, May 1, 2015 (May 1, 2015), pp. 826-838.
Moll, et al., "Split 2 Protein-Ligation Generates Active IL-6-Type Hyper-Cytokines from Inactive Precursors", ACS Synthetic Biology, vol. 6, No. 12, Dec. 15, 2017 (Dec. 15, 2017), pp. 2260-2272.
Ruiz-Gomez, et al., "Rational Structure-Based Rescaffolding Approach to De Novo Design of Interleukin 10 (IL-10) Receptor-1 Mimetics", PLOS One, vol. 11, No. 4, Apr. 28, 2016 (Apr. 28, 2016), p. e0154046.
Silva, et al., "De novo design of potent and selective mimics of IL-2 and IL-15", Nature, vol. 565, No. 7738, Jan. 1, 2019 (Jan. 1, 2019), pp. 186-191.
Ventez, "Engineered Cytokine Derivatives for Targeted Cancer Immunotherapy," Research Collection Doctoral Thesis, Jan. 1, 2016 (Jan. 1, 2016), pp. 1-167.
International Search report for PCT/US2019/062198, mailed May 7, 2020.
Boersma, et al. "Bispecific designed ankyrin repeat proteins (DARPins) targeting epidermal growth factor receptor Inhibit A431 cell proliferation and receptor recycling." J Biol. Chem. 286, 41273-41285 (2011).
Charych, D. H. et al. "NKTR-214, an Engineered Cytokine with Biased IL2 Receptor Binding, Increased Tumor Exposure, and Marked Efficacy in Mouse Tumor Models," Clin. Cancer Res. 22, 680-690 (2016).
Dougan, M. et al. Targeting Cytokine Therapy to the Pancreatic Tumor Microenvironment Using PD-LI-Specific VHHs. Cancer Immunol Res 6, 389-401 (2018).
Gillies, S. D. et al. "A low-toxicity IL-2-based immunocytokine retains antitumor activity despite its high degree ofIL-2 receptor selectivity," Clin. Cancer Res. 17, 3673-3685 (2011).
Hutmacher, et al., "Antibody-cytokine fusion proteins: Biopharmaceuticals with immunomodulatory properties for cancer therapy," Adv. Drug Deliv. Rev. (2018). doi: 10.1016/j.addr.2018.09.002.
Kang, et al. "Tumor-Targeted Delivery of IL-2 by NKG2D Leads to Accumulation of Antigen-Specific CD8+ T Cells in the Tumor Loci and Enhanced Anti-Tumor Effects," PLOS One vol. 7 Issue: 4 e35141 (2012).
Klein, C. et al. "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology 6, e1277306 (2017).
Letourneau, S. et al. "IL-2/anti-IL-2 antibody complexes show strong biological activity by avoiding interaction with IL-2 receptor alpha subunit CD25," Proc. Natl. Acad Sci. US.A. 107, 2171-2176 (2010).
Levin, et al., "Exploiting a natural conformational switch to engineer an interleukin-2 'superkine'." Nature vol. 19 Issue: 7395, p. 529-533 (2012).
Puskas, J. et al. "Development of an attenuated interleukin-2 fusion protein that can be activated by tumour-expressed proteases," Immunology 133, 206-220 (2011).
Sim, et al., "IL2 Variant Circumvents ICOS+ Regulatory T-cell Expansion and Promotes NK Cell Activation," Cancer Immunology Research vol. 4, Issue 11, p. 983-994 (2016).
Sockolosky, et al. "Selective targeting of engineered T cells using orthogonal IL-2 cytokine-receptor complexes," Science vol. 359, Issue 6379, p. 1037-1042 (2018).
Tzeng, et al. "Antigen specificity can be irrelevant to immunocytokine efficacy and biodistribution," Proc. Natl. A.cad Sci. U.S.A. 112, 25 3320-3325 (2015).
Venetz, et al., "Targeted Reconstitution of Cytokine Activity upon ,Antigen Binding using Split Cytokine Antibody Fusion Proteins." J Biol. Chem. 291, 18139-18147 (2016).
Zahnd, C et al. A designed ankyrin repeat protein evolved to picomolar affinity to Her2. J. Afol. Biol. 369, 1015-1028 (2007).

Helix 2' consensus

FIG. 8E

| Position | 8 | 14 | 16 | 28 | 29 | 39 | 41 | 42 | 43 | 52 | 76 | 89 | 93 | 98 |
|---|---|---|---|---|---|---|---|---|---|---|---|---|---|---|
| Codon(s) used | YWC | YWC | MTS / GCG | CMG | AAC / CCC | THT | KYT | RRA | BTT | TWC / ATG | ACT / GAT | GAW / CGT | MTC | AWC |
| Combinatorial mutations | Y / F / H | Y / F / H | M / L / T / A | P / Q | N / S | F / Y / S | A / S / F / V | K / R / G / E | F / L / V / Y / M | F

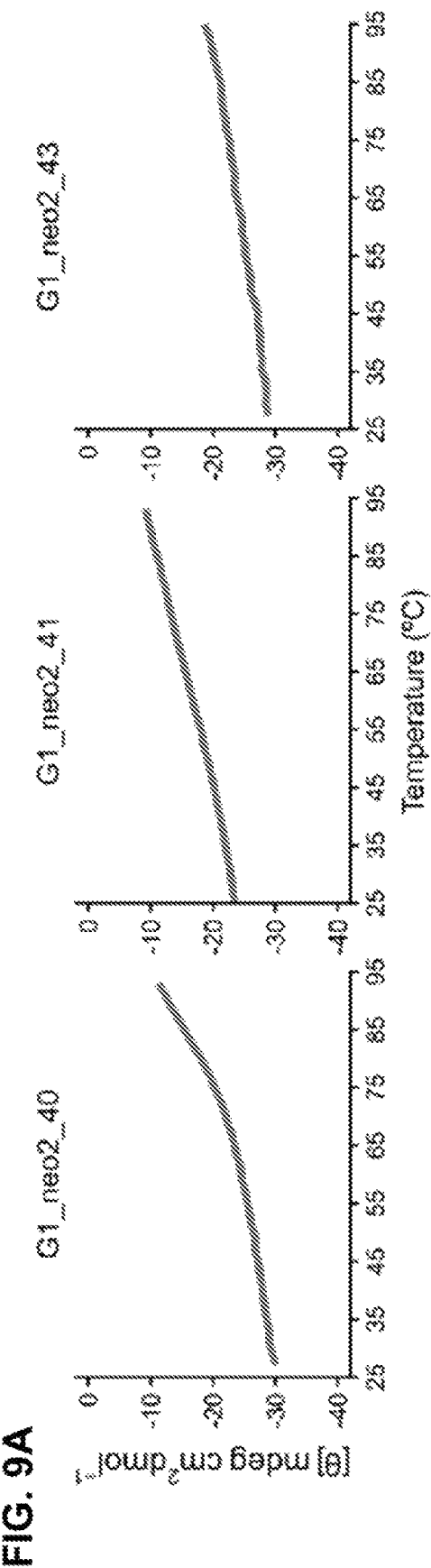
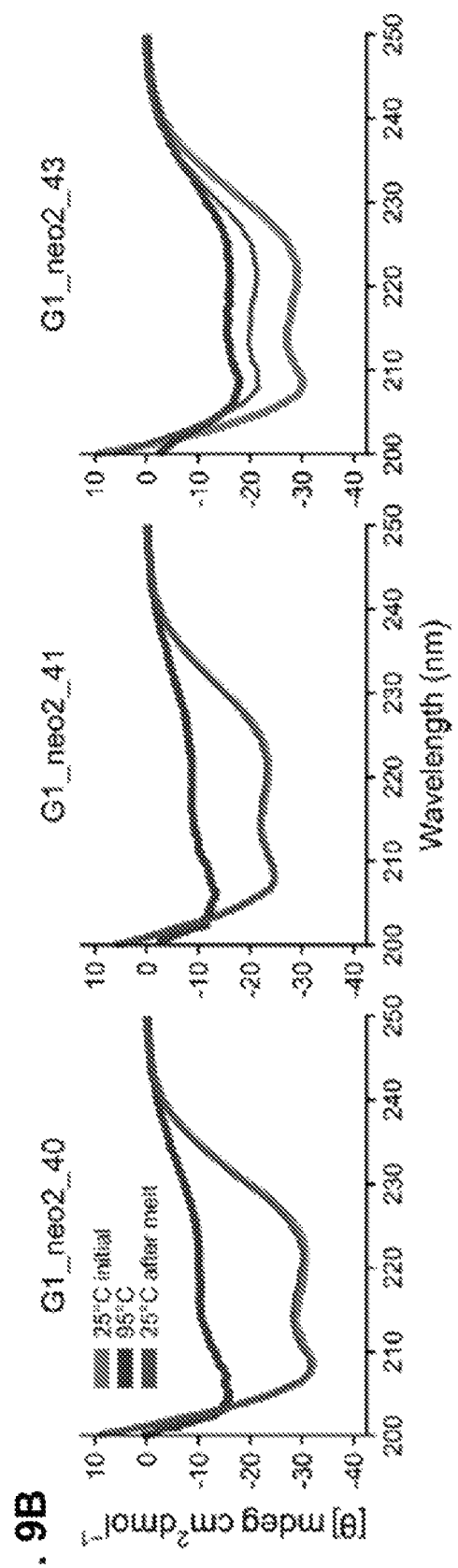
FIG. 9A
FIG. 9B

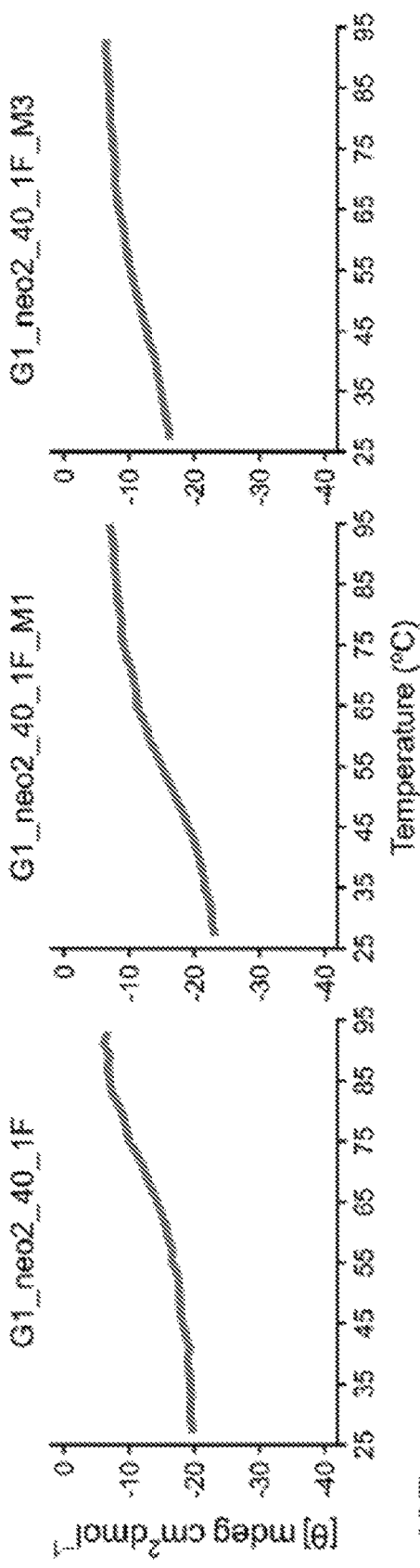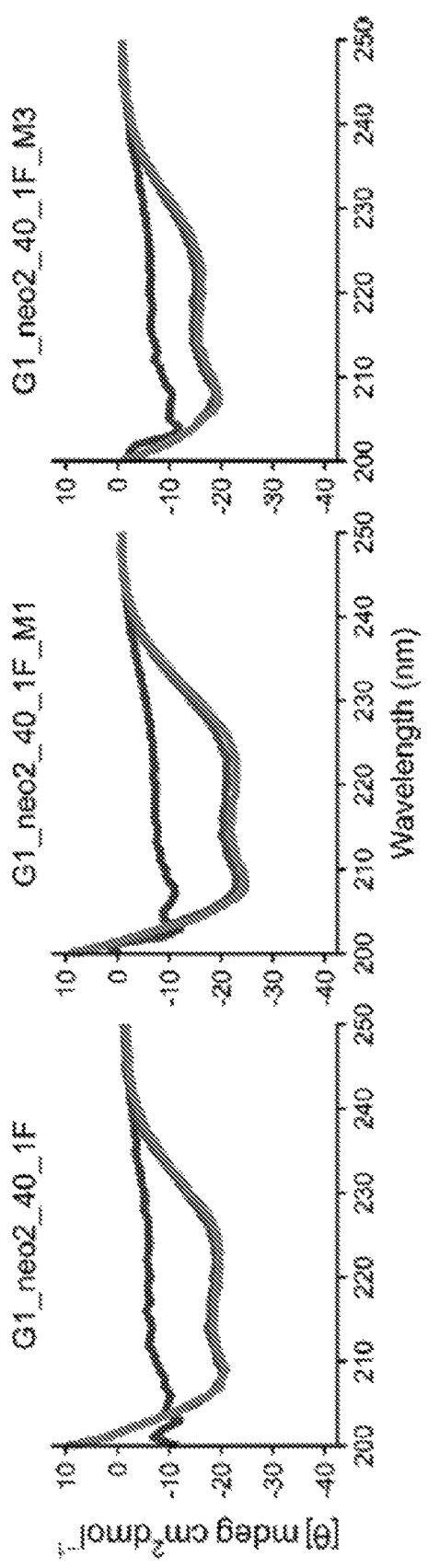
FIG. 10A
FIG. 10B

FIG. 18B K562 cells

SEQUENCE LISTING

```
<160> NUMBER OF SEQ IDS: 328

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Glu His Ala Leu Tyr Asp Ala Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Tyr Ala Phe Asn Phe Glu Leu Ile
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic
```

<400> SEQUENCE: 3

Ile Thr Ile Leu Gln Ser Trp Ile Phe
1               5

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Pro Lys Lys Lys Ile Gln Leu His Ala Glu His Ala Leu Tyr Asp Ala
1               5                   10                  15

Leu Met Ile Leu Asn Ile
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic

<400> SEQUENCE: 5

Leu Glu Asp Tyr Ala Phe Asn Phe Glu Leu Ile Leu Glu Glu Ile Ala
1               5                   10                  15

Arg Leu Phe Glu Ser Gly
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic

<400> SEQUENCE: 6

Glu Asp Glu Gln Glu Glu Met Ala Asn Ala Ile Ile Thr Ile Leu Gln
1               5                   10                  15

Ser Trp Ile Phe Ser
            20

<210> SEQ ID NO 7
<211> LENGTH: 19
<212> TYPE: PRT
<213> ORGANISM: Artificial Sequence
<220> FEATURE:
<223> OTHER INFORMATION: Synthetic

<400> SEQUENCE: 7

Lys Asp Glu Ala Glu Lys Ala Lys Arg Met Lys Glu Trp Met Lys Arg
1               5                   10                  15

Ile Lys Thr

<210> SEQ ID NO 8
<211> LENGTH: 22
<212> TYPE: PRT
<213> ORGANISM: Artificial Sequence
<220> FEATURE:
<223> OTHER INFORMATION: Synthetic

<400> SEQUENCE: 8

Pro Lys Lys Lys Ile Gln Ile Met Ala Glu Ala Leu Lys Asp Ala
1               5                   10                  15

Leu Ser Ile Leu Asn Ile
            20

<210> SEQ ID NO 9
<211> LENGTH: 22
<212> TYPE: PRT
<213> ORGANISM: Artificial Sequence
<220> FEATURE:
<223> OTHER INFORMATION: Synthetic

<400> SEQUENCE: 9

Leu Glu Arg Phe Ala Lys Arg Phe Glu Arg Asn Leu Trp Gly Ile Ala
1               5                   10                  15

Arg Leu Phe Glu Ser Gly
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic

<400> SEQUENCE: 10

Glu Asp Glu Gln Glu Glu Met Ala Asn Ala Ile Ile Thr Ile Leu Gln
1               5                   10                  15

Ser Trp Phe Phe Ser
            20

<210> SEQ ID NO 11
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 11

Ser Thr Lys Lys Trp Gln Leu Gln Ala Glu His Ala Leu Leu Asp Trp
1               5                   10                  15

Gln Met Ala Leu Asn Lys Xaa Xaa Xaa Xaa Xaa Glu Asn Leu Asn Arg
            20                  25                  30

Ala Ile Thr Ala Ala Gln Ser Trp Ile Ser Xaa Xaa Xaa Xaa Xaa Leu
        35                  40                  45

Asp Lys Ala Glu Asp Ile Arg Arg Asn Ser Asp Gln Ala Arg Arg Glu
    50                  55                  60

Ala Glu Lys Xaa Xaa Xaa Xaa Xaa Arg Asp Leu Ile Ser Asn Ala Gln
65                  70                  75                  80

Val Ile Leu Leu Glu Ala Arg

```
                        85

<210> SEQ ID NO 12
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 12

Ser Thr Lys Lys Trp Gln Leu Gln Ala Glu His Ala Leu Leu Asp Trp
1               5                   10                  15

Gln Met Ala Leu Asn Lys Xaa Xaa Xaa Xaa Xaa Glu Asn Leu Asn Arg
                20                  25                  30

Ala Ile Thr Ala Ala Gln Ser Cys Ile Ser Xaa Xaa Xaa Xaa Xaa Leu
            35                  40                  45

Asp Lys Ala Glu Asp Ile Arg Arg Asn Ser Asp Gln Ala Arg Arg Glu
50                  55                  60

Ala Glu Lys Xaa Xaa Xaa Xaa Xaa Arg Asp Leu Ile Ser Asn Ala Gln
65                  70                  75                  80

Val Ile Leu Leu Glu Ala Arg
                85

<210> SEQ ID NO 13
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 13

Ser Thr Lys Lys Trp Gln Leu Gln Ala Glu His Ala Leu Leu Asp Trp
1               5                   10                  15

Gln Met Ala Leu Asn Lys Xaa Xaa Xaa Xaa Xaa Glu Asn Leu Asn Arg
                20                  25                  30

Ala Ile Thr Ala Ala Gln Ser Trp Ile Ser Xaa Xaa Xaa Xaa Xaa Cys
            35                  40                  45
```

```
Asp Lys Ala Glu Asp Ile Arg Arg Asn Ser Asp Gln Ala Arg Arg Glu
    50                  55                  60

Ala Glu Lys Xaa Xaa Xaa Xaa Arg Asp Leu Ile Ser Asn Ala Gln
65                  70                  75                  80

Val Ile Leu Leu Glu Ala Cys
                85
```

<210> SEQ ID NO 14
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 14

```
Ser Thr Lys Lys Leu Gln Leu Gln Ala Glu His Phe Leu Leu Asp Val
1               5                   10                  15

Gln Met Ile Leu Asn Glu Xaa Xaa Xaa Xaa Glu Glu Leu Asn Arg
            20                  25                  30

Ala Ile Thr Asp Ala Gln Ser Trp Ile Ser Xaa Xaa Xaa Xaa Leu
        35                  40                  45

Asp Arg Ala Glu Glu Leu Ala Arg Asn Leu Glu Lys Val Arg Asp Glu
    50                  55                  60

Ala Leu Lys Xaa Xaa Xaa Xaa Arg Asp Leu Val Ser Asn Ala Lys
65                  70                  75                  80

Val Ile Ala Leu Glu Leu Lys
                85
```

<210> SEQ ID NO 15
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 15

```
Ser Thr Lys Lys Leu Gln Leu Gln Ala Glu His Phe Leu Leu Asp Val
1               5                   10                  15
```

```
Gln Met Ile Leu Asn Glu Xaa Xaa Xaa Xaa Xaa Glu Glu Leu Asn Arg
            20                  25                  30

Cys Ile Thr Asp Ala Gln Ser Trp Ile Ser Xaa Xaa Xaa Xaa Xaa Leu
            35                  40                  45

Asp Arg Ala Glu Glu Cys Ala Arg Asn Leu Glu Lys Val Arg Asp Glu
        50                  55                  60

Ala Leu Lys Xaa Xaa Xaa Xaa Xaa Arg Asp Leu Val Ser Asn Ala Lys
65                  70                  75                  80

Val Ile Ala Leu Glu Leu Lys
                85

<210> SEQ ID NO 16
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 16

Ser Thr Lys Lys Leu Gln Leu Gln Ala Glu His Phe Leu Leu Asp Val
1               5                   10                  15

Gln Met Ile Leu Asn Glu Xaa Xaa Xaa Xaa Xaa Glu Glu Leu Asn Arg
            20                  25                  30

Ala Ile Thr Asp Ala Gln Ser Cys Ile Ser Xaa Xaa Xaa Xaa Xaa Leu
            35                  40                  45

Asp Arg Ala Glu Glu Leu Ala Arg Asn Leu Glu Lys Val Arg Asp Glu
        50                  55                  60

Ala Leu Lys Xaa Xaa Xaa Xaa Xaa Arg Asp Leu Val Ser Asn Ala Lys
65                  70                  75                  80

Val Ile Ala Leu Glu Leu Lys
                85

<210> SEQ ID NO 17
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
```

```
<223> OTHER INFORMATION: Xaa, when present, can be any naturally
      occurring amino acid or is optionally absent

<400> SEQUENCE: 17

Ser Thr Lys Lys Leu Gln Leu Gln Ala Glu His Phe Leu Leu Asp Val
1               5                   10                  15

Gln Met Ile Leu Asn Glu Xaa Xaa Xaa Xaa Glu Glu Leu Asn Arg
            20                  25                  30

Ala Ile Thr Asp Ala Gln Ser Trp Ile Ser Xaa Xaa Xaa Xaa Leu
            35                  40                  45

Asp Arg Ala Glu Glu Leu Cys Arg Asn Leu Glu Lys Val Arg Asp Glu
        50                  55                  60

Ala Leu Lys Xaa Xaa Xaa Xaa Arg Asp Leu Val Ser Asn Ala Cys
65              70                  75                  80

Val Ile Ala Leu Glu Leu Lys
                85

<210> SEQ ID NO 18
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 18

Ser Thr Lys Lys Leu Gln Leu Gln Ala Glu His Ala Leu Leu Asp Ala
1               5                   10                  15

Gln Met Met Leu Asn Arg Xaa Xaa Xaa Xaa Xaa Glu Lys Leu Asn Arg
            20                  25                  30

Ile Ile Thr Thr Met Gln Ser Trp Ile Ser Xaa Xaa Xaa Xaa Leu
            35                  40                  45

Asp Gly Ala Lys Glu Leu Ala Lys Glu Val Glu Glu Leu Arg Gln Glu
        50                  55                  60

Ala Glu Lys Xaa Xaa Xaa Xaa Xaa Arg Asp Leu Ala Ser Asn Leu Lys
65              70                  75                  80

Val Ile Leu Leu Glu Leu Ala
                85

<210> SEQ ID NO 19
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
```

```
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 19

Ser Thr Lys Lys Leu Gln Leu Gln Ala Glu His Ala Leu Leu Asp Ala
1               5                   10                  15

Gln Met Met Leu Asn Arg Xaa Xaa Xaa Xaa Xaa Glu Lys Leu Asn Arg
            20                  25                  30

Ile Ile Thr Thr Met Gln Ser Cys Ile Ser Xaa Xaa Xaa Xaa Xaa Leu
        35                  40                  45

Asp Gly Ala Lys Glu Leu Ala Lys Glu Val Glu Leu Arg Gln Glu
    50                  55                  60

Ala Glu Lys Xaa Xaa Xaa Xaa Xaa Arg Asp Leu Ala Ser Asn Leu Lys
65                  70                  75                  80

Val Ile Leu Leu Glu Leu Ala
                85

<210> SEQ ID NO 20
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 20

Ser Thr Lys Lys Ile Gln Leu Gln Leu Glu His Ala Leu Leu Asp Val
1               5                   10                  15

Gln Met Ala Leu Asn Arg Xaa Xaa Xaa Xaa Glu Ser Leu Asn Arg
            20                  25                  30

Met Ile Thr Trp Leu Gln Ser Trp Ile Ser Xaa Xaa Xaa Xaa Xaa Leu
        35                  40                  45

Asp Asn Ala Gln Glu Met Ala Lys Glu Ala Lys Ile Arg Lys Glu
    50                  55                  60

Met Glu Lys Xaa Xaa Xaa Xaa Xaa Arg Asp Leu Ile Ser Asn Ile Ile
65                  70                  75                  80

Val Ile Leu Leu Glu Leu Ser
                85

<210> SEQ ID NO 21
<211> LENGTH: 87
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 21

Ser Thr Lys Lys Ile Gln Leu Gln Leu Glu His Ala Leu Leu Asp Val
1               5                   10                  15

Gln Met Ala Leu Asn Arg Xaa Xaa Xaa Xaa Xaa Glu Ser Leu Asn Arg
            20                  25                  30

Met Ile Thr Trp Leu Gln Ser Cys Ile Ser Xaa Xaa Xaa Xaa Xaa Leu
        35                  40                  45

Asp Asn Ala Gln Glu Met Ala Lys Glu Ala Glu Lys Ile Arg Lys Glu
50                  55                  60

Met Glu Lys Xaa Xaa Xaa Xaa Xaa Arg Asp Leu Ile Ser Asn Ile Ile
65                  70                  75                  80

Val Ile Leu Leu Glu Leu Ser
                85

<210> SEQ ID NO 22
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 22

Ser Thr Lys Lys Ile Gln Leu Gln Leu Glu His Ala Leu Leu Asp Val
1               5                   10                  15

Gln Met Ala Leu Asn Arg Xaa Xaa Xaa Xaa Xaa Glu Ser Leu Asn Arg
            20                  25                  30

Met Ile Thr Trp Leu Gln Ser Trp Ile Ser Xaa Xaa Xaa Xaa Xaa Leu
        35                  40                  45

Asp Asn Ala Gln Glu Met Cys Lys Glu Ala Glu Lys Ile Arg Lys Glu
50                  55                  60

Met Glu Lys Xaa Xaa Xaa Xaa Xaa Arg Asp Leu Ile Ser Asn Ile Cys
65                  70                  75                  80

Val Ile Leu Leu Glu Leu Ser
                85
```

<210> SEQ ID NO 23
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
    occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
    occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
    occurring amino acid or is optionally absent

<400> SEQUENCE: 23

Ser Thr Lys Lys Thr Gln Leu Leu Ala Glu His Ala Leu Leu Asp Ala
1               5                   10                  15

Phe Met Met Leu Asn Val Xaa Xaa Xaa Xaa Glu Lys Leu Asn Arg
                20                  25                  30

Ile Ile Thr Thr Met Gln Ser Trp Ile Tyr Xaa Xaa Xaa Xaa Ala
            35                  40                  45

Asp Gly Ala Lys Glu Leu Ala Lys Glu Val Glu Leu Glu Gln Glu
    50                  55                  60

Tyr Glu Lys Xaa Xaa Xaa Xaa Xaa Glu Asp Asp Ala Ser Asn Leu Lys
65                  70                  75                  80

Val Ile Leu Leu Glu Leu Ala
                85

<210> SEQ ID NO 24
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
    occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
    occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
    occurring amino acid or is optionally absent

<400> SEQUENCE: 24

Ser Thr Lys Lys Thr Gln Leu Leu Ala Glu His Ala Leu Leu Asp Ala
1               5                   10                  15

His Met Met Leu Asn Met Xaa Xaa Xaa Xaa Glu Lys Leu Asn Arg
                20                  25                  30

Ile Ile Thr Thr Met Gln Ser Trp Ile His Xaa Xaa Xaa Xaa Xaa Gly
            35                  40                  45

Asp Gly Ala Gln Glu Leu Ala Lys Glu Val Glu Glu Leu Glu Gln Glu

```
                    50                  55                  60
Tyr Glu Lys Xaa Xaa Xaa Xaa Glu Asp Glu Ala Ser Asn Leu Lys
 65                  70                  75                  80

Val Ile Leu Leu Glu Leu Ala
                85
```

<210> SEQ ID NO 25
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(37)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absentt

<400> SEQUENCE: 25

```
Ser Thr Lys Lys Thr Gln Leu Leu Ala Glu His Ala Leu Leu Asp Ala
  1               5                  10                  15

Phe Met Met Leu Asn Met Xaa Xaa Xaa Xaa Xaa Glu Lys Leu Asn Arg
                 20                  25                  30

Ile Ile Thr Thr Met Gln Ser Trp Ile Phe Xaa Xaa Xaa Xaa Xaa Gly
             35                  40                  45

Asp Gly Ala Lys Glu Leu Ala Lys Glu Val Glu Glu Leu Glu Gln Glu
         50                  55                  60

Phe Glu Lys Xaa Xaa Xaa Xaa Xaa Glu Asp Glu Ala Ser Asn Leu Lys
 65                  70                  75                  80

Val Ile Leu Leu Glu Leu Ala
                85
```

<210> SEQ ID NO 26
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 26

```
Ser Thr Lys Lys Thr Gln Leu Leu Ala Glu His Ala Leu Leu Asp Ala
  1               5                  10                  15
```

```
Leu Met Met Leu Asn Met Xaa Xaa Xaa Xaa Glu Lys Leu Asn Arg
                20                  25                  30

Ile Ile Thr Thr Met Gln Ser Trp Ile Phe Xaa Xaa Xaa Xaa Gly
            35                  40                  45

Asp Gly Ala Gln Glu Leu Ala Lys Glu Val Glu Leu Glu Gln Glu
        50                  55                  60

Leu Glu Lys Xaa Xaa Xaa Xaa Glu Asp Tyr Ala Ser Asn Leu Lys
65                  70                  75                  80

Val Ile Leu Leu Glu Leu Ala
                85

<210> SEQ ID NO 27
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 27

Ser Thr Lys Lys Thr Gln Leu Leu Ala Glu His Ala Leu Leu Asp Ala
1               5                   10                  15

His Met Met Leu Asn Val Xaa Xaa Xaa Xaa Xaa Glu Lys Leu Asn Arg
                20                  25                  30

Ile Ile Thr Thr Met Gln Ser Trp Ile Tyr Xaa Xaa Xaa Xaa Xaa Arg
            35                  40                  45

Asp Gly Ala Gln Glu Leu Ala Lys Glu Val Glu Leu Glu Gln Glu
        50                  55                  60

Leu Glu Lys Xaa Xaa Xaa Xaa Xaa Asp Asp Asp Ala Ser Asn Leu Lys
65                  70                  75                  80

Val Ile Leu Leu Glu Leu Ala
                85

<210> SEQ ID NO 28
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
``` occurring amino acid or is optionally absent

<400> SEQUENCE: 28

Ser Thr Lys Lys Thr Gln Leu Leu Ala Glu His Ala Leu Leu Asp Ala
1               5                   10                  15

Leu Met Met Leu Asn Leu Xaa Xaa Xaa Xaa Xaa Glu Lys Leu Asn Arg
            20                  25                  30

Ile Ile Thr Thr Met Gln Ser Trp Ile Phe Xaa Xaa Xaa Xaa Xaa Gly
        35                  40                  45

Asp Gly Ala Gln Glu Leu Ala Lys Glu Val Glu Glu Leu Glu Gln Glu
    50                  55                  60

His Glu Lys Xaa Xaa Xaa Xaa Xaa Glu Asp Tyr Ala Ser Asn Leu Lys
65                  70                  75                  80

Val Ile Leu Leu Glu Leu Ala
                85

<210> SEQ ID NO 29
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 29

Ser Thr Lys Lys Thr Gln Leu Leu Ala Glu His Ala Leu Leu Asp Ala
1               5                   10                  15

Tyr Met Met Leu Asn Met Xaa Xaa Xaa Xaa Xaa Glu Lys Leu Asn Arg
            20                  25                  30

Ile Ile Thr Thr Met Gln Ser Trp Ile Leu Xaa Xaa Xaa Xaa Xaa Ser
        35                  40                  45

Asp Gly Ala Gln Glu Leu Ala Lys Glu Val Glu Glu Leu Glu Gln Glu
    50                  55                  60

Leu Glu Lys Xaa Xaa Xaa Xaa Xaa Asp Asp Asp Ala Ser Asn Leu Lys
65                  70                  75                  80

Val Ile Leu Leu Glu Leu Ala
                85

<210> SEQ ID NO 30
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE

```
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 30

Ser Thr Lys Lys Thr His Leu Leu Ala Glu His Ala Leu Leu Asp Ala
1               5                   10                  15

Tyr Met Met Leu Asn Val Xaa Xaa Xaa Xaa Xaa Glu Lys Leu Asn Arg
            20                  25                  30

Ile Ile Thr Thr Met Gln Ser Trp Ile Phe Xaa Xaa Xaa Xaa Xaa Gly
        35                  40                  45

Asp Gly Ala Lys Glu Leu Ala Lys Glu Val Glu Glu Leu Glu Gln Glu
    50                  55                  60

Phe Glu Lys Xaa Xaa Xaa Xaa Xaa Asp Asp Asp Ala Ser Asn Leu Lys
65                  70                  75                  80

Val Ile Leu Leu Glu Leu Ala
                85

<210> SEQ ID NO 31
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 31

Ser Thr Lys Lys Thr Gln Leu Leu Ala Glu His Ala Leu Leu Asp Ala
1               5                   10                  15

Tyr Met Met Leu Asn Leu Xaa Xaa Xaa Xaa Xaa Glu Lys Leu Asn Arg
            20                  25                  30

Ile Ile Thr Thr Met Gln Ser Trp Ile Phe Xaa Xaa Xaa Xaa Xaa Ala
        35                  40                  45

Asp Gly Ala Gln Glu Leu Ala Ile Glu Val Glu Glu Leu Glu Gln Glu
    50                  55                  60

Tyr Glu Lys Xaa Xaa Xaa Xaa Xaa Asp Asp Tyr Ala Ser Asn Leu Lys
65                  70                  75                  80

Val Ile Leu Leu Glu Leu Ala
                85

<210> SEQ ID NO 32
<211> LENGTH: 87
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 32

Ser Thr Lys Lys Thr Gln Leu Met Ala Glu His Ala Leu Leu Asp Ala
1               5                   10                  15

Phe Met Met Leu Asn Xaa Xaa Xaa Xaa Xaa Xaa Glu Lys Leu Asn Arg
            20                  25                  30

Ile Ile Thr Thr Met Gln Ser Trp Ile Phe Xaa Xaa Xaa Xaa Xaa Gly
            35                  40                  45

Asp Asp Ala Gln Glu Leu Ala Lys Glu Val Glu Glu Leu Glu Gln Glu
        50                  55                  60

Leu Glu Lys Xaa Xaa Xaa Xaa Xaa Asp Asp Asp Ala Ser Asn Leu Lys
65                  70                  75                  80

Val Ile Leu Leu Glu Leu Ala
                85

<210> SEQ ID NO 33
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 33

Ser Thr Lys Lys Thr Gln Leu Leu Ile Glu His Ala Leu Leu Asp Ala
1               5                   10                  15

Leu Asp Met Ser Arg Xaa Xaa Xaa Xaa Xaa Xaa Glu Lys Leu Ser Arg
            20                  25                  30

Ile Ile Thr Thr Met Gln Ser Trp Ile Phe Xaa Xaa Xaa Xaa Xaa Gly
            35                  40                  45

Asp Gly Ala Gln Gln Leu Ala Lys Glu Val Glu Glu Leu Glu Gln Glu
        50                  55                  60

His Glu Lys Xaa Xaa Xaa Xaa Xaa Glu Asp Glu Ala Ser Asn Leu Lys
65                  70                  75                  80

Val Ile Leu Leu Glu Leu Ala
                85
```

```
<210> SEQ ID NO 34
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 34

Ser Thr Lys Lys Thr Gln Leu Leu Leu Glu His Ala Leu Leu Asp Ala
1               5                   10                  15

Leu His Met Arg Arg Xaa Xaa Xaa Xaa Xaa Xaa Glu Lys Leu Ser Arg
                20                  25                  30

Ile Ile Thr Thr Met Gln Ser Trp Ile Phe Xaa Xaa Xaa Xaa Xaa Gly
            35                  40                  45

Asp Gly Ala Gln Glu Leu Ala Lys Glu Val Glu Gly Leu Glu Gln Glu
        50                  55                  60

His Glu Lys Arg Gly Arg Asp Val Glu Asp Ala Ser Asn Leu Lys
65                  70                  75                  80

Val Ile Leu Leu Glu Leu Ala
                85

<210> SEQ ID NO 35
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 35

Ser Thr Lys Lys Thr Gln Leu Leu Ile Glu His Ala Leu Leu Asp Ala
1               5                   10                  15

Leu Asn Met Arg Lys Xaa Xaa Xaa Xaa Xaa Xaa Glu Lys Leu Ser Arg
                20                  25                  30

Ile Ile Thr Asp Met Gln Ser Trp Ile Phe Xaa Xaa Xaa Xaa Xaa Gly
            35                  40                  45

Asp Gly Ala Gln Gln Leu Ala Lys Glu Val Glu Glu Leu Glu Gln Glu
        50                  55                  60
```

His Glu Lys Xaa Xaa Xaa Xaa Xaa Glu Asp Tyr Ala Ser Asn Leu Lys
 65                  70                  75                  80

Val Ile Leu Leu Glu Leu Ala
                85

<210> SEQ ID NO 36
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 36

Ser Thr Lys Lys Thr Gln Leu Leu Leu Glu His Ala Leu Leu Asp Ala
 1               5                  10                  15

Leu His Met Ser Arg Xaa Xaa Xaa Xaa Xaa Xaa Glu Lys Leu Asn Arg
                20                  25                  30

Ile Ile Thr Asp Met Gln Ser Trp Ile Phe Xaa Xaa Xaa Xaa Xaa Gly
            35                  40                  45

Asp Gly Ala Gln Asp Leu Ala Lys Glu Val Glu Leu Glu Gln Glu
        50                  55                  60

His Glu Lys Xaa Xaa Xaa Xaa Xaa Glu Asp Tyr Ala Ser Asn Leu Lys
 65                  70                  75                  80

Val Ile Leu Leu Glu Leu Ala
                85

<210> SEQ ID NO 37
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 37

Ser Thr Lys Lys Thr Gln Leu Leu Ile Glu His Ala Leu Leu Asp Ala
 1               5                  10                  15

Leu His Met Ser Arg Xaa Xaa Xaa Xaa Xaa Xaa Glu Lys Leu Ser Arg

```
            20                  25                  30
Ile Ile Thr Thr Met Gln Ser Trp Ile Phe Xaa Xaa Xaa Xaa Xaa Gly
        35                  40                  45

Asp Gly Ala Gln His Leu Ala Lys Glu Val Glu Glu Leu Glu Gln Glu
    50                  55                  60

His Glu Lys Xaa Xaa Xaa Xaa Xaa Glu Asp Glu Ala Ser Asn Leu Lys
65                  70                  75                  80

Val Ile Leu Leu Glu Leu Ala
                85

<210> SEQ ID NO 38
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 38

Ser Thr Lys Lys Thr Gln Leu Leu Ile Glu His Ala Leu Leu Asp Ala
1               5                   10                  15

Leu His Met Lys Arg Xaa Xaa Xaa Xaa Xaa Xaa Glu Lys Leu Asn Arg
            20                  25                  30

Ile Ile Thr Asn Met Gln Ser Trp Ile Phe Xaa Xaa Xaa Xaa Xaa Gly
        35                  40                  45

Asp Gly Ala Gln Asp Leu Ala Lys Glu Val Glu Glu Leu Glu Gln Glu
    50                  55                  60

His Glu Lys Xaa Xaa Xaa Xaa Xaa Glu Asp Tyr Ala Ser Asn Leu Lys
65                  70                  75                  80

Val Ile Leu Leu Glu Leu Ala
                85

<210> SEQ ID NO 39
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent
```

<400> SEQUENCE: 39

Ser Thr Glu Lys Thr Gln Leu Ala Ala Glu His Ala Leu Arg Asp Ala
1               5                   10                  15

Leu Met Leu Lys His Leu Xaa Xaa Xaa Xaa Xaa Glu Lys Leu Ala Arg
            20                  25                  30

Ile Ile Thr Thr Met Gln Ser Trp Gln Phe Xaa Xaa Xaa Xaa Xaa Gly
        35                  40                  45

Asp Gly Ala Gln Glu Leu Ala Lys Glu Val Glu Glu Leu Gln Gln Glu
    50                  55                  60

His Glu Val Xaa Xaa Xaa Xaa Xaa Glu Asp Tyr Ala Ser Asn Leu Lys
65                  70                  75                  80

Val Ile Leu Leu His Leu Ala
                85

<210> SEQ ID NO 40
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 40

Ser Thr Lys Asn Thr Gln Leu Ala Ala Glu Asp Ala Leu Leu Asp Ala
1               5                   10                  15

Leu Met Leu Arg Asn Leu Xaa Xaa Xaa Xaa Xaa Glu Lys Leu Ala Arg
            20                  25                  30

Ile Ile Thr Thr Met Gln Ser Trp Gln Phe Xaa Xaa Xaa Xaa Xaa Gly
        35                  40                  45

Asp Gly Ala Gln Glu Leu Ala Lys Glu Val Glu Glu Leu Gln Gln Glu
    50                  55                  60

His Glu Glu Xaa Xaa Xaa Xaa Xaa Glu Asp Tyr Ala Ser Asn Leu Lys
65                  70                  75                  80

Val Ile Leu Leu Gln Leu Ala
                85

<210> SEQ ID NO 41
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)

```
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 41

Ser Thr Glu Lys Thr Gln His Ala Ala Glu Asp Ala Leu Arg Asp Ala
1               5                   10                  15

Leu Met Leu Arg Asn Leu Xaa Xaa Xaa Xaa Xaa Glu Lys Leu Ala Arg
            20                  25                  30

Ile Ile Thr Thr Met Gln Ser Trp Gln Phe Xaa Xaa Xaa Xaa Xaa Gly
        35                  40                  45

Asp Gly Ala Gln Glu Leu Ala Lys Glu Val Glu Glu Leu Gln Gln Glu
    50                  55                  60

His Glu Val Xaa Xaa Xaa Xaa Xaa Glu Asp Tyr Ala Ser Asn Leu Lys
65                  70                  75                  80

Val Ile Leu Leu Gln Leu Ala
                85

<210> SEQ ID NO 42
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(30)
<223> OTHER INFORMATION: Xaa, when present, can be any naturally
      occurring amino acid or is optionally absent
<220> FEATURE:
<221> NAME/KEY: MISC_FEATURE
<222> LOCATION: (45)..(49)
<223> OTHER INFORMATION: Xaa, when present, can be any naturally
      occurring amino acid or is optionally absent
<220> FEATURE:
<221> NAME/KEY: MISC_FEATURE
<222> LOCATION: (69)..(72)
<223> OTHER INFORMATION: Xaa, when present, can be any naturally
      occurring amino acid or is optionally absent

<400> SEQUENCE: 42

Thr Gln Lys Lys Gln Gln Leu Leu Ala Glu His Ala Leu Leu Asp Ala
1               5                   10                  15

Leu Met Ile Leu Asn Met Xaa Xaa Xaa Xaa Xaa Xaa Xaa Xaa Asn Arg
            20                  25                  30

Met Ile Thr Ile Ala Gln Ser Trp Ile Phe Thr Gly Xaa Xaa Xaa Xaa
        35                  40                  45

Xaa Glu Ala Lys Glu Met Ile Lys Met Ala Glu Gln Ala Glu Glu Glu
    50                  55                  60

Ala Arg Arg Glu Xaa Xaa Xaa Xaa Glu Asp Tyr Val Ser Asn Leu Lys
65                  70                  75                  80

Val Ile Leu Lys Glu Ile Ala
                85

<210> SEQ ID NO 43
<211> LENGTH: 87
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 43

Thr Thr Lys Lys Tyr Gln Leu Leu Val Glu His Ala Leu Leu Asp Ala
1               5                   10                  15

Leu Met Met Leu Asn Leu Xaa Xaa Xaa Xaa Xaa Xaa Lys Met Asn Arg
            20                  25                  30

Ile Ile Thr Thr Met Gln Ser Trp Ile Phe Xaa Xaa Xaa Xaa Xaa Xaa
        35                  40                  45

Asp Gln Ala Glu Glu Leu Ala Lys Leu Val Glu Glu Leu Arg Glu Glu
    50                  55                  60

Phe Arg Lys Xaa Xaa Xaa Xaa Xaa Xaa Asp Tyr Ala Ser Asn Leu Lys
65                  70                  75                  80

Val Ile Leu Lys Glu Leu Ser
                85

<210> SEQ ID NO 44
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 44

Thr Thr Lys Lys Ile Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Leu Gln Ser Trp Ile Phe Xaa Xaa Xaa Xaa Xaa Xaa
        35                  40                  45

Asp Arg Ala Arg Glu Leu Ala Lys Leu Leu Glu Glu Ile Arg Glu Glu
    50                  55                  60

Met Arg Lys Xaa Xaa Xaa Xaa Xaa Xaa Asp Tyr Val Ser Asn Met Ile
65                  70                  75                  80

Val Ile Ile Arg Glu Leu Ala
                85
```

```
<210> SEQ ID NO 45
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 45

Thr Lys Lys Lys Ile Gln Leu Leu Ala Glu His Val Leu Leu Asp Leu
1               5                   10                  15

Leu Met Met Leu Asn Leu Xaa Xaa Xaa Xaa Xaa Xaa Lys Met Asn Arg
            20                  25                  30

Leu Ile Thr Ile Val Gln Ser Trp Ile Phe Xaa Xaa Xaa Xaa Xaa Xaa
        35                  40                  45

Asp Gln Ala Glu Glu Met Ala Lys Trp Val Glu Leu Arg Glu Glu
    50                  55                  60

Phe Arg Lys Xaa Xaa Xaa Xaa Xaa Asp Tyr Ala Ser Asn Val Lys
65                  70                  75                  80

Val Ile Leu Lys Glu Leu Ser
                85

<210> SEQ ID NO 46
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 46

Thr Lys Lys Lys Tyr Gln Leu Leu Ile Glu His Leu Leu Leu Asp Ala
1               5                   10                  15

Leu Met Val Leu Asn Met Xaa Xaa Xaa Xaa Xaa Xaa Lys Leu Asn Arg
            20                  25                  30

Ile Ile Thr Ile Leu Gln Ser Trp Ile Phe Xaa Xaa Xaa Xaa Xaa Xaa
        35                  40                  45

Asp Leu Ala Glu Glu Met Glu Lys Leu Met Gln Glu Ile Glu Glu Glu
    50                  55                  60
```

```
Leu Arg Arg Xaa Xaa Xaa Xaa Xaa Xaa Asp Tyr Met Ser Asn Met Arg
 65                  70                  75                  80

Val Ile Ile Lys Glu Leu Ser
                85

<210> SEQ ID NO 47
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 47

Thr Lys Lys Lys Leu Gln Leu Leu Val Glu His Leu Leu Leu Asp Met
 1               5                  10                  15

Leu Met Ile Leu Asn Met Xaa Xaa Xaa Xaa Xaa Xaa Lys Leu Asn Arg
                20                  25                  30

Leu Ile Thr Glu Leu Gln Ser Trp Ile Phe Xaa Xaa Xaa Xaa Xaa Xaa
                35                  40                  45

Asp Lys Ala Glu Glu Met Trp Lys Ile Met Glu Ile Glu Lys Glu
     50                  55                  60

Leu Arg Glu Xaa Xaa Xaa Xaa Xaa Xaa Asp Tyr Met Ser Asn Ala Lys
 65                  70                  75                  80

Val Ile Ile Lys Glu Leu Ser
                85

<210> SEQ ID NO 48
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 48

Thr Ser Lys Lys Gln Gln Leu Leu Ala Glu His Ala Leu Leu Asp Ala
 1               5                  10                  15

Leu Met Ile Leu Asn Ile Xaa Xaa Xaa Xaa Xaa Xaa Ala Val Asn Arg
                20                  25                  30
```

Ala Ile Thr Trp Leu Gln Ser Trp Ile Phe Xaa Xaa Xaa Xaa Xaa Xaa
            35                  40                  45

Asp Gln Ala Glu Glu Met Arg Lys Leu Ala Glu Gln Ile Arg Glu Glu
    50                  55                  60

Met Arg Lys Xaa Xaa Xaa Xaa Xaa Xaa Asp Tyr Val Ser Asn Leu Glu
65                  70                  75                  80

Val Ile Ala Lys Glu Leu Ser
                85

<210> SEQ ID NO 49
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 49

Thr Lys Lys Lys Tyr Gln Leu Leu Ile Glu His Leu Leu Leu Asp Leu
1               5                   10                  15

Leu Met Val Leu Asn Met Xaa Xaa Xaa Xaa Xaa Xaa Lys Ile Asn Arg
            20                  25                  30

Leu Ile Thr Trp Leu Gln Ser Trp Ile Phe Xaa Xaa Xaa Xaa Xaa Xaa
            35                  40                  45

Asp Leu Ala Glu Glu Met Tyr Lys Ile Leu Glu Glu Leu Arg Glu Glu
    50                  55                  60

Met Arg Glu Xaa Xaa Xaa Xaa Xaa Xaa Asp Tyr Met Ser Asn Met Arg
65                  70                  75                  80

Val Ile Val Lys Glu Leu Ser
                85

<210> SEQ ID NO 50
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent -continued

<400> SEQUENCE: 50

Thr Lys Lys Lys Trp Gln Leu Leu Ile Glu His Leu Leu Asp Leu
1               5                   10                  15

Leu Met Ile Leu Asn Leu Xaa Xaa Xaa Xaa Xaa Xaa Lys Leu Asn Arg
            20                  25                  30

Leu Ile Thr Trp Leu Gln Ser Trp Ile Phe Xaa Xaa Xaa Xaa Xaa Xaa
            35                  40                  45

Asp Leu Ala Glu Glu Met Lys Lys Met Met Asp Glu Ile Glu Asp Glu
            50                  55                  60

Leu Arg Glu Xaa Xaa Xaa Xaa Xaa Xaa Asp Tyr Met Ser Asn Ala Lys
65                  70                  75                  80

Val Ile Ile Lys Glu Leu Ser
                85

<210> SEQ ID NO 51
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 51

Thr Lys Lys Lys Ile Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
            35                  40                  45

Asp Gln Ala Glu Glu Leu Ser Lys Leu Val Glu Glu Ile Arg Glu Glu
            50                  55                  60

Met Arg Lys Xaa Xaa Xaa Xaa Xaa Xaa Asp Tyr Val Ser Asn Leu Lys
65                  70                  75                  80

Val Ile Leu Asp Glu Leu Ser
                85

<210> SEQ ID NO 52
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (24)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally

```
                   occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 52

Thr Glu Lys Lys Leu Gln Leu Leu Val Glu His Ala Leu Leu Asp Ala
1               5                   10                  15

Leu Met Ile Leu Asn Leu Trp Xaa Xaa Xaa Xaa Lys Leu Asn Arg
            20                  25                  30

Ile Ile Thr Thr Met Gln Ser Trp Ile Phe Xaa Xaa Xaa Xaa Xaa
            35                  40                  45

Asp Lys Ala Glu Glu Leu Ala Lys Leu Val Glu Glu Leu Arg Glu Glu
            50                  55                  60

Ala Arg Glu Xaa Xaa Xaa Xaa Xaa Asp Tyr Val Ser Asn Leu Lys
65              70                  75                  80

Val Ile Leu Lys Glu Leu Ser
                85

<210> SEQ ID NO 53
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 53

Thr Lys Lys Tyr Gln Leu Leu Met Glu His Leu Leu Leu Asp Leu
1               5                   10                  15

Leu Met Val Leu Asn Met Xaa Xaa Xaa Xaa Xaa Lys Leu Asn Arg
            20                  25                  30

Leu Ile Thr Ile Ile Gln Ser Trp Ile Phe Xaa Xaa Xaa Xaa Xaa
            35                  40                  45

Asp Lys Ala Glu Glu Met Ala Lys Met Leu Lys Glu Ile Glu Asp Glu
            50                  55                  60

Leu Arg Glu Xaa Xaa Xaa Xaa Xaa Xaa Asp Tyr Met Ser Asn Met Ile
65              70                  75                  80

Val Ile Met Lys Glu Leu Ser
                85

<210> SEQ ID NO 54
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 54

Thr Thr Lys Lys Ile Gln Leu Leu Val Glu His Ala Leu Leu Asp Ala
1               5                   10                  15

Leu Met Leu Leu Asn Leu Xaa Xaa Xaa Xaa Xaa Xaa Lys Met Asn Arg
            20                  25                  30

Ile Ile Thr Thr Met Gln Ser Trp Ile Phe Xaa Xaa Xaa Xaa Xaa Xaa
        35                  40                  45

Asp Gln Ala Gln Glu Leu Ala Lys Leu Val Glu Glu Leu Arg Glu Glu
    50                  55                  60

Phe Arg Lys Xaa Xaa Xaa Xaa Xaa Xaa Asp Tyr Val Ser Asn Leu Lys
65                  70                  75                  80

Val Ile Leu Glu Glu Leu Ser
                85

<210> SEQ ID NO 55
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 55

Thr Lys Lys Lys Ile Gln Leu Leu Val Glu His Ala Leu Leu Asp Ala
1               5                   10                  15

Leu Met Met Leu Asn Leu Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Gln Ala Glu Glu Leu Ala Lys Leu Val Arg Glu Leu Arg Glu Glu
    50                  55                  60

Phe Arg Lys Xaa Xaa Xaa Xaa Xaa Xaa Asp Tyr Ala Ser Asn Leu Glu
65                  70                  75                  80

Val Ile Leu Arg Glu Leu Ser
                85

<210> SEQ ID NO 56
```

<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 56

Thr Lys Lys Lys Ile Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
                20                  25                  30

Ile Ile Thr Thr Met Gln Ser Trp Ile Phe Xaa Xaa Xaa Xaa Xaa Xaa
            35                  40                  45

Asp Arg Ala Arg Glu Leu Ala Lys Leu Val Glu Glu Ile Arg Asp Glu
        50                  55                  60

Met Glu Lys Xaa Xaa Xaa Xaa Xaa Xaa Asp Tyr Val Ser Asn Leu Lys
65                  70                  75                  80

Val Ile Leu Glu Glu Leu Ala
                85

<210> SEQ ID NO 57
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 57

Thr Lys Lys Lys Tyr Gln Leu Leu Ile Glu His Val Leu Leu Asp Leu
1               5                   10                  15

Leu Met Leu Leu Asn Leu Xaa Xaa Xaa Xaa Xaa Xaa Lys Met Asn Arg
                20                  25                  30

Leu Ile Thr Ile Leu Gln Ser Trp Ile Phe Xaa Xaa Xaa Xaa Xaa Xaa
            35                  40                  45

Asp Lys Ala Glu Glu Met Ala Lys Leu Leu Lys Glu Leu Arg Glu Glu
        50                  55                  60

Phe Arg Glu Xaa Xaa Xaa Xaa Xaa Xaa Asp Tyr Ile Ser Asn Ala Ile 65                  70                  75                  80

Val Ile Leu Lys Glu Leu Ser
                85

<210> SEQ ID NO 58
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 58

Thr Lys Lys Lys Ile Gln Leu Leu Val Glu His Ala Leu Leu Asp Ala
1               5                   10                  15

Leu Met Met Leu Asn Leu Xaa Xaa Xaa Xaa Xaa Lys Leu Asn Arg
                20                  25                  30

Ile Ile Thr Thr Met Gln Ser Trp Ile Phe Xaa Xaa Xaa Xaa Xaa Xaa
                35                  40                  45

Asp Arg Ala Glu Glu Leu Ala Lys Leu Val Glu Glu Leu Arg Glu Glu
            50                  55                  60

Phe Arg Lys Xaa Xaa Xaa Xaa Xaa Xaa Asp Tyr Ala Ser Asn Leu Lys
65                  70                  75                  80

Val Ile Leu Lys Glu Leu Ser
                85

<210> SEQ ID NO 59
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 59

Thr Lys Lys Lys Ile Gln Leu Leu Val Glu His Ala Leu Leu Asp Ala
1               5                   10                  15

Leu Met Met Leu Asn Leu Xaa Xaa Xaa Xaa Xaa Xaa Lys Leu Asn Arg
                20                  25                  30

```
Ile Ile Thr Thr Met Gln Ser Trp Ile Phe Xaa Xaa Xaa Xaa Xaa
            35                  40                  45

Asp Gln Ala Arg Glu Leu Ala Lys Leu Val Glu Glu Leu Arg Glu Glu
 50                  55                  60

Phe Arg Lys Xaa Xaa Xaa Xaa Xaa Xaa Asp Tyr Ala Ser Asn Leu Lys
 65                  70                  75                  80

Val Ile Leu Glu Glu Leu Ala
                85
```

<210> SEQ ID NO 60
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: vnt
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 60

```
Thr Lys Lys Lys Leu Gln Leu Leu Val Glu His Ala Leu Leu Asp Ala
 1               5                  10                  15

Leu Met Leu Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
            35                  40                  45

Asp Gln Ala Glu Glu Leu Ala Lys Leu Val Glu Ile Arg Glu Glu
 50                  55                  60

Leu Arg Lys Xaa Xaa Xaa Xaa Xaa Xaa Asp Tyr Val Ser Asn Leu Lys
 65                  70                  75                  80

Val Ile Leu Lys Glu Leu Ser
                85
```

<210> SEQ ID NO 61
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 61

-continued

```
Thr Thr Lys Lys Tyr Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
            35                  40                  45

Asp Gln Ala Glu Glu Leu Ala Lys Leu Val Arg Glu Ile Arg Glu Glu
            50                  55                  60

Met Arg Lys Xaa Xaa Xaa Xaa Xaa Xaa Asp Tyr Val Ser Asn Leu Glu
65                  70                  75                  80

Val Ile Leu Arg Glu Leu Ser
                85
```

<210> SEQ ID NO 62
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 62

```
Thr Lys Lys Lys Ile Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
            35                  40                  45

Asp Arg Ala Glu Glu Leu Ala Lys Leu Val Arg Glu Ile Arg Glu Glu
            50                  55                  60

Met Arg Lys Xaa Xaa Xaa Xaa Xaa Xaa Asp Tyr Val Ser Asn Leu Glu
65                  70                  75                  80

Val Ile Leu Arg Glu Leu Ser
                85
```

<210> SEQ ID NO 63
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:

```
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 63

Thr Lys Lys Tyr Gln Leu Leu Ile Glu His Leu Leu Leu Asp Leu
1               5                  10                  15

Leu Met Ile Leu Asn Leu Xaa Xaa Xaa Xaa Xaa Xaa Lys Leu Asn Arg
                20                  25                  30

Leu Ile Thr Trp Leu Gln Ser Trp Ile Phe Arg Xaa Xaa Xaa Xaa Xaa
            35                  40                  45

Asp Lys Ala Glu Glu Trp Ala Lys Ile Leu Lys Glu Ile Arg Glu Glu
50                  55                  60

Leu Arg Glu Xaa Xaa Xaa Xaa Xaa Xaa Asp Tyr Met Ser Asn Ala Ile
65                  70                  75                  80

Val Ile Met Lys Glu Leu Ser
                85

<210> SEQ ID NO 64
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 64

Thr Asp Lys Lys Leu Gln Leu Leu Val Glu His Leu Leu Leu Asp Leu
1               5                  10                  15

Leu Met Met Leu Asn Leu Xaa Xaa Xaa Xaa Xaa Xaa Lys Met Asn Arg
                20                  25                  30

Leu Ile Thr Ile Ala Gln Ser Trp Ile Phe Thr Xaa Xaa Xaa Xaa Xaa
            35                  40                  45

Asp Leu Ala Arg Glu Met Ile Lys Leu Leu Glu Glu Thr Glu Asp Glu
50                  55                  60

Asn Arg Lys Xaa Xaa Xaa Xaa Xaa Xaa Asp Tyr Val Ser Asn Ala Arg
65                  70                  75                  80

Val Ile Ala Lys Glu Leu Glu
                85

<210> SEQ ID NO 65
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
``` occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 65

Thr Lys Lys Lys Ile Gln Leu Leu Val Glu His Ala Leu Leu Asp Ala
1               5                   10                  15

Leu Met Leu Leu Asn Leu Xaa Xaa Xaa Xaa Xaa Lys Met Asn Arg
                20                  25                  30

Ile Ile Thr Thr Met Gln Ser Trp Ile Phe Xaa Xaa Xaa Xaa Xaa Xaa
            35                  40                  45

Asp Gln Ala Glu Glu Leu Ala Lys Leu Val Glu Glu Leu Lys Glu Glu
            50                  55                  60

Phe Lys Lys Xaa Xaa Xaa Xaa Xaa Xaa Asp Tyr Val Ser Asn Leu Lys
65                  70                  75                  80

Val Ile Leu Lys Glu Leu Ser
                85

<210> SEQ ID NO 66
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 66

Thr Lys Lys Lys Tyr Gln Leu Leu Ile Glu His Ala Leu Leu Asp Ala
1               5                   10                  15

Leu Met Ile Leu Asn Leu Xaa Xaa Xaa Xaa Xaa Xaa Lys Leu Asn Arg
                20                  25                  30

Ile Ile Thr Thr Met Gln Ser Trp Ile Phe Thr Xaa Xaa Xaa Xaa Xaa
            35                  40                  45

Asp Lys Ala Glu Glu Leu Glu Lys Leu Ala Lys Glu Ile Glu Asp Glu
            50                  55                  60

Ala Arg Glu Xaa Xaa Xaa Xaa Xaa Xaa Asp Tyr Met Ser Asn Leu Arg
65                  70                  75                  80

Val Ile Leu Lys Glu Leu Ser
                85

<210> SEQ ID NO 67
<211> LENGTH: 87
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 67

Thr Lys Lys Lys Ala Gln Leu Leu Ala Glu His Ala Leu Leu Asp Ala
1               5                   10                  15

Leu Met Leu Leu Asn Leu Xaa Xaa Xaa Xaa Xaa Xaa Arg Leu Asn Arg
            20                  25                  30

Ile Ile Thr Trp Leu Gln Ser Ile Ile Phe Thr Xaa Xaa Xaa Xaa Xaa
        35                  40                  45

Asp Met Val Lys Glu Ala Val Lys Leu Ala Asp Glu Ile Glu Asp Glu
    50                  55                  60

Met Arg Lys Xaa Xaa Xaa Xaa Xaa Xaa Asp Tyr Val Ser Asn Leu Arg
65                  70                  75                  80

Val Ile Leu Gln Glu Leu Ala
                85

<210> SEQ ID NO 68
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 68

Thr Gln Lys Lys Asn Gln Leu Leu Ala Glu His Leu Leu Leu Asp Ala
1               5                   10                  15

Leu Met Val Leu Asn Gln Xaa Xaa Xaa Xaa Xaa Val Ala Asn Arg
            20                  25                  30

Ile Ile Thr Trp Ala Gln Ser Trp Ile Phe Glu Xaa Xaa Xaa Xaa Xaa
        35                  40                  45

Asn Lys Ala Glu Glu Ala Lys Lys Leu Ala Lys Lys Leu Glu Glu Glu
    50                  55                  60

Met Arg Lys Xaa Xaa Xaa Xaa Xaa Xaa Asp Tyr Ile Ser Asn Met Lys
65                  70                  75                  80
```

Val Ile Ala Glu Glu Met Ser
            85

<210> SEQ ID NO 69
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(29)
<223> OTHER INFORMATION: Xaa, when present, can be any naturally
      occurring amino acid or is optionally absent
<220> FEATURE:
<221> NAME/KEY: MISC_FEATURE
<222> LOCATION: (46)..(50)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(80)
<223> OTHER INFORMATION: Xaa, when present, can be any naturally
      occurring amino acid or is optionally absent

<400> SEQUENCE: 69

Glu Asp Tyr Tyr Ser Asn Leu Lys Val Ile Leu Glu Glu Leu Ala Arg
1               5                   10                  15

Glu Met Glu Arg Xaa Xaa Xaa Xaa Xaa Xaa Xaa Xaa Trp Arg Gln
            20                  25                  30

Trp Lys Lys Ile Val Glu Arg Ile Arg Gln Ile Arg Ser Xaa Xaa Xaa
            35                  40                  45

Xaa Xaa Asn Glu Ala Lys Glu Leu Leu Asn Arg Leu Ile Thr Tyr Ile
50                  55                  60

Gln Ser Gln Ile Phe Glu Ile Ser Glu Arg Ile Arg Xaa Xaa Xaa Xaa
65                  70                  75                  80

Glu Lys Lys Glu Glu Ser Trp Lys Lys Trp Gln Leu Leu Glu His
            85                  90                  95

Ala Leu Leu Asp Val Leu Met Leu Leu Asn Asp
            100                 105

<210> SEQ ID NO 70
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (55)..(56)
<223> OTHER INFORMATION: Xaa, when present, can be any naturally
      occurring amino acid or is optionally absent
<220> FEATURE:
<221> NAME/KEY: MISC_FEATURE
<222> LOCATION: (79)..(82)
<223> OTHER INFORMATION: Xaa, when present, can be any naturally
      occurring amino acid or is optionally absent

<400> SEQUENCE: 70

Pro Glu Lys Lys Arg Gln Leu Leu Leu Glu His Ile Leu Leu Asp Ala
1               5                   10                  15

Leu Met Leu Leu Asn Leu Xaa Xaa Xaa Xaa Xaa Xaa Asn Thr Glu Ser
            20                  25                  30

```
Lys Phe Glu Asp Tyr Ile Ser Asn Ala Glu Val Ile Ala Glu Leu
            35                  40                  45

Ala Lys Leu Met Glu Ser Xaa Xaa Leu Ser Asp Glu Ala Glu Lys Phe
 50                  55                  60

Lys Lys Ile Lys Gln Trp Leu Arg Glu Val Trp Arg Ile Trp Xaa Xaa
 65                  70                  75                  80

Xaa Xaa Trp Ser Thr Leu Glu Asp Lys Ala Arg Glu Leu Leu Asn Arg
             85                  90                  95

Ile Ile Thr Thr Ile Gln Ser Gln Ile Phe Tyr
            100                 105

<210> SEQ ID NO 71
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(31)
<223> OTHER INFORMATION: Xaa, when present, can be any naturally
      occurring amino acid or is optionally absent
<220> FEATURE:
<221> NAME/KEY: MISC_FEATURE
<222> LOCATION: (55)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (80)..(83)
<223> OTHER INFORMATION: Xaa, when present, can be any naturally
      occurring amino acid or is optionally absent

<400> SEQUENCE: 71

Pro Glu Lys Lys Arg Gln Leu Leu Glu His Ile Leu Leu Asp Leu
 1               5                  10                  15

Leu Met Ile Leu Asn Met Ile Glu Xaa Xaa Xaa Xaa Xaa Xaa Ser
             20                  25                  30

Glu Met Glu Asp Tyr Trp Ser Asn Val Arg Val Ile Leu Arg Glu Leu
            35                  40                  45

Ala Arg Leu Met Glu Glu Xaa Xaa Xaa Lys Glu Leu Ser Glu Leu Met
 50                  55                  60

Glu Arg Met Arg Lys Ile Val Glu Lys Ile Arg Gln Ile Val Thr Xaa
 65                  70                  75                  80

Xaa Xaa Xaa Leu Asp Thr Ala Arg Glu Trp Leu Asn Arg Leu Ile Thr
             85                  90                  95

Trp Ile Gln Ser Leu Ile Phe Arg
            100

<210> SEQ ID NO 72
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (55)..(57)
<223> OTHER INFORMATION: Xaa, when present, can be any naturally
      occurring amino acid or is optionally absent
```

```
<220> FEATURE:
<221> NAME/KEY: MISC_FEATURE
<222> LOCATION: (80)..(83)
<223> OTHER INFORMATION: Xaa, when present, can be any naturally
      occurring amino acid or is optionally absent

<400> SEQUENCE: 72

Pro Glu Lys Lys Arg Gln Leu Leu Leu Glu His Ile Leu Leu Asp Leu
1               5                   10                  15

Leu Met Ile Leu Asn Met Xaa Xaa Xaa Xaa Xaa Xaa Asn Thr Glu Ser
            20                  25                  30

Glu Met Glu Asp Tyr Trp Ser Asn Val Arg Val Ile Leu Arg Glu Leu
        35                  40                  45

Ala Arg Leu Met Glu Glu Xaa Xaa Xaa Lys Glu Leu Ser Glu Leu Met
    50                  55                  60

Glu Arg Met Arg Lys Ile Val Glu Lys Ile Arg Gln Ile Val Thr Xaa
65                  70                  75                  80

Xaa Xaa Xaa Leu Asp Thr Ala Arg Glu Trp Leu Asn Arg Leu Ile Thr
                85                  90                  95

Trp Ile Gln Ser Leu Ile Phe Arg
            100

<210> SEQ ID NO 73
<211> LENGTH: 96
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (47)..(50)
<223> OTHER INFORMATION: Xaa, when present, can be any naturally
      occurring amino acid or is optionally absent
<220> FEATURE:
<221> NAME/KEY: MISC_FEATURE
<222> LOCATION: (72)..(75)
<223> OTHER INFORMATION: Xaa, when present, can be any naturally
      occurring amino acid or is optionally absent

<400> SEQUENCE: 73

Pro Glu Lys Lys Arg Gln Leu Leu Ala Glu His Leu Leu Leu Asp Val
1               5                   10                  15

Leu Met Met Leu Asn Xaa Xaa Xaa Xaa Xaa Xaa Asp Tyr Ala Ser Asn
            20                  25                  30

Ala Gln Val Ile Ala Asp Glu Phe Arg Glu Leu Ala Arg Glu Xaa Xaa
        35                  40                  45

Xaa Xaa Asp Glu Ala Lys Lys Ala Glu Lys Ile Ile Glu Ala Leu Glu
    50                  55                  60

Arg Ala Arg Glu Trp Leu Leu Xaa Xaa Xaa Xaa Lys Glu Lys Ala Lys
65                  70                  75                  80

Glu Ala Leu Asn Arg Ala Ile Thr Ile Ala Gln Ser Trp Ile Phe Asn
                85                  90                  95

<210> SEQ ID NO 74
<211> LENGTH: 104
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (55)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (80)..(83)
<223> OTHER INFORMATION: Xaa, when present, can be any naturally
      occurring amino acid or is optionally absent

<400> SEQUENCE: 74

Pro Glu Lys Lys Arg Gln Leu Leu Glu His Leu Leu Asp Leu
1               5                   10                  15

Leu Met Ile Leu Asn Xaa Xaa Xaa Xaa Xaa Lys Asn Ile Glu Ser
                20              25                  30

Asp Trp Glu Asp Tyr Met Ser Asn Ile Glu Val Ile Glu Leu
            35                  40                  45

Arg Lys Ile Met Glu Ser Xaa Xaa Xaa Ser Glu Lys Ala Lys Glu Trp
50                  55                  60

Lys Arg Met Lys Gln Trp Val Arg Arg Ile Leu Glu Ile Val Lys Xaa
65                  70                  75                  80

Xaa Xaa Xaa Leu Glu Glu Ala Lys Glu Trp Leu Asn Arg Leu Ile Thr
                85                  90                  95

Ile Val Gln Ser Glu Ile Phe Glu
                100

<210> SEQ ID NO 75
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (55)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (80)..(83)
<223> OTHER INFORMATION: Xaa, when present, can be any naturally
      occurring amino acid or is optionally absent

<400> SEQUENCE: 75

Trp Glu Lys Lys Arg Gln Leu Leu Glu His Leu Leu Asp Leu
1               5                   10                  15

Leu Met Ile Leu Asn Xaa Xaa Xaa Xaa Xaa Gln Asn Thr Glu Ser
                20              25                  30

Leu Met Glu Asp Tyr Met Ser Asn Ala Lys Val Ile Val Glu Glu Leu
            35                  40                  45

Ala Arg Met Met Arg Ser Xaa Xaa Xaa Glu Asp Lys Ala Arg Glu Trp
50                  55                  60

Glu Glu Met Lys Lys Arg Ile Glu Glu Ile Arg Gln Ile Ile Gln Xaa
65                  70                  75                  80
```

```
Xaa Xaa Xaa Lys Glu Arg Ala Lys Glu Glu Leu Asn Arg Leu Ile Thr
            85                  90                  95

Tyr Val Gln Ser Glu Ile Phe Arg
            100

<210> SEQ ID NO 76
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 76

Pro Lys Lys Lys Ile Gln Leu Leu Ala Glu His Ala Leu Leu Asp Ala
1               5                   10                  15

Leu Met Ile Leu Asn Xaa Xaa Xaa Xaa Xaa Xaa Gln Asn Ala Glu Glu
            20                  25                  30

Lys Leu Glu Asp Tyr Ala Ser Asn Val Glu Val Ile Leu Glu Glu Ile
            35                  40                  45

Ala Arg Leu Met Glu Ser Gly Xaa Xaa Lys Asp Glu Ala Glu Lys Ala
        50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Arg Ile Ile Thr Leu Leu Gln Ser
            85                  90                  95

Trp Ile Phe Ser
            100

<210> SEQ ID NO 77
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (54)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 77

Pro Glu Lys Lys Arg Gln Leu Leu Ala Glu His Ala Leu Leu Asp Ala
1               5                   10                  15
```

```
Leu Met Ile Leu Asn Xaa Xaa Xaa Xaa Xaa Xaa Gln Asn Ala Glu Glu
            20                  25                  30

Lys Leu Glu Asp Tyr Met Ser Asn Val Glu Val Ile Met Glu Glu Phe
            35                  40                  45

Ala Arg Met Met Arg Xaa Xaa Xaa Xaa Ser Glu Ala Glu Asn Ala
50                      55                  60

Glu Arg Ile Lys Lys Trp Val Arg Lys Ala Ser Ser Xaa Xaa Xaa Ser
65                  70                  75                  80

Glu Glu Gln Arg Glu Met Met Asn Arg Ala Ile Thr Leu Met Gln Ser
                85                  90                  95

Trp Ile Phe Glu
            100

<210> SEQ ID NO 78
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(58)
<223> OTHER INFORMATION: Xaa, when present, can be any naturally
      occurring amino acid or is optionally absent
<220> FEATURE:
<221> NAME/KEY: MISC_FEATURE
<222> LOCATION: (75)..(78)
<223> OTHER INFORMATION: Xaa, when present, can be any naturally
      occurring amino acid or is optionally absent

<400> SEQUENCE: 78

Pro Glu Lys Lys Arg Gln Leu Leu Ala Glu His Leu Leu Leu Asp Ala
1               5                   10                  15

Leu Met Val Leu Asn Met Xaa Xaa Xaa Xaa Xaa Xaa Asn Thr Glu Glu
            20                  25                  30

Lys Leu Glu Asp Tyr Ile Ser Asn Met Lys Val Ile Ile Lys Glu Met
            35                  40                  45

Ile Glu Leu Met Arg Ser Leu Xaa Xaa Xaa Glu Glu Ala Glu Lys Trp
50                      55                  60

Lys Glu Ala Leu Lys Ala Val Glu Lys Ile Xaa Xaa Xaa Xaa Asp Ser
65                  70                  75                  80

Glu Thr Ala Arg Glu Leu Ala Asn Arg Ile Ile Thr Leu Ala Gln Ser
                85                  90                  95

Ala Ile Phe Tyr
            100

<210> SEQ ID NO 79
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
```

```
<222> LOCATION: (56)..(58)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(78)
<223> OTHER INFORMATION: Xaa, when present, can be any naturally
      occurring amino acid or is optionally absent

<400> SEQUENCE: 79

Pro Glu Lys Lys Arg Gln Leu Leu Ala Glu His Ala Leu Leu Asp Ala
1               5                   10                  15

Leu Met Phe Leu Asn Leu Xaa Xaa Xaa Xaa Xaa Xaa Gln Ala Glu Glu
            20                  25                  30

Lys Ile Glu Asp Tyr Ala Ser Asn Leu Arg Val Ile Ala Glu Glu Leu
        35                  40                  45

Ala Arg Leu Phe Glu Asn Leu Xaa Xaa Xaa Asp Glu Ala Gln Lys Ala
    50                  55                  60

Lys Asp Ile Lys Glu Leu Ala Glu Arg Ala Arg Ser Xaa Xaa Ser Ser
65                  70                  75                  80

Glu Lys Arg Lys Glu Ala Met Asn Arg Ala Ile Thr Ile Leu Gln Ser
                85                  90                  95

Met Ile Phe Arg
            100

<210> SEQ ID NO 80
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(58)
<223> OTHER INFORMATION: Xaa, when present, can be any naturally
      occurring amino acid or is optionally absentt
<220> FEATURE:
<221> NAME/KEY: MISC_FEATURE
<222> LOCATION: (75)..(78)
<223> OTHER INFORMATION: Xaa, when present, can be any naturally
      occurring amino acid or is optionally absent

<400> SEQUENCE: 80

Pro Glu Lys Lys Arg Gln Leu Leu Ala Glu His Ala Leu Leu Asp Ala
1               5                   10                  15

Leu Met Ile Leu Asn Ile Xaa Xaa Xaa Xaa Xaa Asp Asn Thr Glu Ser
            20                  25                  30

Lys Leu Glu Asp Tyr Ile Ser Asn Leu Lys Val Ile Leu Glu Glu Ile
        35                  40                  45

Ala Arg Leu Met Glu Ser Leu Xaa Xaa Xaa Asp Glu Ala Glu Lys Ala
    50                  55                  60

Lys Glu Ala Met Arg Leu Ala Asp Lys Ala Xaa Xaa Xaa Xaa Ser Glu
65                  70                  75                  80

Glu Glu Lys Lys Glu Ala Met Asn Arg Val Ile Thr Trp Ala Gln Ser
                85                  90                  95

Trp Ile Phe Asn
            100
```

```
<210> SEQ ID NO 81
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(29)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(58)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 81

Pro Glu Lys Lys Arg Gln Leu Leu Ala Glu His Ala Leu Leu Asp Ala
1               5                   10                  15

Leu Met Met Leu Asn Ile Xaa Xaa Xaa Xaa Xaa Xaa Xaa Ala Glu Glu
            20                  25                  30

Lys Leu Glu Asp Tyr Trp Ser Asn Leu Ile Val Ile Leu Arg Glu Ile
        35                  40                  45

Ala Lys Leu Met Glu Ser Leu Xaa Xaa Xaa Asp Ala Glu Lys Ala
    50                  55                  60

Lys Glu Ala Ala Arg Trp Ala Glu Glu Ala Arg Thr Xaa Xaa Xaa Lys
65                  70                  75                  80

Asp Gln Arg Arg Glu Leu Ala Asn Arg Ile Ile Thr Leu Leu Gln Ser
                85                  90                  95

Trp Ile Phe Ser
            100

<210> SEQ ID NO 82
<211> LENGTH: 99
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (55)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (76)..(78)
<223> OTHER INFORMATION: Xaa, when present, can be any naturally
      occurring amino acid or is optionally absent

<400> SEQUENCE: 82

Glu Lys Lys Arg Gln Leu Leu Ala Glu His Leu Leu Leu Asp Ala Leu
1               5                   10                  15

Met Ile Leu Asn Ile Ile Glu Thr Asn Glu Gln Asn Ala Glu Ser Lys
            20                  25                  30

Leu Glu Asp Tyr Ile Ser Asn Ala Lys Val Ile Leu Asp Glu Phe Arg
        35                  40                  45

Glu Met Ala Arg Asp Leu Xaa Xaa Xaa Asp Glu Ala Lys Lys Ala Glu
    50                  55                  60

Lys Met Lys Arg Trp Leu Glu Lys Met Arg Ser Xaa Xaa Xaa Ser Asp
65                  70                  75                  80
```

Glu Arg Arg Glu Trp Ala Asn Arg Met Ile Thr Thr Ala Gln Ser Trp
                85                  90                  95

Ile Phe Asn

<210> SEQ ID NO 83
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (44)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 83

Thr Asn Lys Lys Ala Gln Leu His Ala Glu Phe Ala Leu His Asp Ala
1               5                   10                  15

Leu Met Leu Leu Asn Leu Xaa Xaa Xaa Xaa Xaa Arg Leu Asn Arg
                20                  25                  30

Ile Ile Thr Trp Leu Gln Ser Ile Ile Phe Tyr Xaa Xaa Xaa Xaa Xaa
            35                  40                  45

Asp Met Val Lys Glu Ala Val Lys Asp Ala Asp Glu Ile Glu Asp Glu
    50                  55                  60

Met Arg Lys Xaa Xaa Xaa Xaa Xaa Xaa Asp Tyr Val Ser Asn Leu Arg
65                  70                  75                  80

Leu Ile Leu Gln Glu Leu Ala
                85

<210> SEQ ID NO 84
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (44)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 84

Thr Asn Lys Glu Ala Gln Leu His Ala Glu Phe Ala Leu Tyr Asp Ala
1               5                   10                  15

Leu Met Leu Leu Asn Leu Xaa Xaa Xaa Xaa Xaa Xaa Arg Leu Asn Arg
                20                  25                  30

Ile Ile Thr Trp Leu Gln Ser Ile Ile Phe Tyr Xaa Xaa Xaa Xaa Xaa
            35                  40                  45

Asp Met Val Lys Glu Ala Val Lys Leu Ala Asp Glu Ile Glu Asp Glu
        50                  55                  60

Met Arg Lys Xaa Xaa Xaa Xaa Xaa Asp Tyr Val Val Asn Leu Arg
 65                  70                  75                  80

Leu Ile Leu Gln Glu Leu Ala
                85

<210> SEQ ID NO 85
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (44)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 85

Thr Lys Lys Asp Ala Glu Leu Leu Ala Glu Phe Ala Leu Tyr Asp Ala
 1               5                  10                  15

Leu Met Leu Leu Asn Leu Xaa Xaa Xaa Xaa Xaa Arg Leu Asn Glu
                20                  25                  30

Ile Ile Thr Trp Leu Gln Ser Ile Ile Phe Tyr Xaa Xaa Xaa Xaa Xaa
            35                  40                  45

Asp Met Val Lys Glu Ala Val Lys Leu Ala Asp Glu Ile Glu Asp Glu
        50                  55                  60

Met Arg Lys Xaa Xaa Xaa Xaa Xaa Asp Tyr Val Ser Asn Leu Arg
 65                  70                  75                  80

Leu Ile Leu Gln Glu Leu Ala
                85

<210> SEQ ID NO 86
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 86

Thr Asn Lys Lys Ala Gln Leu His Ala Glu Phe Ala Leu Tyr Asp Ala
1               5                   10                  15

Leu Met Leu Leu Asn Leu Xaa Xaa Xaa Xaa Xaa Xaa Arg Leu Asn Asp
            20                  25                  30

Ile Ile Thr Trp Leu Gln Ser Ile Phe Xaa Xaa Xaa Xaa Xaa
        35                  40                  45

Asp Met Val Lys Glu Ala Val Lys Leu Ala Asp Glu Ile Glu Asp Glu
    50                  55                  60

Met Arg Lys Xaa Xaa Xaa Xaa Xaa Asp Tyr Val Val Asn Leu Arg
65                  70                  75                  80

Tyr Ile Leu Gln Glu Leu Ala
                85

<210> SEQ ID NO 87
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(24)
<223> OTHER INFORMATION: Xaa, when present, can be any naturally
      occurring amino acid or is optionally absent
<220> FEATURE:
<221> NAME/KEY: MISC_FEATURE
<222> LOCATION: (46)..(50)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(80)
<223> OTHER INFORMATION: Xaa, when present, can be any naturally
      occurring amino acid or is optionally absent

<400> SEQUENCE: 87

Glu Asp Tyr Tyr Ser Asn Leu Lys Leu Ile Leu Glu Glu Leu Ala Arg
1               5                   10                  15

Glu Met Glu Arg Xaa Xaa Xaa Xaa Asp Lys Ala Glu Gly Trp Arg Gln
            20                  25                  30

Trp Lys Lys Ile Val Glu Arg Ile Arg Gln Ile Arg Ser Xaa Xaa Xaa
            35                  40                  45

Xaa Xaa Asn Glu Ala Lys Glu Leu Leu Asn Arg Leu Ile Thr Tyr Ile
    50                  55                  60

Gln Ser Gln Ile Phe Glu Val Leu His Gly Val Gly Xaa Xaa Xaa Xaa
65                  70                  75                  80

Glu Lys Lys Glu Glu Ser Trp Lys Lys Trp Asp Leu Leu Glu His
                85                  90                  95

Ala Leu Leu Asp Val Leu Met Leu Leu Asn Asp
                100                 105

<210> SEQ ID NO 88
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(24)
<223> OTHER INFORMATION: Xaa, when present, can be any naturally
      occurring amino acid or is optionally absent
<220> FEATURE:

```
<221> NAME/KEY: MISC_FEATURE
<222> LOCATION: (46)..(50)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(80)
<223> OTHER INFORMATION: Xaa, when present, can be any naturally
      occurring amino acid or is optionally absent

<400> SEQUENCE: 88

Glu Asp Tyr Tyr Ser Asn Leu Lys Val Ile Leu Glu Glu Leu Ala Arg
1               5                   10                  15

Glu Met Glu Arg Xaa Xaa Xaa Xaa Asp Lys Ala Glu Glu Trp Arg Gln
            20                  25                  30

Trp Lys Lys Ile Val Glu Arg Ile Arg Gln Ile Arg Ser Xaa Xaa Xaa
        35                  40                  45

Xaa Xaa Asn Glu Ala Lys Glu Leu Leu Asn Glu Leu Ile Thr Tyr Ile
    50                  55                  60

Gln Ser Gln Ile Phe Glu Val Ile Glu Arg Glu Gly Xaa Xaa Xaa Xaa
65              70                  75                  80

Glu Lys Lys Glu Glu Ser Trp Lys Lys Trp Glu Leu His Leu Glu His
                85                  90                  95

Ala Leu Leu Asp Val Leu Met Leu Leu Asn Asp
                100                 105

<210> SEQ ID NO 89
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(24)
<223> OTHER INFORMATION: Xaa, when present, can be any naturally
      occurring amino acid or is optionally absent
<220> FEATURE:
<221> NAME/KEY: MISC_FEATURE
<222> LOCATION: (46)..(50)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(80)
<223> OTHER INFORMATION: Xaa, when present, can be any naturally
      occurring amino acid or is optionally absent

<400> SEQUENCE: 89

Glu Asp Tyr Tyr Ser Asn Leu Lys Leu Ile Leu Glu Glu Leu Ala Arg
1               5                   10                  15

Glu Met Glu Arg Xaa Xaa Xaa Xaa Asp Lys Ala Glu Glu Trp Arg Gln
            20                  25                  30

Trp Lys Lys Ile Val Glu Arg Ile Arg Gln Ile Arg Ser Xaa Xaa Xaa
        35                  40                  45

Xaa Xaa Asn Glu Ala Lys Glu Leu Leu Asn Arg Leu Ile Thr Tyr Ile
    50                  55                  60

Gln Ser Gln Ile Phe Glu Val Leu Glu Gly Val Gly Xaa Xaa Xaa Xaa
65              70                  75                  80

Glu Lys Lys Glu Glu Ser Trp Lys Lys Trp Glu Leu His Leu Glu His
                85                  90                  95

Ala Leu Leu Asp Val Leu Met Leu Leu Asn Asp
                100                 105
```

```
<210> SEQ ID NO 90
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 90

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 91
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 91

Pro Lys Lys Lys Ile Gln Leu Leu Ala Glu His Ala Leu Phe Asp Leu
1               5                   10                  15

Leu Met Ile Leu Asn Ile Xaa Xaa Xaa Xaa Xaa Xaa Xaa Xaa Xaa Xaa
            20                  25                  30

Lys Leu Glu Asp Tyr Ala Tyr Asn Ala Gly Val Ile Leu Glu Glu Ile
        35                  40                  45
```

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Asp Xaa Xaa Xaa Glu
65                  70                  75                  80

Asp Glu Gln Glu Glu Met Ala Asn Glu Ile Ile Thr Ile Leu Gln Ser
                85                  90                  95

Trp Asn Phe Ser
            100

<210> SEQ ID NO 92
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 92

Pro Lys Lys Lys Ile Gln Ile Thr Ala Glu Glu Ala Leu Lys Asp Ala
1               5                   10                  15

Leu Ser Ile Leu Asn Ile Xaa Xaa Xaa Xaa Xaa Xaa Xaa Xaa Xaa Xaa
            20                  25                  30

Gln Leu Glu Arg Phe Ala Lys Arg Phe Glu Arg Asn Leu Trp Gly Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 93
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)

<223> OTHER INFORMATION: Xaa, when present, can be any naturally
      occurring amino acid or is optionally absent

<400> SEQUENCE: 93

```
Pro Lys Lys Lys Ile Gln Ile Met Ala Glu Glu Ala Leu Lys Asp Ala
1               5                   10                  15

Leu Ser Ile Leu Asn Ile Xaa Xaa Xaa Xaa Xaa Xaa Xaa Xaa Xaa Xaa
            20                  25                  30

Gln Leu Glu Arg Phe Ala Lys Arg Phe Glu Arg Asn Leu Trp Gly Ile
            35                  40                  45

Ala Arg Leu Phe Glu Ser Gly Xaa Xaa Lys Asp Glu Ala Glu Lys Ala
50                      55                  60

Lys Arg Met Ile Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Phe Phe Ser
            100
```

<210> SEQ ID NO 94
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally
      occurring amino acid or is optionally absent
<220> FEATURE:
<221> NAME/KEY: MISC_FEATURE
<222> LOCATION: (55)..(56)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 94

```
Pro Lys Lys Lys Ile Gln Leu Tyr Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Glu Leu Glu Asp Tyr Ala Phe Asn Phe Glu Leu Ile Leu Glu Glu Ile
            35                  40                  45

Ala Arg Leu Phe Glu Ser Xaa Xaa Gln Lys Asp Glu Ala Glu Lys Ala
50                      55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 95
<211> LENGTH: 5
<212> TYPE: PRT
<213> ORGANISM: Artificial Sequence
<220> FEATURE:
<223> OTHER INFORMATION: Synthetic

```
<400> SEQUENCE: 95

Gly Gly Gly Gly Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic

<400> SEQUENCE: 96

Gly Ser Gly Gly Gly
1               5

<210> SEQ ID NO 97
<211> LENGTH: 6
<212> TYPE: PRT
<213> ORGANISM: Artificial Sequence
<220> FEATURE:
<223> OTHER INFORMATION: Synthetic

<400> SEQUENCE: 97

Gly Gly Gly Gly Gly Gly
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic

<400> SEQUENCE: 98

Gly Gly Ser Gly Gly Gly
1               5

<210> SEQ ID NO 99
<211> LENGTH: 16
<212> TYPE: PRT
<213> ORGANISM: Artificial Sequence
<220> FEATURE:
<223> OTHER INFORMATION: Synthetic

<400> SEQUENCE: 99

Gly Gly Ser Gly Gly Ser Gly Gly Gly Ser Gly Gly Ser Gly Ser Gly
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic

<400> SEQUENCE: 100

Gly Ser Gly Gly Ser Gly Gly Gly Ser Gly Gly Ser Gly Ser Gly
1               5                   10                  15

<210> SEQ ID NO 101
<211> LENGTH: 30
<212> TYPE: PRT
<213> ORGANISM: Artificial Sequence
<220> FEATURE:
<223> OTHER INFORMATION: Synthetic
```

```
<400> SEQUENCE: 101

Gly Gly Ser Gly Gly Ser Gly Gly Ser Gly Gly Ser Gly Gly Gly
1               5                   10                  15

Gly Ser Gly Gly Ser Gly Gly Ser Gly Gly Gly Ser
            20                  25                  30

<210> SEQ ID NO 102
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: X is Q, E, or S

<400> SEQUENCE: 102

Gly Gly Gly Gly Xaa
1               5

<210> SEQ ID NO 103
<211> LENGTH: 87
<212> TYPE: PRT
<213> ORGANISM: Artificial Sequence
<220> FEATURE:
<223> OTHER INFORMATION: Synthetic

<400> SEQUENCE: 103

Ser Thr Lys Lys Trp Gln Leu Gln Ala Glu His Ala Leu Leu Asp Trp
1               5                   10                  15

Gln Met Ala Leu Asn Lys Ser Pro Glu Pro Asn Glu Asn Leu Asn Arg
            20                  25                  30

Ala Ile Thr Ala Ala Gln Ser Trp Ile Ser Thr Gly Lys Ile Asp Leu
        35                  40                  45

Asp Lys Ala Glu Asp Ile Arg Arg Asn Ser Asp Gln Ala Arg Arg Glu
    50                  55                  60

Ala Glu Lys Arg Gly Ile Asp Val Arg Asp Leu Ile Ser Asn Ala Gln
65                  70                  75                  80

Val Ile Leu Leu Glu Ala Arg
                85

<210> SEQ ID NO 104
<211> LENGTH: 87
<212> TYPE: PRT
<213> ORGANISM: Artificial Sequence
<220> FEATURE:
<223> OTHER INFORMATION: Synthetic

<400> SEQUENCE: 104

Ser Thr Lys Lys Trp Gln Leu Gln Ala Glu His Ala Leu Leu Asp Trp
1               5                   10                  15

Gln Met Ala Leu Asn Lys Ser Pro Glu Pro Asn Glu Asn Leu Asn Arg
            20                  25                  30

Ala Ile Thr Ala Ala Gln Ser Cys Ile Ser Thr Gly Lys Cys Asp Leu
        35                  40                  45

Asp Lys Ala Glu Asp Ile Arg Arg Asn Ser Asp Gln Ala Arg Arg Glu
    50                  55                  60

Ala Glu Lys Arg Gly Ile Asp Val Arg Asp Leu Ile Ser Asn Ala Gln
65                  70                  75                  80

Val Ile Leu Leu Glu Ala Arg
```

<210> SEQ ID NO 105
<211> LENGTH: 87
<212> TYPE: PRT
<213> ORGANISM: Artificial Sequence
<220> FEATURE:
<223> OTHER INFORMATION: Synthetic

<400> SEQUENCE: 105

Ser Thr Lys Lys Trp Gln Leu Gln Ala Glu His Ala Leu Leu Asp Trp
1               5                   10                  15

Gln Met Ala Leu Asn Lys Ser Pro Glu Pro Asn Glu Asn Leu Asn Arg
            20                  25                  30

Ala Ile Thr Ala Ala Gln Ser Trp Ile Ser Thr Gly Lys Ile Asp Cys
        35                  40                  45

Asp Lys Ala Glu Asp Ile Arg Arg Asn Ser Asp Gln Ala Arg Arg Glu
    50                  55                  60

Ala Glu Lys Arg Gly Ile Asp Val Arg Asp Leu Ile Ser Asn Ala Gln
65                  70                  75                  80

Val Ile Leu Leu Glu Ala Cys
            85

<210> SEQ ID NO 106
<211> LENGTH: 87
<212> TYPE: PRT
<213> ORGANISM: Artificial Sequence
<220> FEATURE:
<223> OTHER INFORMATION: Synthetic

<400> SEQUENCE: 106

Ser Thr Lys Lys Leu Gln Leu Gln Ala Glu His Phe Leu Leu Asp Val
1               5                   10                  15

Gln Met Ile Leu Asn Glu Ser Pro Glu Pro Asn Glu Glu Leu Asn Arg
            20                  25                  30

Ala Ile Thr Asp Ala Gln Ser Trp Ile Ser Thr Gly Lys Ile Asp Leu
        35                  40                  45

Asp Arg Ala Glu Glu Leu Ala Arg Asn Leu Glu Lys Val Arg Asp Glu
    50                  55                  60

Ala Leu Lys Arg Gly Ile Asp Val Arg Asp Leu Val Ser Asn Ala Lys
65                  70                  75                  80

Val Ile Ala Leu Glu Leu Lys
            85

<210> SEQ ID NO 107
<211> LENGTH: 87
<212> TYPE: PRT
<213> ORGANISM: Artificial Sequence
<220> FEATURE:
<223> OTHER INFORMATION: Synthetic

<400> SEQUENCE: 107

Ser Thr Lys Lys Leu Gln Leu Gln Ala Glu His Phe Leu Leu Asp Val
1               5                   10                  15

Gln Met Ile Leu Asn Glu Ser Pro Glu Pro Asn Glu Glu Leu Asn Arg
            20                  25                  30

Cys Ile Thr Asp Ala Gln Ser Trp Ile Ser Thr Gly Lys Ile Asp Leu
        35                  40                  45

Asp Arg Ala Glu Glu Cys Ala Arg Asn Leu Glu Lys Val Arg Asp Glu
    50                  55                  60

```
Ala Leu Lys Arg Gly Ile Asp Val Arg Asp Leu Val Ser Asn Ala Lys
 65                  70                  75                  80

Val Ile Ala Leu Glu Leu Lys
                85
```

<210> SEQ ID NO 108
<211> LENGTH: 87
<212> TYPE: PRT
<213> ORGANISM: Artificial Sequence
<220> FEATURE:
<223> OTHER INFORMATION: Synthetic

<400> SEQUENCE: 108

```
Ser Thr Lys Lys Leu Gln Leu Gln Ala Glu His Phe Leu Leu Asp Val
 1               5                  10                  15

Gln Met Ile Leu Asn Glu Ser Pro Glu Pro Asn Glu Glu Leu Asn Arg
                20                  25                  30

Ala Ile Thr Asp Ala Gln Ser Cys Ile Ser Thr Gly Lys Cys Asp Leu
            35                  40                  45

Asp Arg Ala Glu Glu Leu Ala Arg Asn Leu Glu Lys Val Arg Asp Glu
        50                  55                  60

Ala Leu Lys Arg Gly Ile Asp Val Arg Asp Leu Val Ser Asn Ala Lys
 65                  70                  75                  80

Val Ile Ala Leu Glu Leu Lys
                85
```

<210> SEQ ID NO 109
<211> LENGTH: 87
<212> TYPE: PRT
<213> ORGANISM: Artificial Sequence
<220> FEATURE:
<223> OTHER INFORMATION: Synthetic

<400> SEQUENCE: 109

```
Ser Thr Lys Lys Leu Gln Leu Gln Ala Glu His Phe Leu Leu Asp Val
 1               5                  10                  15

Gln Met Ile Leu Asn Glu Ser Pro Glu Pro Asn Glu Glu Leu Asn Arg
                20                  25                  30

Ala Ile Thr Asp Ala Gln Ser Trp Ile Ser Thr Gly Lys Ile Asp Leu
            35                  40                  45

Asp Arg Ala Glu Glu Leu Cys Arg Asn Leu Glu Lys Val Arg Asp Glu
        50                  55                  60

Ala Leu Lys Arg Gly Ile Asp Val Arg Asp Leu Val Ser Asn Ala Cys
 65                  70                  75                  80

Val Ile Ala Leu Glu Leu Lys
                85
```

<210> SEQ ID NO 110
<211> LENGTH: 87
<212> TYPE: PRT
<213> ORGANISM: Artificial Sequence
<220> FEATURE:
<223> OTHER INFORMATION: Synthetic

<400> SEQUENCE: 110

```
Ser Thr Lys Lys Leu Gln Leu Gln Ala Glu His Ala Leu Leu Asp Ala
 1               5                  10                  15

Gln Met Met Leu Asn Arg Ser Pro Glu Pro Asn Glu Lys Leu Asn Arg
                20                  25                  30
```

Ile Ile Thr Thr Met Gln Ser Trp Ile Ser Thr Gly Lys Ile Asp Leu
            35                  40                  45

Asp Gly Ala Lys Glu Leu Ala Lys Glu Val Glu Glu Leu Arg Gln Glu
 50                  55                  60

Ala Glu Lys Arg Gly Ile Asp Val Arg Asp Leu Ala Ser Asn Leu Lys
 65                  70                  75                  80

Val Ile Leu Leu Glu Leu Ala
                85

<210> SEQ ID NO 111
<211> LENGTH: 87
<212> TYPE: PRT
<213> ORGANISM: Artificial Sequence
<220> FEATURE:
<223> OTHER INFORMATION: Synthetic

<400> SEQUENCE: 111

Ser Thr Lys Lys Leu Gln Leu Gln Ala Glu His Ala Leu Leu Asp Ala
 1               5                  10                  15

Gln Met Met Leu Asn Arg Ser Pro Glu Pro Asn Glu Lys Leu Asn Arg
                20                  25                  30

Ile Ile Thr Thr Met Gln Ser Cys Ile Ser Thr Gly Lys Cys Asp Leu
            35                  40                  45

Asp Gly Ala Lys Glu Leu Ala Lys Glu Val Glu Glu Leu Arg Gln Glu
 50                  55                  60

Ala Glu Lys Arg Gly Ile Asp Val Arg Asp Leu Ala Ser Asn Leu Lys
 65                  70                  75                  80

Val Ile Leu Leu Glu Leu Ala
                85

<210> SEQ ID NO 112
<211> LENGTH: 87
<212> TYPE: PRT
<213> ORGANISM: Artificial Sequence
<220> FEATURE:
<223> OTHER INFORMATION: Synthetic

<400> SEQUENCE: 112

Ser Thr Lys Lys Ile Gln Leu Gln Leu Glu His Ala Leu Leu Asp Val
 1               5                  10                  15

Gln Met Ala Leu Asn Arg Ser Pro Glu Pro Asn Glu Ser Leu Asn Arg
                20                  25                  30

Met Ile Thr Trp Leu Gln Ser Trp Ile Ser Thr Gly Lys Ile Asp Leu
            35                  40                  45

Asp Asn Ala Gln Glu Met Ala Lys Glu Ala Glu Lys Ile Arg Lys Glu
 50                  55                  60

Met Glu Lys Arg Gly Ile Asp Val Arg Asp Leu Ile Ser Asn Ile Ile
 65                  70                  75                  80

Val Ile Leu Leu Glu Leu Ser
                85

<210> SEQ ID NO 113
<211> LENGTH: 87
<212> TYPE: PRT
<213> ORGANISM: Artificial Sequence
<220> FEATURE:
<223> OTHER INFORMATION: Synthetic

<400> SEQUENCE: 113

Ser Thr Lys Lys Ile Gln Leu Gln Leu Glu His Ala Leu Leu Asp Val

```
                1               5                   10                  15
Gln Met Ala Leu Asn Arg Ser Pro Glu Pro Asn Glu Ser Leu Asn Arg
            20                  25                  30

Met Ile Thr Trp Leu Gln Ser Cys Ile Ser Thr Gly Lys Cys Asp Leu
            35                  40                  45

Asp Asn Ala Gln Glu Met Ala Lys Glu Ala Glu Lys Ile Arg Lys Glu
            50                  55                  60

Met Glu Lys Arg Gly Ile Asp Val Arg Asp Leu Ile Ser Asn Ile Ile
65                  70                  75                  80

Val Ile Leu Leu Glu Leu Ser
                85
```

<210> SEQ ID NO 114
<211> LENGTH: 87
<212> TYPE: PRT
<213> ORGANISM: Artificial Sequence
<220> FEATURE:
<223> OTHER INFORMATION: Synthetic

<400> SEQUENCE: 114

```
Ser Thr Lys Lys Ile Gln Leu Gln Leu Glu His Ala Leu Leu Asp Val
1               5                   10                  15

Gln Met Ala Leu Asn Arg Ser Pro Glu Pro Asn Glu Ser Leu Asn Arg
            20                  25                  30

Met Ile Thr Trp Leu Gln Ser Trp Ile Ser Thr Gly Lys Ile Asp Leu
            35                  40                  45

Asp Asn Ala Gln Glu Met Cys Lys Glu Ala Glu Lys Ile Arg Lys Glu
            50                  55                  60

Met Glu Lys Arg Gly Ile Asp Val Arg Asp Leu Ile Ser Asn Ile Cys
65                  70                  75                  80

Val Ile Leu Leu Glu Leu Ser
                85
```

<210> SEQ ID NO 115
<211> LENGTH: 87
<212> TYPE: PRT
<213> ORGANISM: Artificial Sequence
<220> FEATURE:
<223> OTHER INFORMATION: Synthetic

<400> SEQUENCE: 115

```
Ser Thr Lys Lys Thr Gln Leu Leu Ala Glu His Ala Leu Leu Asp Ala
1               5                   10                  15

Phe Met Met Leu Asn Val Val Pro Glu Pro Asn Glu Lys Leu Asn Arg
            20                  25                  30

Ile Ile Thr Thr Met Gln Ser Trp Ile Tyr Thr Gly Lys Ile Asp Ala
            35                  40                  45

Asp Gly Ala Lys Glu Leu Ala Lys Glu Val Glu Glu Leu Glu Gln Glu
            50                  55                  60

Tyr Glu Lys Arg Gly Ile Asp Val Glu Asp Ala Ser Asn Leu Lys
65                  70                  75                  80

Val Ile Leu Leu Glu Leu Ala
                85
```

<210> SEQ ID NO 116
<211> LENGTH: 87
<212> TYPE: PRT
<213> ORGANISM: Artificial Sequence
<220> FEATURE:

<223> OTHER INFORMATION: Synthetic

<400> SEQUENCE: 116

Ser Thr Lys Lys Thr Gln Leu Leu Ala Glu His Ala Leu Leu Asp Ala
1               5                   10                  15

His Met Met Leu Asn Met Leu Pro Glu Pro Asn Glu Lys Leu Asn Arg
            20                  25                  30

Ile Ile Thr Thr Met Gln Ser Trp Ile His Thr Gly Lys Ile Asp Gly
        35                  40                  45

Asp Gly Ala Gln Glu Leu Ala Lys Glu Val Glu Leu Glu Gln Glu
    50                  55                  60

Tyr Glu Lys Arg Gly Ile Asp Val Glu Asp Ala Ser Asn Leu Lys
65                  70                  75                  80

Val Ile Leu Leu Glu Leu Ala
                85

<210> SEQ ID NO 117
<211> LENGTH: 87
<212> TYPE: PRT
<213> ORGANISM: Artificial Sequence
<220> FEATURE:
<223> OTHER INFORMATION: Synthetic

<400> SEQUENCE: 117

Ser Thr Lys Lys Thr Gln Leu Leu Ala Glu His Ala Leu Leu Asp Ala
1               5                   10                  15

Phe Met Met Leu Asn Met Val Pro Glu Pro Asn Glu Lys Leu Asn Arg
            20                  25                  30

Ile Ile Thr Thr Met Gln Ser Trp Ile Phe Thr Gly Lys Ile Asp Gly
        35                  40                  45

Asp Gly Ala Lys Glu Leu Ala Lys Glu Val Glu Leu Glu Gln Glu
    50                  55                  60

Phe Glu Lys Arg Gly Ile Asp Val Glu Asp Ala Ser Asn Leu Lys
65                  70                  75                  80

Val Ile Leu Leu Glu Leu Ala
                85

<210> SEQ ID NO 118
<211> LENGTH: 87
<212> TYPE: PRT
<213> ORGANISM: Artificial Sequence
<220> FEATURE:
<223> OTHER INFORMATION: Synthetic

<400> SEQUENCE: 118

Ser Thr Lys Lys Thr Gln Leu Leu Ala Glu His Ala Leu Leu Asp Ala
1               5                   10                  15

Leu Met Met Leu Asn Met Val Pro Glu Pro Asn Glu Lys Leu Asn Arg
            20                  25                  30

Ile Ile Thr Thr Met Gln Ser Trp Ile Phe Thr Gly Lys Ile Asp Gly
        35                  40                  45

Asp Gly Ala Gln Glu Leu Ala Lys Glu Val Glu Leu Glu Gln Glu
    50                  55                  60

Leu Glu Lys Arg Gly Ile Asp Val Glu Asp Tyr Ala Ser Asn Leu Lys
65                  70                  75                  80

Val Ile Leu Leu Glu Leu Ala
                85

```
<210> SEQ ID NO 119
<211> LENGTH: 87
<212> TYPE: PRT
<213> ORGANISM: Artificial Sequence
<220> FEATURE:
<223> OTHER INFORMATION: Synthetic

<400> SEQUENCE: 119
```

Ser Thr Lys Lys Thr Gln Leu Leu Ala Glu His Ala Leu Leu Asp Ala
1               5                   10                  15

His Met Met Leu Asn Val Val Pro Glu Pro Asn Glu Lys Leu Asn Arg
            20                  25                  30

Ile Ile Thr Thr Met Gln Ser Trp Ile Tyr Thr Gly Lys Ile Asp Arg
        35                  40                  45

Asp Gly Ala Gln Glu Leu Ala Lys Glu Val Glu Glu Leu Glu Gln Glu
    50                  55                  60

Leu Glu Lys Arg Gly Ile Asp Val Asp Asp Ala Ser Asn Leu Lys
65                  70                  75                  80

Val Ile Leu Leu Glu Leu Ala
                85

```
<210> SEQ ID NO 120
<211> LENGTH: 87
<212> TYPE: PRT
<213> ORGANISM: Artificial Sequence
<220> FEATURE:
<223> OTHER INFORMATION: Synthetic

<400> SEQUENCE: 120
```

Ser Thr Lys Lys Thr Gln Leu Leu Ala Glu His Ala Leu Leu Asp Ala
1               5                   10                  15

Leu Met Met Leu Asn Leu Leu Pro Glu Pro Asn Glu Lys Leu Asn Arg
            20                  25                  30

Ile Ile Thr Thr Met Gln Ser Trp Ile Phe Thr Gly Lys Ile Asp Gly
        35                  40                  45

Asp Gly Ala Gln Glu Leu Ala Lys Glu Val Glu Glu Leu Glu Gln Glu
    50                  55                  60

His Glu Lys Arg Gly Ile Asp Val Glu Asp Tyr Ala Ser Asn Leu Lys
65                  70                  75                  80

Val Ile Leu Leu Glu Leu Ala
                85

```
<210> SEQ ID NO 121
<211> LENGTH: 87
<212> TYPE: PRT
<213> ORGANISM: Artificial Sequence
<220> FEATURE:
<223> OTHER INFORMATION: Synthetic

<400> SEQUENCE: 121
```

Ser Thr Lys Lys Thr Gln Leu Leu Ala Glu His Ala Leu Leu Asp Ala
1               5                   10                  15

Tyr Met Met Leu Asn Met Val Pro Glu Pro Asn Glu Lys Leu Asn Arg
            20                  25                  30

Ile Ile Thr Thr Met Gln Ser Trp Ile Leu Thr Gly Lys Ile Asp Ser
        35                  40                  45

Asp Gly Ala Gln Glu Leu Ala Lys Glu Val Glu Glu Leu Glu Gln Glu
    50                  55                  60

Leu Glu Lys Arg Gly Ile Asp Val Asp Asp Ala Ser Asn Leu Lys
65                  70                  75                  80

```
Val Ile Leu Leu Glu Leu Ala
                85

<210> SEQ ID NO 122
<211> LENGTH: 87
<212> TYPE: PRT
<213> ORGANISM: Artificial Sequence
<220> FEATURE:
<223> OTHER INFORMATION: Synthetic

<400> SEQUENCE: 122

Ser Thr Lys Lys Thr His Leu Ala Glu His Ala Leu Leu Asp Ala
1               5                   10                  15

Tyr Met Met Leu Asn Val Met Pro Glu Pro Asn Glu Lys Leu Asn Arg
                20                  25                  30

Ile Ile Thr Thr Met Gln Ser Trp Ile Phe Thr Gly Lys Ile Asp Gly
                35                  40                  45

Asp Gly Ala Lys Glu Leu Ala Lys Glu Val Glu Glu Leu Glu Gln Glu
            50                  55                  60

Phe Glu Lys Arg Gly Ile Asp Val Asp Asp Ala Ser Asn Leu Lys
65              70                  75                  80

Val Ile Leu Leu Glu Leu Ala
                85

<210> SEQ ID NO 123
<211> LENGTH: 87
<212> TYPE: PRT
<213> ORGANISM: Artificial Sequence
<220> FEATURE:
<223> OTHER INFORMATION: Synthetic

<400> SEQUENCE: 123

Ser Thr Lys Lys Thr Gln Leu Ala Glu His Ala Leu Leu Asp Ala
1               5                   10                  15

Tyr Met Met Leu Asn Leu Val Pro Glu Pro Asn Glu Lys Leu Asn Arg
                20                  25                  30

Ile Ile Thr Thr Met Gln Ser Trp Ile Phe Thr Gly Lys Ile Asp Ala
                35                  40                  45

Asp Gly Ala Gln Glu Leu Ala Ile Glu Val Glu Glu Leu Glu Gln Glu
            50                  55                  60

Tyr Glu Lys Arg Gly Ile Asp Val Asp Asp Tyr Ala Ser Asn Leu Lys
65              70                  75                  80

Val Ile Leu Leu Glu Leu Ala
                85

<210> SEQ ID NO 124
<211> LENGTH: 87
<212> TYPE: PRT
<213> ORGANISM: Artificial Sequence
<220> FEATURE:
<223> OTHER INFORMATION: Synthetic

<400> SEQUENCE: 124

Ser Thr Lys Lys Thr Gln Leu Met Ala Glu His Ala Leu Leu Asp Ala
1               5                   10                  15

Phe Met Met Leu Asn Val Leu Pro Glu Pro Asn Glu Lys Leu Asn Arg
                20                  25                  30

Ile Ile Thr Thr Met Gln Ser Trp Ile Phe Thr Gly Lys Ile Asp Gly
                35                  40                  45
```

```
Asp Asp Ala Gln Glu Leu Ala Lys Glu Val Glu Glu Leu Glu Gln Glu
        50                  55                  60

Leu Glu Lys Arg Gly Ile Asp Val Asp Asp Ala Ser Asn Leu Lys
65                  70                  75                  80

Val Ile Leu Leu Glu Leu Ala
                85

<210> SEQ ID NO 125
<211> LENGTH: 87
<212> TYPE: PRT
<213> ORGANISM: Artificial Sequence
<220> FEATURE:
<223> OTHER INFORMATION: Synthetic

<400> SEQUENCE: 125

Ser Thr Lys Lys Thr Gln Leu Leu Ile Glu His Ala Leu Leu Asp Ala
1               5                   10                  15

Leu Asp Met Ser Arg Asn Leu Pro Glu Pro Asn Glu Lys Leu Ser Arg
                20                  25                  30

Ile Ile Thr Thr Met Gln Ser Trp Ile Phe Thr Gly Lys Ile Asp Gly
                35                  40                  45

Asp Gly Ala Gln Gln Leu Ala Lys Glu Val Glu Glu Leu Glu Gln Glu
        50                  55                  60

His Glu Lys Arg Gly Glu Asp Val Glu Asp Ala Ser Asn Leu Lys
65                  70                  75                  80

Val Ile Leu Leu Glu Leu Ala
                85

<210> SEQ ID NO 126
<211> LENGTH: 87
<212> TYPE: PRT
<213> ORGANISM: Artificial Sequence
<220> FEATURE:
<223> OTHER INFORMATION: Synthetic

<400> SEQUENCE: 126

Ser Thr Lys Lys Thr Gln Leu Leu Glu His Ala Leu Leu Asp Ala
1               5                   10                  15

Leu His Met Arg Arg Asn Leu Pro Glu Pro Asn Glu Lys Leu Ser Arg
                20                  25                  30

Ile Ile Thr Thr Met Gln Ser Trp Ile Phe Thr Gly Lys Ile Asp Gly
                35                  40                  45

Asp Gly Ala Gln Glu Leu Ala Lys Glu Val Glu Glu Leu Glu Gln Glu
        50                  55                  60

His Glu Lys Arg Gly Arg Asp Val Glu Asp Asp Ala Ser Asn Leu Lys
65                  70                  75                  80

Val Ile Leu Leu Glu Leu Ala
                85

<210> SEQ ID NO 127
<211> LENGTH: 87
<212> TYPE: PRT
<213> ORGANISM: Artificial Sequence
<220> FEATURE:
<223> OTHER INFORMATION: Synthetic

<400> SEQUENCE: 127

Ser Thr Lys Lys Thr Gln Leu Leu Ile Glu His Ala Leu Leu Asp Ala
1               5                   10                  15

Leu Asn Met Arg Lys Lys Leu Pro Glu Pro Asn Glu Lys Leu Ser Arg
```

20                  25                  30

Ile Ile Thr Asp Met Gln Ser Trp Ile Phe Thr Gly Lys Ile Asp Gly
            35                  40                  45

Asp Gly Ala Gln Gln Leu Ala Lys Glu Val Glu Glu Leu Glu Gln Glu
        50                  55                  60

His Glu Lys Arg Gly Gly Asp Val Glu Asp Tyr Ala Ser Asn Leu Lys
65                  70                  75                  80

Val Ile Leu Leu Glu Leu Ala
                85

<210> SEQ ID NO 128
<211> LENGTH: 87
<212> TYPE: PRT
<213> ORGANISM: Artificial Sequence
<220> FEATURE:
<223> OTHER INFORMATION: Synthetic

<400> SEQUENCE: 128

Ser Thr Lys Lys Thr Gln Leu Leu Leu Glu His Ala Leu Leu Asp Ala
1               5                   10                  15

Leu His Met Ser Arg Glu Leu Pro Glu Pro Asn Glu Lys Leu Asn Arg
            20                  25                  30

Ile Ile Thr Asp Met Gln Ser Trp Ile Phe Thr Gly Lys Ile Asp Gly
            35                  40                  45

Asp Gly Ala Gln Asp Leu Ala Lys Glu Val Glu Leu Glu Gln Glu
        50                  55                  60

His Glu Lys Arg Gly Gly Asp Val Glu Asp Tyr Ala Ser Asn Leu Lys
65                  70                  75                  80

Val Ile Leu Leu Glu Leu Ala
                85

<210> SEQ ID NO 129
<211> LENGTH: 87
<212> TYPE: PRT
<213> ORGANISM: Artificial Sequence
<220> FEATURE:
<223> OTHER INFORMATION: Synthetic

<400> SEQUENCE: 129

Ser Thr Lys Lys Thr Gln Leu Leu Ile Glu His Ala Leu Leu Asp Ala
1               5                   10                  15

Leu His Met Ser Arg Lys Leu Pro Glu Pro Asn Glu Lys Leu Ser Arg
            20                  25                  30

Ile Ile Thr Thr Met Gln Ser Trp Ile Phe Thr Gly Lys Ile Asp Gly
            35                  40                  45

Asp Gly Ala Gln His Leu Ala Lys Glu Val Glu Glu Leu Glu Gln Glu
        50                  55                  60

His Glu Lys Arg Gly Gly Glu Val Glu Asp Glu Ala Ser Asn Leu Lys
65                  70                  75                  80

Val Ile Leu Leu Glu Leu Ala
                85

<210> SEQ ID NO 130
<211> LENGTH: 87
<212> TYPE: PRT
<213> ORGANISM: Artificial Sequence
<220> FEATURE:
<223> OTHER INFORMATION: Synthetic

<400> SEQUENCE: 130

```
Ser Thr Lys Lys Thr Gln Leu Leu Ile Glu His Ala Leu Leu Asp Ala
1               5                   10                  15

Leu His Met Lys Arg Lys Leu Pro Glu Pro Asn Glu Lys Leu Asn Arg
            20                  25                  30

Ile Ile Thr Asn Met Gln Ser Trp Ile Phe Thr Glu Lys Ile Asp Gly
            35                  40                  45

Asp Gly Ala Gln Asp Leu Ala Lys Glu Val Glu Leu Glu Gln Glu
            50                  55                  60

His Glu Lys Arg Gly Gln Asp Val Glu Asp Tyr Ala Ser Asn Leu Lys
65                  70                  75                  80

Val Ile Leu Leu Glu Leu Ala
                85

<210> SEQ ID NO 131
<211> LENGTH: 87
<212> TYPE: PRT
<213> ORGANISM: Artificial Sequence
<220> FEATURE:
<223> OTHER INFORMATION: Synthetic

<400> SEQUENCE: 131

Ser Thr Glu Lys Thr Gln Leu Ala Ala Glu His Ala Leu Arg Asp Ala
1               5                   10                  15

Leu Met Leu Lys His Leu Leu Asn Glu Pro Asn Glu Lys Leu Ala Arg
            20                  25                  30

Ile Ile Thr Thr Met Gln Ser Trp Gln Phe Thr Gly Lys Ile Asp Gly
            35                  40                  45

Asp Gly Ala Gln Glu Leu Ala Lys Glu Val Glu Glu Leu Gln Gln Glu
            50                  55                  60

His Glu Val Arg Gly Ile Asp Val Glu Asp Tyr Ala Ser Asn Leu Lys
65                  70                  75                  80

Val Ile Leu Leu His Leu Ala
                85

<210> SEQ ID NO 132
<211> LENGTH: 87
<212> TYPE: PRT
<213> ORGANISM: Artificial Sequence
<220> FEATURE:
<223> OTHER INFORMATION: Synthetic

<400> SEQUENCE: 132

Ser Thr Lys Asn Thr Gln Leu Ala Ala Glu Asp Ala Leu Leu Asp Ala
1               5                   10                  15

Leu Met Leu Arg Asn Leu Leu Asn Glu Pro Asn Glu Lys Leu Ala Arg
            20                  25                  30

Ile Ile Thr Thr Met Gln Ser Trp Gln Phe Thr Glu Lys Ile Asp Gly
            35                  40                  45

Asp Gly Ala Gln Glu Leu Ala Lys Glu Val Glu Glu Leu Gln Gln Glu
            50                  55                  60

His Glu Glu Arg Gly Ile Asp Val Glu Asp Tyr Ala Ser Asn Leu Lys
65                  70                  75                  80

Val Ile Leu Leu Gln Leu Ala
                85

<210> SEQ ID NO 133
<211> LENGTH: 87
<212> TYPE: PRT
```

<213> ORGANISM: Artificial Sequence
<220> FEATURE:
<223> OTHER INFORMATION: Synthetic

<400> SEQUENCE: 133

Ser Thr Glu Lys Thr Gln His Ala Ala Glu Asp Ala Leu Arg Asp Ala
1               5                   10                  15

Leu Met Leu Arg Asn Leu Leu Asn Glu Pro Asn Glu Lys Leu Ala Arg
            20                  25                  30

Ile Ile Thr Thr Met Gln Ser Trp Gln Phe Thr Glu Lys Ile Asp Gly
        35                  40                  45

Asp Gly Ala Gln Glu Leu Ala Lys Glu Val Glu Leu Gln Gln Glu
    50                  55                  60

His Glu Val Arg Gly Ile Asp Val Glu Asp Tyr Ala Ser Asn Leu Lys
65                  70                  75                  80

Val Ile Leu Leu Gln Leu Ala
                85

<210> SEQ ID NO 134
<211> LENGTH: 87
<212> TYPE: PRT
<213> ORGANISM: Artificial Sequence
<220> FEATURE:
<223> OTHER INFORMATION: Synthetic

<400> SEQUENCE: 134

Thr Gln Lys Lys Gln Gln Leu Leu Ala Glu His Ala Leu Leu Asp Ala
1               5                   10                  15

Leu Met Ile Leu Asn Met Leu Lys Thr Ser Ser Glu Ala Val Asn Arg
            20                  25                  30

Met Ile Thr Ile Ala Gln Ser Trp Ile Phe Thr Gly Thr Ser Asn Pro
        35                  40                  45

Glu Glu Ala Lys Glu Met Ile Lys Met Ala Glu Gln Ala Glu Glu Glu
    50                  55                  60

Ala Arg Arg Glu Gly Val Asp Thr Glu Asp Tyr Val Ser Asn Leu Lys
65                  70                  75                  80

Val Ile Leu Lys Glu Ile Ala
                85

<210> SEQ ID NO 135
<211> LENGTH: 87
<212> TYPE: PRT
<213> ORGANISM: Artificial Sequence
<220> FEATURE:
<223> OTHER INFORMATION: Synthetic

<400> SEQUENCE: 135

Thr Thr Lys Lys Tyr Gln Leu Leu Val Glu His Ala Leu Leu Asp Ala
1               5                   10                  15

Leu Met Met Leu Asn Leu Ser Ser Glu Ser Asn Glu Lys Met Asn Arg
            20                  25                  30

Ile Ile Thr Thr Met Gln Ser Trp Ile Phe Thr Gly Thr Phe Asp Pro
        35                  40                  45

Asp Gln Ala Glu Glu Leu Ala Lys Leu Val Glu Glu Leu Arg Glu Glu
    50                  55                  60

Phe Arg Lys Arg Gly Ile Asp Thr Glu Asp Tyr Ala Ser Asn Leu Lys
65                  70                  75                  80

Val Ile Leu Lys Glu Leu Ser
                85

<210> SEQ ID NO 136
<211> LENGTH: 87
<212> TYPE: PRT
<213> ORGANISM: Artificial Sequence
<220> FEATURE:
<223> OTHER INFORMATION: Synthetic

<400> SEQUENCE: 136

```
Thr Thr Lys Lys Ile Gln Leu Leu Val Glu His Ala Leu Leu Asp Ala
1               5                   10                  15

Leu Met Ile Leu Asn Leu Ser Ser Glu Ser Asn Glu Lys Leu Asn Arg
            20                  25                  30

Ile Ile Thr Thr Leu Gln Ser Trp Ile Phe Arg Gly Glu Ile Asp Pro
        35                  40                  45

Asp Arg Ala Arg Glu Leu Ala Lys Leu Leu Glu Glu Ile Arg Glu Glu
    50                  55                  60

Met Arg Lys Arg Gly Ile Asp Thr Glu Asp Tyr Val Ser Asn Met Ile
65                  70                  75                  80

Val Ile Ile Arg Glu Leu Ala
                85
```

<210> SEQ ID NO 137
<211> LENGTH: 87
<212> TYPE: PRT
<213> ORGANISM: Artificial Sequence
<220> FEATURE:
<223> OTHER INFORMATION: Synthetic

<400> SEQUENCE: 137

```
Thr Lys Lys Lys Ile Gln Leu Leu Ala Glu His Val Leu Leu Asp Leu
1               5                   10                  15

Leu Met Met Leu Asn Leu Ser Ser Glu Ser Asn Glu Lys Met Asn Arg
            20                  25                  30

Leu Ile Thr Ile Val Gln Ser Trp Ile Phe Thr Gly Thr Ile Asp Pro
        35                  40                  45

Asp Gln Ala Glu Glu Met Ala Lys Trp Val Glu Glu Leu Arg Glu Glu
    50                  55                  60

Phe Arg Lys Arg Gly Ile Asp Thr Glu Asp Tyr Ala Ser Asn Val Lys
65                  70                  75                  80

Val Ile Leu Lys Glu Leu Ser
                85
```

<210> SEQ ID NO 138
<211> LENGTH: 87
<212> TYPE: PRT
<213> ORGANISM: Artificial Sequence
<220> FEATURE:
<223> OTHER INFORMATION: Synthetic

<400> SEQUENCE: 138

```
Thr Lys Lys Lys Tyr Gln Leu Leu Ile Glu His Leu Leu Leu Asp Ala
1               5                   10                  15

Leu Met Val Leu Asn Met Ser Ser Glu Ser Asn Glu Lys Leu Asn Arg
            20                  25                  30

Ile Ile Thr Ile Leu Gln Ser Trp Ile Phe Thr Gly Thr Trp Asp Pro
        35                  40                  45

Asp Leu Ala Glu Glu Met Glu Lys Leu Met Gln Glu Ile Glu Glu Glu
    50                  55                  60
```

```
Leu Arg Arg Arg Gly Ile Asp Thr Glu Asp Tyr Met Ser Asn Met Arg
65                  70                  75                  80

Val Ile Ile Lys Glu Leu Ser
                85
```

<210> SEQ ID NO 139
<211> LENGTH: 87
<212> TYPE: PRT
<213> ORGANISM: Artificial Sequence
<220> FEATURE:
<223> OTHER INFORMATION: Synthetic

<400> SEQUENCE: 139

```
Thr Lys Lys Leu Gln Leu Leu Val Glu His Leu Leu Leu Asp Met
1               5                   10                  15

Leu Met Ile Leu Asn Met Ser Ser Glu Ser Asn Glu Lys Leu Asn Arg
                20                  25                  30

Leu Ile Thr Glu Leu Gln Ser Trp Ile Phe Arg Gly Glu Ile Asp Pro
            35                  40                  45

Asp Lys Ala Glu Glu Met Trp Lys Ile Met Glu Gly Ile Glu Lys Glu
        50                  55                  60

Leu Arg Glu Arg Gly Ile Asp Thr Glu Asp Tyr Met Ser Asn Ala Lys
65                  70                  75                  80

Val Ile Ile Lys Glu Leu Ser
                85
```

<210> SEQ ID NO 140
<211> LENGTH: 87
<212> TYPE: PRT
<213> ORGANISM: Artificial Sequence
<220> FEATURE:
<223> OTHER INFORMATION: Synthetic

<400> SEQUENCE: 140

```
Thr Ser Lys Lys Gln Gln Leu Leu Ala Glu His Ala Leu Leu Asp Ala
1               5                   10                  15

Leu Met Ile Leu Asn Ile Ser Ser Glu Ser Ser Glu Ala Val Asn Arg
                20                  25                  30

Ala Ile Thr Trp Leu Gln Ser Trp Ile Phe Lys Gly Thr Val Asn Pro
            35                  40                  45

Asp Gln Ala Glu Glu Met Arg Lys Leu Ala Glu Gln Ile Arg Glu Glu
        50                  55                  60

Met Arg Lys Arg Gly Ile Asp Thr Glu Asp Tyr Val Ser Asn Leu Glu
65                  70                  75                  80

Val Ile Ala Lys Glu Leu Ser
                85
```

<210> SEQ ID NO 141
<211> LENGTH: 87
<212> TYPE: PRT
<213> ORGANISM: Artificial Sequence
<220> FEATURE:
<223> OTHER INFORMATION: Synthetic

<400> SEQUENCE: 141

```
Thr Lys Lys Lys Tyr Gln Leu Leu Ile Glu His Leu Leu Leu Asp Leu
1               5                   10                  15

Leu Met Val Leu Asn Met Ser Ser Glu Ser Asn Glu Lys Ile Asn Arg
                20                  25                  30

Leu Ile Thr Trp Leu Gln Ser Trp Ile Phe Thr Gly Thr Tyr Asp Pro
```

```
                35                  40                  45
Asp Leu Ala Glu Glu Met Tyr Lys Ile Leu Glu Glu Leu Arg Glu Glu
        50                  55                  60
Met Arg Glu Arg Gly Ile Asp Thr Glu Asp Tyr Met Ser Asn Met Arg
65                  70                  75                  80
Val Ile Val Lys Glu Leu Ser
                85

<210> SEQ ID NO 142
<211> LENGTH: 87
<212> TYPE: PRT
<213> ORGANISM: Artificial Sequence
<220> FEATURE:
<223> OTHER INFORMATION: Synthetic

<400> SEQUENCE: 142

Thr Lys Lys Lys Trp Gln Leu Leu Ile Glu His Leu Leu Asp Leu
1               5                   10                  15

Leu Met Ile Leu Asn Leu Ser Ser Glu Ser Asn Glu Lys Leu Asn Arg
                20                  25                  30

Leu Ile Thr Trp Leu Gln Ser Trp Ile Phe Thr Gly Thr Tyr Asp Pro
            35                  40                  45

Asp Leu Ala Glu Glu Met Lys Lys Met Met Asp Glu Ile Glu Asp Glu
        50                  55                  60

Leu Arg Glu Arg Gly Ile Asp Thr Glu Asp Tyr Met Ser Asn Ala Lys
65                  70                  75                  80

Val Ile Ile Lys Glu Leu Ser
                85

<210> SEQ ID NO 143
<211> LENGTH: 87
<212> TYPE: PRT
<213> ORGANISM: Artificial Sequence
<220> FEATURE:
<223> OTHER INFORMATION: Synthetic

<400> SEQUENCE: 143

Thr Lys Lys Lys Ile Gln Leu Leu Val Glu His Ala Leu Leu Asp Ala
1               5                   10                  15

Leu Met Ile Leu Asn Leu Ser Ser Glu Ser Asn Glu Lys Leu Asn Arg
                20                  25                  30

Ile Ile Thr Thr Met Gln Ser Trp Ile Phe Thr Gly Thr Ile Asp Pro
            35                  40                  45

Asp Gln Ala Glu Glu Leu Ser Lys Leu Val Glu Glu Ile Arg Glu Glu
        50                  55                  60

Met Arg Lys Arg Gly Ile Asp Thr Glu Asp Tyr Val Ser Asn Leu Lys
65                  70                  75                  80

Val Ile Leu Asp Glu Leu Ser
                85

<210> SEQ ID NO 144
<211> LENGTH: 87
<212> TYPE: PRT
<213> ORGANISM: Artificial Sequence
<220> FEATURE:
<223> OTHER INFORMATION: Synthetic

<400> SEQUENCE: 144

Thr Glu Lys Lys Leu Gln Leu Leu Val Glu His Ala Leu Leu Asp Ala
1               5                   10                  15
```

```
Leu Met Ile Leu Asn Leu Trp Ser Glu Ser Asn Glu Lys Leu Asn Arg
            20                  25                  30

Ile Ile Thr Thr Met Gln Ser Trp Ile Phe Thr Gly Arg Ile Asp Pro
        35                  40                  45

Asp Lys Ala Glu Glu Leu Ala Lys Leu Val Glu Leu Arg Glu Glu
 50                  55                  60

Ala Arg Glu Arg Gly Ile Asp Thr Glu Asp Tyr Val Ser Asn Leu Lys
 65                  70                  75                  80

Val Ile Leu Lys Glu Leu Ser
                85

<210> SEQ ID NO 145
<211> LENGTH: 87
<212> TYPE: PRT
<213> ORGANISM: Artificial Sequence
<220> FEATURE:
<223> OTHER INFORMATION: Synthetic

<400> SEQUENCE: 145

Thr Lys Lys Lys Tyr Gln Leu Leu Met Glu His Leu Leu Asp Leu
 1               5                  10                  15

Leu Met Val Leu Asn Met Ser Ser Glu Ser Asn Glu Lys Leu Asn Arg
            20                  25                  30

Leu Ile Thr Ile Ile Gln Ser Trp Ile Phe Thr Gly Thr Trp Asp Pro
        35                  40                  45

Asp Lys Ala Glu Glu Met Ala Lys Met Leu Lys Glu Ile Glu Asp Glu
 50                  55                  60

Leu Arg Glu Arg Gly Ile Asp Thr Glu Asp Tyr Met Ser Asn Met Ile
 65                  70                  75                  80

Val Ile Met Lys Glu Leu Ser
                85

<210> SEQ ID NO 146
<211> LENGTH: 87
<212> TYPE: PRT
<213> ORGANISM: Artificial Sequence
<220> FEATURE:
<223> OTHER INFORMATION: Synthetic

<400> SEQUENCE: 146

Thr Thr Lys Lys Ile Gln Leu Leu Val Glu His Ala Leu Leu Asp Ala
 1               5                  10                  15

Leu Met Leu Leu Asn Leu Ser Ser Glu Ser Asn Glu Lys Met Asn Arg
            20                  25                  30

Ile Ile Thr Thr Met Gln Ser Trp Ile Phe Glu Gly Arg Ile Asp Pro
        35                  40                  45

Asp Gln Ala Gln Glu Leu Ala Lys Leu Val Glu Glu Leu Arg Glu Glu
 50                  55                  60

Phe Arg Lys Arg Gly Ile Asp Thr Glu Asp Tyr Val Ser Asn Leu Lys
 65                  70                  75                  80

Val Ile Leu Glu Glu Leu Ser
                85

<210> SEQ ID NO 147
<211> LENGTH: 87
<212> TYPE: PRT
<213> ORGANISM: Artificial Sequence
<220> FEATURE:
<223> OTHER INFORMATION: Synthetic
```

<400> SEQUENCE: 147

Thr Lys Lys Lys Ile Gln Leu Leu Val Glu His Ala Leu Leu Asp Ala
1               5                   10                  15

Leu Met Met Leu Asn Leu Ser Ser Glu Ser Asn Glu Lys Leu Asn Arg
            20                  25                  30

Ile Ile Thr Thr Met Gln Ser Trp Ile Phe Thr Gly Thr Ile Asp Pro
        35                  40                  45

Asp Gln Ala Glu Glu Leu Ala Lys Leu Val Arg Glu Leu Arg Glu Glu
    50                  55                  60

Phe Arg Lys Arg Gly Ile Asp Thr Glu Asp Tyr Ala Ser Asn Leu Glu
65                  70                  75                  80

Val Ile Leu Arg Glu Leu Ser
                85

<210> SEQ ID NO 148
<211> LENGTH: 87
<212> TYPE: PRT
<213> ORGANISM: Artificial Sequence
<220> FEATURE:
<223> OTHER INFORMATION: Synthetic

<400> SEQUENCE: 148

Thr Lys Lys Lys Ile Gln Leu Leu Val Glu His Ala Leu Leu Asp Ala
1               5                   10                  15

Leu Met Ile Leu Asn Leu Ser Ser Lys Ser Asn Glu Lys Leu Asn Arg
            20                  25                  30

Ile Ile Thr Thr Met Gln Ser Trp Ile Phe Asn Gly Thr Ile Asp Pro
        35                  40                  45

Asp Arg Ala Arg Glu Leu Ala Lys Leu Val Glu Glu Ile Arg Asp Glu
    50                  55                  60

Met Glu Lys Asn Gly Ile Asp Thr Glu Asp Tyr Val Ser Asn Leu Lys
65                  70                  75                  80

Val Ile Leu Glu Glu Leu Ala
                85

<210> SEQ ID NO 149
<211> LENGTH: 87
<212> TYPE: PRT
<213> ORGANISM: Artificial Sequence
<220> FEATURE:
<223> OTHER INFORMATION: Synthetic

<400> SEQUENCE: 149

Thr Lys Lys Lys Tyr Gln Leu Leu Ile Glu His Val Leu Leu Asp Leu
1               5                   10                  15

Leu Met Leu Leu Asn Leu Ser Ser Glu Ser Asn Glu Lys Met Asn Arg
            20                  25                  30

Leu Ile Thr Ile Leu Gln Ser Trp Ile Phe Thr Gly Thr Tyr Asp Pro
        35                  40                  45

Asp Lys Ala Glu Glu Met Ala Lys Leu Leu Lys Glu Leu Arg Glu Glu
    50                  55                  60

Phe Arg Glu Arg Gly Ile Asp Thr Glu Asp Tyr Ile Ser Asn Ala Ile
65                  70                  75                  80

Val Ile Leu Lys Glu Leu Ser
                85

<210> SEQ ID NO 150

```
<211> LENGTH: 87
<212> TYPE: PRT
<213> ORGANISM: Artificial Sequence
<220> FEATURE:
<223> OTHER INFORMATION: Synthetic

<400> SEQUENCE: 150

Thr Lys Lys Lys Ile Gln Leu Leu Val Glu His Ala Leu Leu Asp Ala
1               5                   10                  15

Leu Met Met Leu Asn Leu Ser Ser Glu Ser Asn Glu Lys Leu Asn Arg
            20                  25                  30

Ile Ile Thr Thr Met Gln Ser Trp Ile Phe Thr Gly Thr Ile Asp Pro
        35                  40                  45

Asp Arg Ala Glu Glu Leu Ala Lys Leu Val Glu Glu Leu Arg Glu Glu
    50                  55                  60

Phe Arg Lys Arg Gly Ile Asp Thr Glu Asp Tyr Ala Ser Asn Leu Lys
65                  70                  75                  80

Val Ile Leu Lys Glu Leu Ser
                85

<210> SEQ ID NO 151
<211> LENGTH: 87
<212> TYPE: PRT
<213> ORGANISM: Artificial Sequence
<220> FEATURE:
<223> OTHER INFORMATION: Synthetic

<400> SEQUENCE: 151

Thr Lys Lys Lys Ile Gln Leu Leu Val Glu His Ala Leu Leu Asp Ala
1               5                   10                  15

Leu Met Met Leu Asn Leu Ser Ser Glu Ser Asn Glu Lys Leu Asn Arg
            20                  25                  30

Ile Ile Thr Thr Met Gln Ser Trp Ile Phe Asn Gly Thr Ile Asp Pro
        35                  40                  45

Asp Gln Ala Arg Glu Leu Ala Lys Leu Val Glu Glu Leu Arg Glu Glu
    50                  55                  60

Phe Arg Lys Arg Gly Ile Asp Thr Glu Asp Tyr Ala Ser Asn Leu Lys
65                  70                  75                  80

Val Ile Leu Glu Glu Leu Ala
                85

<210> SEQ ID NO 152
<211> LENGTH: 87
<212> TYPE: PRT
<213> ORGANISM: Artificial Sequence
<220> FEATURE:
<223> OTHER INFORMATION: Synthetic

<400> SEQUENCE: 152

Thr Lys Lys Lys Leu Gln Leu Leu Val Glu His Ala Leu Leu Asp Ala
1               5                   10                  15

Leu Met Leu Leu Asn Leu Ser Ser Glu Ser Asn Glu Lys Leu Asn Arg
            20                  25                  30

Ile Ile Thr Thr Met Gln Ser Trp Ile Phe Thr Gly Thr Val Asp Pro
        35                  40                  45

Asp Gln Ala Glu Glu Leu Ala Lys Leu Val Glu Glu Ile Arg Glu Glu
    50                  55                  60

Leu Arg Lys Arg Gly Ile Asp Thr Glu Asp Tyr Val Ser Asn Leu Lys
65                  70                  75                  80
```

Val Ile Leu Lys Glu Leu Ser
            85

<210> SEQ ID NO 153
<211> LENGTH: 87
<212> TYPE: PRT
<213> ORGANISM: Artificial Sequence
<220> FEATURE:
<223> OTHER INFORMATION: Synthetic

<400> SEQUENCE: 153

Thr Thr Lys Lys Tyr Gln Leu Leu Val Glu His Ala Leu Leu Asp Ala
1               5                   10                  15

Leu Met Ile Leu Asn Leu Ser Ser Glu Ser Asn Glu Lys Leu Asn Arg
            20                  25                  30

Ile Ile Thr Thr Met Gln Ser Trp Ile Phe Thr Gly Thr Phe Asp Pro
        35                  40                  45

Asp Gln Ala Glu Glu Leu Ala Lys Leu Val Arg Glu Ile Arg Glu Glu
    50                  55                  60

Met Arg Lys Arg Gly Ile Asp Thr Glu Asp Tyr Val Ser Asn Leu Glu
65                  70                  75                  80

Val Ile Leu Arg Glu Leu Ser
            85

<210> SEQ ID NO 154
<211> LENGTH: 87
<212> TYPE: PRT
<213> ORGANISM: Artificial Sequence
<220> FEATURE:
<223> OTHER INFORMATION: Synthetic

<400> SEQUENCE: 154

Thr Lys Lys Lys Ile Gln Leu Leu Val Glu His Ala Leu Leu Asp Ala
1               5                   10                  15

Leu Met Ile Leu Asn Leu Ser Ser Glu Ser Asn Glu Lys Leu Asn Arg
            20                  25                  30

Ile Ile Thr Thr Met Gln Ser Trp Ile Phe Thr Gly Thr Ile Asp Pro
        35                  40                  45

Asp Arg Ala Glu Glu Leu Ala Lys Leu Val Arg Glu Ile Arg Glu Glu
    50                  55                  60

Met Arg Lys Arg Gly Ile Asp Thr Glu Asp Tyr Val Ser Asn Leu Glu
65                  70                  75                  80

Val Ile Leu Arg Glu Leu Ser
            85

<210> SEQ ID NO 155
<211> LENGTH: 87
<212> TYPE: PRT
<213> ORGANISM: Artificial Sequence
<220> FEATURE:
<223> OTHER INFORMATION: Synthetic

<400> SEQUENCE: 155

Thr Lys Lys Lys Tyr Gln Leu Leu Ile Glu His Leu Leu Leu Asp Leu
1               5                   10                  15

Leu Met Ile Leu Asn Leu Ser Ser Glu Ser Asn Glu Lys Leu Asn Arg
            20                  25                  30

Leu Ile Thr Trp Leu Gln Ser Trp Ile Phe Arg Gly Glu Trp Asp Pro
        35                  40                  45

Asp Lys Ala Glu Glu Trp Ala Lys Ile Leu Lys Glu Ile Arg Glu Glu

```
                50                  55                  60
Leu Arg Glu Arg Gly Ile Asp Thr Glu Asp Tyr Met Ser Asn Ala Ile
 65                  70                  75                  80

Val Ile Met Lys Glu Leu Ser
                85

<210> SEQ ID NO 156
<211> LENGTH: 87
<212> TYPE: PRT
<213> ORGANISM: Artificial Sequence
<220> FEATURE:
<223> OTHER INFORMATION: Synthetic

<400> SEQUENCE: 156

Thr Asp Lys Lys Leu Gln Leu Leu Val Glu His Leu Leu Asp Leu
 1               5                  10                  15

Leu Met Met Leu Asn Leu Ser Ser Lys Ser Asn Glu Lys Met Asn Arg
                20                  25                  30

Leu Ile Thr Ile Ala Gln Ser Trp Ile Phe Thr Gly Lys Val Asp Pro
             35                  40                  45

Asp Leu Ala Arg Glu Met Ile Lys Leu Leu Glu Glu Thr Glu Asp Glu
         50                  55                  60

Asn Arg Lys Asn Gly Ile Asp Thr Glu Asp Tyr Val Ser Asn Ala Arg
 65                  70                  75                  80

Val Ile Ala Lys Glu Leu Glu
                85

<210> SEQ ID NO 157
<211> LENGTH: 87
<212> TYPE: PRT
<213> ORGANISM: Artificial Sequence
<220> FEATURE:
<223> OTHER INFORMATION: Synthetic

<400> SEQUENCE: 157

Thr Lys Lys Lys Ile Gln Leu Leu Val Glu His Ala Leu Leu Asp Ala
 1               5                  10                  15

Leu Met Leu Leu Asn Leu Ser Ser Glu Ser Asn Glu Lys Met Asn Arg
                20                  25                  30

Ile Ile Thr Thr Met Gln Ser Trp Ile Phe Thr Gly Thr Ile Asp Pro
             35                  40                  45

Asp Gln Ala Glu Glu Leu Ala Lys Leu Val Glu Glu Leu Lys Glu Glu
         50                  55                  60

Phe Lys Lys Arg Gly Ile Asp Thr Glu Asp Tyr Val Ser Asn Leu Lys
 65                  70                  75                  80

Val Ile Leu Lys Glu Leu Ser
                85

<210> SEQ ID NO 158
<211> LENGTH: 87
<212> TYPE: PRT
<213> ORGANISM: Artificial Sequence
<220> FEATURE:
<223> OTHER INFORMATION: Synthetic

<400> SEQUENCE: 158

Thr Lys Lys Lys Tyr Gln Leu Leu Ile Glu His Ala Leu Leu Asp Ala
 1               5                  10                  15

Leu Met Ile Leu Asn Leu Trp Ser Glu Ser Asn Glu Lys Leu Asn Arg
                20                  25                  30
```

```
Ile Ile Thr Thr Met Gln Ser Trp Ile Phe Thr Gly Thr Tyr Asp Pro
            35                  40                  45

Asp Lys Ala Glu Glu Leu Glu Lys Leu Ala Lys Ile Glu Asp Glu
 50                  55                  60

Ala Arg Glu Arg Gly Ile Asp Thr Glu Asp Tyr Met Ser Asn Leu Arg
 65                  70                  75                  80

Val Ile Leu Lys Glu Leu Ser
                85

<210> SEQ ID NO 159
<211> LENGTH: 87
<212> TYPE: PRT
<213> ORGANISM: Artificial Sequence
<220> FEATURE:
<223> OTHER INFORMATION: Synthetic

<400> SEQUENCE: 159

Thr Lys Lys Lys Ala Gln Leu Leu Ala Glu His Ala Leu Leu Asp Ala
 1               5                  10                  15

Leu Met Leu Leu Asn Leu Ser Ser Glu Ser Asn Glu Arg Leu Asn Arg
                20                  25                  30

Ile Ile Thr Trp Leu Gln Ser Ile Ile Phe Thr Gly Thr Tyr Asp Pro
            35                  40                  45

Asp Met Val Lys Glu Ala Val Lys Leu Ala Asp Glu Ile Glu Asp Glu
 50                  55                  60

Met Arg Lys Arg Gly Ile Asp Thr Glu Asp Tyr Val Ser Asn Leu Arg
 65                  70                  75                  80

Val Ile Leu Gln Glu Leu Ala
                85

<210> SEQ ID NO 160
<211> LENGTH: 87
<212> TYPE: PRT
<213> ORGANISM: Artificial Sequence
<220> FEATURE:
<223> OTHER INFORMATION: Synthetic

<400> SEQUENCE: 160

Thr Gln Lys Lys Asn Gln Leu Leu Ala Glu His Leu Leu Leu Asp Ala
 1               5                  10                  15

Leu Met Val Leu Asn Gln Ser Ser Glu Ser Ser Glu Val Ala Asn Arg
                20                  25                  30

Ile Ile Thr Trp Ala Gln Ser Trp Ile Phe Glu Gly Arg Val Asp Pro
            35                  40                  45

Asn Lys Ala Glu Glu Ala Lys Lys Leu Ala Lys Lys Leu Glu Glu Glu
 50                  55                  60

Met Arg Lys Arg Gly Ile Asp Met Glu Asp Tyr Ile Ser Asn Met Lys
 65                  70                  75                  80

Val Ile Ala Glu Glu Met Ser
                85

<210> SEQ ID NO 161
<211> LENGTH: 107
<212> TYPE: PRT
<213> ORGANISM: Artificial Sequence
<220> FEATURE:
<223> OTHER INFORMATION: Synthetic

<400> SEQUENCE: 161
```

```
Glu Asp Tyr Tyr Ser Asn Leu Lys Val Ile Leu Glu Glu Leu Ala Arg
1               5                   10                  15

Glu Met Glu Arg Asn Gly Leu Ser Asp Lys Ala Glu Gly Trp Arg Gln
            20                  25                  30

Trp Lys Lys Ile Val Glu Arg Ile Arg Gln Ile Arg Ser Asn Asn Ser
                35                  40                  45

Asp Leu Asn Glu Ala Lys Glu Leu Leu Asn Arg Leu Ile Thr Tyr Ile
    50                  55                  60

Gln Ser Gln Ile Phe Glu Ile Ser Glu Arg Ile Arg Glu Thr Asp Gln
65                  70                  75                  80

Glu Lys Lys Glu Glu Ser Trp Lys Lys Trp Gln Leu Leu Leu Glu His
                85                  90                  95

Ala Leu Leu Asp Val Leu Met Leu Leu Asn Asp
                100                 105

<210> SEQ ID NO 162
<211> LENGTH: 107
<212> TYPE: PRT
<213> ORGANISM: Artificial Sequence
<220> FEATURE:
<223> OTHER INFORMATION: Synthetic

<400> SEQUENCE: 162

Pro Glu Lys Lys Arg Gln Leu Leu Glu His Ile Leu Leu Asp Ala
1               5                   10                  15

Leu Met Leu Leu Asn Leu Leu Glu Thr Asn Pro Gln Asn Thr Glu Ser
            20                  25                  30

Lys Phe Glu Asp Tyr Ile Ser Asn Ala Glu Val Ile Ala Glu Glu Leu
                35                  40                  45

Ala Lys Leu Met Glu Ser Leu Gly Leu Ser Asp Glu Ala Glu Lys Phe
    50                  55                  60

Lys Lys Ile Lys Gln Trp Leu Arg Glu Val Trp Arg Ile Trp Ser Ser
65                  70                  75                  80

Thr Asn Trp Ser Thr Leu Glu Asp Lys Ala Arg Glu Leu Leu Asn Arg
                85                  90                  95

Ile Ile Thr Thr Ile Gln Ser Gln Ile Phe Tyr
            100                 105

<210> SEQ ID NO 163
<211> LENGTH: 104
<212> TYPE: PRT
<213> ORGANISM: Artificial Sequence
<220> FEATURE:
<223> OTHER INFORMATION: Synthetic

<400> SEQUENCE: 163

Pro Glu Lys Lys Arg Gln Leu Leu Glu His Ile Leu Leu Asp Leu
1               5                   10                  15

Leu Met Ile Leu Asn Met Ile Glu Thr Asn Arg Glu Asn Thr Glu Ser
            20                  25                  30

Glu Met Glu Asp Tyr Trp Ser Asn Val Arg Val Ile Leu Arg Glu Leu
                35                  40                  45

Ala Arg Leu Met Glu Glu Leu Asn Tyr Lys Glu Leu Ser Glu Leu Met
    50                  55                  60

Glu Arg Met Arg Lys Ile Val Glu Lys Ile Arg Gln Ile Val Thr Asn
65                  70                  75                  80

Asn Ser Ser Leu Asp Thr Ala Arg Glu Trp Leu Asn Arg Leu Ile Thr
                85                  90                  95
```

```
Trp Ile Gln Ser Leu Ile Phe Arg
            100

<210> SEQ ID NO 164
<211> LENGTH: 104
<212> TYPE: PRT
<213> ORGANISM: Artificial Sequence
<220> FEATURE:
<223> OTHER INFORMATION: Synthetic

<400> SEQUENCE: 164

Pro Glu Lys Lys Arg Gln Leu Leu Ala Glu His Ala Leu Leu Asp Ala
1               5                   10                  15

Leu Met Leu Leu Asn Ile Ile Glu Thr Asn Ser Lys Asn Thr Glu Ser
            20                  25                  30

Lys Met Glu Asp Tyr Val Ser Asn Leu Glu Val Ile Leu Thr Glu Phe
        35                  40                  45

Lys Lys Leu Ala Glu Lys Leu Asn Phe Ser Glu Glu Ala Glu Arg Ala
    50                  55                  60

Glu Arg Met Lys Arg Trp Ala Arg Lys Ala Tyr Gln Met Met Thr Leu
65                  70                  75                  80

Asp Leu Ser Leu Asp Lys Ala Lys Glu Met Leu Asn Arg Ile Ile Thr
                85                  90                  95

Ile Leu Gln Ser Ile Ile Phe Asn
            100

<210> SEQ ID NO 165
<211> LENGTH: 96
<212> TYPE: PRT
<213> ORGANISM: Artificial Sequence
<220> FEATURE:
<223> OTHER INFORMATION: Synthetic

<400> SEQUENCE: 165

Pro Glu Lys Lys Arg Gln Leu Leu Ala Glu His Leu Leu Leu Asp Val
1               5                   10                  15

Leu Met Met Leu Asn Gly Asn Ala Ser Leu Lys Asp Tyr Ala Ser Asn
            20                  25                  30

Ala Gln Val Ile Ala Asp Glu Phe Arg Glu Leu Ala Arg Glu Leu Gly
        35                  40                  45

Leu Thr Asp Glu Ala Lys Lys Ala Glu Lys Ile Ile Glu Ala Leu Glu
    50                  55                  60

Arg Ala Arg Glu Trp Leu Leu Asn Asn Lys Asp Lys Glu Lys Ala Lys
65                  70                  75                  80

Glu Ala Leu Asn Arg Ala Ile Thr Ile Ala Gln Ser Trp Ile Phe Asn
                85                  90                  95

<210> SEQ ID NO 166
<211> LENGTH: 104
<212> TYPE: PRT
<213> ORGANISM: Artificial Sequence
<220> FEATURE:
<223> OTHER INFORMATION: Synthetic

<400> SEQUENCE: 166

Pro Glu Lys Lys Arg Gln Leu Leu Leu Glu His Leu Leu Leu Asp Leu
1               5                   10                  15

Leu Met Ile Leu Asn Met Leu Arg Thr Asn Pro Lys Asn Ile Glu Ser
            20                  25                  30
```

```
Asp Trp Glu Asp Tyr Met Ser Asn Ile Glu Val Ile Glu Glu Leu
            35                  40                  45

Arg Lys Ile Met Glu Ser Leu Gly Arg Ser Lys Ala Lys Glu Trp
 50                  55                  60

Lys Arg Met Lys Gln Trp Val Arg Arg Ile Leu Glu Ile Val Lys Asn
 65                  70                  75                  80

Asn Ser Asp Leu Glu Glu Ala Lys Glu Trp Leu Asn Arg Leu Ile Thr
                85                  90                  95

Ile Val Gln Ser Glu Ile Phe Glu
            100

<210> SEQ ID NO 167
<211> LENGTH: 104
<212> TYPE: PRT
<213> ORGANISM: Artificial Sequence
<220> FEATURE:
<223> OTHER INFORMATION: Synthetic

<400> SEQUENCE: 167

Trp Glu Lys Lys Arg Gln Leu Leu Glu His Leu Leu Leu Asp Leu
 1               5                  10                  15

Leu Met Ile Leu Asn Met Trp Arg Thr Asn Pro Gln Asn Thr Glu Ser
                20                  25                  30

Leu Met Glu Asp Tyr Met Ser Asn Ala Lys Val Ile Val Glu Glu Leu
            35                  40                  45

Ala Arg Met Met Arg Ser Gln Gly Leu Glu Asp Lys Ala Arg Glu Trp
 50                  55                  60

Glu Glu Met Lys Lys Arg Ile Glu Ile Arg Gln Ile Ile Gln Asn
 65                  70                  75                  80

Asn Ser Ser Lys Glu Arg Ala Lys Glu Glu Leu Asn Arg Leu Ile Thr
                85                  90                  95

Tyr Val Gln Ser Glu Ile Phe Arg
            100

<210> SEQ ID NO 168
<211> LENGTH: 100
<212> TYPE: PRT
<213> ORGANISM: Artificial Sequence
<220> FEATURE:
<223> OTHER INFORMATION: Synthetic

<400> SEQUENCE: 168

Pro Lys Lys Lys Ile Gln Leu Leu Ala Glu His Ala Leu Leu Asp Ala
 1               5                  10                  15

Leu Met Ile Leu Asn Ile Val Lys Thr Asn Ser Gln Asn Ala Glu Glu
                20                  25                  30

Lys Leu Glu Asp Tyr Ala Ser Asn Val Glu Val Ile Leu Glu Glu Ile
            35                  40                  45

Ala Arg Leu Met Glu Ser Gly Asp Gln Lys Asp Glu Ala Glu Lys Ala
 50                  55                  60

Lys Arg Met Lys Glu Trp Met Lys Arg Ile Lys Thr Thr Ala Ser Glu
 65                  70                  75                  80

Asp Glu Gln Glu Glu Met Ala Asn Arg Ile Ile Thr Leu Leu Gln Ser
                85                  90                  95

Trp Ile Phe Ser
            100

<210> SEQ ID NO 169
```

```
<211> LENGTH: 100
<212> TYPE: PRT
<213> ORGANISM: Artificial Sequence
<220> FEATURE:
<223> OTHER INFORMATION: Synthetic

<400> SEQUENCE: 169

Pro Glu Lys Lys Arg Gln Leu Leu Ala Glu His Ala Leu Leu Asp Ala
1               5                   10                  15

Leu Met Ile Leu Asn Ile Leu Gln Thr Asn Pro Gln Asn Ala Glu Glu
            20                  25                  30

Lys Leu Glu Asp Tyr Met Ser Asn Val Glu Val Ile Met Glu Glu Phe
        35                  40                  45

Ala Arg Met Met Arg Asn Gly Asp Arg Ser Glu Glu Ala Glu Asn Ala
    50                  55                  60

Glu Arg Ile Lys Lys Trp Val Arg Lys Ala Ser Ser Thr Ala Ser Ser
65                  70                  75                  80

Glu Glu Gln Arg Glu Met Met Asn Arg Ala Ile Thr Leu Met Gln Ser
                85                  90                  95

Trp Ile Phe Glu
            100

<210> SEQ ID NO 170
<211> LENGTH: 100
<212> TYPE: PRT
<213> ORGANISM: Artificial Sequence
<220> FEATURE:
<223> OTHER INFORMATION: Synthetic

<400> SEQUENCE: 170

Pro Glu Lys Lys Arg Gln Leu Leu Ala Glu His Leu Leu Leu Asp Ala
1               5                   10                  15

Leu Met Val Leu Asn Met Leu Thr Thr Asn Ser Lys Asn Thr Glu Glu
            20                  25                  30

Lys Leu Glu Asp Tyr Ile Ser Asn Met Lys Val Ile Ile Lys Glu Met
        35                  40                  45

Ile Glu Leu Met Arg Ser Leu Gly Arg Leu Glu Glu Ala Glu Lys Trp
    50                  55                  60

Lys Glu Ala Leu Lys Ala Val Glu Lys Ile Gly Ser Arg Met Asp Ser
65                  70                  75                  80

Glu Thr Ala Arg Glu Leu Ala Asn Arg Ile Ile Thr Leu Ala Gln Ser
                85                  90                  95

Ala Ile Phe Tyr
            100

<210> SEQ ID NO 171
<211> LENGTH: 100
<212> TYPE: PRT
<213> ORGANISM: Artificial Sequence
<220> FEATURE:
<223> OTHER INFORMATION: Synthetic

<400> SEQUENCE: 171

Pro Glu Lys Lys Arg Gln Leu Leu Ala Glu His Ala Leu Leu Asp Ala
1               5                   10                  15

Leu Met Phe Leu Asn Leu Val Glu Thr Asn Pro Asp Gln Ala Glu Glu
            20                  25                  30

Lys Ile Glu Asp Tyr Ala Ser Asn Leu Arg Val Ile Ala Glu Glu Leu
        35                  40                  45
```

Ala Arg Leu Phe Glu Asn Leu Gly Arg Leu Asp Glu Ala Gln Lys Ala
 50                  55                  60

Lys Asp Ile Lys Glu Leu Ala Glu Arg Ala Arg Ser Arg Val Ser Ser
 65                  70                  75                  80

Glu Lys Arg Lys Glu Ala Met Asn Arg Ala Ile Thr Ile Leu Gln Ser
                 85                  90                  95

Met Ile Phe Arg
            100

<210> SEQ ID NO 172
<211> LENGTH: 100
<212> TYPE: PRT
<213> ORGANISM: Artificial Sequence
<220> FEATURE:
<223> OTHER INFORMATION: Synthetic

<400> SEQUENCE: 172

Pro Glu Lys Lys Arg Gln Leu Leu Ala Glu His Ala Leu Leu Asp Ala
 1               5                  10                  15

Leu Met Ile Leu Asn Ile Ile Arg Thr Asn Ser Asp Asn Thr Glu Ser
                20                  25                  30

Lys Leu Glu Asp Tyr Ile Ser Asn Leu Lys Val Ile Leu Glu Glu Ile
             35                  40                  45

Ala Arg Leu Met Glu Ser Leu Gly Leu Ser Asp Glu Ala Glu Lys Ala
 50                  55                  60

Lys Glu Ala Met Arg Leu Ala Asp Lys Ala Gly Ser Thr Ala Ser Glu
 65                  70                  75                  80

Glu Glu Lys Lys Glu Ala Met Asn Arg Val Ile Thr Trp Ala Gln Ser
                 85                  90                  95

Trp Ile Phe Asn
            100

<210> SEQ ID NO 173
<211> LENGTH: 100
<212> TYPE: PRT
<213> ORGANISM: Artificial Sequence
<220> FEATURE:
<223> OTHER INFORMATION: Synthetic

<400> SEQUENCE: 173

Pro Glu Lys Lys Arg Gln Leu Leu Ala Glu His Ala Leu Leu Asp Ala
 1               5                  10                  15

Leu Met Met Leu Asn Ile Leu Arg Thr Asn Pro Asp Asn Ala Glu Glu
                20                  25                  30

Lys Leu Glu Asp Tyr Trp Ser Asn Leu Ile Val Ile Leu Arg Glu Ile
             35                  40                  45

Ala Lys Leu Met Glu Ser Leu Gly Leu Thr Asp Glu Ala Glu Lys Ala
 50                  55                  60

Lys Glu Ala Ala Arg Trp Ala Glu Glu Ala Arg Thr Thr Ala Ser Lys
 65                  70                  75                  80

Asp Gln Arg Arg Glu Leu Ala Asn Arg Ile Ile Thr Leu Leu Gln Ser
                 85                  90                  95

Trp Ile Phe Ser
            100

<210> SEQ ID NO 174
<211> LENGTH: 100
<212> TYPE: PRT
<213> ORGANISM: Artificial Sequence

```
<220> FEATURE:
<223> OTHER INFORMATION: Synthetic

<400> SEQUENCE: 174

Pro Glu Lys Lys Arg Gln Leu Leu Ala Glu His Leu Leu Leu Asp Ala
1               5                   10                  15

Leu Met Ile Leu Asn Ile Ile Glu Thr Asn Gln Asn Ala Glu Ser
            20                  25                  30

Lys Leu Glu Asp Tyr Ile Ser Asn Ala Lys Val Ile Leu Asp Glu Phe
        35                  40                  45

Arg Glu Met Ala Arg Asp Leu Gly Leu Leu Asp Glu Ala Lys Lys Ala
    50                  55                  60

Glu Lys Met Lys Arg Trp Leu Glu Lys Met Arg Ser Asn Ala Ser Ser
65                  70                  75                  80

Asp Glu Arg Arg Glu Trp Ala Asn Arg Met Ile Thr Thr Ala Gln Ser
                85                  90                  95

Trp Ile Phe Asn
            100

<210> SEQ ID NO 175
<211> LENGTH: 87
<212> TYPE: PRT
<213> ORGANISM: Artificial Sequence
<220> FEATURE:
<223> OTHER INFORMATION: Synthetic

<400> SEQUENCE: 175

Thr Asn Lys Glu Ala Gln Leu His Ala Glu Phe Ala Leu Tyr Asp Ala
1               5                   10                  15

Leu Met Leu Leu Asn Leu Ser Ser Glu Ser Asn Glu Arg Leu Asn Arg
            20                  25                  30

Ile Ile Thr Trp Leu Gln Ser Ile Ile Phe Tyr Glu Thr Tyr Asp Pro
        35                  40                  45

Asp Met Val Lys Glu Ala Val Lys Leu Ala Asp Glu Ile Glu Asp Glu
    50                  55                  60

Met Arg Lys Arg Lys Ile Asp Thr Glu Asp Tyr Val Val Asn Leu Arg
65                  70                  75                  80

Leu Ile Leu Gln Glu Leu Ala
                85

<210> SEQ ID NO 176
<211> LENGTH: 87
<212> TYPE: PRT
<213> ORGANISM: Artificial Sequence
<220> FEATURE:
<223> OTHER INFORMATION: Synthetic

<400> SEQUENCE: 176

Thr Lys Lys Asp Ala Glu Leu Leu Ala Glu Phe Ala Leu Tyr Asp Ala
1               5                   10                  15

Leu Met Leu Leu Asn Leu Ser Ser Glu Ser Asn Glu Arg Leu Asn Glu
            20                  25                  30

Ile Ile Thr Trp Leu Gln Ser Ile Ile Phe Tyr Gly Thr Tyr Asp Pro
        35                  40                  45

Asp Met Val Lys Glu Ala Val Lys Leu Ala Asp Glu Ile Glu Asp Glu
    50                  55                  60

Met Arg Lys Arg Gly Ile Asp Thr Glu Asp Tyr Val Ser Asn Leu Arg
65                  70                  75                  80
```

Leu Ile Leu Gln Glu Leu Ala
                85

<210> SEQ ID NO 177
<211> LENGTH: 87
<212> TYPE: PRT
<213> ORGANISM: Artificial Sequence
<220> FEATURE:
<223> OTHER INFORMATION: Synthetic

<400> SEQUENCE: 177

Thr Asn Lys Lys Ala Gln Leu His Ala Glu Phe Ala Leu Tyr Asp Ala
1               5                   10                  15

Leu Met Leu Leu Asn Leu Ser Ser Glu Ser Asn Glu Arg Leu Asn Asp
            20                  25                  30

Ile Ile Thr Trp Leu Gln Ser Ile Ile Phe Thr Gly Thr Tyr Asp Pro
        35                  40                  45

Asp Met Val Lys Glu Ala Val Lys Leu Ala Asp Glu Ile Glu Asp Glu
    50                  55                  60

Met Arg Lys Arg Lys Ile Asp Thr Glu Asp Tyr Val Val Asn Leu Arg
65                  70                  75                  80

Tyr Ile Leu Gln Glu Leu Ala
                85

<210> SEQ ID NO 178
<211> LENGTH: 107
<212> TYPE: PRT
<213> ORGANISM: Artificial Sequence
<220> FEATURE:
<223> OTHER INFORMATION: Synthetic

<400> SEQUENCE: 178

Glu Asp Tyr Tyr Ser Asn Leu Lys Leu Ile Leu Glu Glu Leu Ala Arg
1               5                   10                  15

Glu Met Glu Arg Asn Gly Leu Ser Asp Lys Ala Glu Glu Trp Arg Gln
            20                  25                  30

Trp Lys Lys Ile Val Glu Arg Ile Arg Gln Ile Arg Ser Asn Asn Ser
        35                  40                  45

Asp Leu Asn Glu Ala Lys Glu Leu Leu Asn Arg Leu Ile Thr Tyr Ile
    50                  55                  60

Gln Ser Gln Ile Phe Glu Val Leu His Gly Val Gly Glu Thr Asp Gln
65                  70                  75                  80

Glu Lys Lys Glu Glu Ser Trp Lys Lys Trp Asp Leu Leu Glu His
            85                  90                  95

Ala Leu Leu Asp Val Leu Met Leu Leu Asn Asp
            100                 105

<210> SEQ ID NO 179
<211> LENGTH: 107
<212> TYPE: PRT
<213> ORGANISM: Artificial Sequence
<220> FEATURE:
<223> OTHER INFORMATION: Synthetic

<400> SEQUENCE: 179

Glu Asp Tyr Tyr Ser Asn Leu Lys Val Ile Leu Glu Glu Leu Ala Arg
1               5                   10                  15

Glu Met Glu Arg Asn Gly Leu Ser Asp Lys Ala Glu Glu Trp Arg Gln
            20                  25                  30

Trp Lys Lys Ile Val Glu Arg Ile Arg Gln Ile Arg Ser Asn Asn Ser

```
                    35                  40                  45

Asp Leu Asn Glu Ala Lys Glu Leu Leu Asn Glu Leu Ile Thr Tyr Ile
         50                  55                  60

Gln Ser Gln Ile Phe Glu Val Ile Glu Arg Glu Gly Glu Thr Asp Gln
 65                  70                  75                  80

Glu Lys Lys Glu Glu Ser Trp Lys Lys Trp Glu Leu His Leu Glu His
                     85                  90                  95

Ala Leu Leu Asp Val Leu Met Leu Leu Asn Asp
                100                 105

<210> SEQ ID NO 180
<211> LENGTH: 107
<212> TYPE: PRT
<213> ORGANISM: Artificial Sequence
<220> FEATURE:
<223> OTHER INFORMATION: Synthetic

<400> SEQUENCE: 180

Glu Asp Tyr Tyr Ser Asn Leu Lys Leu Ile Leu Glu Glu Leu Ala Arg
 1               5                  10                  15

Glu Met Glu Arg Asn Gly Leu Ser Asp Lys Ala Glu Glu Trp Arg Gln
                20                  25                  30

Trp Lys Lys Ile Val Glu Arg Ile Arg Gln Ile Arg Ser Asn Asn Ser
            35                  40                  45

Asp Leu Asn Glu Ala Lys Glu Leu Leu Asn Arg Leu Ile Thr Tyr Ile
         50                  55                  60

Gln Ser Gln Ile Phe Glu Val Leu Glu Gly Val Gly Glu Thr Asp Gln
 65                  70                  75                  80

Glu Lys Lys Glu Glu Ser Trp Lys Lys Trp Glu Leu His Leu Glu His
                     85                  90                  95

Ala Leu Leu Asp Val Leu Met Leu Leu Asn Asp
                100                 105

<210> SEQ ID NO 181
<211> LENGTH: 100
<212> TYPE: PRT
<213> ORGANISM: Artificial Sequence
<220> FEATURE:
<223> OTHER INFORMATION: Synthetic

<400> SEQUENCE: 181

Pro Lys Lys Lys Ile Gln Leu His Ala Glu His Ala Leu Tyr Asp Ala
 1               5                  10                  15

Leu Met Ile Leu Asn Ile Val Lys Thr Asn Ser Pro Pro Ala Glu Glu
                20                  25                  30

Lys Leu Glu Asp Tyr Ala Phe Asn Phe Glu Leu Ile Leu Glu Glu Ile
            35                  40                  45

Ala Arg Leu Phe Glu Ser Gly Asp Gln Lys Asp Glu Ala Glu Lys Ala
         50                  55                  60

Lys Arg Met Lys Glu Trp Met Lys Arg Ile Lys Thr Thr Ala Ser Glu
 65                  70                  75                  80

Asp Glu Gln Glu Glu Met Ala Asn Ala Ile Ile Thr Ile Leu Gln Ser
                     85                  90                  95

Trp Ile Phe Ser
            100

<210> SEQ ID NO 182
<211> LENGTH: 100
```

```
<212> TYPE: PRT
<213> ORGANISM: Artificial Sequence
<220> FEATURE:
<223> OTHER INFORMATION: Synthetic

<400> SEQUENCE: 182

Pro Lys Lys Lys Ile Gln Leu Leu Ala Glu His Ala Leu Phe Asp Leu
1               5                   10                  15

Leu Met Ile Leu Asn Ile Val Lys Thr Asn Ser Gln Asn Ala Glu Glu
            20                  25                  30

Lys Leu Glu Asp Tyr Ala Tyr Asn Ala Gly Val Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Asp Thr Ala Ser Glu
65                  70                  75                  80

Asp Glu Gln Glu Glu Met Ala Asn Glu Ile Ile Thr Ile Leu Gln Ser
                85                  90                  95

Trp Asn Phe Ser
            100

<210> SEQ ID NO 183
<211> LENGTH: 100
<212> TYPE: PRT
<213> ORGANISM: Artificial Sequence
<220> FEATURE:
<223> OTHER INFORMATION: Synthetic

<400> SEQUENCE: 183

Pro Lys Lys Lys Ile Gln Ile Thr Ala Glu Glu Ala Leu Lys Asp Ala
1               5                   10                  15

Leu Ser Ile Leu Asn Ile Val Lys Thr Asn Ser Pro Pro Ala Glu Glu
            20                  25                  30

Gln Leu Glu Arg Phe Ala Lys Arg Phe Glu Arg Asn Leu Trp Gly Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 184
<211> LENGTH: 100
<212> TYPE: PRT
<213> ORGANISM: Artificial Sequence
<220> FEATURE:
<223> OTHER INFORMATION: Synthetic

<400> SEQUENCE: 184

Pro Lys Lys Lys Ile Gln Ile Met Ala Glu Glu Ala Leu Lys Asp Ala
1               5                   10                  15

Leu Ser Ile Leu Asn Ile Val Lys Thr Asn Ser Pro Pro Ala Glu Glu
            20                  25                  30

Gln Leu Glu Arg Phe Ala Lys Arg Phe Glu Arg Asn Leu Trp Gly Ile
        35                  40                  45

Ala Arg Leu Phe Glu Ser Gly Asp Gln Lys Asp Glu Ala Glu Lys Ala
```

```
            50                  55                  60
Lys Arg Met Ile Glu Trp Met Lys Arg Ile Lys Thr Thr Ala Ser Glu
 65                  70                  75                  80

Asp Glu Gln Glu Glu Met Ala Asn Ala Ile Ile Thr Ile Leu Gln Ser
                 85                  90                  95

Trp Phe Phe Ser
            100

<210> SEQ ID NO 185

<400> SEQUENCE: 185

000

<210> SEQ ID NO 186
<211> LENGTH: 130
<212> TYPE: PRT
<213> ORGANISM: Artificial Sequence
<220> FEATURE:
<223> OTHER INFORMATION: Synthetic

<400> SEQUENCE: 186

Gly Pro Gly Ser His Leu Glu Gln Leu Leu Met Asp Leu Gln Glu Leu
  1               5                  10                  15

Leu Ser Arg Met Glu Asn Tyr Arg Asn Leu Lys Leu Pro Arg Met Leu
                 20                  25                  30

Thr Phe Lys Phe Tyr Leu Pro Lys Gln Ala Thr Glu Leu Lys Asp Leu
             35                  40                  45

Gln Cys Leu Glu Asp Glu Leu Gly Pro Leu Arg His Val Leu Asp Leu
 50                  55                  60

Thr Gln Ser Lys Ser Phe Gln Leu Glu Asp Ala Glu Asn Phe Ile Ser
 65                  70                  75                  80

Asn Ile Arg Val Thr Val Val Lys Leu Lys Gly Ser Asp Asn Thr Phe
                 85                  90                  95

Glu Cys Gln Phe Asp Asp Glu Ser Ala Thr Val Val Asp Phe Leu Arg
                100                 105                 110

Arg Trp Ile Ala Phe Cys Gln Ser Ile Ile Ser Thr Ser Pro Gln Ala
            115                 120                 125

Ala Ala
    130

<210> SEQ ID NO 187
<211> LENGTH: 133
<212> TYPE: PRT
<213> ORGANISM: Artificial Sequence
<220> FEATURE:
<223> OTHER INFORMATION: Synthetic

<400> SEQUENCE: 187

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala His Ser Lys Asn Phe His Phe
 65                  70                  75                  80
```

```
Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Leu Thr Phe Cys Gln Ser Ile
        115                 120                 125

Ile Ser Thr Leu Thr
        130

<210> SEQ ID NO 188
<211> LENGTH: 100
<212> TYPE: PRT
<213> ORGANISM: Artificial Sequence
<220> FEATURE:
<223> OTHER INFORMATION: Synthetic

<400> SEQUENCE: 188

Pro Lys Lys Lys Ile Gln Leu Leu Ala Glu His Ala Leu Leu Asp Ala
1               5                   10                  15

Leu Met Ile Leu Asn Ile Val Lys Thr Asn Ser Gln Asn Ala Glu Glu
            20                  25                  30

Lys Leu Glu Asp Tyr Ala Ser Asn Val Glu Val Ile Leu Glu Glu Ile
        35                  40                  45

Ala Arg Leu Met Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Arg Ile Ile Thr Leu Leu Gln Ser
                85                  90                  95

Trp Ile Phe Ser
            100

<210> SEQ ID NO 189
<211> LENGTH: 101
<212> TYPE: PRT
<213> ORGANISM: Artificial Sequence
<220> FEATURE:
<223> OTHER INFORMATION: Synthetic

<400> SEQUENCE: 189

Pro Lys Lys Lys Ile Gln Leu His Ala Glu His Ala Leu Tyr Asp Ala
1               5                   10                  15

Leu Lys Met Ile Leu Asn Ile Val Lys Thr Asn Ser Pro Pro Ala Glu
            20                  25                  30

Glu Lys Leu Glu Asp Tyr Ala Phe Asn Phe Glu Leu Ile Leu Glu Glu
        35                  40                  45

Ile Ala Arg Leu Phe Glu Ser Gly Asp Gln Lys Asp Glu Ala Glu Lys
    50                  55                  60

Ala Lys Arg Met Lys Glu Trp Met Lys Arg Ile Lys Thr Thr Ala Ser
65                  70                  75                  80

Glu Asp Glu Gln Glu Glu Met Ala Asn Ala Ile Ile Thr Ile Leu Gln
                85                  90                  95

Ser Trp Ile Phe Ser
            100

<210> SEQ ID NO 190
<211> LENGTH: 100
<212> TYPE: PRT
```

<213> ORGANISM: Artificial Sequence
<220> FEATURE:
<223> OTHER INFORMATION: Synthetic

<400> SEQUENCE: 190

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Cys Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 191
<211> LENGTH: 100
<212> TYPE: PRT
<213> ORGANISM: Artificial Sequence
<220> FEATURE:
<223> OTHER INFORMATION: Synthetic

<400> SEQUENCE: 191

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Cys Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 192
<211> LENGTH: 100
<212> TYPE: PRT
<213> ORGANISM: Artificial Sequence
<220> FEATURE:
<223> OTHER INFORMATION: Synthetic

<400> SEQUENCE: 192

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

```
Lys Arg Met Lys Glu Trp Met Lys Arg Ile Lys Thr Thr Ala Ser Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 193
<211> LENGTH: 100
<212> TYPE: PRT
<213> ORGANISM: Artificial Sequence
<220> FEATURE:
<223> OTHER INFORMATION: Synthetic

<400> SEQUENCE: 193

Pro Lys Lys Lys Ile Gln Leu His Ala Glu His Ala Leu Tyr Asp Ala
 1               5                  10                  15

Leu Met Ile Leu Asn Ile Val Lys Thr Asn Ser Pro Pro Ala Glu Glu
                 20                  25                  30

Lys Leu Glu Asp Tyr Ala Phe Asn Phe Glu Leu Ile Leu Glu Glu Ile
                 35                  40                  45

Ala Arg Leu Phe Glu Ser Gly Asp Gln Cys Asp Glu Ala Glu Lys Ala
 50                  55                  60

Lys Arg Met Lys Glu Trp Met Lys Arg Ile Lys Thr Thr Ala Ser Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 194
<211> LENGTH: 100
<212> TYPE: PRT
<213> ORGANISM: Artificial Sequence
<220> FEATURE:
<223> OTHER INFORMATION: Synthetic

<400> SEQUENCE: 194

Pro Lys Lys Lys Ile Gln Leu His Ala Glu His Ala Leu Tyr Asp Ala
 1               5                  10                  15

Leu Met Ile Leu Asn Ile Val Lys Thr Asn Ser Pro Pro Ala Glu Glu
                 20                  25                  30

Lys Leu Glu Asp Tyr Ala Phe Asn Phe Glu Leu Ile Leu Glu Glu Ile
                 35                  40                  45

Ala Arg Leu Phe Glu Ser Gly Asp Gln Lys Cys Glu Ala Glu Lys Ala
 50                  55                  60

Lys Arg Met Lys Glu Trp Met Lys Arg Ile Lys Thr Thr Ala Ser Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 195
<211> LENGTH: 100
<212> TYPE: PRT
<213> ORGANISM: Artificial Sequence
<220> FEATURE:
<223> OTHER INFORMATION: Synthetic
```

<400> SEQUENCE: 195

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Cys Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 196
<211> LENGTH: 100
<212> TYPE: PRT
<213> ORGANISM: Artificial Sequence
<220> FEATURE:
<223> OTHER INFORMATION: Synthetic

<400> SEQUENCE: 196

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Cys Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 197
<211> LENGTH: 100
<212> TYPE: PRT
<213> ORGANISM: Artificial Sequence
<220> FEATURE:
<223> OTHER INFORMATION: Synthetic

<400> SEQUENCE: 197

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Cys Trp Met Lys Arg Ile Lys Thr Thr Ala Ser Glu
65                  70                  75                  80

```
Asp Glu Gln Glu Glu Met Ala Asn Ala Ile Ile Thr Ile Leu Gln Ser
                85                  90                  95

Trp Ile Phe Ser
            100

<210> SEQ ID NO 198
<211> LENGTH: 100
<212> TYPE: PRT
<213> ORGANISM: Artificial Sequence
<220> FEATURE:
<223> OTHER INFORMATION: Synthetic

<400> SEQUENCE: 198

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 199
<211> LENGTH: 100
<212> TYPE: PRT
<213> ORGANISM: Artificial Sequence
<220> FEATURE:
<223> OTHER INFORMATION: Synthetic

<400> SEQUENCE: 199

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Cys Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 200
<211> LENGTH: 100
<212> TYPE: PRT
<213> ORGANISM: Artificial Sequence
<220> FEATURE:
<223> OTHER INFORMATION: Synthetic

<400> SEQUENCE: 200
```

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 201
<211> LENGTH: 100
<212> TYPE: PRT
<213> ORGANISM: Artificial Sequence
<220> FEATURE:
<223> OTHER INFORMATION: Synthetic

<400> SEQUENCE: 201

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Cys Met Ala Asn Ala Ile Ile Thr Ile Leu Gln Ser
                85                  90                  95

Trp Ile Phe Ser
            100

<210> SEQ ID NO 202
<211> LENGTH: 100
<212> TYPE: PRT
<213> ORGANISM: Artificial Sequence
<220> FEATURE:
<223> OTHER INFORMATION: Synthetic

<400> SEQUENCE: 202

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Cys Leu Phe Glu Ser Gly Asp Gln Lys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95
```

```
Trp Ile Phe Ser
            100

<210> SEQ ID NO 203
<211> LENGTH: 100
<212> TYPE: PRT
<213> ORGANISM: Artificial Sequence
<220> FEATURE:
<223> OTHER INFORMATION: Synthetic

<400> SEQUENCE: 203

Pro Lys Lys Lys Ile Gln Leu His Ala Glu His Ala Leu Tyr Asp Ala
1               5                  10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Cys Ser Gly Asp Gln Lys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 204
<211> LENGTH: 100
<212> TYPE: PRT
<213> ORGANISM: Artificial Sequence
<220> FEATURE:
<223> OTHER INFORMATION: Synthetic

<400> SEQUENCE: 204

Pro Lys Lys Lys Ile Gln Leu His Ala Glu His Ala Leu Tyr Asp Ala
1               5                  10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 205
<211> LENGTH: 100
<212> TYPE: PRT
<213> ORGANISM: Artificial Sequence
<220> FEATURE:
<223> OTHER INFORMATION: Synthetic

<400> SEQUENCE: 205

Pro Lys Lys Lys Ile Gln Leu His Ala Glu His Ala Leu Tyr Asp Ala
1               5                  10                  15
```

-continued

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
                35                  40                  45

Ala Arg Leu Phe Glu Ser Gly Asp Gln Cys Asp Glu Ala Glu Lys Ala
 50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 206
<211> LENGTH: 100
<212> TYPE: PRT
<213> ORGANISM: Artificial Sequence
<220> FEATURE:
<223> OTHER INFORMATION: Synthetic

<400> SEQUENCE: 206

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
                35                  40                  45

Ala Arg Leu Phe Glu Ser Gly Asp Gln Lys Cys Glu Ala Glu Lys Ala
 50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 207
<211> LENGTH: 100
<212> TYPE: PRT
<213> ORGANISM: Artificial Sequence
<220> FEATURE:
<223> OTHER INFORMATION: Synthetic

<400> SEQUENCE: 207

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
                35                  40                  45

Ala Arg Leu Phe Glu Ser Gly Asp Gln Lys Asp Glu Ala Cys Lys Ala
 50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

```
<210> SEQ ID NO 208
<211> LENGTH: 100
<212> TYPE: PRT
<213> ORGANISM: Artificial Sequence
<220> FEATURE:
<223> OTHER INFORMATION: Synthetic

<400> SEQUENCE: 208

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Cys Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 209
<211> LENGTH: 100
<212> TYPE: PRT
<213> ORGANISM: Artificial Sequence
<220> FEATURE:
<223> OTHER INFORMATION: Synthetic

<400> SEQUENCE: 209

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Cys Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 210
<211> LENGTH: 100
<212> TYPE: PRT
<213> ORGANISM: Artificial Sequence
<220> FEATURE:
<223> OTHER INFORMATION: Synthetic

<400> SEQUENCE: 210

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30
```

```
Lys Leu Glu Asp Tyr Ala Phe Asn Phe Glu Leu Ile Leu Glu Glu Ile
         35                  40                  45

Ala Arg Leu Phe Cys Ser Gly Asp Gln Lys Asp Glu Ala Glu Lys Ala
 50                  55                  60

Lys Arg Met Lys Glu Trp Met Lys Arg Ile Lys Thr Thr Ala Ser Glu
 65                  70                  75                  80

Asp Cys Gln Glu Glu Met Ala Asn Ala Ile Ile Thr Ile Leu Gln Ser
                 85                  90                  95

Trp Ile Phe Ser
            100

<210> SEQ ID NO 211
<211> LENGTH: 100
<212> TYPE: PRT
<213> ORGANISM: Artificial Sequence
<220> FEATURE:
<223> OTHER INFORMATION: Synthetic

<400> SEQUENCE: 211

Pro Lys Lys Lys Ile Gln Leu His Ala Glu His Ala Leu Tyr Asp Ala
 1               5                  10                  15

Leu Met Ile Leu Asn Ile Val Lys Thr Asn Ser Pro Pro Ala Glu Glu
             20                  25                  30

Lys Leu Glu Asp Tyr Ala Phe Asn Phe Glu Leu Ile Leu Glu Glu Ile
         35                  40                  45

Ala Arg Leu Phe Glu Ser Gly Cys Gln Lys Asp Glu Ala Glu Lys Ala
 50                  55                  60

Lys Arg Met Lys Glu Trp Met Lys Arg Ile Lys Thr Thr Ala Ser Glu
 65                  70                  75                  80

Asp Cys Gln Glu Glu Met Ala Asn Ala Ile Ile Thr Ile Leu Gln Ser
                 85                  90                  95

Trp Ile Phe Ser
            100

<210> SEQ ID NO 212
<211> LENGTH: 100
<212> TYPE: PRT
<213> ORGANISM: Artificial Sequence
<220> FEATURE:
<223> OTHER INFORMATION: Synthetic

<400> SEQUENCE: 212

Pro Lys Lys Lys Ile Gln Leu His Ala Glu His Ala Leu Tyr Asp Ala
 1               5                  10                  15

Leu Met Ile Leu Asn Ile Val Lys Thr Asn Ser Pro Pro Ala Glu Glu
             20                  25                  30

Lys Leu Glu Asp Tyr Ala Phe Asn Phe Glu Leu Ile Leu Glu Glu Ile
         35                  40                  45

Ala Arg Leu Phe Glu Ser Gly Asp Gln Cys Asp Glu Ala Glu Lys Ala
 50                  55                  60

Lys Arg Met Lys Glu Trp Met Lys Arg Ile Lys Thr Thr Ala Ser Glu
 65                  70                  75                  80

Asp Cys Gln Glu Glu Met Ala Asn Ala Ile Ile Thr Ile Leu Gln Ser
                 85                  90                  95

Trp Ile Phe Ser
            100

<210> SEQ ID NO 213
```

```
<211> LENGTH: 100
<212> TYPE: PRT
<213> ORGANISM: Artificial Sequence
<220> FEATURE:
<223> OTHER INFORMATION: Synthetic

<400> SEQUENCE: 213

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Cys Glu Ala Glu Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 214
<211> LENGTH: 100
<212> TYPE: PRT
<213> ORGANISM: Artificial Sequence
<220> FEATURE:
<223> OTHER INFORMATION: Synthetic

<400> SEQUENCE: 214

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Cys Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 215
<211> LENGTH: 100
<212> TYPE: PRT
<213> ORGANISM: Artificial Sequence
<220> FEATURE:
<223> OTHER INFORMATION: Synthetic

<400> SEQUENCE: 215

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45
```

```
Ala Arg Leu Phe Glu Ser Gly Asp Gln Lys Asp Glu Ala Glu Lys Ala
    50                  55                  60

Lys Cys Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 216
<211> LENGTH: 100
<212> TYPE: PRT
<213> ORGANISM: Artificial Sequence
<220> FEATURE:
<223> OTHER INFORMATION: Synthetic

<400> SEQUENCE: 216

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Cys Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 217
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 217

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Cys Leu Phe Glu Ser Gly Xaa Xaa Lys Asp Glu Ala Glu Lys Ala
    50                  55                  60
```

```
Lys Arg Met Lys Glu Trp Met Lys Arg Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 218
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 218

Pro Lys Lys Lys Ile Gln Leu His Ala Glu His Ala Leu Tyr Asp Ala
  1               5                  10                  15

Leu Met Ile Leu Asn Ile Xaa Xaa Xaa Xaa Xaa Xaa Xaa Xaa Xaa Xaa
                 20                  25                  30

Xaa Leu Glu Asp Tyr Ala Phe Asn Phe Glu Leu Ile Leu Glu Glu Ile
             35                  40                  45

Ala Arg Leu Phe Cys Ser Gly Xaa Xaa Lys Asp Glu Ala Glu Lys Ala
 50                  55                  60

Lys Arg Met Lys Glu Trp Met Lys Arg Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 219
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 219

Pro Lys Lys Lys Ile Gln Leu His Ala Glu His Ala Leu Tyr Asp Ala
  1               5                  10                  15
```

```
Leu Met Ile Leu Asn Ile Xaa Xaa Xaa Xaa Xaa Xaa Xaa Xaa Xaa
             20                  25                  30

Xaa Leu Glu Asp Tyr Ala Phe Asn Phe Glu Leu Ile Leu Glu Ile
         35                  40                  45

Ala Arg Leu Phe Glu Ser Gly Cys Gln Lys Asp Glu Ala Glu Lys Ala
50                      55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 220
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 220

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
             20                  25                  30

Xaa Leu Glu Asp Tyr Ala Phe Asn Phe Glu Leu Ile Leu Glu Ile
         35                  40                  45

Ala Arg Leu Phe Glu Ser Gly Xaa Xaa Cys Asp Glu Ala Glu Lys Ala
50                      55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 221
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
```

<223> OTHER INFORMATION: Xaa, when present, can be any naturally
     occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
     occurring amino acid or is optionally absent

<400> SEQUENCE: 221

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Cys Glu Ala Glu Lys Ala
    50                  55                  60

Lys Arg Met Lys Glu Trp Met Lys Arg Ile Lys Thr Xaa Xaa Xaa Glu
65              70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 222
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
     occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
     occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
     occurring amino acid or is optionally absent

<400> SEQUENCE: 222

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Cys Lys Ala
    50                  55                  60

Lys Arg Met Lys Glu Trp Met Lys Arg Ile Lys Thr Xaa Xaa Xaa Glu
65              70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 223

<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 223

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Cys Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 224
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 224

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala

```
                50                  55                  60
Lys Arg Met Lys Cys Trp Met Lys Arg Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 225
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 225

Pro Lys Lys Lys Ile Gln Leu His Ala Glu His Ala Leu Tyr Asp Ala
 1               5                  10                  15

Leu Met Ile Leu Asn Ile Xaa Xaa Xaa Xaa Xaa Xaa Xaa Xaa Xaa Xaa
                20                  25                  30

Xaa Leu Glu Asp Tyr Ala Phe Asn Phe Glu Leu Ile Leu Glu Glu Ile
            35                  40                  45

Ala Arg Leu Phe Glu Ser Gly Xaa Xaa Lys Asp Glu Ala Glu Lys Ala
         50                  55                  60

Lys Arg Met Lys Glu Trp Met Lys Cys Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 226
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent

<400> SEQUENCE: 226

Pro Lys Lys Lys Ile Gln Leu His Ala Glu His Ala Leu Tyr Asp Ala
 1               5                  10                  15
```

```
Leu Met Ile Leu Asn Ile Xaa Xaa Xaa Xaa Xaa Xaa Xaa Xaa Xaa
                20                  25                  30

Xaa Leu Glu Asp Tyr Ala Phe Asn Phe Glu Leu Ile Leu Glu Ile
            35                  40                  45

Ala Arg Leu Phe Glu Ser Gly Xaa Xaa Lys Asp Glu Ala Glu Lys Ala
 50                  55                  60

Lys Arg Met Lys Glu Trp Met Lys Arg Ile Lys Thr Cys Ala Ser Glu
 65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 227
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 227

Pro Lys Lys Lys Ile Gln Leu His Ala Glu His Ala Leu Tyr Asp Ala
 1                   5                  10                  15

Leu Met Ile Leu Asn Ile Xaa Xaa Xaa Xaa Xaa Xaa Xaa Xaa Xaa
                20                  25                  30

Xaa Leu Glu Asp Tyr Ala Phe Asn Phe Glu Leu Ile Leu Glu Ile
            35                  40                  45

Ala Arg Leu Phe Glu Ser Gly Xaa Xaa Lys Asp Glu Ala Glu Lys Ala
 50                  55                  60

Lys Arg Met Lys Glu Trp Met Lys Arg Ile Lys Thr Xaa Xaa Xaa Glu
 65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 228
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
```

```
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 228

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
50                  55                  60

Lys Arg Met Lys Glu Trp Met Lys Arg Ile Lys Thr Xaa Xaa Xaa Glu
65                  70                  75                  80

Asp Glu Gln Glu Cys Met Ala Asn Ala Ile Ile Thr Ile Leu Gln Ser
                85                  90                  95

Trp Ile Phe Ser
            100

<210> SEQ ID NO 229
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 229

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Cys Leu Phe Glu Ser Gly Xaa Xaa Lys Asp Glu Ala Glu Lys Ala
50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

```
<210> SEQ ID NO 230
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 230

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Cys Ser Gly Xaa Xaa Lys Asp Glu Ala Glu Lys Ala
    50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 231
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 231

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Cys Ile Lys Thr Xaa Xaa Xaa Glu
65                  70                  75                  80
```

```
Asp Glu Gln Glu Glu Met Ala Asn Ala Ile Ile Thr Ile Leu Gln Ser
                85                  90                  95

Trp Ile Phe Ser
            100

<210> SEQ ID NO 232
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 232

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
                20                  25                  30

Xaa Leu Glu Asp Tyr Ala Phe Asn Phe Glu Leu Ile Leu Glu Glu Ile
            35                  40                  45

Ala Arg Leu Phe Glu Ser Gly Xaa Xaa Cys Asp Glu Ala Glu Lys Ala
        50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 233
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 233

Pro Lys Lys Lys Ile Gln Leu His Ala Glu His Ala Leu Tyr Asp Ala
```

```
                1               5                  10                 15
Leu Met Ile Leu Asn Ile Xaa Xaa Xaa Xaa Xaa Xaa Xaa Xaa Xaa
                20                 25                 30

Xaa Leu Glu Asp Tyr Ala Phe Asn Phe Glu Leu Ile Leu Glu Glu Ile
        35                 40                 45

Ala Arg Leu Phe Glu Ser Gly Xaa Xaa Lys Cys Glu Ala Lys Ala
    50                 55                 60

Lys Arg Met Lys Glu Trp Met Lys Cys Ile Lys Thr Xaa Xaa Xaa Glu
65                  70                 75                 80

Asp Glu Gln Glu Glu Met Ala Asn Ala Ile Ile Thr Ile Leu Gln Ser
                85                 90                 95

Trp Ile Phe Ser
            100

<210> SEQ ID NO 234
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 234

Pro Lys Lys Lys Ile Gln Leu His Ala Glu His Ala Leu Tyr Asp Ala
1               5                  10                 15

Leu Met Ile Leu Asn Ile Xaa Xaa Xaa Xaa Xaa Xaa Xaa Xaa Xaa
                20                 25                 30

Xaa Leu Glu Asp Tyr Ala Phe Asn Phe Glu Leu Ile Leu Glu Glu Ile
        35                 40                 45

Ala Arg Leu Phe Glu Ser Gly Xaa Xaa Lys Asp Glu Ala Cys Lys Ala
    50                 55                 60

Lys Arg Met Lys Glu Trp Met Lys Cys Ile Lys Thr Xaa Xaa Xaa Glu
65                  70                 75                 80

Asp Glu Gln Glu Glu Met Ala Asn Ala Ile Ile Thr Ile Leu Gln Ser
                85                 90                 95

Trp Ile Phe Ser
            100

<210> SEQ ID NO 235
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
```

```
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 235

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Cys Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 236
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 236

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Cys Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100
```

```
<210> SEQ ID NO 237
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 237

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Cys Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 238
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 238

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Arg Ile Lys Thr Xaa Xaa Xaa Glu
```

```
                65                  70                  75                  80
Asp Cys Gln Glu Glu Met Ala Asn Ala Ile Ile Thr Ile Leu Gln Ser
                    85                  90                  95

Trp Ile Phe Ser
            100

<210> SEQ ID NO 239
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 239

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
                20                  25                  30

Xaa Leu Glu Asp Tyr Ala Phe Asn Phe Glu Leu Ile Leu Glu Glu Ile
            35                  40                  45

Ala Arg Leu Phe Glu Ser Gly Xaa Xaa Cys Asp Glu Ala Glu Lys Ala
        50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                    85                  90                  95

Trp Ile Phe Ser
            100

<210> SEQ ID NO 240
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 240
```

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Cys Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 241
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 241

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Cys Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 242
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
```

```
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 242

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
                35                  40                  45

Ala Arg Leu Phe Glu Ser Gly Xaa Xaa Lys Asp Glu Ala Glu Lys Ala
 50                  55                  60

Lys Cys Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
                100

<210> SEQ ID NO 243
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 243

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
                35                  40                  45

Ala Arg Leu Phe Glu Ser Gly Xaa Xaa Lys Asp Glu Ala Glu Lys Ala
 50                  55                  60

Lys Arg Met Lys Cys Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
                100
```

-continued

```
<210> SEQ ID NO 244
<211> LENGTH: 726
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(25)
<223> OTHER INFORMATION: Optional His tag
<220> FEATURE:
<221> NAME/KEY: MISC_FEATURE
<222> LOCATION: (26)..(609)
<223> OTHER INFORMATION: Mouse serum albumin
<220> FEATURE:
<221> NAME/KEY: MISC_FEATURE
<222> LOCATION: (610)..(626)
<223> OTHER INFORMATION: Linker
<220> FEATURE:
<221> NAME/KEY: MISC_FEATURE
<222> LOCATION: (627)..(726)
<223> OTHER INFORMATION: Neo2/15

<400> SEQUENCE: 244

Gly Ser Asp Gly Gly Ser His His His His His Gly Ser Gly Ser
1               5                   10                  15

Glu Asn Leu Tyr Phe Gln Gly Ser Gly Glu Ala His Lys Ser Glu Ile
            20                  25                  30

Ala His Arg Tyr Asn Asp Leu Gly Glu Gln His Phe Lys Gly Leu Val
        35                  40                  45

Leu Ile Ala Phe Ser Gln Tyr Leu Gln Lys Cys Ser Tyr Asp Glu His
    50                  55                  60

Ala Lys Leu Val Gln Glu Val Thr Asp Phe Ala Lys Thr Cys Val Ala
65                  70                  75                  80

Asp Glu Ser Ala Ala Asn Cys Asp Lys Ser Leu His Thr Leu Phe Gly
                85                  90                  95

Asp Lys Leu Cys Ala Ile Pro Asn Leu Arg Glu Asn Tyr Gly Glu Leu
            100                 105                 110

Ala Asp Cys Cys Thr Lys Gln Glu Pro Glu Arg Asn Glu Cys Phe Leu
        115                 120                 125

Gln His Lys Asp Asp Asn Pro Ser Leu Pro Pro Phe Glu Arg Pro Glu
    130                 135                 140

Ala Glu Ala Met Cys Thr Ser Phe Lys Glu Asn Pro Thr Thr Phe Met
145                 150                 155                 160

Gly His Tyr Leu His Glu Val Ala Arg Arg His Pro Tyr Phe Tyr Ala
                165                 170                 175

Pro Glu Leu Leu Tyr Tyr Ala Glu Gln Tyr Asn Glu Ile Leu Thr Gln
            180                 185                 190

Cys Cys Ala Glu Ala Asp Lys Glu Ser Cys Leu Thr Pro Lys Leu Asp
        195                 200                 205

Gly Val Lys Glu Lys Ala Leu Val Ser Ser Val Arg Gln Arg Met Lys
    210                 215                 220

Cys Ser Ser Met Gln Lys Phe Gly Glu Arg Ala Phe Lys Ala Trp Ala
225                 230                 235                 240

Val Ala Arg Leu Ser Gln Thr Phe Pro Asn Ala Asp Phe Ala Glu Ile
                245                 250                 255

Thr Lys Leu Ala Thr Asp Leu Thr Lys Val Asn Lys Glu Cys Cys His
            260                 265                 270

Gly Asp Leu Leu Glu Cys Ala Asp Asp Arg Ala Glu Leu Ala Lys Tyr
```

-continued

```
                275                 280                 285
Met Cys Glu Asn Gln Ala Thr Ile Ser Ser Lys Leu Gln Thr Cys Cys
    290                 295                 300
Asp Lys Pro Leu Leu Lys Lys Ala His Cys Leu Ser Glu Val Glu His
305                 310                 315                 320
Asp Thr Met Pro Ala Asp Leu Pro Ala Ile Ala Ala Asp Phe Val Glu
                    325                 330                 335
Asp Gln Glu Val Cys Lys Asn Tyr Ala Glu Ala Lys Asp Val Phe Leu
                340                 345                 350
Gly Thr Phe Leu Tyr Glu Tyr Ser Arg Arg His Pro Asp Tyr Ser Val
                355                 360                 365
Ser Leu Leu Leu Arg Leu Ala Lys Lys Tyr Glu Ala Thr Leu Glu Lys
    370                 375                 380
Cys Cys Ala Glu Ala Asn Pro Pro Ala Cys Tyr Gly Thr Val Leu Ala
385                 390                 395                 400
Glu Phe Gln Pro Leu Val Glu Glu Pro Lys Asn Leu Val Lys Thr Asn
                    405                 410                 415
Cys Asp Leu Tyr Glu Lys Leu Gly Glu Tyr Gly Phe Gln Asn Ala Ile
                420                 425                 430
Leu Val Arg Tyr Thr Gln Lys Ala Pro Gln Val Ser Thr Pro Thr Leu
                435                 440                 445
Val Glu Ala Ala Arg Asn Leu Gly Arg Val Gly Thr Lys Cys Cys Thr
    450                 455                 460
Leu Pro Glu Asp Gln Arg Leu Pro Cys Val Glu Asp Tyr Leu Ser Ala
465                 470                 475                 480
Ile Leu Asn Arg Val Cys Leu Leu His Glu Lys Thr Pro Val Ser Glu
                    485                 490                 495
His Val Thr Lys Cys Cys Ser Gly Ser Leu Val Glu Arg Arg Pro Cys
                500                 505                 510
Phe Ser Ala Leu Thr Val Asp Glu Thr Tyr Val Pro Lys Glu Phe Lys
                515                 520                 525
Ala Glu Thr Phe Thr Phe His Ser Asp Ile Cys Thr Leu Pro Glu Lys
    530                 535                 540
Glu Lys Gln Ile Lys Lys Gln Thr Ala Leu Ala Glu Leu Val Lys His
545                 550                 555                 560
Lys Pro Lys Ala Thr Ala Glu Gln Leu Lys Thr Val Met Asp Asp Phe
                    565                 570                 575
Ala Gln Phe Leu Asp Thr Cys Cys Lys Ala Ala Asp Lys Asp Thr Cys
                580                 585                 590
Phe Ser Thr Glu Gly Pro Asn Leu Val Thr Arg Cys Lys Asp Ala Leu
                595                 600                 605
Ala Gly Gly Gly Ser Gly Gly Ser Gly Gly Ser Gly Gly Ser Gly
    610                 615                 620
Ser Gly Pro Lys Lys Lys Ile Gln Leu His Ala Glu His Ala Leu Tyr
625                 630                 635                 640
Asp Ala Leu Met Ile Leu Asn Ile Val Lys Thr Asn Ser Pro Pro Ala
                    645                 650                 655
Glu Glu Lys Leu Glu Asp Tyr Ala Phe Asn Phe Glu Leu Ile Leu Glu
                660                 665                 670
Glu Ile Ala Arg Leu Phe Glu Ser Gly Asp Gln Lys Asp Glu Ala Glu
                675                 680                 685
Lys Ala Lys Arg Met Lys Glu Trp Met Lys Arg Ile Lys Thr Thr Ala
    690                 695                 700
```

-continued

Ser Glu Asp Glu Gln Glu Glu Met Ala Asn Ala Ile Ile Thr Ile Leu
705                 710                 715                 720

Gln Ser Trp Ile Phe Ser
            725

<210> SEQ ID NO 245
<211> LENGTH: 87
<212> TYPE: PRT
<213> ORGANISM: Artificial Sequence
<220> FEATURE:
<223> OTHER INFORMATION: Synthetic

<400> SEQUENCE: 245

Thr Asn Lys Lys Ala Gln Leu His Ala Glu Phe Ala Leu His Asp Ala
1               5                   10                  15

Leu Met Leu Leu Asn Leu Ser Ser Glu Ser Asn Glu Arg Leu Asn Arg
            20                  25                  30

Ile Ile Thr Trp Leu Gln Ser Ile Ile Phe Tyr Gly Thr Tyr Asp Pro
        35                  40                  45

Asp Met Val Lys Glu Ala Val Lys Asp Ala Asp Glu Ile Glu Asp Glu
    50                  55                  60

Met Arg Lys Arg Gly Ile Asp Thr Glu Asp Tyr Val Ser Asn Leu Arg
65                  70                  75                  80

Leu Ile Leu Gln Glu Leu Ala
            85

<210> SEQ ID NO 246
<211> LENGTH: 100
<212> TYPE: PRT
<213> ORGANISM: Artificial Sequence
<220> FEATURE:
<223> OTHER INFORMATION: Synthetic

<400> SEQUENCE: 246

Pro Lys Lys Lys Ile Gln Leu Tyr Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Glu Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
            85                  90                  95

Trp Ile Phe Ser
            100

<210> SEQ ID NO 247
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:

```
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 247

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 248
<211> LENGTH: 22
<212> TYPE: PRT
<213> ORGANISM: Artificial Sequence
<220> FEATURE:
<223> OTHER INFORMATION: Synthetic peptide

<400> SEQUENCE: 248

Ser Thr Lys Lys Thr Gln Leu Gln Leu Glu His Leu Leu Leu Asp Leu
1               5                   10                  15

Gln Met Ile Leu Asn Gly
            20

<210> SEQ ID NO 249
<211> LENGTH: 15
<212> TYPE: PRT
<213> ORGANISM: Artificial Sequence
<220> FEATURE:
<223> OTHER INFORMATION: Synthetic peptide

<400> SEQUENCE: 249

Asn Trp Val Asn Val Ile Ser Asp Leu Lys Lys Ile Glu Asp Leu
1               5                   10                  15

<210> SEQ ID NO 250
<211> LENGTH: 22
<212> TYPE: PRT
<213> ORGANISM: Artificial Sequence
<220> FEATURE:
<223> OTHER INFORMATION: Synthetic peptide

<400> SEQUENCE: 250

Pro Arg Asp Leu Ile Ser Asn Ile Asn Val Ile Val Leu Glu Leu Lys
1               5                   10                  15

Gly Ser Glu Thr Thr Phe
            20
```

```
<210> SEQ ID NO 251
<211> LENGTH: 22
<212> TYPE: PRT
<213> ORGANISM: Artificial Sequence
<220> FEATURE:
<223> OTHER INFORMATION: Synthetic peptide

<400> SEQUENCE: 251

Ile His Asp Thr Val Glu Asn Leu Ile Ile Leu Ala Asn Asn Ser Leu
1               5                   10                  15

Ser Ser Asn Gly Asn Val
            20

<210> SEQ ID NO 252
<211> LENGTH: 19
<212> TYPE: PRT
<213> ORGANISM: Artificial Sequence
<220> FEATURE:
<223> OTHER INFORMATION: Synthetic peptide

<400> SEQUENCE: 252

Ala Thr Glu Leu Lys His Leu Gln Cys Leu Glu Glu Glu Leu Lys Pro
1               5                   10                  15

Leu Glu Glu

<210> SEQ ID NO 253
<211> LENGTH: 19
<212> TYPE: PRT
<213> ORGANISM: Artificial Sequence
<220> FEATURE:
<223> OTHER INFORMATION: Synthetic peptide

<400> SEQUENCE: 253

Ser Cys Lys Val Thr Ala Met Lys Cys Phe Leu Leu Glu Leu Gln Val
1               5                   10                  15

Ile Ser Leu

<210> SEQ ID NO 254
<211> LENGTH: 21
<212> TYPE: PRT
<213> ORGANISM: Artificial Sequence
<220> FEATURE:
<223> OTHER INFORMATION: Synthetic peptide

<400> SEQUENCE: 254

Thr Ala Thr Ile Val Glu Phe Leu Asn Arg Trp Ile Thr Phe Cys Gln
1               5                   10                  15

Ser Ile Ile Ser Thr
            20

<210> SEQ ID NO 255
<211> LENGTH: 21
<212> TYPE: PRT
<213> ORGANISM: Artificial Sequence
<220> FEATURE:
<223> OTHER INFORMATION: Synthetic peptide

<400> SEQUENCE: 255

Glu Lys Asn Ile Lys Glu Phe Leu Gln Ser Phe Val His Ile Val Gln
1               5                   10                  15

Met Phe Ile Asn Thr
            20

<210> SEQ ID NO 256
```

```
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (23)..(27)
<223> OTHER INFORMATION: Optional

<400> SEQUENCE: 256

Pro Lys Lys Lys Ile Gln Leu His Ala Glu His Ala Leu Tyr Asp Ala
1               5                   10                  15

Leu Met Ile Leu Asn Ile Val Lys Thr Asn Ser
            20                  25

<210> SEQ ID NO 257
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(9)
<223> OTHER INFORMATION: Optional
<220> FEATURE:
<221> NAME/KEY: MISC_FEATURE
<222> LOCATION: (32)..(33)
<223> OTHER INFORMATION: Optional
<220> FEATURE:
<221> NAME/KEY: MISC_FEATURE
<222> LOCATION: (53)..(55)
<223> OTHER INFORMATION: Optional

<400> SEQUENCE: 257

Thr Asn Ser Pro Pro Ala Glu Glu Lys Leu Glu Asp Tyr Ala Phe Asn
1               5                   10                  15

Phe Glu Leu Ile Leu Glu Glu Ile Ala Arg Leu Phe Glu Ser Gly Asp
            20                  25                  30

Gln Lys Asp Glu Ala Glu Lys Ala Lys Arg Met Lys Glu Trp Met Lys
        35                  40                  45

Arg Ile Lys Thr Thr Ala Ser Glu Asp Glu Gln Glu Glu Met Ala Asn
    50                  55                  60

Ala Ile Ile Thr Ile Leu Gln Ser Trp Ile Phe Ser
65                  70                  75

<210> SEQ ID NO 258
<211> LENGTH: 79
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (23)..(33)
<223> OTHER INFORMATION: Optional
<220> FEATURE:
<221> NAME/KEY: MISC_FEATURE
<222> LOCATION: (56)..(57)
<223> OTHER INFORMATION: Optional

<400> SEQUENCE: 258

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30
```

```
Lys Leu Glu Asp Tyr Ala Phe Asn Phe Glu Leu Ile Leu Glu Glu Ile
            35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser
65                  70                  75
```

<210> SEQ ID NO 259
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Optional

<400> SEQUENCE: 259

```
Thr Thr Ala Ser Glu Asp Glu Gln Glu Glu Met Ala Asn Ala Ile Ile
1               5                   10                  15

Thr Ile Leu Gln Ser Trp Ile Phe Ser
            20                  25
```

<210> SEQ ID NO 260
<211> LENGTH: 56
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (23)..(33)
<223> OTHER INFORMATION: Optional
<220> FEATURE:
<221> NAME/KEY: MISC_FEATURE
<222> LOCATION: (55)..(56)
<223> OTHER INFORMATION: Optional

<400> SEQUENCE: 260

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
            35                  40                  45

Ala Arg Leu Phe Glu Ser Gly Asp
    50                  55
```

<210> SEQ ID NO 261
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (22)..(24)
<223> OTHER INFORMATION: Optional

<400> SEQUENCE: 261

```
Asp Gln Lys Asp Glu Ala Glu Lys Ala Lys Arg Met Lys Glu Trp Met
1               5                   10                  15

Lys Arg Ile Lys Thr Thr Ala Ser Glu Asp Glu Gln Glu Glu Met Ala
            20                  25                  30
```

Asn Ala Ile Ile Thr Ile Leu Gln Ser Trp Ile Phe Ser
            35                  40                  45

<210> SEQ ID NO 262
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (23)..(27)
<223> OTHER INFORMATION: Optional

<400> SEQUENCE: 262

Pro Lys Lys Lys Ile Gln Ile Met Ala Glu Glu Ala Leu Lys Asp Ala
1               5                   10                  15

Leu Ser Ile Leu Asn Ile Val Lys Thr Asn Ser
            20                  25

<210> SEQ ID NO 263
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: Optional
<220> FEATURE:
<221> NAME/KEY: MISC_FEATURE
<222> LOCATION: (32)..(33)
<223> OTHER INFORMATION: Optional
<220> FEATURE:
<221> NAME/KEY: MISC_FEATURE
<222> LOCATION: (53)..(55)
<223> OTHER INFORMATION: Optional

<400> SEQUENCE: 263

Thr Asn Ser Pro Pro Ala Glu Glu Gln Leu Glu Arg Phe Ala Lys Arg
1               5                   10                  15

Phe Glu Arg Asn Leu Trp Gly Ile Ala Arg Leu Phe Glu Ser Gly Asp
            20                  25                  30

Gln Lys Asp Glu Ala Glu Lys Ala Lys Arg Met Ile Glu Trp Met Lys
        35                  40                  45

Arg Ile Lys Thr Thr Ala Ser Glu Asp Glu Gln Glu Glu Met Ala Asn
    50                  55                  60

Ala Ile Ile Thr Ile Leu Gln Ser Trp Phe Phe Ser
65                  70                  75

<210> SEQ ID NO 264
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (53)..(55)
<223> OTHER INFORMATION: Xaa can be any naturally occurring amino acid

<400> SEQUENCE: 264

Xaa Xaa Xaa Xaa Xaa Xaa Xaa Xaa Xaa Leu Glu Asp Tyr Ala Phe Asn
1               5                   10                  15

Phe Glu Leu Ile Leu Glu Glu Ile Ala Arg Leu Phe Glu Ser Gly Xaa
            20                  25                  30

Xaa Lys Asp Glu Ala Glu Lys Ala Lys Arg Met Lys Glu Trp Met Lys
        35                  40                  45

Arg Ile Lys Thr Xaa Xaa Glu Asp Glu Gln Glu Glu Met Ala Asn
    50                  55                  60

Ala Ile Ile Thr Ile Leu Gln Ser Trp Ile Phe Ser
65                  70                  75

<210> SEQ ID NO 265
<211> LENGTH: 79
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid

<400> SEQUENCE: 265

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Thr Ala Ser
65                  70                  75

<210> SEQ ID NO 266
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Xaa can be any naturally occurring amino acid

<400> SEQUENCE: 266

Xaa Xaa Xaa Xaa Xaa Asp Glu Gln Glu Glu Met Ala Asn Ala Ile Ile
1               5                   10                  15

Thr Ile Leu Gln Ser Trp Ile Phe Ser
            20                  25

<210> SEQ ID NO 267
<211> LENGTH: 58
<212> TYPE: PRT
<213> ORGANISM: Artificial Sequence
<220> FEATURE:
<223> OTHER INFORMATION: Synthetic peptide
<220> FEATURE:

```
<221> NAME/KEY: misc_feature
<222> LOCATION: (23)..(33)
<223> OTHER INFORMATION: Xaa can be any naturally occurring amino acid
<220> F

```
<223> OTHER INFORMATION: Xaa can be any naturally occurring amino acid
<220> FEATURE:
<221> NAME/KEY: misc_feature
<222> LOCATION: (53)..(55)
<223> OTHER INFORMATION: Xaa can be any naturally occurring amino acid

<400> SEQUENCE: 270

Xaa Xaa Xaa Xaa Xaa Xaa Xaa Gln Leu Glu Arg Phe Ala Lys Arg
1               5                   10                  15

Phe Glu Arg Asn Leu Trp Gly Ile Ala Arg Leu Phe Glu Ser Gly Xaa
                20                  25                  30

Xaa Lys Asp Glu Ala Glu Lys Ala Lys Arg Met Ile Glu Trp Met Lys
        35                  40                  45

Arg Ile Lys Thr Xaa Xaa Xaa Glu Asp Glu Gln Glu Met Ala Asn
    50                  55                  60

Ala Ile Ile Thr Ile Leu Gln Ser Trp Phe Phe Ser
65                  70                  75

<210> SEQ ID NO 271
<211> LENGTH: 22
<212> TYPE: PRT
<213> ORGANISM: Artificial Sequence
<220> FEATURE:
<223> OTHER INFORMATION: Synthetic peptide

<400> SEQUENCE: 271

Ser Thr Lys Lys Trp Gln Leu Gln Ala Glu His Ala Leu Leu Asp Trp
1               5                   10                  15

Gln Met Ala Leu Asn Lys
            20

<210> SEQ ID NO 272
<211> LENGTH: 15
<212> TYPE: PRT
<213> ORGANISM: Artificial Sequence
<220> FEATURE:
<223> OTHER INFORMATION: Synthetic peptide

<400> SEQUENCE: 272

Glu Asn Leu Asn Arg Ala Ile Thr Ala Ala Gln Ser Trp Ile Ser
1               5                   10                  15

<210> SEQ ID NO 273
<211> LENGTH: 20
<212> TYPE: PRT
<213> ORGANISM: Artificial Sequence
<220> FEATURE:
<223> OTHER INFORMATION: Synthetic peptide

<400> SEQUENCE: 273

Leu Asp Lys Ala Glu Asp Ile Arg Arg Asn Ser Asp Gln Ala Arg Arg
1               5                   10                  15

Glu Ala Glu Lys
            20

<210> SEQ ID NO 274
<211> LENGTH: 15
<212> TYPE: PRT
<213> ORGANISM: Artificial Sequence
<220> FEATURE:
<223> OTHER INFORMATION: Synthetic peptide

<400> SEQUENCE: 274

Arg Asp Leu Ile Ser Asn Ala Gln Val Ile Leu Leu Glu Ala Arg
```

```
<210> SEQ ID NO 275
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 275

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Cys Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 276
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 276

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Cys Ser Gly Xaa Xaa Lys Asp Glu Ala Glu Lys Ala
    50                  55                  60
```

```
Lys Arg Met Lys Glu Trp Met Lys Arg Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 277
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 277

Pro Lys Lys Lys Ile Gln Leu His Ala Glu His Ala Leu Tyr Asp Ala
 1               5                  10                  15

Leu Met Ile Leu Asn Ile Xaa Xaa Xaa Xaa Xaa Xaa Xaa Xaa Xaa
                 20                  25                  30

Xaa Leu Glu Asp Tyr Ala Phe Asn Phe Glu Leu Ile Leu Glu Glu Ile
             35                  40                  45

Ala Arg Leu Phe Glu Ser Gly Cys Gln Lys Asp Glu Ala Glu Lys Ala
 50                  55                  60

Lys Arg Met Lys Glu Trp Met Lys Arg Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 278
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 278

Pro Lys Lys Lys Ile Gln Leu His Ala Glu His Ala Leu Tyr Asp Ala
 1               5                  10                  15

Leu Met Ile Leu Asn Ile Xaa Xaa Xaa Xaa Xaa Xaa Xaa Xaa Xaa
                 20                  25                  30

Xaa Leu Glu Asp Tyr Ala Phe Asn Phe Glu Leu Ile Leu Glu Glu Ile
             35                  40                  45
```

```
Ala Arg Leu Phe Glu Ser Gly Xaa Xaa Cys Asp Glu Ala Glu Lys Ala
 50                  55                  60

Lys Arg Met Lys Glu Trp Met Lys Arg Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 279
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 279

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa
             20                  25                  30

Xaa Leu Glu Asp Tyr Ala Phe Asn Phe Glu Leu Ile Leu Glu Glu Ile
             35                  40                  45

Ala Arg Leu Phe Glu Ser Gly Xaa Xaa Lys Cys Glu Ala Glu Lys Ala
 50                  55                  60

Lys Arg Met Lys Glu Trp Met Lys Arg Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 280
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 280

Pro Lys Lys Lys Ile Gln Leu His Ala Glu His Ala Leu Tyr Asp Ala
1               5                   10                  15
```

```
Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Cys Lys Ala
50                      55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 281
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 281

Pro Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
50                      55                  60

Lys Cys Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 282
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
```

<222> LOCATION: (77)..(79)
<223> OTHER INFORMATION: Xaa can be any naturally occurring amino acid

<400> SEQUENCE: 282

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
                35                  40                  45

Ala Arg Leu Phe Glu Ser Gly Xaa Xaa Lys Asp Glu Ala Glu Lys Ala
        50                  55                  60

Lys Arg Met Lys Cys Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 283
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 283

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
                35                  40                  45

Ala Arg Leu Phe Glu Ser Gly Xaa Xaa Lys Asp Glu Ala Glu Lys Ala
        50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 284
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)

<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid

<400> SEQUENCE: 284

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Cys Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 285
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 285

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 286
<211> LENGTH: 100
<212> TYPE: PRT
<213> ORGANISM: Artificial Sequence
<220> FEATURE:
<223> OTHER INFORMATION: Synthetic peptide

```
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 286

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
            35                  40                  45

Ala Arg Leu Phe Glu Ser Gly Xaa Xaa Lys Asp Glu Ala Glu Lys Ala
50                  55                  60

Lys Arg Met Lys Glu Trp Met Lys Arg Ile Lys Thr Xaa Xaa Xaa Glu
65                  70                  75                  80

Asp Glu Gln Glu Cys Met Ala Asn Ala Ile Ile Thr Ile Leu Gln Ser
                85                  90                  95

Trp Ile Phe Ser
            100

<210> SEQ ID NO 287
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 287

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
            35                  40                  45

Ala Cys Leu Phe Glu Ser Gly Xaa Xaa Lys Asp Glu Ala Glu Lys Ala
50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 288
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 288

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
            35                  40                  45

Ala Arg Leu Phe Cys Ser Gly Xaa Xaa Lys Asp Glu Ala Glu Lys Ala
50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 289
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 289

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
            35                  40                  45

Ala Arg Leu Phe Glu Ser Gly Cys Gln Lys Asp Glu Ala Glu Lys Ala
50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 290
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 290

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Cys Asp Glu Ala Glu Lys Ala
    50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 291
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 291

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Cys Glu Ala Glu Lys Ala
    50                  55                  60

```
Lys Arg Met Lys Glu Trp Met Lys Cys Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 292
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 292

Pro Lys Lys Lys Ile Gln Leu His Ala Glu His Ala Leu Tyr Asp Ala
 1               5                   10                  15

Leu Met Ile Leu Asn Ile Xaa Xaa Xaa Xaa Xaa Xaa Xaa Xaa Xaa
                 20                  25                  30

Xaa Leu Glu Asp Tyr Ala Phe Asn Phe Glu Leu Ile Leu Glu Glu Ile
         35                  40                  45

Ala Arg Leu Phe Glu Ser Gly Xaa Xaa Lys Asp Glu Ala Glu Lys Ala
 50                  55                  60

Lys Cys Met Lys Glu Trp Met Lys Cys Ile Lys Thr Xaa Xaa Xaa Glu
 65                  70                  75                  80

Asp Glu Gln Glu Glu Met Ala Asn Ala Ile Ile Thr Ile Leu Gln Ser
                 85                  90                  95

Trp Ile Phe Ser
            100

<210> SEQ ID NO 293
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 293

Pro Lys Lys Lys Ile Gln Leu His Ala Glu His Ala Leu Tyr Asp Ala
 1               5                   10                  15

Leu Met Ile Leu Asn Ile Xaa Xaa Xaa Xaa Xaa Xaa Xaa Xaa Xaa Xaa
```

```
            20                  25                  30
Xaa Leu Glu Asp Tyr Ala Phe Asn Phe Glu Leu Ile Leu Glu Glu Ile
            35                  40                  45

Ala Cys Leu Phe Glu Ser Gly Xaa Xaa Lys Asp Glu Ala Glu Lys Ala
        50                  55                  60

Lys Arg Met Lys Glu Trp Met Lys Arg Ile Lys Thr Xaa Xaa Xaa Glu
 65                 70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 294
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 294

Pro Lys Lys Lys Ile Gln Leu His Ala Glu His Ala Leu Tyr Asp Ala
 1               5                  10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
            35                  40                  45

Ala Arg Leu Phe Cys Ser Gly Xaa Xaa Lys Asp Glu Ala Glu Lys Ala
        50                  55                  60

Lys Arg Met Lys Glu Trp Met Lys Arg Ile Lys Thr Xaa Xaa Xaa Glu
 65                 70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 295
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 295

Pro Lys Lys Lys Ile Gln Leu His Ala Glu His Ala Leu Tyr Asp Ala
```

```
                1               5                   10                  15
Leu Met Ile Leu Asn Ile Xaa Xaa Xaa Xaa Xaa Xaa Xaa Xaa Xaa
                20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 296
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 296

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
                20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Cys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 297
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
```

```
<221> NAME/KEY: misc_feature
<222> LOCATION: (77)..(79)
<223> OTHER INFORMATION: Xaa can be any naturally occurring amino acid

<400> SEQUENCE: 297

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Cys Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 298
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 298

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Cys Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 299
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 299

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
            35                  40                  45

Ala Arg Leu Phe Glu Ser Gly Xaa Xaa Lys Asp Glu Ala Glu Lys Ala
 50                  55                  60

Lys Cys Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 300
<211> LENGTH: 100
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 300

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
            35                  40                  45

Ala Arg Leu Phe Glu Ser Gly Xaa Xaa Lys Asp Glu Ala Glu Lys Ala
 50                  55                  60

Lys Arg Met Lys Cys Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100

<210> SEQ ID NO 301
```

```
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(27)
<223> OTHER INFORMATION: Xaa can be any naturally occurring amino acid

<400> SEQUENCE: 301

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa
            20                  25

<210> SEQ ID NO 302

<400> SEQUENCE: 302

000

<210> SEQ ID NO 303
<211> LENGTH: 14
<212> TYPE: PRT
<213> ORGANISM: Artificial Sequence
<220> FEATURE:
<223> OTHER INFORMATION: Synthetic peptide

<400> SEQUENCE: 303

Leu Asn Asp Ile Phe Glu Ala Gln Lys Ile Glu Trp His Glu
1               5                   10

<210> SEQ ID NO 304
<211> LENGTH: 276
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(24)
<223> OTHER INFORMATION: Optional
<220> FEATURE:
<221> NAME/KEY: MISC_FEATURE
<222> LOCATION: (101)..(120)
<223> OTHER INFORMATION: Optional

<400> SEQUENCE: 304

Met Gly Ser His His His His His Gly Ser Gly Ser Glu Asn Leu
1               5                   10                  15

Tyr Phe Gln Gly Ser Gly Gly Thr Asn Ser Pro Pro Ala Glu Glu
            20                  25                  30

Lys Leu Glu Asp Tyr Ala Phe Asn Phe Glu Leu Ile Leu Glu Glu Ile
                35                  40                  45

Ala Arg Leu Phe Glu Ser Gly Asp Gln Lys Asp Glu Ala Glu Lys Ala
            50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser Gly Ser Gly Gly Ser Gly Gly Gly Ser Gly Gly Ser
            100                 105                 110

Gly Ser Gly Gly Ser Gly Gly Gly Asp Leu Gly Lys Lys Leu Leu Glu
            115                 120                 125
```

```
Ala Ala Arg Ala Gly Gln Asp Asp Glu Val Arg Ile Leu Met Ala Asn
        130                 135                 140

Gly Ala Asp Val Asn Ala Asp Thr Trp Gly Trp Thr Pro Leu His
145                 150                 155                 160

Leu Ala Ala Tyr Gln Gly His Leu Glu Ile Val Glu Val Leu Leu Lys
                165                 170                 175

Asn Gly Ala Asp Val Asn Ala Tyr Asp Tyr Ile Gly Trp Thr Pro Leu
            180                 185                 190

His Leu Ala Ala Asp Gly His Leu Glu Ile Val Glu Val Leu Leu Lys
        195                 200                 205

Asn Gly Ala Asp Val Asn Ala Ser Asp Tyr Ile Gly Asp Thr Pro Leu
            210                 215                 220

His Leu Ala Ala His Asn Gly His Leu Glu Ile Val Glu Val Leu Leu
225                 230                 235                 240

Lys His Gly Ala Asp Val Asn Ala Gln Asp Lys Phe Gly Lys Thr Ala
                245                 250                 255

Phe Asp Ile Ser Ile Asp Asn Gly Asn Glu Asp Leu Ala Glu Ile Leu
            260                 265                 270

Gln Lys Leu Asn
        275

<210> SEQ ID NO 305
<211> LENGTH: 190
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(24)
<223> OTHER INFORMATION: Optional
<220> FEATURE:
<221> NAME/KEY: MISC_FEATURE
<222> LOCATION: (149)..(163)
<223> OTHER INFORMATION: Optional

<400> SEQUENCE: 305

Met Gly Ser His His His His His Gly Ser Gly Ser Glu Asn Leu
1               5                   10                  15

Tyr Phe Gln Gly Ser Gly Ser Gly Asp Leu Gly Lys Lys Leu Leu Glu
                20                  25                  30

Ala Ala Arg Ala Gly Gln Asp Asp Glu Val Arg Ile Leu Met Ala Asn
            35                  40                  45

Gly Ala Asp Val Asn Ala Lys Asp Glu Tyr Gly Leu Thr Pro Leu Tyr
50                  55                  60

Leu Ala Thr Ala His Gly His Leu Glu Ile Val Glu Val Leu Leu Lys
65                  70                  75                  80

Asn Gly Ala Asp Val Asn Ala Val Asp Ala Ile Gly Phe Thr Pro Leu
                85                  90                  95

His Leu Ala Ala Phe Ile Gly His Leu Glu Ile Ala Glu Val Leu Leu
            100                 105                 110

Lys His Gly Ala Asp Val Asn Ala Gln Asp Lys Phe Gly Lys Thr Ala
        115                 120                 125

Phe Asp Ile Ser Ile Gly Asn Gly Asn Glu Asp Leu Ala Glu Ile Leu
    130                 135                 140

Gln Lys Leu Asn Gly Ser Gly Gly Ser Gly Gly Ser Gly Gly Ser
145                 150                 155                 160
```

Gly Ser Gly Pro Lys Lys Ile Gln Leu His Ala Glu His Ala Leu
                165                 170                 175

Tyr Asp Ala Leu Met Ile Leu Asn Ile Val Lys Thr Asn Ser
                180                 185                 190

<210> SEQ ID NO 306
<211> LENGTH: 239
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(24)
<223> OTHER INFORMATION: Optional
<220> FEATURE:
<221> NAME/KEY: MISC_FEATURE
<222> LOCATION: (149)..(163)
<223> OTHER INFORMATION: Optional

<400> SEQUENCE: 306

Met Gly Ser His His His His Gly Ser Gly Ser Glu Asn Leu
1               5                   10                  15

Tyr Phe Gln Gly Ser Gly Ser Gly Asp Leu Gly Lys Lys Leu Leu Glu
                20                  25                  30

Ala Ala Arg Ala Gly Gln Asp Asp Glu Val Arg Ile Leu Met Ala Asn
            35                  40                  45

Gly Ala Asp Val Asn Ala Lys Asp Glu Tyr Gly Leu Thr Pro Leu Tyr
        50                  55                  60

Leu Ala Thr Ala His Gly His Leu Glu Ile Val Glu Val Leu Leu Lys
65                  70                  75                  80

Asn Gly Ala Asp Val Asn Ala Val Asp Ala Ile Gly Phe Thr Pro Leu
                85                  90                  95

His Leu Ala Ala Phe Ile Gly His Leu Glu Ile Ala Glu Val Leu Leu
            100                 105                 110

Lys His Gly Ala Asp Val Asn Ala Gln Asp Lys Phe Gly Lys Thr Ala
        115                 120                 125

Phe Asp Ile Ser Ile Gly Asn Gly Asn Glu Asp Leu Ala Glu Ile Leu
130                 135                 140

Gln Lys Leu Asn Gly Ser Gly Ser Gly Gly Ser Gly Ser
145                 150                 155                 160

Gly Ser Gly Thr Asn Ser Pro Pro Ala Glu Lys Leu Glu Asp Tyr
            165                 170                 175

Ala Phe Asn Phe Glu Leu Ile Leu Glu Glu Ile Ala Arg Leu Phe Glu
        180                 185                 190

Ser Gly Asp Gln Lys Asp Glu Ala Glu Lys Ala Lys Arg Met Lys Glu
    195                 200                 205

Trp Met Lys Arg Ile Lys Thr Thr Ala Ser Glu Asp Glu Gln Glu Glu
210                 215                 220

Met Ala Asn Ala Ile Ile Thr Ile Leu Gln Ser Trp Ile Phe Ser
225                 230                 235

<210> SEQ ID NO 307
<211> LENGTH: 276
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(24)

<223> OTHER INFORMATION: Optional
<220> FEATURE:
<221> NAME/KEY: MISC_FEATURE
<222> LOCATION: (101)..(120)
<223> OTHER INFORMATION: Optional

<400> SEQUENCE: 307

Met Gly Ser His His His His His His Gly Ser Gly Ser Glu Asn Leu
1               5                   10                  15

Tyr Phe Gln Gly Ser Gly Gly Thr Asn Ser Pro Pro Ala Glu Glu
            20                  25                  30

Lys Leu Glu Asp Tyr Ala Phe Asn Phe Glu Leu Ile Leu Glu Glu Ile
                35                  40                  45

Ala Arg Leu Phe Glu Ser Gly Asp Gln Lys Asp Glu Ala Glu Lys Ala
        50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser Gly Ser Gly Ser Gly Gly Ser Gly Gly Ser
            100                 105                 110

Gly Ser Gly Gly Ser Gly Gly Asp Leu Gly Lys Lys Leu Leu Glu
        115                 120                 125

Ala Ala Arg Ala Gly Gln Asp Asp Glu Val Arg Ile Leu Met Ala Asn
    130                 135                 140

Gly Ala Asp Val Asn Ala Asp Asp Thr Trp Gly Trp Thr Pro Leu His
145                 150                 155                 160

Leu Ala Ala Tyr Gln Gly His Leu Glu Ile Val Glu Val Leu Leu Lys
                165                 170                 175

Asn Gly Ala Asp Val Asn Ala Tyr Asp Tyr Ile Gly Trp Thr Pro Leu
            180                 185                 190

His Leu Ala Ala Asp Gly His Leu Glu Ile Val Glu Val Leu Leu Lys
        195                 200                 205

Asn Gly Ala Asp Val Asn Ala Ser Asp Tyr Ile Gly Asp Thr Pro Leu
210                 215                 220

His Leu Ala Ala His Asn Gly His Leu Glu Ile Val Glu Val Leu Leu
225                 230                 235                 240

Lys His Gly Ala Asp Val Asn Ala Gln Asp Lys Phe Gly Lys Thr Ala
                245                 250                 255

Phe Asp Ile Ser Ile Asp Asn Gly Asn Glu Asp Leu Ala Glu Ile Leu
            260                 265                 270

Gln Lys Leu Asn
        275

<210> SEQ ID NO 308
<211> LENGTH: 245
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(24)
<223> OTHER INFORMATION: Optional
<220> FEATURE:
<221> NAME/KEY: MISC_FEATURE
<222> LOCATION: (70)..(89)
<223> OTHER INFORMATION: Optional

<400> SEQUENCE: 308

```
Met Gly Ser His His His His His Gly Ser Gly Ser Glu Asn Leu
1               5                   10                  15

Tyr Phe Gln Gly Ser Gly Gly Gly Asp Gln Lys Asp Glu Ala Glu Lys
                20                  25                  30

Ala Lys Arg Met Lys Glu Trp Met Lys Arg Ile Lys Thr Thr Ala Ser
            35                  40                  45

Glu Asp Glu Gln Glu Glu Met Ala Asn Ala Ile Ile Thr Ile Leu Gln
50                      55                  60

Ser Trp Ile Phe Ser Gly Ser Gly Gly Ser Gly Gly Ser Gly Gly
65                  70                  75                  80

Ser Gly Ser Gly Gly Ser Gly Gly Asp Leu Gly Lys Lys Leu Leu
                85                  90                  95

Glu Ala Ala Arg Ala Gly Gln Asp Asp Glu Val Arg Ile Leu Met Ala
                100                 105                 110

Asn Gly Ala Asp Val Asn Ala Asp Asp Thr Trp Gly Trp Thr Pro Leu
            115                 120                 125

His Leu Ala Ala Tyr Gln Gly His Leu Glu Ile Val Glu Val Leu Leu
130                 135                 140

Lys Asn Gly Ala Asp Val Asn Ala Tyr Asp Tyr Ile Gly Trp Thr Pro
145                 150                 155                 160

Leu His Leu Ala Ala Asp Gly His Leu Glu Ile Val Glu Val Leu Leu
            165                 170                 175

Lys Asn Gly Ala Asp Val Asn Ala Ser Asp Tyr Ile Gly Asp Thr Pro
                180                 185                 190

Leu His Leu Ala Ala His Asn Gly His Leu Glu Ile Val Glu Val Leu
            195                 200                 205

Leu Lys His Gly Ala Asp Val Asn Ala Gln Asp Lys Phe Gly Lys Thr
210                 215                 220

Ala Phe Asp Ile Ser Ile Asp Asn Gly Asn Glu Asp Leu Ala Glu Ile
225                 230                 235                 240

Leu Gln Lys Leu Asn
            245

<210> SEQ ID NO 309
<211> LENGTH: 225
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(24)
<223> OTHER INFORMATION: Optional
<220> FEATURE:
<221> NAME/KEY: MISC_FEATURE
<222> LOCATION: (49)..(69)
<223> OTHER INFORMATION: Optional

<400> SEQUENCE: 309

Met Gly Ser His His His His His Gly Ser Gly Ser Glu Asn Leu
1               5                   10                  15

Tyr Phe Gln Gly Ser Gly Gly Gly Thr Thr Ala Ser Glu Asp Glu Gln
                20                  25                  30

Glu Glu Met Ala Asn Ala Ile Ile Thr Ile Leu Gln Ser Trp Ile Phe
            35                  40                  45

Ser Gly Ser Gly Gly Ser Gly Gly Gly Ser Gly Gly Ser Gly
50                  55                  60
```

```
Gly Ser Gly Gly Gly Asp Leu Gly Lys Lys Leu Leu Glu Ala Ala Arg
 65                  70                  75                  80

Ala Gly Gln Asp Asp Glu Val Arg Ile Leu Met Ala Asn Gly Ala Asp
                 85                  90                  95

Val Asn Ala Asp Asp Thr Trp Gly Trp Thr Pro Leu His Leu Ala Ala
            100                 105                 110

Tyr Gln Gly His Leu Glu Ile Val Glu Val Leu Leu Lys Asn Gly Ala
        115                 120                 125

Asp Val Asn Ala Tyr Asp Tyr Ile Gly Trp Thr Pro Leu His Leu Ala
    130                 135                 140

Ala Asp Gly His Leu Glu Ile Val Glu Val Leu Leu Lys Asn Gly Ala
145                 150                 155                 160

Asp Val Asn Ala Ser Asp Tyr Ile Gly Asp Thr Pro Leu His Leu Ala
                165                 170                 175

Ala His Asn Gly His Leu Glu Ile Val Glu Val Leu Leu Lys His Gly
            180                 185                 190

Ala Asp Val Asn Ala Gln Asp Lys Phe Gly Lys Thr Ala Phe Asp Ile
        195                 200                 205

Ser Ile Asp Asn Gly Asn Glu Asp Leu Ala Glu Ile Leu Gln Lys Leu
    210                 215                 220

Asn
225

<210> SEQ ID NO 310
<211> LENGTH: 218
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(24)
<223> OTHER INFORMATION: Optional
<220> FEATURE:
<221> NAME/KEY: MISC_FEATURE
<222> LOCATION: (149)..(163)
<223> OTHER INFORMATION: Optional

<400> SEQUENCE: 310

Met Gly Ser His His His His His His Gly Ser Gly Ser Glu Asn Leu
1               5                   10                  15

Tyr Phe Gln Gly Ser Gly Ser Gly Asp Leu Gly Lys Lys Leu Leu Glu
            20                  25                  30

Ala Ala Arg Ala Gly Gln Asp Asp Glu Val Arg Ile Leu Met Ala Asn
        35                  40                  45

Gly Ala Asp Val Asn Ala Lys Asp Glu Tyr Gly Leu Thr Pro Leu Tyr
    50                  55                  60

Leu Ala Thr Ala His Gly His Leu Glu Ile Val Glu Val Leu Leu Lys
65                  70                  75                  80

Asn Gly Ala Asp Val Asn Ala Val Asp Ala Ile Gly Phe Thr Pro Leu
                85                  90                  95

His Leu Ala Ala Phe Ile Gly His Leu Glu Ile Ala Glu Val Leu Leu
            100                 105                 110

Lys His Gly Ala Asp Val Asn Ala Gln Asp Lys Phe Gly Lys Thr Ala
        115                 120                 125

Phe Asp Ile Ser Ile Gly Asn Gly Asn Glu Asp Leu Ala Glu Ile Leu
    130                 135                 140

Gln Lys Leu Asn Gly Ser Gly Gly Ser Gly Gly Ser Gly Gly Ser
```

```
                145                 150                 155                 160
Gly Ser Gly Pro Lys Lys Ile Gln Leu His Ala Glu His Ala Leu
                165                 170                 175

Tyr Asp Ala Leu Met Ile Leu Asn Ile Val Lys Thr Asn Ser Pro Pro
            180                 185                 190

Ala Glu Glu Lys Leu Glu Asp Tyr Ala Phe Asn Phe Glu Leu Ile Leu
                195                 200                 205

Glu Glu Ile Ala Arg Leu Phe Glu Ser Gly
            210                 215

<210> SEQ ID NO 311
<211> LENGTH: 241
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(24)
<223> OTHER INFORMATION: Optional
<220> FEATURE:
<221> NAME/KEY: MISC_FEATURE
<222> LOCATION: (148)..(163)
<223> OTHER INFORMATION: Optional

<400> SEQUENCE: 311

Met Gly Ser His His His His His Gly Ser Gly Ser Glu Asn Leu
1               5                   10                  15

Tyr Phe Gln Gly Ser Gly Ser Gly Asp Leu Gly Lys Lys Leu Leu Glu
                20                  25                  30

Ala Ala Arg Ala Gly Gln Asp Asp Glu Val Arg Ile Leu Met Ala Asn
            35                  40                  45

Gly Ala Asp Val Asn Ala Lys Asp Glu Tyr Gly Leu Thr Pro Leu Tyr
        50                  55                  60

Leu Ala Thr Ala His Gly His Leu Glu Ile Val Glu Val Leu Leu Lys
65                  70                  75                  80

Asn Gly Ala Asp Val Asn Ala Val Asp Ala Ile Gly Phe Thr Pro Leu
                85                  90                  95

His Leu Ala Ala Phe Ile Gly His Leu Glu Ile Ala Glu Val Leu Leu
            100                 105                 110

Lys His Gly Ala Asp Val Asn Ala Gln Asp Lys Phe Gly Lys Thr Ala
        115                 120                 125

Phe Asp Ile Ser Ile Gly Asn Gly Asn Glu Asp Leu Ala Glu Ile Leu
130                 135                 140

Gln Lys Leu Asn Gly Ser Gly Ser Gly Gly Ser Gly Gly Ser
145                 150                 155                 160

Gly Ser Gly Pro Lys Lys Ile Gln Leu His Ala Glu His Ala Leu
                165                 170                 175

Tyr Asp Ala Leu Met Ile Leu Asn Ile Val Lys Thr Asn Ser Pro Pro
            180                 185                 190

Ala Glu Glu Lys Leu Glu Asp Tyr Ala Phe Asn Phe Glu Leu Ile Leu
                195                 200                 205

Glu Glu Ile Ala Arg Leu Phe Glu Ser Gly Asp Gln Lys Asp Glu Ala
            210                 215                 220

Glu Lys Ala Lys Arg Met Lys Glu Trp Met Lys Arg Ile Lys Thr Thr
225                 230                 235                 240

Ala
```

```
<210> SEQ ID NO 312
<211> LENGTH: 56
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (23)..(32)
<223> OTHER INFORMATION: Optional
<220> FEATURE:
<221> NAME/KEY: MISC_FEATURE
<222> LOCATION: (55)..(56)
<223> OTHER INFORMATION: Optional

<400> SEQUENCE: 312

Pro Lys Lys Lys Ile Gln Ile Met Ala Glu Glu Ala Leu Lys Asp Ala
1               5                   10                  15

Leu Ser Ile Leu Asn Ile Val Lys Thr Asn Ser Pro Ala Glu Glu
            20                  25                  30

Gln Leu Glu Arg Phe Ala Lys Arg Phe Glu Arg Asn Leu Trp Gly Ile
        35                  40                  45

Ala Arg Leu Phe Glu Ser Gly Asp
    50                  55

<210> SEQ ID NO 313
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Optional
<220> FEATURE:
<221> NAME/KEY: MISC_FEATURE
<222> LOCATION: (21)..(25)
<223> OTHER INFORMATION: Optional

<400> SEQUENCE: 313

Asp Gln Lys Asp Glu Ala Glu Lys Ala Lys Arg Met Ile Glu Trp Met
1               5                   10                  15

Lys Arg Ile Lys Thr Thr Ala Ser Glu Asp Glu Gln Glu Glu Met Ala
            20                  25                  30

Asn Ala Ile Ile Thr Ile Leu Gln Ser Trp Phe Phe Ser
        35                  40                  45

<210> SEQ ID NO 314
<211> LENGTH: 56
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(32)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid

<400> SEQUENCE: 314

Pro Lys Lys Lys Ile Gln Ile Met Ala Glu Glu Ala Leu Lys Asp Ala
1               5                   10                  15

Leu Ser Ile Leu Asn Ile Xaa Xaa Xaa Xaa Xaa Xaa Xaa Xaa Xaa Xaa
```

```
                    20                  25                  30

Gln Leu Glu Arg Phe Ala Lys Arg Phe Glu Arg Asn Leu Trp Gly Ile
        35                  40                  45

Ala Arg Leu Phe Glu Ser Xaa Xaa
    50                  55

<210> SEQ ID NO 315
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Optional
<220> FEATURE:
<221> NAME/KEY: misc_feature
<222> LOCATION: (21)..(24)
<223> OTHER INFORMATION: Xaa can be any naturally occurring amino acid

<400> SEQUENCE: 315

Xaa Xaa Lys Asp Glu Ala Glu Lys Ala Lys Arg Met Ile Glu Trp Met
1               5                   10                  15

Lys Arg Ile Lys Xaa Xaa Xaa Xaa Glu Asp Glu Gln Glu Glu Met Ala
            20                  25                  30

Asn Ala Ile Ile Thr Ile Leu Gln Ser Trp Phe Phe Ser
        35                  40                  45

<210> SEQ ID NO 316
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (23)..(33)
<223> OTHER INFORMATION: Optional
<220> FEATURE:
<221> NAME/KEY: MISC_FEATURE
<222> LOCATION: (55)..(57)
<223> OTHER INFORMATION: Optional
<220> FEATURE:
<221> NAME/KEY: MISC_FEATURE
<222> LOCATION: (76)..(78)
<223> OTHER INFORMATION: Optional

<400> SEQUENCE: 316

Pro Lys Lys Lys Ile Gln Ile Met Ala Glu Glu Ala Leu Lys Asp Ala
1               5                   10                  15

Leu Ser Ile Leu Asn Ile Val Lys Thr Asn Ser Pro Pro Ala Glu Glu
            20                  25                  30

Gln Leu Glu Arg Phe Ala Lys Arg Phe Glu Arg Asn Leu Trp Gly Ile
        35                  40                  45

Ala Arg Leu Phe Glu Ser Gly Asp Gln Lys Asp Glu Ala Glu Lys Ala
    50                  55                  60

Lys Arg Met Ile Glu Trp Met Lys Arg Ile Lys Thr Thr Ala
65                  70                  75

<210> SEQ ID NO 317
<211> LENGTH: 25
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(5)
<223> OTHER INFORMATION: Optional

<400> SEQUENCE: 317

Thr Thr Ala Ser Glu Asp Glu Gln Glu Glu Met Ala Asn Ala Ile Ile
1               5                   10                  15

Thr Ile Leu Gln Ser Trp Phe Phe Ser
            20                  25

<210> SEQ ID NO 318
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (55)..(57)
<223> OTHER INFORMATION: Xaa can be any naturally occurring amino acid
<220> FEATURE:
<221> NAME/KEY: misc_feature
<222> LOCATION: (76)..(78)
<223> OTHER INFORMATION: Xaa can be any naturally occurring amino acid

<400> SEQUENCE: 318

Pro Lys Lys Lys Ile Gln Ile Met Ala Glu Glu Ala Leu Lys Asp Ala
1               5                   10                  15

Leu Ser Ile Leu Asn Ile Xaa Xaa Xaa Xaa Xaa Xaa Xaa Xaa Xaa Xaa
            20                  25                  30

Xaa Leu Glu Arg Phe Ala Lys Arg Phe Glu Arg Asn Leu Trp Gly Ile
            35                  40                  45

Ala Arg Leu Phe Glu Ser Xaa Xaa Xaa Lys Asp Glu Ala Glu Lys Ala
        50                  55                  60

Lys Arg Met Ile Glu Trp Met Lys Arg Ile Lys Xaa Xaa Xaa
65                  70                  75

<210> SEQ ID NO 319
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Optional

<400> SEQUENCE: 319

Xaa Xaa Xaa Xaa Xaa Asp Glu Gln Glu Glu Met Ala Asn Ala Ile Ile
1               5                   10                  15

Thr Ile Leu Gln Ser Trp Phe Phe Ser
            20                  25

<210> SEQ ID NO 320
<211> LENGTH: 17
<212> TYPE: PRT
<213> ORGANISM: Artificial Sequence
<220> FEATURE:
<223> OTHER INFORMATION: Synthetic peptide

<400> SEQUENCE: 320
```

Gln Leu His Ala Glu His Ala Leu Tyr Asp Ala Leu Met Ile Leu Asn
1               5                   10                  15

Ile

<210> SEQ ID NO 321
<211> LENGTH: 21
<212> TYPE: PRT
<213> ORGANISM: Artificial Sequence
<220> FEATURE:
<223> OTHER INFORMATION: Synthetic peptide

<400> SEQUENCE: 321

Leu Glu Asp Tyr Ala Phe Asn Phe Glu Leu Ile Leu Glu Glu Ile Ala
1               5                   10                  15

Arg Leu Phe Glu Ser
            20

<210> SEQ ID NO 322
<211> LENGTH: 20
<212> TYPE: PRT
<213> ORGANISM: Artificial Sequence
<220> FEATURE:
<223> OTHER INFORMATION: Synthetic peptide

<400> SEQUENCE: 322

Asp Glu Gln Glu Glu Met Ala Asn Ala Ile Ile Thr Ile Leu Gln Ser
1               5                   10                  15

Trp Ile Phe Ser
            20

<210> SEQ ID NO 323
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (23)..(27)
<223> OTHER INFORMATION: Optional

<400> SEQUENCE: 323

Pro Lys Lys Lys Ile Gln Leu His Ala Glu His Ala Leu Tyr Asp Ala
1               5                   10                  15

Leu Met Ile Leu Asn Ile Val Gly Gly Ser Ser
            20                  25

<210> SEQ ID NO 324
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(4)
<223> OTHER INFORMATION: Optional

<400> SEQUENCE: 324

Ser Lys Glu Ala Ile Gln Leu His Ala Glu His Ala Leu Tyr Asp Ala
1               5                   10                  15

Leu Met Ile Leu Asn Ile Val Lys Thr Asn Ser
            20                  25

```
<210> SEQ ID NO 325
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Optional

<400> SEQUENCE: 325

Pro Ile Gln Leu His Ala Glu His Ala Leu Tyr Asp Ala Leu Met Ile
1               5                   10                  15

Leu Asn Ile Val
            20

<210> SEQ ID NO 326
<211> LENGTH: 69
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Optional
<220> FEATURE:
<221> NAME/KEY: MISC_FEATURE
<222> LOCATION: (25)..(26)
<223> OTHER INFORMATION: Optional
<220> FEATURE:
<221> NAME/KEY: MISC_FEATURE
<222> LOCATION: (46)..(48)
<223> OTHER INFORMATION: Optional

<400> SEQUENCE: 326

Pro Lys Leu Glu Asp Tyr Ala Phe Asn Phe Glu Leu Ile Leu Glu Glu
1               5                   10                  15

Ile Ala Arg Leu Phe Glu Ser Gly Asp Gln Lys Asp Glu Ala Glu Lys
                20                  25                  30

Ala Lys Arg Met Lys Glu Trp Met Lys Arg Ile Lys Thr Thr Ala Ser
            35                  40                  45

Glu Asp Glu Gln Glu Glu Met Ala Asn Ala Ile Ile Thr Ile Leu Gln
    50                  55                  60

Ser Trp Ile Phe Ser
65

<210> SEQ ID NO 327
<211> LENGTH: 77
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Optional
<220> FEATURE:
<221> NAME/KEY: MISC_FEATURE
<222> LOCATION: (28)..(33)
<223> OTHER INFORMATION: Optional
<220> FEATURE:
<221> NAME/KEY: MISC_FEATURE
<222> LOCATION: (52)..(57)
<223> OTHER INFORMATION: Optional

<400> SEQUENCE: 327

Gly Gly Ser Ser Gly Gly Leu Glu Asp Tyr Ala Phe Asn Phe Glu Leu
```

```
1               5                   10                  15
Ile Leu Glu Glu Ile Ala Arg Leu Phe Glu Ser Gly Gly Ser Ser Gly
                20                  25                  30

Gly Lys Asp Glu Ala Glu Lys Ala Lys Arg Met Lys Glu Trp Met Lys
        35                  40                  45

Arg Ile Thr Gly Gly Ser Ser Gly Gly Asp Glu Gln Glu Glu Met Ala
    50                  55                  60

Asn Ala Ile Ile Thr Ile Leu Gln Ser Trp Ile Phe Ser
65                  70                  75

<210> SEQ ID NO 328
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Optional
<220> FEATURE:
<221> NAME/KEY: MISC_FEATURE
<222> LOCATION: (28)..(35)
<223> OTHER INFORMATION: Optional
<220> FEATURE:
<221> NAME/KEY: MISC_FEATURE
<222> LOCATION: (51)..(56)
<223> OTHER INFORMATION: Optional

<400> SEQUENCE: 328

Gly Gly Ser Ser Gly Gly Leu Glu Asp Tyr Ala Phe Asn Phe Glu Leu
1               5                   10                  15

Ile Leu Glu Glu Ile Ala Arg Leu Phe Glu Ser Gly Gly Ser Ser Gly
                20                  25                  30

Gly Gly Gly Glu Ala Glu Lys Ala Lys Arg Met Lys Glu Trp Met Lys
        35                  40                  45

Arg Ile Gly Gly Ser Ser Gly Gly Asp Glu Gln Glu Glu Met Ala Asn
    50                  55                  60

Ala Ile Ile Thr Ile Leu Gln Ser Trp Ile Phe Ser
65                  70                  75
```

SPLIT INTERLEUKIN MIMETICS AND THEIR USE

CROSS REFERENCE

This application is a U.S. national phase of International Application No. PCT/US2019/062198, filed on Nov. 19, 2019, which claims priority to U.S. Provisional Application No. 62/770,152, filed Nov. 20, 2018, both of which are incorporated by reference herein in their entirety.

BACKGROUND

The considerable potential of central immune cytokine interleukins such as IL-2 and IL-4 for cancer treatment has sparked numerous efforts to improve their therapeutic properties by mutation and/or chemical modification. However, because these approaches are closely tied to native IL-2 or IL-4, they cannot eliminate undesirable properties such as low stability and binding to the IL-2 receptor a subunit (IL-2Rα), to IL-4 receptor $\alpha\gamma_c$ heterodimer (IL-4Rα$\gamma_c$), or to IL-13 receptor a subunit (IL-13Rα).

SUMMARY

In one aspect the disclosure provides non-naturally occurring conditionally active receptor agonists, comprising a first polypeptide component and a second polypeptide component, wherein the first polypeptide component and the second polypeptide component are not present in a fusion protein, wherein in total the first polypeptide component and the second polypeptide component comprise domains X1, X2, X3, and X4, wherein:
  (a) X1 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (PKKKIQ)LHAEHALYDAL(MILNI) (SEQ ID NO: 4);
  (b) X2 is any helical peptide domain at least 8 amino acids in length:
  (c) X3 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (LE)DYAFNFELILEE(IARLFESG) (SEQ ID NO:5); and
  (d) X4 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (EDEQEEMANAI)ITILQSWIF(S) (SEQ ID NO:6).
  wherein:
    (i) amino acid residues in parentheses may be present or absent;
    (ii) the first polypeptide component comprises at least one of X1, X2, X3, and X4 but does not comprise each of X1, X2, X3, and X4; and
    (iii) the second polypeptide component comprises each of X1, X2, X3, and X4 that is not present in the first polypeptide component;
  wherein the first polypeptide component and the second polypeptide component are not active receptor agonists individually, and wherein the first polypeptide component and the second polypeptide interact to form an active agonist of IL-2 receptor $\beta\gamma_c$ heterodimer (IL-2R$\beta\gamma_c$), IL-4 receptor $\alpha\gamma_c$ heterodimer (IL-4Rα$\gamma_c$), IL-13 alpha, or IL-4Ralpha/IL13Ralpha heterodimer.

Numerous embodiments of the first and second polypeptides are provided herein. In exemplary embodiments,
  (i) the first polypeptide component includes one of X1, X2, X3, and X4, and the second polypeptide component includes the three of X1, X2, X3, and X4 that am not present in the first polypeptide component; or
  (ii) the first polypeptide component includes two of X1, X2, X3, and X4, and the second polypeptide component includes the two of X1, X2, X3, and X4 that are not present in the first polypeptide component. In other exemplary embodiments,
  (i) the first polypeptide comprises X1 and the second polypeptide comprises X2, X3, and X4;
  (ii) the first polypeptide comprises X2 and the second polypeptide comprises X1, X3, and X4;
  (iii) the first polypeptide comprises X3 and the second polypeptide comprises X1, X2, and X4;
  (iv) the first polypeptide comprises X4 and the second polypeptide comprises X1, X2, and X3;
  (v) the first polypeptide comprises X1 and X2, and the second polypeptide comprises X3 and X4;
  (vi) the first polypeptide comprises X1 and X3, and the second polypeptide comprises X2 and X4;
  (vii) the first polypeptide comprises X1 and X4, and the second polypeptide comprises X2 and X3;
  (viii) the first polypeptide comprises X2 and X3, and the second polypeptide comprises X1 and X4;
  (ix) the first polypeptide comprises X2 and X4, and the second polypeptide comprises X1 and X3;
  (x) the first polypeptide comprises X3 and X4, and the second polypeptide comprises X1 and X2;
  (xi) the first polypeptide comprises X1, X2, and X3 and the second polypeptide comprises X4;
  (xii) the first polypeptide comprises X1, X2, and X4 and the second polypeptide comprises X3;
  (xiii) the first polypeptide comprises X1, X3, and X4 and the second polypeptide comprises X2; or
  (xiv) the first polypeptide comprises X2, X3, and X4 and the second polypeptide comprises X1.

In other exemplary embodiments, the first polypeptide component and the second polypeptide component may be non-covalently associated, and/or the first polypeptide component and the second polypeptide component may be indirectly bound to each other through a receptor. In a further exemplary embodiment, the first polypeptide component further comprises a first targeting domain and/or the second polypeptide component further comprises a second targeting domain; in some embodiments, the first targeting domain, when present, is a translational fusion with the first polypeptide, and wherein the second targeting domain, when present, is a translational fusion with the second polypeptide. In some embodiments, the targeting domains may bind to a cell surface protein.

In another aspect, the disclosure provides polypeptides comprising 1, 2, or 3, but not all 4 domains X1, X2, X3, and X4, wherein:
  (a) X1, when present, is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (PKKKIQ)LHAEHALYDAL(MILNI); (SEQ ID NO: 4);
  (b) X2, when present, is any helical peptide domain;
  (c) X3, when present, is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (LE)D<u>Y</u>AF<u>N</u>FEL<u>I</u>LEE(<u>I</u>ARLFESG) (SEQ ID NO:5); and (d) X4, when present, is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (EDEQEEMANAI)<u>I</u>TILQS<u>W</u>IF(S) (SEQ ID NO:6);

amino acid residues in parentheses may be present or absent. Numerous embodiments of the polypeptides are provided. In some exemplary embodiments, the polypeptide comprises:

(i) a polypeptide comprising X1 and excluding X2, X3, and X4;
(ii) a polypeptide comprising X2 and excluding X1, X3, and X4;
(iii) a polypeptide comprising X3 and excluding X1, X2, and X4;
(iv) a polypeptide comprising X4 and excluding X1, X2, and X3;
(v) a polypeptide comprising X1 and X2, and excluding X3 and X4;
(vi) a polypeptide comprising X1 and X3, and excluding X2 and X4;
(vii) a polypeptide comprising X1 and X4, and excluding X2 and X3;
(viii) a polypeptide comprising X2 and X3, and excluding X1 and X4;
(ix) a polypeptide comprising X2 and X4, and excluding X1 and X3;
(x) a polypeptide comprising X3 and X4, and excluding X1 and X2;
(xi) a polypeptide comprising X1, X2, and X3 and excluding X4;
(xii) a polypeptide comprising X1, X2, and X4 and excluding X3;
(xiii) a polypeptide comprising X1, X3, and X4 and excluding X2; and
(xiv) a polypeptide comprising X2, X3, and X4 and excluding X1.

In another exemplary embodiment, the polypeptide further comprises a targeting domain, including but not limited to the targeting domain being a translational fusion with the polypeptide. In some embodiments, the targeting domains may bind to a cell surface protein.

In other aspects, the disclosure provides nucleic acids encoding the polypeptide, first polypeptide, or second polypeptide of any embodiment disclosed; expression vectors comprising the nucleic acids operatively linked to a promoter; host cells comprising the nucleic acids and/or expression vectors disclosed herein, and pharmaceutical composition, comprising the conditionally active receptor agonist, polypeptide, nucleic acid, expression vector, or host cell of any embodiment disclosed, and a pharmaceutically acceptable carrier.

The disclosure also provides methods for treating cancer, comprising administering to a subject in need thereof the conditionally active receptor agonist of any embodiment disclosed herein, under conditions wherein the first polypeptide component and the second polypeptide component interact at cells of the tumor to treat the cancer.

In another aspect, the disclosure provides the conditionally active receptor agonist, polypeptide, nucleic acid, expression vector, host cell, or pharmaceutical composition of any embodiment disclosed for use as a medicament for treating cancer and/or for modulating an immune response in a subject.

In a further aspect, the disclosure provides methods for agonizing the IL-2 receptor or the IL-4 receptor, comprising administering to a subject the conditionally active receptor agonist of any embodiment disclosed herein, under conditions wherein the first polypeptide component and the second polypeptide component interact at the receptor.

DESCRIPTION OF THE DRAWINGS

The following figures are in accordance with example embodiments:

FIG. 1A) The designed non-split mimetics have four helices; three mimetic IL-2 interactions with hIL-2Rβ $\gamma_c$, while the fourth holds the first three in place. Top: in the first generation of designs, each of the core elements of IL-2 (helices H1-H4) were independently idealized using fragment-assembly from a clustered ideal fragment database (size: 4 a.a.); bottom: in the second generation of designs the core elements were instead built using parametric equations that recapitulate the shape of each disembodied helix, allowing changes in the length of each helix by +/−8 a.a.; FIG. 1B) Pairs of helices were reconnected using ideal loop fragments (size: 4 a.a, or 7 a.a., for gen-1 and gen-2 respectively, see Methods), representative examples are shown with newly built elements connecting each pair of helices; FIG. 1C) The helix hairpins generated in FIG. 1B were assembled in all possible combinations to generate fully connected protein backbones.

FIG. 3A) Neo-2/15 structurally aligned into the structure of IL-4 in complex with IL4Rα and $\gamma_c$ (from PDB code 3BPL). Fourteen IL-4 residues that contact IL-4Rα and that were grafted into Neo-2/15 are labeled. FIG. 3B) Neoleukin-4 (Neo-4), a new protein with sixteen amino acid mutations compared to Neo-2/15. These mutations are labeled; thirteen of these were derived from the IL-4 residues depicted in panel "a)" that mediate contact with IL-4Rα, and three of them (HBM, K681 and 198F, underlined in the figure) were introduced by directed evolution using random mutagenesis and screening for high binding affinity variants. FIG. 3C) Biolayer interferometry data showing that Neo-4, like IL-4, binds to IL-4Rα alone, has no affinity for $\gamma_c$ alone, but binds to $\gamma_c$ when IL-4Rα is present in solution.

FIG. 5A-5C) Heatmaps for G1_neo2_40 single-site mutagenesis library showing enrichment at specific positions after consecutive rounds of increasing selection with FIG. 5A) 50 nM, FIG. 5B) 2 nM, and FIG. 5C) 0.1 nM IL-2Rβ $\gamma_c$ heterodimer. Based on these enrichment data, a combinatorial library was designed with nucleotide diversity $1.5 \times 10^6$. FIG. 5D) Amino acid residues available in the initial combinatorial library are depicted indicating residues predicted to be advantageous (shown above the original sequence) and deleterious (shown below the original sequence; in the depiction of the original sequence, black indicates residues that are represented in the combinatorial library and gray, residues not represented in the combinatorial library.

FIG. 6C) 0.1 nM, and FIG. 6D) 0.1 nM IL-2Rβ $\gamma_c$ heterodimer. Based on these enrichment data, a combinatorial library was designed with nucleotide diversity $5.3 \times 10^6$. FIG. 6E) Amino acid residues available in the initial combinatorial library are depicted indicating residues predicted to be advantageous; black indicates residues in the starting sequence represented in the combinatorial library.

FIG. 7C) 0.1 nM, and FIG. 7D) 0.1 nM IL-2Rβ $\gamma_c$, heterodimer. Based on these enrichment data, a combinatorial library was designed with nucleotide diversity $2.9 \times 10^6$. FIG. 7E) Amino acid residues available in the initial combinatorial library are depicted indicating residues predicted to be advantageous; black indicates residues in the starting sequence represented in the combinatorial library.

FIG. 8A-8E. Experimental optimization of G2_neo2_40_1F_seq36. Heatmaps for G2 neo2_40_1F_seq36 single-site mutagenesis library showing enrichment at specific positions after consecutive rounds of increasing selection with FIG. 8A) 10 nM, FIG. 8B) 1 nM, FIG. 8C) 0.1 nM, and FIG. 8D) 0.1 nM IL-2Rβ $\gamma_c$, heterodimer. Based on these enrichment data, a combinatorial library was designed with nucleotide diversity $2.7 \times 10^6$. FIG. 8E) Amino acid residues available in the initial combinatorial library are depicted indicating residues predicted to be advantageous; black indicates residues in the starting sequence represented in the combinatorial library.

FIG. 9A-9B. Circular Dichroism (CD) thermal denaturation experiments for multiple IL-2/IL-15 de novo designed mimetics, generation-1. FIG. 9A) Thermal denaturation curves and FIG. 9B) wavelength scans.

FIG. 10A-10B. Circular Dichroism (CD) thermal denaturation experiments for multiple IL-2/IL-15 de novo designed mimetics, generation-1 experimentally optimized. FIG. 10A) Thermal denaturation curves and FIG. 10B) wavelength scans.

FIG. 11A and FIG. 11C) Thermal denaturation curves and FIG. 11B and FIG. 11D) wavelength scans.

FIG. 12A) SDS Tris-Tricine gel electrophoresis showing expression and purification over affinity column. FIG. 12B) Circular dichroism at 222 nm during thermal melting from 25° C. to 95° C., showing robust temperature stability. FIG. 12C) Circular dichroism wavelength scans at 25° C., 95° C. and then again 25° C., showing that neoleukin-2/15 does not fully melt at 95° C. and refolds fully after cooling back to 25° C.

FIG. 13A) Schematic showing point mutant positions in neoleukin-2/15 that can individually be mutated to cysteine without interfering with expression of the protein or binding to IL-2Rβγc. Positions were chosen to avoid interference with receptor binding. FIG. 13B) Association kinetics of Neolukin-2/15 cysteine mutants with IL-2Rβ$\gamma_c$, measured using biolayer interferometry. All of the variants associate with receptor approximately similarly to Neo-2/15.

FIG. 14A) SDS Tris-Tricine gel electrophoresis showing expression and purification over affinity column. FIG. 14B) Circular dichroism at 222 nm during thermal melting from 25° C. to 95° C., showing robust temperature stability. FIG. 14C) Circular dichroism wavelength scans at 25° C., 95° C. and then again 25° C., showing that neoleukin-4 does not fully melt at 95° C. and refolds fully after cooling back to 25° C.

Figure 16A:
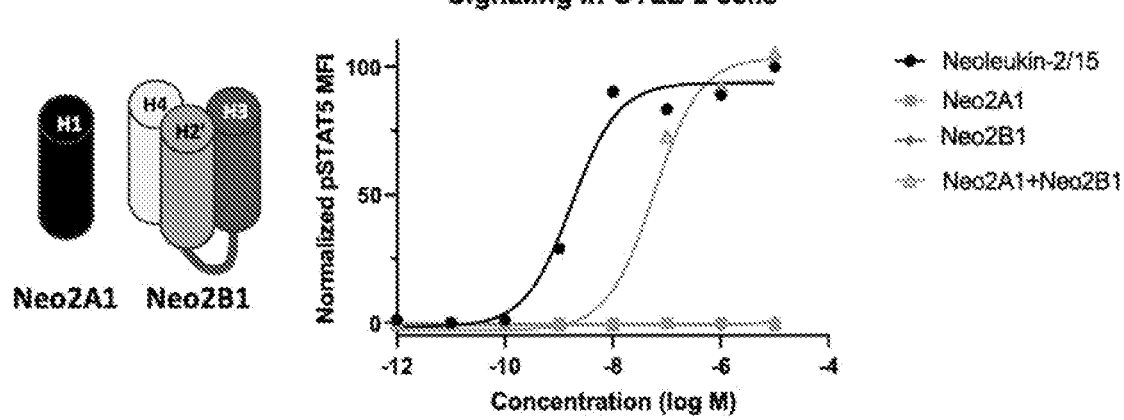
Figure 16B:
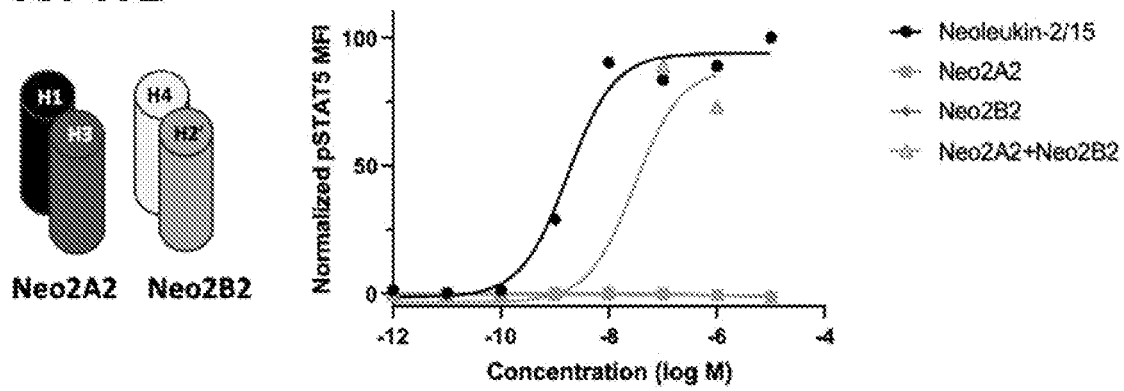
Figure 16C:
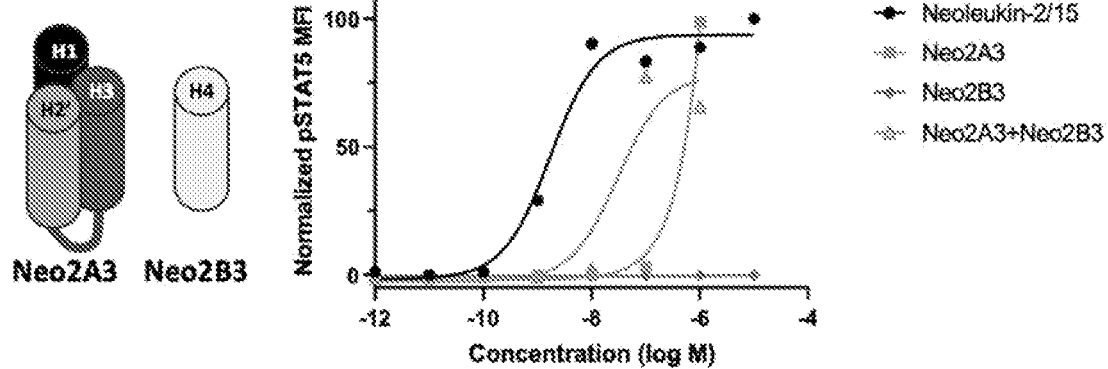

FIG. 16A-C. Split-Neo-2/15 variants stimulate cell signaling by STAT5 phosphorylation in murine CTLL-2 cell lines. a. CTLL-2 cells were starved in cytokine-free media (RPMI, 10% FBS, +1 mM sodium pyruvate, +2 mM L-glutamine, 1% P/S) for 2 hours before the assay. Cells were plated in a 96-well plate and re-suspended in RPMI medium containing serial dilutions of protein samples: Neoleukin-2/15, Neo2A1, Neo2B1, and Neo2A1+Neo2B1 at equimolar ratios. Cells were stimulated for 15 min at 37° C. and immediately fixed by addition of formaldehyde to 1.5% and 10 min incubation at room temperature. Cells were permeabilized by resuspension in cold 100% methanol for 30 min at 4° C. Fixed and permeabilized cells were washed twice with FACS buffer (PBS pH 7.2 containing 0.1% bovine serum albumin) and incubated with Alexa™ Fluor 647-conjugated anti-STAT5 pY694 (BD Biosciences) diluted 1:50 in FACS buffer for 2 h at room temperature. Cells were then washed twice in FACS buffer and mean fluorescence intensity (MFI) was determined on a Guava easyCyte™ flow cytometer (Millipore). Dose-response curves were fitted to a logistic model and half-maximal effective concentration (EC50 values) were calculated using GraphPad Prism data analysis software after subtraction of the MFI of unstimulated cells and normalization to the maximum signal intensity. b. Bio-Layer Interferometry binding assay of Neo-2/15 split into helixes H1-H3+H2'-H4 (Neo2A3 and Neo2B3 respectively), following the aforementioned experimental protocol. c. Bio-Layer Interferometry binding assay of Neo-2/15 split into helixes H1-H3-HT+H4 (Neo2A2 and Neo2B2 respectively), following the aforementioned experimental protocol.

Figure 17A:
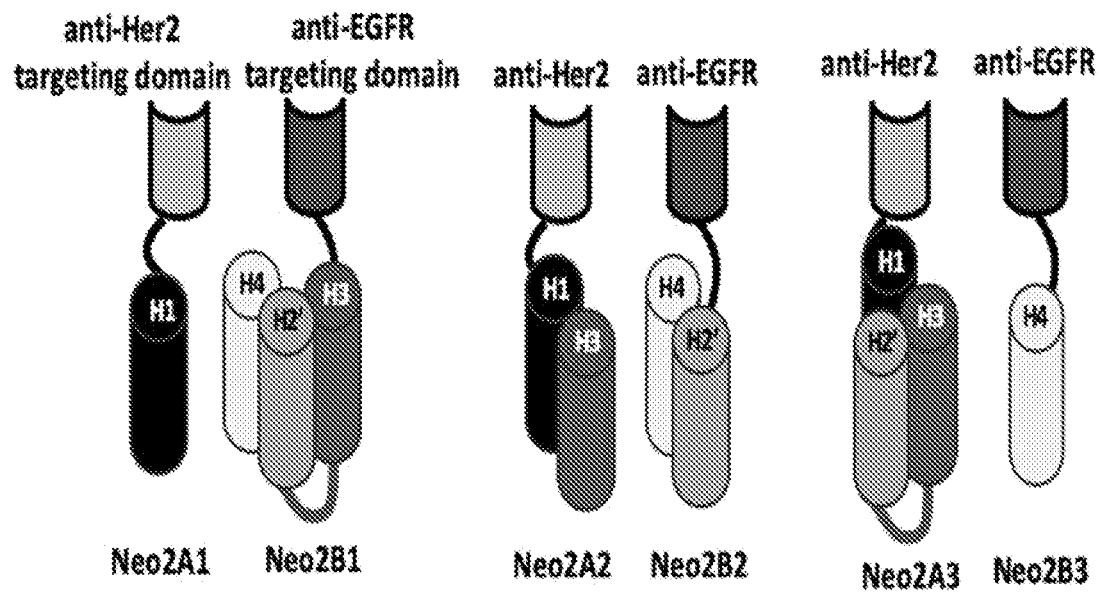
Figure 17B:
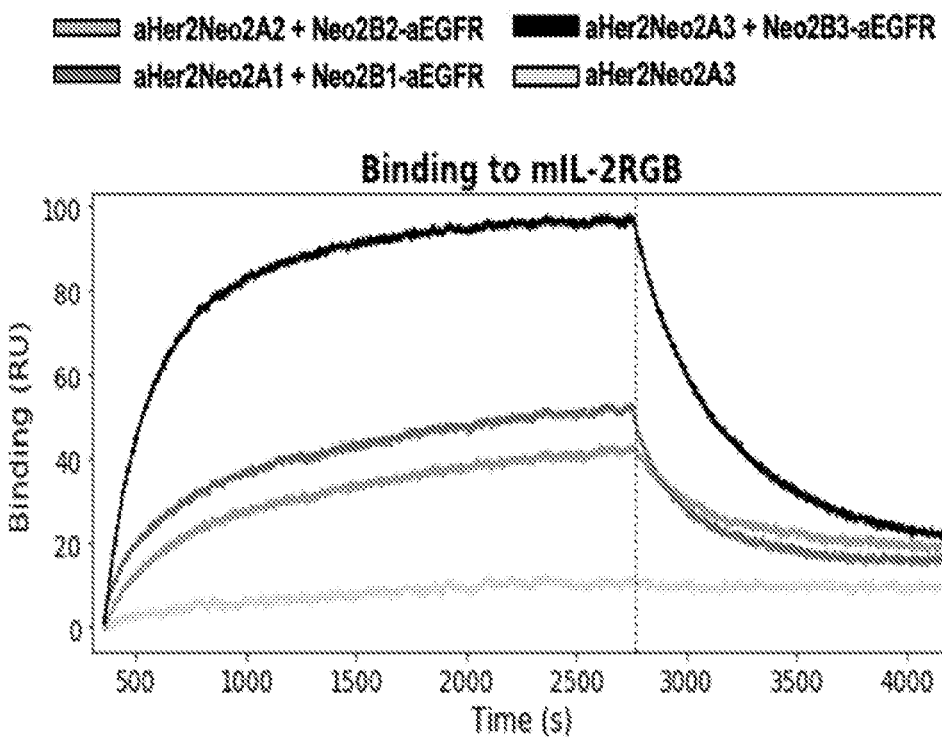

FIG. 17A-B. Fusions of split-Neo2/15 variants to targeting domains bind to the IL-2Receptor. a. Neo2A and Neo2B split protein variants fused to anti-EGFR and anti-Her2 DARPin targeting domains. b. Bio-Layer Interferometry binding assay of split-Neo-2/15 protein fusions to mouse IL-2 Receptor. Binding data were collected in an Octet RED96 (ForteBio) and processed using ForteBio™ Data Analysis Software version 9.0.0.10. Biotinylated target receptor human γc was immobilized on streptavidin-coated biosensors (SA ForteBio) at 1 μg/ml in binding buffer (10 mM HEPES (pH 7.4), 150 mM NaCl, 3 mM EDTA, 0.05% surfactant P20, 0.5% non-fat dry milk) for 300 seconds. After loading the target receptor onto the biosensor, baseline measurement was performed dipping the biosensors in binding buffer alone, then, the binding kinetics were monitored by dipping the biosensors in wells containing the target protein (association step) and then dipping the sensors back into baseline/buffer (dissociation). For the association step, analyte proteins (i.e. aHer2Neo2A1+Neo2B1-aEGFR, aHer2Neo2A2+Neo2B2-aEGFR, aHer2Neo2A3+Neo2B3-aEGFR) were diluted in equimolar amounts from concentrated stocks into binding buffer to a final concentration of 100 nM. Mouse IL-2Rβ was also added in solution at saturating concentration (250 nM).

Figure 18A:
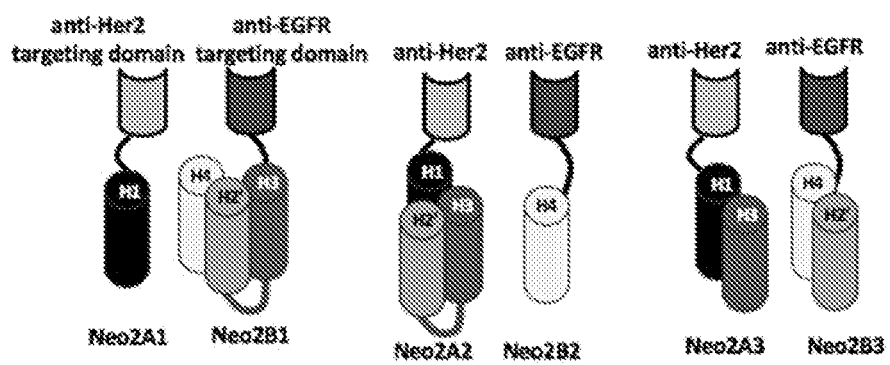
Figure 18A:
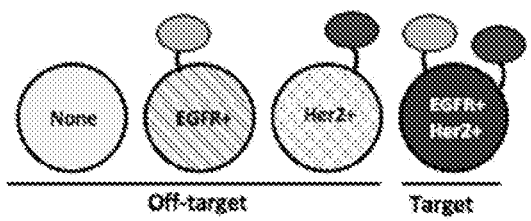
Figure 18C:
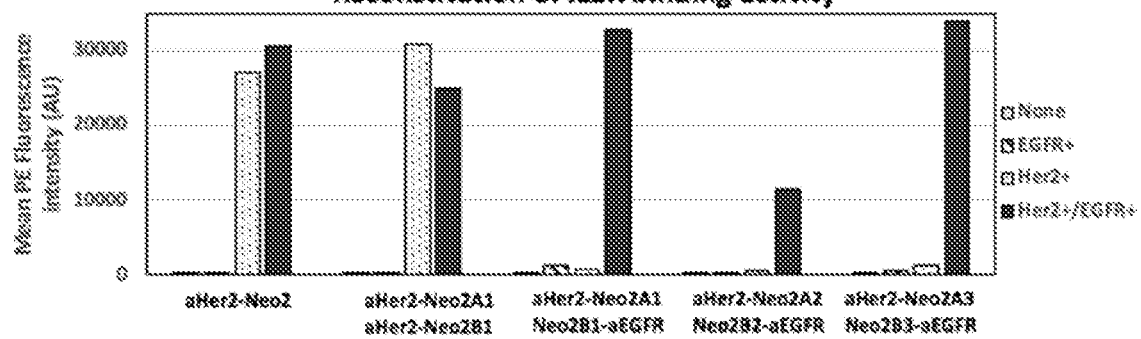

FIG. 18A-C. Targeted reconstitution of split-Neoleukin-2/15 on the surface of K562 cells expressing Her2 and EGFR. a. Neo2A and Neo2B split protein variants fused to anti-EGFR and anti-Her2 DARPin targeting domains. b. Engineered K562 tumor cell lines transduced for expression of Her2+/eGFP+, EGFR+/iRFP+ or Her2+/eGFP+ and EGFR+/iRFP+ surface markers. c. Functional reconstitution assay of Her2-targeted Neo2A variants (aHer2Neo2A1, aHer2Neo2A2 and aHer2Neo2A3) and EGFR-targeted Neo2B variants (Neo2B1-aEGFR, Neo2B2-aEGFR and Neo2B3-aEGFR) to the surface of the four aforementioned K562 cell lines. All cell lines were mixed in equivalent ratio (50,000 of each cell type per well) and transferred to a V-bottom plate at 200.000 cells/well. The cells were incubated for 30 minutes at room temperature with an equimolar ratio of anti-Her2-Neo2, anti-Her2-Neo2A+anti-EGFR-Neo2B variants, to a final concentration of 10 nM in FACS buffer (PBS (Gibco), 0.5% BSA). The cells were then washed twice (PBS (Gibco), 0.5% BSA) and subsequently incubated for 5 minutes with the following components: 50 nM of biotinylated soluble human common gamma receptor, 50 nM of soluble human IL-2Rβ and 15 nM of streptavidin-phycoerythrin conjugate (SAPE). Cells were washed again and analyzed by flow cytometry in a LSRII instrument. Her2+ cells were sorted for eGFP fluorescence (Ex/Em=488/508), EGFR+ cells were sorted for iRFP fluorescence (Ex/Em=637/670), Her2+/EGFR+ cells were identified by simultaneous expression of eGFP and iRFP. Reconstitution of Neoleukin-2/15 activity and binding to the IL-2 receptor was identified by analyzing PE (Ex/Em=561/582) fluorescence on the surface of each subset of cells.

Figure 19A:
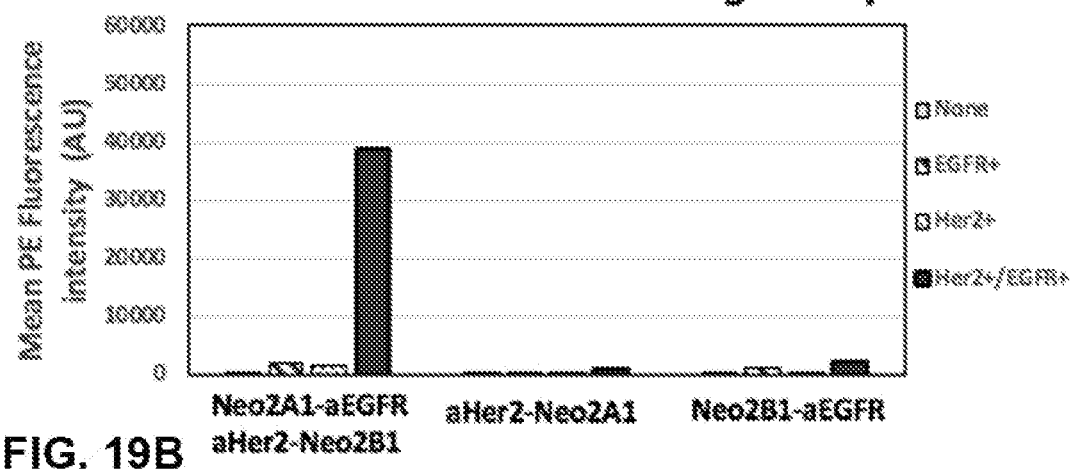
Figure 19B:
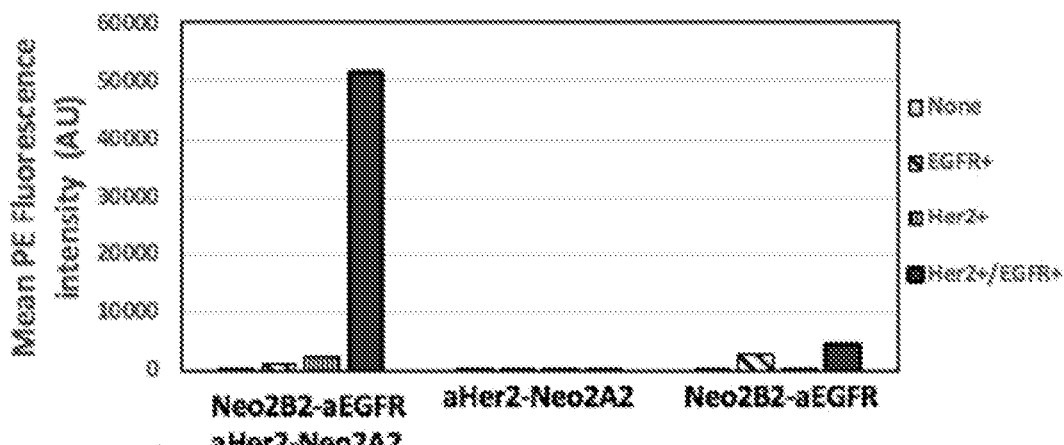
Figure 19C:
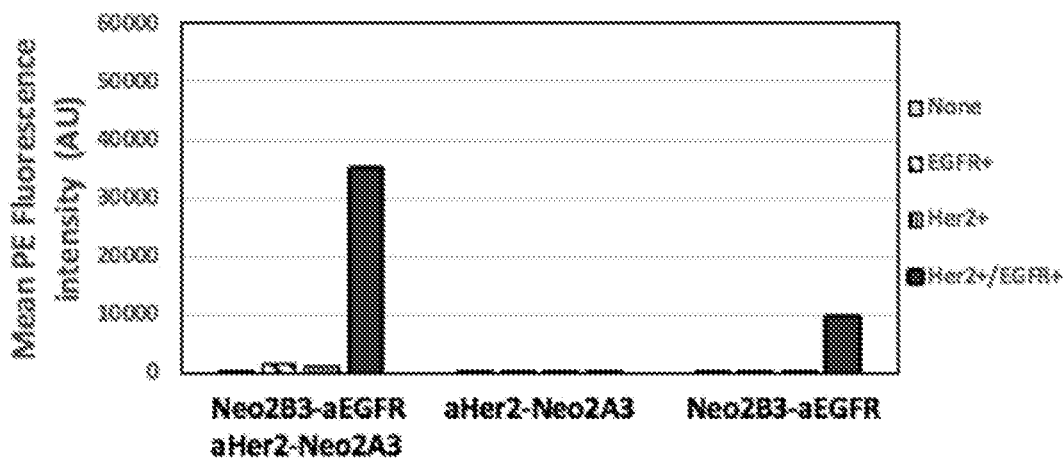

FIG. 19A-C. Both fragments of the split-Neo-2/15 variants are necessary to enable functional reconstitution on the surface of K562 cells expressing Her2 and EGFR. a. Functional reconstitution assay of Her2-targeted Neo2A variants (aHer2-Neo2A1) and EGFR-targeted Neo2B variants (Neo2B1-aEGFR) to the surface of four K562 cell lines expressing the following markers: None, Her2+/eGFP+, EGFR+/iRFP+, Her2+/eGFP+/EGFR+/iRFP+. All cell lines were mixed in equivalent ratio (50,000 of each cell type per well) and transferred to a V-bottom plate at 200.000 cells/well. The cells were incubated for 30 minutes at room temperature with anti-Her2-Neo2A1, Neo2B1-antiEGFR or anti-Her2-Neo2A1+Neo2B1-antiEGFR to a final concentration of 810 nM in FACS buffer (PBS (Gibco), 0.5% BSA). The cells were then washed twice (PBS (Gibco), 0.5% BSA) and subsequently incubated for 5 minutes with the following components: 50 nM of biotinylated soluble human common gamma receptor, 50 nM of soluble human IL-2Rβ and 15 nM of streptavidin-phycoerythrin conjugate (SAPE). Cells were washed again and analyzed by flow cytometry in a LSRII instrument. Her2+ cells were sorted for eGFP fluorescence (Ex/Em=488/508), EGFR+ cells were sorted for iRFP fluorescence (Ex/Em=637/670), Her2+/EGFR+ cells were identified by simultaneous expression of eGFP and iRFP. Reconstitution of Neoleukin-2/15 activity and binding to the IL-2 receptor was identified by analyzing PE (Ex/Em=561/582) fluorescence on the surface of each subset of cells. As observed, both fragments are necessary to reconstitute functional Neoleukin-2/15 activity on the surface of double positive cells. b. Same assay described in (a) using aHer2-Neo2A2 and Neo2B2-aEGFR. c. Same assay described in (a) using aHer2-Neo2A3 and Neo2B3-aEGFR.

Figure 20A:
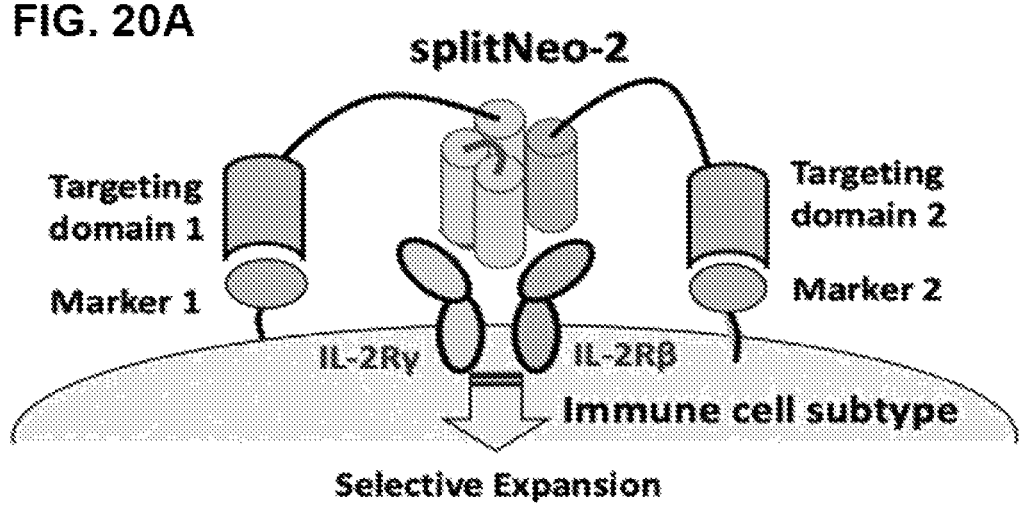
Figure 20B:
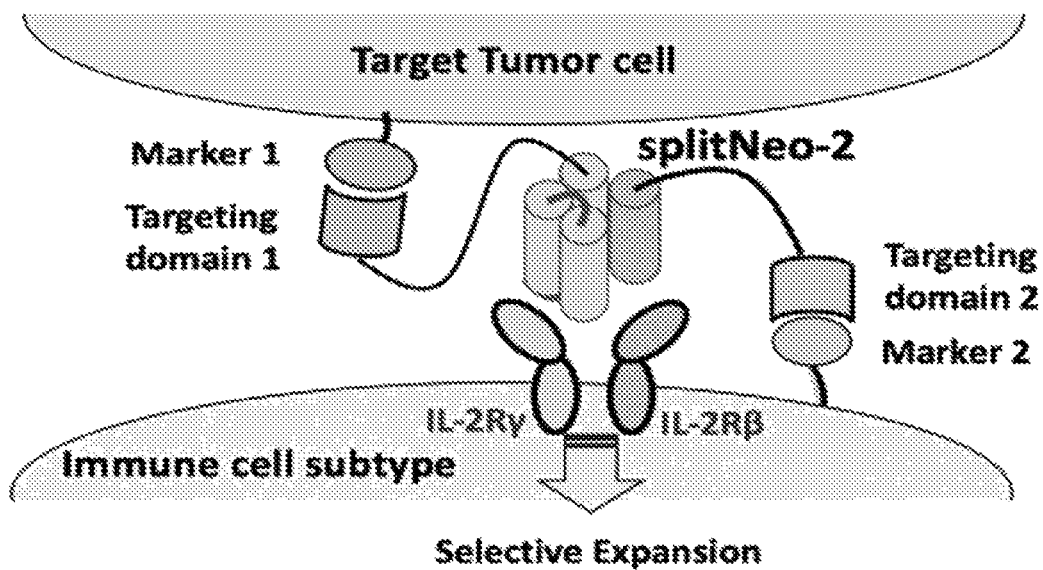

FIG. 20A-B. Illustration of alternative modes of action of the splitNeo-2 platform for highly-specific activation of immune cell subtypes. a. Selective targeting of splitNeo-2 to two surface markers to stimulate the expansion of a specific immune cell subtype (e.g. CD8+, CAR T cells or Regulatory T cells) b. Simultaneous tumor and T cell targeting by the split Neoleukin-2/15 system to induce immune cell subset specific proliferation in the environment of target tumor cells.

Figure 21:
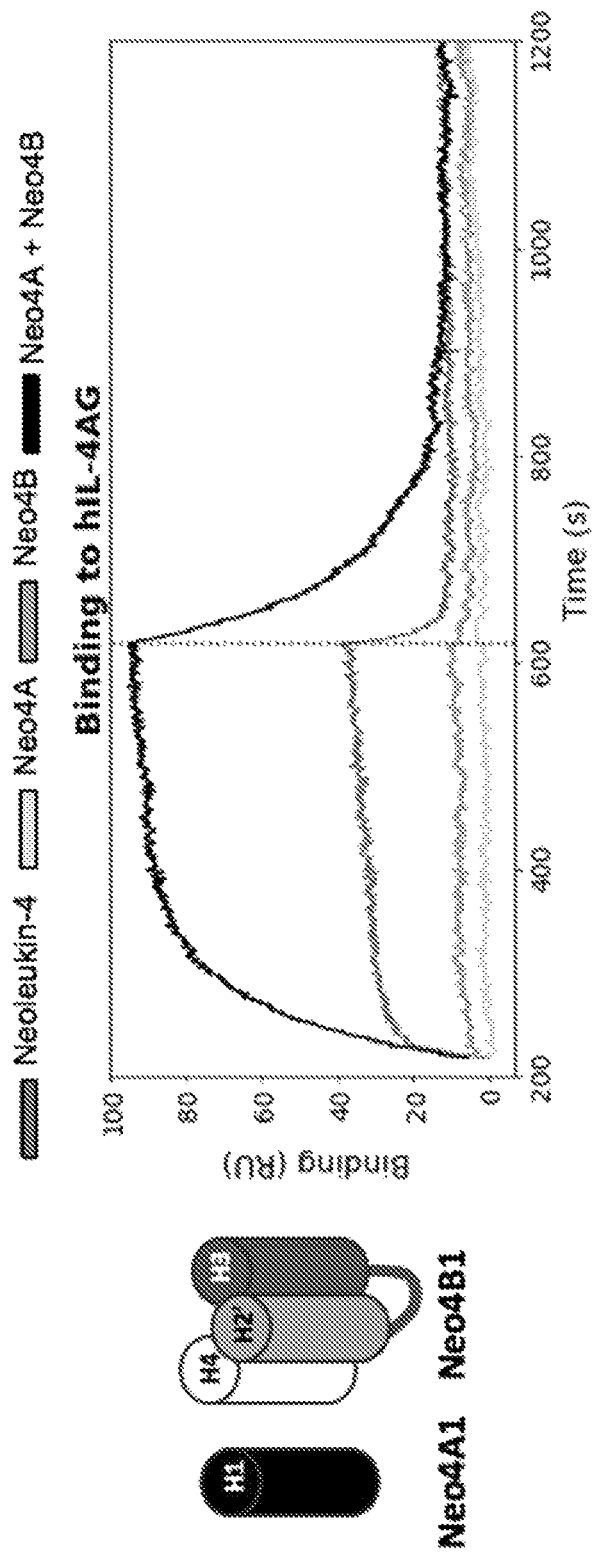

FIG. 21A. Neoleukin-4 split fragments can reconstitute full activity when combined. Bio-Layer Interferometry binding assay of Neo-4 split into helices H1 (Neo4A1) +H3-H2'-H4 (Neo4B1) to human IL-4 Receptor. Binding data were collected in an Octet RED96 (ForteBio) and processed using ForteBio™ Data Analysis Software version 9.0.0.10. Biotinylated target receptor human γc was immobilized on streptavidin-coated biosensors (SA ForteBio) at 1 µg/ml in binding buffer (10 mM HEPES (pH 7.4), 150 mM NaCl, 3 mM EDTA, 0.05% surfactant P20, 0.5% non-fat dry milk) for 300 seconds. After loading the target receptor onto the biosensor, baseline measurement was performed in binding buffer alone, then, the binding kinetics were monitored by dipping the biosensors in wells containing the target protein at the indicated concentration (association step) and then dipping the sensors back into baseline/buffer (dissociation). For the association step, analyte proteins (i.e. Neoleukin-4, Neo4A1, Neo4B1 and an equimolar ratio of Neo4A1+ Neo4B1) were diluted from concentrated stocks into binding buffer to a final concentration of 100 nM, human IL-4Rα was also added in solution at saturating concentration (250 nM).

DETAILED DESCRIPTION

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense: that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met: M), phenylalanine (Phe; F), praline (Pro; P), serine (Ser; S), threonine (Thr; 1), tryptophan (Trp; W), tyrosine (Tyr; Y), and valine (Val; V).

All embodiments of any aspect of the invention can be used in combination, unless the context clearly dictates otherwise.

In a first aspect, the disclosure provides non-naturally occurring conditionally active receptor agonists, comprising a first polypeptide component and a second polypeptide component, wherein the first polypeptide component and the second polypeptide component are not present in a fusion protein, wherein in total the first polypeptide component and the second polypeptide component comprise domains X1, X2, X3, and X4, wherein:
(a) X1 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (PKKKIQ) LHAEHALYDAL(MILNI) (SEQ ID NO: 4);
(b) X2 is any helical peptide domain;
(c) X3 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (LE) DYAFNFELILEE((IARLFESG) (SEQ ID NO:5); and
(d) X4 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (EDEQEE-MANAI)ITILQSWIF(S) (SEQ ID NO:6). wherein:
(i) amino acid residues in parentheses may be present or absent;
(ii) the first polypeptide component comprises at least one of X1, X2, X3. and X4 but does not comprise each of X1, X2, X3, and X4; and
(iii) the second polypeptide component comprises each of X1, X2, X3. and X4 that is not present in the first polypeptide component;
wherein the first polypeptide component and the second polypeptide component are not active receptor agonists individually, and wherein the first polypeptide component and the second polypeptide interact to form an active agonist of IL-2 receptor $\beta\gamma_c$ heterodimer (IL-2R$\beta\gamma_c$), IL-4 receptor $\alpha\gamma_c$ heterodimer (IL-4R$\alpha\gamma_c$), IL-13 alpha, or IL-4Ralpha/IL13Ralpha heterodimer.

As shown in the examples that follow, as described in detail in PCT application serial no. PCT/US2019/038703 filed Jun. 29, 2019, and as described in Silva et al., Nature 565, pg. 186, Jan. 10, 2019, polypeptides that include all of X1-X4 were previously shown to be (a) mimetics of IL-2 and interleukin-15 (IL-15) that bind to the IL-2 receptor $\beta\gamma_c$ heterodimer (IL-2R$\beta\gamma_c$), but have no binding site for IL-2Rα or IL-15Rα, or (b) mimetics of IL-4 that bind to the IL-4 receptor ay, heterodimer (IL-4R$\alpha\gamma_c$) or IL-13 receptor a subunit (IL-13Rα) (natural IL-4 and the IL-4 mimetics described herein cross-react with IL-13 receptor, forming an IL-4Rα/IL13Rα heterodimer). The full length polypeptides were shown to be hyper-stable, bind to human and mouse IL-2R$\beta\gamma_c$, or IL-4R$\alpha\gamma_c$ with higher affinity than the natural cytokines, and elicit downstream cell signaling independent of IL-2Rα and IL-15Rα, or independent of IL-13Rα. The full length polypeptides can be used, for example, to treat cancer.

In contrast, the present disclosure surprisingly demonstrates conditionally active receptor agonists comprising the recited separate first and second polypeptides that individually are not receptor agonists, but which can interact non-covalently to form an active agonist of IL-2 receptor $\beta\gamma_c$ heterodimer (IL-2R$\beta\gamma_c$), IL-4 receptor $\alpha\gamma_c$ heterodimer (IL-4R$\alpha\gamma_c$), IL-13 alpha, or IL-4Ralpha/IL13Ralpha heterodimer. The affinity of this non-covalent interaction between the "split components" (i.e.: the first polypeptide and the second polypeptide) is such that the interaction only occurs in the presence of the appropriate receptor, and also only when both split components are co-localized. Thus, the conditionally active receptor agonists of the current disclosure can be used for any uses that the polypeptides that include all of X1-X4 can be used for. Furthermore, the conditionally active receptor agonists enable co-localization-dependent reconstitution of the agonist, and thus, conditional-activation of the receptor.

The term protein mimetic as used herein refers to a protein that imitates certain aspects of the function of another protein. The two proteins typically have different amino acid sequence and/or different structures. Provided herein, among other things, conditionally active mimetics of IL-2 and IL-15. The aspects of the function of IL-2 and IL-15 that these conditionally active mimetics imitate is the induction of heterodimerization of IL-2Rβγ$_c$, leading to phosphorylation of STAT5. Because IL-2 and IL-15 both signal through heterodimerization of IL-2Rβγ$_c$, these conditionally active mimetics imitate this biological function of both IL-2 and IL-15. These conditionally active mimetics may be referred to herein as mimetics of IL-2, of IL-15, or of both IL-2 and IL-15.

Also provided are conditionally active mimetics of IL-4. These conditionally active mimetics are capable of imitating certain functions of IL-4. The function of IL-4 that these mimetics imitate is the induction of heterodimerization of IL-4Rαγ$_c$ (and/or heterodimerization of IL-4Rα/IL-13Rα).

In one embodiment, the first polypeptide component and the second polypeptide interact to form an agonist of the IL-2 receptor βγ$_c$ heterodimer (IL-2Rβγ$_c$). In another embodiment, the first polypeptide component and the second polypeptide interact to form an agonist of the IL-4 receptor αγ$_c$ heterodimer (IL-4Rαγ$_c$), IL-13 alpha, or IL-4Ralpha/IL13Ralpha heterodimer.

Native hIL-2 comprises four helices connected by long irregular loops. The N-terminal helix (H1) interacts with both the beta and gamma subunits, the third helix (H3) interacts with the beta subunit, and the C-terminal helix (H4) with the gamma subunit; the alpha subunit interacting surface is formed by the irregular second helix (H2) and two long loops, one connecting H1 to H2 and the other connecting H3 and H4. Idealized proteins were designed and produced in which H1, H3 and H4 are replaced by idealized structural domains, including but not limited to helices and beta strands (referred to as domains X1, X3 and X4, respectively) displaying an IL-2Rβγ$_c$, or IL-4Rαγ, interface inspired by H1. H3 and H4, and in which H2 is replaced with an idealized helix (referred to as domain X2) that offers better packing. As shown in the examples, extensive mutational studies have been carried out, demonstrating that the amino acid sequence of each peptide domain each can be extensively modified without loss of binding to the IL-2 or IL-4 receptor, and that the domains can be placed in any order while retaining conditional binding to the IL-2 or IL-4 receptor. The polypeptides may comprise L amino acids and glycine, D-amino acids and glycine, or combinations thereof. As described herein, the idealized proteins can be split into two polypeptides that separately have negligible binding to the relevant receptor but when mixed together can reconstitute receptor activity. The proteins are typically split at sites that won't interfere with the function of the protein (e.g., linker sections in embodiments with linkers). In addition, just as the X1, X2, X3, and X4 domains in the non-split proteins can be looped together in any order, the split proteins can comprise any combination of the domains.

Thus, X1, X2, X3, and X4 may be in any order in the first and second polypeptide; in non-limiting embodiments:

(i) the first polypeptide comprises X1 and the second polypeptide comprises X2, X3, and X4;
(ii) the first polypeptide comprises X2 and the second polypeptide comprises X1, X3, and X4;
(iii) the first polypeptide comprises X3 and the second polypeptide comprises X1, X2, and X4;
(iv) the first polypeptide comprises X4 and the second polypeptide comprises X1, X2, and X3;
(v) the first polypeptide comprises X1 and X2, and the second polypeptide comprises X3 and X4;
(vi) the first polypeptide comprises X1 and X3, and the second polypeptide comprises X2 and X4;
(vii) the first polypeptide comprises X1 and X4, and the second polypeptide comprises X2 and X3;
(viii) the first polypeptide comprises X2 and X3, and the second polypeptide comprises X1 and X4;
(ix) the first polypeptide comprises X2 and X4, and the second polypeptide comprises X1 and X3;
(x) the first polypeptide comprises X3 and X4, and the second polypeptide comprises X1 and X2;
(xi) the first polypeptide comprises X1, X2, and X3 and the second polypeptide comprises X4;
(xii) the first polypeptide comprises X1, X2, and X4 and the second polypeptide comprises X3;
(xiii) the first polypeptide comprises X1, X3, and X4 and the second polypeptide comprises X2; or
(xiv) the first polypeptide comprises X2, X3, and X4 and the second polypeptide comprises X1.

When the first polypeptide and/or the second polypeptide include more than one domain of X1, X2, X3, and X4, the domains may in some embodiments be separated by amino acid linkers of any suitable length or amino acid composition. There is no requirement for linkers; in one embodiment there are no linkers present between any of the domains. In other embodiments, an amino acid linker may be present between 0, 1, or 2 junctions between domains X1, X2, X3, and X4 in the first polypeptide and/or the second polypeptide. The amino acid linkers may be of any length as deemed appropriate for an intended use In some aspects, a linker is at the N terminus or C terminus and is referred to as a linker despite not linking two domains together. In some aspects, the linker is referred to as a linker as it was present in a non-split protein linking two domains together.

In all of these embodiments, X1, X3, and X4 may be any suitable length, meaning each domain may contain any suitable number of additional amino acids other than the peptides of SEQ ID NOS:4, 5, and 6, respectively. The residues in parentheses are optional, and thus may be present or absent. As will be understood by those of skill in the art, this means, for example, that the N-terminal 6 amino acids and the C-terminal 5 amino acid residues of (PKKKIQ) LHAEHALYDAL(MILNI) (SEQ ID NO: 4) are optional. As will be further understood by those of skill in the art: (i) if one N-terminal amino acid is absent, it will be the N-terminal most amino acid (i.e.: the N-terminal P residue in SEQ ID NO:4); (ii) if two N-terminal amino acids are absent, it will be the two N-terminal most amino acids (i.e.: the N-terminal PK dipeptide in SEQ ID NO:4); (iii) if one C-terminal amino acid residue is absent, it will be the C-terminal most amino acid (i.e.: the C-terminal I residue in SEQ ID NO:4); (iv) if two C-terminal amino acid residues are absent, it will be the two C-terminal most amino acids (i.e.: the C-terminal NI dipeptide in SEQ ID NO:4), etc. Thus, it will be clear to those of skill in the art that one or more optional amino acid residues may be absent, and that absent amino acids from the optional residues are contiguous from the relevant peptide terminus, as exemplified above.

In one embodiment, X1 comprises a peptide with identity to the full length of peptide ((PKKKIQ)LHAEHALYDAL (MILNI) (SEQ ID NO: 4); X3 comprises a peptide with identity to the full length of peptide (LE)DYAFNFELILEE ((IARLFESG) (SEQ ID NO:5); and X4 comprises a peptide with identity to the full length of peptide to the full length of peptide (EDEQEEMANAI)ITILQSWIF(S) (SEQ ID NO:6), respectively, of at least 25%, 27%, 30%, 35%, 40%, 45%, 50%, 55%, 60%, 65%, 70%, 75%, 80%, 85%, 90%, 95%, 98%, or 100%.

In various embodiments, X1 is a peptide comprising an amino acid sequence with identity to the full length of peptide ((PKKKIQ)LHAEHALYDAL(MILNI) (SEQ ID NO: 4) or (PKKKI)QLHAEHALYDALMILNI (SEQ ID NO:4), X3 is a peptide comprising an amino acid sequence with identity to the full length of peptide (LE)DYAFNFE-LILEE((IARLFESG) (SEQ ID NO:5) or LEDYAFNFELI-LEEIARLFES(G) (SEQ ID NO:5); and X4 is a peptide comprising an amino acid sequence with identity to the full length of peptide to the full length of peptide (EDEQEE-MANAI)ITILQSWIF(S) (SEQ ID NO:6) or (E)DEQEE-MANAIITILQSWIFS (SEQ ID NO:6), respectively, of at least 25%, 27%, 30%, 35%, 40%, 45%, 50%, 55%, 60%, 65%, 70%, 75%, 80%, 85%, 90%, 95%, 98%, or 100%.

In specific embodiments;
(i) X1 is a peptide comprising an amino acid sequence with identity to the full length of peptide (PKKKIQ) LHAEHALYDAL(MILNI) (SEQ ID NO: 4) or (PKK-KI)QLHAEHALYDALMILNI (SEQ ID NO:4) of at least 70%, X3 is a peptide comprising an amino acid sequence with identity to the full length of peptide (LE)DYAFNFELILEE((IARLFESG) (SEQ ID NO:5) or LEDYAFNFELILEEIARLFES(G) (SEQ ID NO:5) of at least 70%; and X4 is a peptide comprising an amino acid sequence with identity to the full length of peptide to the full length of peptide (EDEQEEMANAI) ITILQSWIF(S) (SEQ ID NO:6) or (E)DEQEEMA-NAIITILQSWIFS (SEQ ID NO:6) of at least 70%;
(ii) X1 is a peptide comprising an amino acid sequence with identity to the full length of peptide (PKKKIQ) LHAEHALYDAL(MILNI) (SEQ ID NO: 4) or (PKK-KI)QLHAEHALYDALMILNI (SEQ ID NO:4) of at least 70%, X3 is a peptide comprising an amino acid sequence with identity to the full length of peptide (LE)DYAFNFELILEE((IARLFESG) (SEQ ID NO:5) or LEDYAFNFELILEEIARLFES(G) (SEQ ID NO:5) of at least 70%; and X4 is a peptide comprising an amino acid sequence with identity to the full length of peptide to the full length of peptide (EDEQEEMANAI) ITILQSWIF(S) (SEQ ID NO:6) or (E)DEQEEMA-NAIITILQSWIFS (SEQ ID NO:6) of at least 70%;
(iii) X1 is a peptide comprising an amino acid sequence with identity to the full length of peptide (PKKKIQ) LHAEHALYDAL(MILNI) (SEQ ID NO: 4) or (PKK-KI)QLHAEHALYDALMILNI (SEQ ID NO:4) of at least 85%, X3 is a peptide comprising an amino acid sequence with identity to the full length of peptide (LE)DYAFNFELILEE((IARLFESG) (SEQ ID NO:5) or LEDYAFNFELILEEIARLFES(G) (SEQ ID NO:5) of at least 85%; and X4 is a peptide comprising an amino acid sequence with identity to the full length of peptide to the full length of peptide (EDEQEEMANAI) ITILQSWIF(S) (SEQ ID NO:6) or (E)DEQEEMA-NAIITILQSWIFS (SEQ ID NO:6) of at least 85%;
(iv) X1 is a peptide comprising an amino acid sequence with 100% identity to the full length of peptide (PKK-KIQ)LHAEHALYDAL(MILNI) (SEQ ID NO: 4) or (PKKKI)QLHAEHALYDALMILNI (SEQ ID NO:4), X3 is a peptide comprising an amino acid sequence with 100% identity to the full length of peptide (LE) DYAFNFELILEE((IARLFESG) (SEQ ID NO:5) or LEDYAFNFELILEEIARLFES(G) (SEQ ID NO:5); and X4 is a peptide comprising an amino acid sequence with 100% identity to the full length of peptide to the full length of peptide (EDEQEEMANAI)IT ILQSWIF(S) (SEQ ID NO:6) or (E)DEQEEMA-NAIITILQSWIFS (SEQ ID NO:6);
(v) X1 is a peptide comprising an amino acid sequence with identity to the full length of peptide (PKKKIQ) LHAEHALYDAL(MILNI) (SEQ ID NO: 4) of at least 85%, X3 is a peptide comprising an amino acid sequence with identity to the full length of peptide (LE)DYAFNFELILEE((IARLFESG) (SEQ ID NO:5) of at least 85%; and X4 is a peptide comprising an amino acid sequence with identity to the full length of peptide to the full length of peptide (EDEQEEMANAI) ITILQSWIF(S) (SEQ ID NO:6) of at least 85%; or (vi) X1 is a peptide comprising an amino acid sequence with 100% identity to the full length of peptide (PKK-KIQ)LHAEHALYDAL(MILNI) (SEQ ID NO: 4), X3 is a peptide comprising an amino acid sequence with 100% identity to the full length of peptide (LE) DYAFNFELILEE((IARLFESG) (SEQ ID NO:5); and X4 is a peptide comprising an amino acid sequence with 100% identity to the full length of peptide to the full length of peptide (EDEQEEMANAI)ITILQSWIF (S) (SEQ ID NO:6).

In these embodiments, different versions of SEQ ID NO: 4, 5, and 6 are shown that have the same primary amino acid sequence but differ in the position of optional residues as noted by the parentheses.

In further embodiments:
X1 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide QLHAE-HALYDALMILNI (SEQ ID NO:320);

X3 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide LEDYAFNFELILE-EIARLFES (SEQ ID NO:321); and/or X4 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide DEQEEMANAIIT-ILQSWIF(S) (SEQ ID NO:322).

In another embodiment where the optional residues of SEQ ID NO:4, SEQ ID NO:5, and SEQ ID NO:6 are present,
(a) X1 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide PKKKIQL-HAEHALYDALMILNI (SEQ ID NO: 4);
(c) X3 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide LEDYAFN-FELILEEIARLFESG (SEQ ID NO:5); and
(d) X4 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide EDEQEE-MANAIITILQSWIFS (SEQ ID NO:6). In another embodiment where select optional residues of SEQ ID NO:4, SEQ ID NO:5, and SEQ ID NO:6 are present,
(a) X1 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide QLHAE-HALYDALMILNI (SEQ ID NO:320);

(c) X3 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide LEDYAFNFELILEEIARLFES (SEQ ID NO:321); and X4 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide or DEQEEMANAIITILQSWIF(S) (SEQ ID NO:322).

In various embodiments where the optional residues of SEQ ID NO:4, SEQ ID NO:5, and SEQ ID NO:6 are present, X1 is a peptide comprising an amino acid sequence with identity to the full length of peptide PKKKIQLHAEHALYDALMILNI (SEQ ID NO: 4), X3 is a peptide comprising an amino acid sequence with identity to the full length of peptide LEDYAFNFELILEEIARLFESG (SEQ ID NO:5) or LEDYAFNFELILEEIARLFES (SEQ ID NO:321); and X4 is a peptide comprising an amino acid sequence with identity to the full length of peptide to the full length of peptide EDEQEEMANAIITILQSWIF(S) (SEQ ID NO:6) or DEQEEMANAIITILQSWIF(S) (SEQ ID NO:322), respectively, of at least 25%, 27%, 30%, 35%, 40%, 45%, 50%, 55%, 60%, 65%, 70%, 75%, 80%, 85%, 90%, 95%, 98%, or 100%.

In specific embodiments;

(i) X1 is a peptide comprising an amino acid sequence with identity to the full length of peptide PKKKIQLHAEHALYDALMILNI (SEQ ID NO: 4) or QLHAEHALYDALMILNI (SEQ ID NO:320) of at least 65%; X3 is a peptide comprising an amino acid sequence with identity to the full length of peptide LEDYAFNFELILEEIARLFESG (SEQ ID NO:5) or LEDYAFNFELILEEIARLFES (SEQ ID NO:321) of at least 65%; and X4 is a peptide comprising an amino acid sequence with identity to the full length of peptide EDEQEEMANAIITILQSWIF(S) (SEQ ID NO:6) or DEQEEMANAIITILQSWIF(S) (SEQ ID NO:322), of at least 65%;

(ii) X1 is a peptide comprising an amino acid sequence with identity to the full length of peptide PKKKIQLHAEHALYDALMILNI (SEQ ID NO: 4) or QLHAEHALYDALMILNI (SEQ ID NO:320) of at least 75%; X3 is a peptide comprising an amino acid sequence with identity to the full length of peptide LEDYAFNFELILEEIARLFESG (SEQ ID NO:5) or LEDYAFNFELILEEIARLFES (SEQ ID NO:321) of at least 75%; and X4 is a peptide comprising an amino acid sequence with identity to the full length of peptide EDEQEEMANAIITILQSWIF(S) (SEQ ID NO:6) or DEQEEMANAIITILQSWIF(S) (SEQ ID NO:322), of at least 75%;

(iii) X1 is a peptide comprising an amino acid sequence with identity to the full length of peptide PKKKIQLHAEHALYDALMILNI (SEQ ID NO: 4) or QLHAEHALYDALMILNI (SEQ ID NO:320) of at least 80%; X3 is a peptide comprising an amino acid sequence with identity to the full length of peptide LEDYAFNFELILEEIARLFESG (SEQ ID NO:5) or LEDYAFNFELILEEIARLFES (SEQ ID NO:321) of at least 80%; and X4 is a peptide comprising an amino acid sequence with identity to the full length of peptide EDEQEEMANAIITILQSWIF(S) (SEQ ID NO:6) or DEQEEMANAIITILQSWIF(S) (SEQ ID NO:322), of at least 80%;

(iv) X1 is a peptide comprising an amino acid sequence with identity to the full length of peptide PKKKIQLHAEHALYDALMILNI (SEQ ID NO: 4) or QLHAEHALYDALMILNI (SEQ ID NO:320) of at least 90%; X3 is a peptide comprising an amino acid sequence with identity to the full length of peptide LEDYAFNFELILEEIARLFESG (SEQ ID NO:5) or LEDYAFNFELILEEIARLFES (SEQ ID NO:321) of at least 90%; and X4 is a peptide comprising an amino acid sequence with identity to the full length of peptide EDEQEEMANAIITILQSWIF(S) (SEQ ID NO:6) or DEQEEMANAIITILQSWIF(S) (SEQ ID NO:322), of at least 90%;

(v) X1 is a peptide comprising an amino acid sequence with identity to the full length of peptide PKKKIQLHAEHALYDALMILNI (SEQ ID NO: 4) or QLHAEHALYDALMILNI (SEQ ID NO:320) of 100%; X3 is a peptide comprising an amino acid sequence with identity to the full length of peptide LEDYAFNFELILEEIARLFESG (SEQ ID NO:5) or LEDYAFNFELILEEIARLFES (SEQ ID NO:321) of 100%; and X4 is a peptide comprising an amino acid sequence with identity to the full length of peptide EDEQEEMANAIITILQSWIF(S) (SEQ ID NO:6) or DEQEEMANAIITILQSWIFS (SEQ ID NO:322), of 100%.

(vi) X1 is a peptide comprising an amino acid sequence with identity to the full length of peptide PKKKIQLHAEHALYDALMILNI (SEQ ID NO: 4) of at least 80%; X3 is a peptide comprising an amino acid sequence with identity to the full length of peptide LEDYAFNFELILEEIARLFESG (SEQ ID NO:5) of at least 80%; and X4 is a peptide comprising an amino acid sequence with identity to the full length of peptide EDEQEEMANAIITILQSWIF(S) (SEQ ID NO:6) of at least 80%;

(vii) X1 is a peptide comprising an amino acid sequence with identity to the full length of peptide PKKKIQLHAEHALYDALMILNI (SEQ ID NO: 4) of at least 90%; X3 is a peptide comprising an amino acid sequence with identity to the full length of peptide LEDYAFNFELILEEIARLFESG (SEQ ID NO:5) of at least 90%; and X4 is a peptide comprising an amino acid sequence with identity to the full length of peptide EDEQEEMANAIITILQSWIF(S) (SEQ ID NO:6), of at least 90%;

(viii) X1 is a peptide comprising an amino acid sequence with identity to the full length of peptide PKKKIQLHAEHALYDALMILNI (SEQ ID NO: 4) of 100%; X3 is a peptide comprising an amino acid sequence with identity to the full length of peptide LEDYAFNFELILEEIARLFESG (SEQ ID NO:5) of 100%; and X4 is a peptide comprising an amino acid sequence with identity to the full length of peptide EDEQEEMANAIITILQSWIF(S) (SEQ ID NO:6) of 100%;

(ix) X1 is a peptide comprising an amino acid sequence with identity to the full length of peptide QLHAEHALYDALMILNI (SEQ ID NO:320) of at least 80%; X3 is a peptide comprising an amino acid sequence with identity to the full length of peptide LEDYAFNFELILEEIARLFES (SEQ ID NO:321) of at least 80%; and X4 is a peptide comprising an amino acid sequence with identity to the full length of peptide DEQEEMANAIITILQSWIF(S) (SEQ ID NO:322), of at least 80%;

(x) X1 is a peptide comprising an amino acid sequence with identity to the full length of peptide QLHAEHALYDALMILNI (SEQ ID NO:320) of at least 90%; X3 is a peptide comprising an amino acid sequence with identity to the full length of peptide LEDYAFNFELILEEIARLFES (SEQ ID NO:321) of at least 90%;

and X4 is a peptide comprising an amino acid sequence with identity to the full length of peptide DEQEEMANAIITILQSWIF(S) (SEQ ID NO:322), of at least 90%; or (xi) X1 is a peptide comprising an amino acid sequence with identity to the full length of peptide QLHAEHALYDALMILNI (SEQ ID NO:320) of 100%; X3 is a peptide comprising an amino acid sequence with identity to the full length of peptide LEDYAFNFELILEEIARLFES (SEQ ID NO:321) of 100%; and X4 is a peptide comprising an amino acid sequence with identity to the full length of peptide DEQEEMANAIITILQSWIFS (SEQ ID NO:322), of 100%.

In one embodiment, the conditionally active receptor agonists are conditionally active receptor agonists IL-2/15 mimetics and
(i) X1 includes 1, 2, 3, 4, or ally of the following: L at residue 7, H at residue 8, H at residue 11, Y at residue 14; M at residue 18 wherein the numbering is relative to SEQ ID NO:4 based on the optional residues being present; and/or
(ii) X3 includes 1, 2, 3, 4, 5, 6, 7, or all 8 of the following: D at residue 3, Y at residue 4, F at residue 6, N at residue 7, L at residue 10, I at residue 11, E at residue 13, or E at residue 14 wherein the numbering is relative to SEQ ID NO:5 based on the optional residues being present. In a further embodiment, (iii) X4 includes I at residue 19 wherein the numbering is relative to SEQ ID NO:6 based on the optional residues being present.

In SEQ ID NO:4, 5, and 6, a number of amino acid residues are marked in bold font. In (PKKKIQ)LHAEHALYDAL(MILNI) (SEQ ID NO: 4): amino acid residues E10, L13, Y14, D15, and L17 (numbered based on optional residues being present) are marked in bold font; In (LE)DYAFNFELILEE((IARLFESG) (SEQ ID NO:5): amino acid residues L1, Y4, N7, L10, I11, and I15 (numbered based on optional residues being present) are marked in bold font; and in (EDEQEEMANAI)ITILQSWIF(S) (SEQ ID NO:6) amino acid residues I12, Q16, and W18 (numbered based on optional residues being present) are marked in bold font.

In one embodiment:
(a) amino acid (AA) substitutions in X1 relative to the AA sequence of SEQ ID NO:4 occur at no more than 3 AA residues marked in bold font, or occur at no more than 2 AA residues marked in bold font, or occur at no more than 1 AA residue marked in bold font, or do not occur at AA residues marked in bold font;
(b) AA substitutions in X3 relative to the AA sequence of SEQ ID NO:5 occur at no more than 3 AA residues marked in bold font, or occur at no more than 2 AA residues marked in bold font, or occur at no more than 1 AA residue marked in bold font, or do not occur at AA residues marked in bold font: and/or
(c) AA substitutions in X4 relative to the AA sequence of SEQ ID NO:6 occur at no more than 2 AA residues marked in bold font, or occur at no more than 1 AA residue marked in bold font, or do not occur at AA residues marked in bold font.

In another embodiment, AA substitutions in X2 relative to the AA sequence of SEQ ID NO:7 do not occur at AA residues marked in bold font.

In another embodiment of conditionally active receptor agonists IL-2 mimetics, amino acid substitutions relative to the reference peptide domains (i.e.: SEQ ID NOS: 4, 5, or 6) do not occur at AA residues marked in bold font. As shown below, SEQ ID NOS:4, 5, and 6 each include residues in bold font that are involved in binding to the receptor:

(PKKKIQ)LHAEHALYDAL(MILNI) (SEQ ID NO: 4): amino acid residues E10, L13, Y14, D15, and L17 (numbered based on optional residues being present) are invariant in this embodiment;
(LE)DYAFNFELILEE((IARLFESG) (SEQ ID NO:5) amino acid residues L1, Y4, N7, L10, I11, and I15 (numbered based on optional residues being present) are invariant in this embodiment; and
(EDEQEEMANAI)ITILQSWIF(S) (SEQ ID NO:6) amino acid residues I12, Q16, and W18 (numbered based on optional residues being present) are invariant in this embodiment.

In a further embodiment, amino acid residue W13 is invariant when X2 comprises is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide KDEAEKAKRMKEWMKRIK(T) (SEQ ID NO:7), wherein residues in parentheses are optional. In one embodiment, the optional residue is present; in another embodiment the optional residue is absent.

In another embodiment of conditionally active receptor agonists IL-2 mimetics, amino acid substitutions relative to the reference peptide domains (i.e.: SEQ ID NOS: 4, 5, or 6) do not occur at more than 3, 2, or 1 AA residues marked in bold font.

In another embodiment, the conditionally active receptor agonists are conditionally active receptor agonists IL-4/IL-13 mimetics, and X1 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical along its length to the peptide PKKKIQIMAEEALKDALSILNI (SEQ ID NO: 8);

X3 is a peptide comprising the amino acid sequence at least 37% 40%, 45%, 50%, 55%, 60%, 65%, 70%, 75%, 80%, 85%, 90%, 95%, 98%, or 100% identical along its length the peptide LERFAKRFERNLWGIARLFESG (SEQ ID NO: 9); and X4 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical along its length to the peptide

```
                                          (SEQ ID NO: 10)
        EDEQEEMANAIITILQSWFFS.
``` wherein
(i) X1 includes I at residue 7. T or M at residue 8, E at residue 11. K at residue 14 and S at residue 18; and
(ii) X3 includes R at residue 3. F at residue 4, K at residue 6, R at residue 7. R at residue 10, N at residue 11, W at residue 13, and G at residue 14.

In a further embodiment, (iii) X4 includes F at residue 19.

In various embodiments, X1 is a peptide comprising the amino acid sequence having identity to the full length of PKKKIQIMAEEALKDALSILNI (SEQ ID NO:8), X3 is a peptide comprising the amino acid sequence having identity to the full length of LERFAKRFERNLWGIARLFESG (SEQ ID NO: 9), and X4 is a peptide comprising the amino acid sequence having identity to the full length of

```
                                          (SEQ ID NO: 10)
        EDEQEEMANAIITILQSWFFS
```

10) that are each at least 25%, 27%, 30%, 35%, 40%, 45%, 50%, 55%, 60%, 65%, 70%, 75%, 80%, 85%, 90%, 95%, 98%, or 100%. In specific embodiments, (i) X1 is a peptide comprising the amino acid sequence at least 65% identical along its length to the peptide PKKKIQIMAEEALKDALSILNI (SEQ ID NO:8); X3 is a peptide comprising the amino acid sequence at least 65% identical along its length the peptide LERFAKRFERNLWGIARLFESG (SEQ ID NO:9); and X4 is a peptide comprising the amino acid sequence at least 65% identical along its length to the peptide EDEQEEMANAIITILQSWFFS (SEQ ID NO:10);

(ii) X1 is a peptide comprising the amino acid sequence at least 75% identical along its length to the peptide PKKKIQIMAEEALKDALSILNI (SEQ ID NO:8); X3 is a peptide comprising the amino acid sequence at least 75% identical along its length the peptide LERFAKRFERNLWGIARLFESG (SEQ ID NO:9); and X4 is a peptide comprising the amino acid sequence at least 75% identical along its length to the peptide EDEQEEMANAIITILQSWFFS (SEQ ID NO:10);

(iii) X1 is a peptide comprising the amino acid sequence at least 80% identical along its length to the peptide PKKKIQIMAEEALKDALSILNI (SEQ ID NO:8); X3 is a peptide comprising the amino acid sequence at least 80% identical along its length the peptide LERFAKRFERNLWGIARLFESG (SEQ ID NO:9); and X4 is a peptide comprising the amino acid sequence at least 80% identical along its length to the peptide EDEQEEMANAIITILQSWFFS (SEQ ID NO:10); or (iv) X1 is a peptide comprising the amino acid sequence at least 90% identical along its length to the peptide PKKKIQIMAEEALKDALSILNI (SEQ ID NO:8); X3 is a peptide comprising the amino acid sequence at least 90% identical along its length the peptide LERFAKRFERNLWGIARLFESG (SEQ ID NO:9); and X4 is a peptide comprising the amino acid sequence at least 90% identical along its length to the peptide EDEQEEMANAIITILQSWFFS (SEQ ID NO:10);

in each case, wherein (A) X1 includes I at residue 7, T or M at residue 8, E at residue 11, K at residue 14 and S at residue 18; and (B) X3 includes R at residue 3, F at residue 4, K at residue 6. R at residue 7, R at residue 10, N at residue 11, W at residue 13. and G at residue 14.

In another embodiment of conditionally active receptor agonists IL-4/IL-13 mimetics, amino acid substitutions relative to the reference peptide domains (i.e.: SEQ ID NOS: 8, 9, or 10) do not occur at AA residues marked in bold font. As shown below, SEQ ID NOS:8, 9, and 10 each include residues in bold font:

PKKKIQIMAEEALKDALSILNI (SEQ ID NO:8): amino acid residues E10, E11, A12, L13, K14, D15, A16, and L17 are invariant in this embodiment LERFAKRFERNLWGIARLFESG (SEQ ID NO: 9): amino acid residues F4, A5, K6, R7, F8, E9, R10, and N11 are invariant in this embodiment

EDEQEEMANAIITILQSWFFS (SEQ ID NO: 10):

amino acid residues I11, I12, T13, I14, L15, Q16, S17, W18, F19, and F20 are invariant in this embodiment In a further embodiment, amino acid residue W13 is invariant when X2 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide KDEAEKAKRMKEWMKRIK(T) (SEQ ID NO:7).

In another embodiment, amino acid substitutions relative to the reference peptide domains are conservative amino acid substitutions. As used herein. "conservative amino acid substitution" means a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are known. Polypeptides comprising conservative amino acid substitutions can be tested in any one of the assays described herein to confirm that a desired activity, e.g. antigen-binding activity and specificity of a native or reference polypeptide is retained. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M): (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine. Met, Ala, Val, Leu, Ile; (2) neutral hydrophilic: Cys, Ser, Thr, Asn, Gln; (3) acidic: Asp, Glu: (4) basic: His, Lys, Arg; (5) residues that influence chain orientation: Gly, Pro; (6) aromatic: Tip, Tyr, Phe. Non-conservative substitutions will entail exchanging a member of one of these classes for another class. Particular conservative substitutions include, for example; Ala into Gly or into Ser; Arg into Lys: Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile: Phe into Met, into Leu or into Tyr: Ser into Thr; Thr into Ser; Trp into Tyr; Tyr into Trp: and/or Phe into Val, into Ile or into Leu.

In one embodiment, amino acid residues in X1 relative to SEQ ID NO:4 are selected from the group consisting of:

| Position 01: | A | F | I | L | M | P | Q | R | S | W |
|---|---|---|---|---|---|---|---|---|---|---|
| Position 02: | A | D | E | G | V | K | | | | |
| Position 03: | D | E | F | W | K | | | | | |
| Position 04: | D | E | K | N | P | R | W | | | |
| Position 05: | D | E | H | I | K | L | M | S | | |
| Position 06: | A | D | E | G | L | P | S | W | Q | |
| Position 07: | D | E | L | Q | Y | I | | | | |
| Position 08: | A | F | H | W | Y | M | T | | | |
| Position 09: | C | F | P | A | | | | | | |
| Position 10: | C | D | E | F | K | P | | | | |
| Position 11: | D | F | H | E | | | | | | |
| Position 12: | A | D | E | P | S | T | V | | | |
| Position 13: | H | I | L | M | P | R | V | W | | |
| Position 14: | F | R | W | Y | K | | | | | |
| Position 15: | D | E | N | Y | | | | | | |
| Position 16: | A | C | L | M | S | | | | | |
| Position 17: | F | I | L | M | P | R | | | | |
| Position 18: | G | M | Q | Y | S | | | | | |
| Position 19: | I | L | M | P | Q | V | | | | |
| Position 20: | A | K | L | M | Q | R | S | | | |
| Position 21: | G | K | N | P | R | S | W | | | |
| Position 22: | D | E | I | K | M | N | W | Y | | |

In one embodiment the conditionally active receptor agonists are conditionally active IL-4 mimetics, and position 7 is I, position 8 is M or T, position 11 is E, position 14 is K, and position 18 is S.

In another embodiment the conditionally active receptor agonists are conditionally active IL-2 mimetics, and 1, 2, 3, 4, or 5 of the following are not true: position 7 is I, position 8 is M or T, position 11 is E, position 14 is K, and position 18 is S.

In another embodiment, amino acid residues in X3 relative to SEQ ID NO:5 are selected from the group consisting of:

| | | | | | | | | | | |
|---|---|---|---|---|---|---|---|---|---|---|
| Position 01: | A | L | | | | | | | | |
| Position 02: | D | E | G | K | M | T | | | | |
| Position 03: | D | E | N | Y | R | | | | | |
| Position 04: | C | D | G | T | Y | F | | | | |
| Position 05: | A | F | H | S | V | W | Y | | | |
| Position 06: | A | F | I | M | T | V | Y | K | | |
| Position 07: | D | K | N | S | T | R | | | | |
| Position 08: | A | C | G | L | M | S | V | F | | |
| Position 09: | C | H | K | L | R | S | T | V | E | |
| Position 10: | F | I | L | M | Y | R | | | | |
| Position 11: | I | L | N | T | Y | | | | | |
| Position 12: | F | K | L | M | S | V | | | | |
| Position 13: | A | D | F | G | I | N | P | Q | S | T | E | W |
| Position 14: | A | E | F | G | H | S | V | | | |
| Position 15: | C | I | L | M | V | W | | | | |
| Position 16: | A | D | G | S | T | V | | | | |
| Position 17: | H | K | L | N | R | | | | | |
| Position 18: | C | D | G | I | L | Q | R | T | W | |
| Position 19: | D | F | M | N | W | | | | | |
| Position 20: | A | C | E | F | G | M | S | Y | | |
| Position 21: | D | E | G | H | L | M | R | S | T | V | W |
| Position 22: | A | D | G | K | N | S | Y | | | |

In another embodiment, the conditionally active receptor agonists are conditionally active IL4/IL-13 mimetics and position 3 is R, position 4 is F, position 6 is K, position 7 is R, position 10 is R, position 11 is N, position 13 is W, and position 14 is G.

In another embodiment, the conditionally active receptor agonists are conditionally active IL-2 mimetics and 1, 2, 3, 4, 5, 6, 7, or all 8 of the following are not true: position 3 is R, position 4 is F, position 6 is K, position 7 is R, position 10 is R, position 11 is N, position 13 is W, and position 14 is G.

In any of such embodiments, the conditionally active receptor agonists further allows for a cysteine at position 17 relative to SEQ ID NO:5 in addition to the amino acid residues of H, K, L, N and R, or at position 20 relative to SEQ ID NO:5 in addition to the amino acid residues of A, C, E, F, G, M, S, and Y. Accordingly, in this embodiment amino acid residues in X3 relative to SEQ ID NO:5 can be selected from the group consisting of:

| | | | | | | | | | | |
|---|---|---|---|---|---|---|---|---|---|---|
| Position 01: | A | L | | | | | | | | |
| Position 02: | D | E | G | K | M | T | | | | |
| Position 03: | D | E | N | Y | R | | | | | |
| Position 04: | C | D | G | T | Y | F | | | | |
| Position 05: | A | F | H | S | V | W | Y | | | |
| Position 06: | A | F | I | M | T | V | Y | K | | |
| Position 07: | D | K | N | S | T | R | | | | |
| Position 08: | A | C | G | L | M | S | V | F | | |
| Position 09: | C | H | K | L | R | S | T | V | E | |
| Position 10: | F | I | L | M | Y | R | | | | |
| Position 11: | I | L | N | T | Y | | | | | |
| Position 12: | F | K | L | M | S | V | | | | |
| Position 13: | A | D | F | G | I | N | P | Q | S | T | E | W |
| Position 14: | A | E | F | G | H | S | V | | | |
| Position 15: | C | I | L | M | V | W | | | | |
| Position 16: | A | D | G | S | T | V | | | | |
| Position 17: | H | K | L | N | R | C | | | | |
| Position 18: | C | D | G | I | L | Q | R | T | W | |
| Position 19: | D | F | M | N | W | | | | | |
| Position 20: | A | C | E | F | G | M | S | Y | C | |
| Position 21: | D | E | G | H | L | M | R | S | T | V | W |
| Position 22: | A | D | G | K | N | S | Y | | | |

In another embodiment, amino acid residues in X4 relative to SEQ ID NO:6 are selected from the group consisting of:

| | | | | | | | | | | |
|---|---|---|---|---|---|---|---|---|---|---|
| Position 01: | D | E | G | K | V | | | | | |
| Position 02: | D | I | M | S | | | | | | |
| Position 03: | E | G | H | K | | | | | | |
| Position 04: | E | G | I | K | Q | R | S | | | |
| Position 05: | A | D | E | G | H | S | V | | | |
| Position 06: | C | D | E | G | I | M | Q | R | T | V |
| Position 07: | C | E | L | M | P | R | T | | | |
| Position 08: | A | F | L | M | W | | | | | |
| Position 09: | A | G | L | N | Q | R | T | | | |
| Position 10: | A | C | D | E | F | H | I | W | | |
| Position 11: | I | M | N | S | V | W | | | | |
| Position 12: | I | K | L | S | V | | | | | |
| Position 13: | C | L | M | R | S | T | | | | |
| Position 14: | I | L | P | T | Y | | | | | |
| Position 15: | F | G | I | L | M | N | V | | | |
| Position 16: | H | K | Q | R | | | | | | |
| Position 17: | C | F | K | S | W | Y | | | | |
| Position 18: | K | Q | T | W | | | | | | |
| Position 19: | C | G | N | I | | | | | | |
| Position 20: | C | F | G | L | Y | | | | | |
| Position 21: | A | F | G | H | S | Y | | | | |

In another embodiment, the conditionally active receptor agonists are conditionally active IL-4/IL-13 mimetics and position 19 is I. In another embodiment, the conditionally active receptor agonists are conditionally active IL-2 mimetics and position 19 is not I.

In any of such embodiments. the conditionally active receptor agonists further allows for a cysteine at position 3 relative to SEQ ID NO:6 in addition to the amino acid residues of E, G, H and K. Accordingly, in this embodiment, amino acid residues in X4 relative to SEQ ID NO:6 can be selected from the group consisting of:

| Position 01: | D | E | G | K | V | | | | |
|---|---|---|---|---|---|---|---|---|---|
| Position 02: | D | I | M | S | | | | | |
| Position 03: | E | G | H | K | C | | | | |
| Position 04: | E | G | I | K | Q | R | S | | |
| Position 05: | A | D | E | G | H | S | V | | |
| Position 06: | C | D | E | G | I | M | Q | R | T | V |
| Position 07: | C | E | L | M | P | R | T | | |
| Position 08: | A | F | L | M | W | | | | |
| Position 09: | A | G | L | N | Q | R | T | | |
| Position 10: | A | C | D | E | F | H | I | W | |
| Position 11: | I | M | N | S | V | W | | | |
| Position 12: | I | K | L | S | V | | | | |
| Position 13: | C | L | M | R | S | T | | | |
| Position 14: | I | L | P | T | Y | | | | |
| Position 15: | F | G | I | L | M | N | V | | |
| Position 16: | H | K | Q | R | | | | | |
| Position 17: | C | F | K | S | W | Y | | | |
| Position 18: | K | Q | T | W | | | | | |
| Position 19: | C | G | N | I | | | | | |
| Position 20: | C | F | G | L | Y | | | | |
| Position 21: | A | F | G | H | S | Y | | | |

As noted herein, domain X2 is a structural domain, and thus any amino acid sequence that connects (i.e.: in the same polypeptide or upon non-covalent interaction of the first and second polypeptide) the relevant other domains and allows them to fold can be used. The length required will depend on the specifics of the first polypeptide and the second polypeptide being used and can be 8 amino acids or longer. In one exemplary and non-limiting embodiment, X2 is a peptide comprising the amino acid sequence at least 20%, 27%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identical along its length to KDEAEKAKRMKEWMKRIK(T) (SEQ ID NO:7) or KDEAEKAKRMKEWMKRIKT (SEQ ID NO:7). In one embodiment, amino acid changes relative to the amino acid sequence of SEQ ID NO:7 are conservative amino acid substitutions. In another embodiment, the W13 amino acid residue is invariant. In a further embodiment, amino acid residues in X2 relative to SEQ ID NO:7 are selected from the group consisting of:

| Position 01: | A | H | L | M | R | S | V | K | | |
|---|---|---|---|---|---|---|---|---|---|---|
| Position 02: | A | D | E | Q | R | S | T | V | W | Y |
| Position 03: | C | E | G | K | L | N | Q | R | W | |
| Position 04: | A | F | G | N | S | T | V | Y | | |
| Position 05: | A | E | G | I | M | R | V | | | |
| Position 06: | C | E | K | L | N | R | V | | | |
| Position 07: | A | C | E | I | L | S | T | V | W | |
| Position 08: | H | K | L | M | S | T | W | Y | | |
| Position 09: | A | I | L | M | Q | S | R | | | |
| Position 10: | A | I | M | S | W | Y | | | | |
| Position 11: | C | I | K | L | S | V | | | | |
| Position 12: | C | E | K | L | P | Q | R | T | | |
| Position 13: | A | D | H | N | W | | | | | |
| Position 14: | A | C | G | I | L | S | T | V | M | |
| Position 15: | A | E | G | I | K | L | M | R | V | |
| Position 16: | G | H | L | R | S | T | V | | | |
| Position 17: | A | I | L | V | | | | | | |
| Position 18: | A | C | D | E | G | H | I | K | M | S |
| Position 19: | D | E | G | L | N | V | T | | | |

In another embodiment, the polypeptides are IL-4/IL-13 mimetics and position 11 is I. In another embodiment, the polypeptides are IL-2 mimetics and position 11 is not I.

In any of such embodiments, the polypeptide further allows for a cysteine at positions 5 or 16 relative to SEQ ID NO:7.

Alternatively, in any of such embodiments, the polypeptide further allows for a cysteine at positions 1, 2, 5, 9 or 16 relative to SEQ ID NO:7

Accordingly, amino acid residues in X2 relative to SEQ ID NO:7 can be selected from the group consisting of:

| Position 01: | A | H | L | M | R | S | V | K | C | |
|---|---|---|---|---|---|---|---|---|---|---|
| Position 02: | A | D | E | Q | R | S | T | V | W | Y | C |
| Position 03: | C | E | G | K | L | N | Q | R | W | |
| Position 04: | A | F | G | N | S | T | V | Y | | |
| Position 05: | A | E | G | I | M | R | V | C | | |
| Position 06: | C | E | K | L | N | R | V | | | |
| Position 07: | A | C | E | I | L | S | T | V | W | |
| Position 08: | H | K | L | M | S | T | W | Y | | |
| Position 09: | A | I | L | M | Q | S | R | C | | |
| Position 10: | A | I | M | S | W | Y | | | | |
| Position 11: | C | I | K | L | S | V | | | | |
| Position 12: | C | E | K | L | P | Q | R | T | | |
| Position 13: | A | D | H | N | W | | | | | |
| Position 14: | A | C | G | I | L | S | T | V | M | |
| Position 15: | A | E | G | I | K | L | M | R | V | |
| Position 16: | G | H | L | R | S | T | V | C | | |
| Position 17: | A | I | L | V | | | | | | |
| Position 18: | A | C | D | E | G | H | I | K | M | S |
| Position 19: | D | E | G | L | N | V | T | | | |

In various specific embodiments:
(i) X2 is a peptide comprising the amino acid sequence at least 70% identical along its length to KDEAEKAKRMKEWMKRIK(T) (SEQ ID NO:7);
(ii) X2 is a peptide comprising the amino acid sequence at least 80% identical along its length to KDEAEKAKRMKEWMKRIK(T) (SEQ ID NO:7);
(iii) X2 is a peptide comprising the amino acid sequence at least 90% identical along its length to KDEAEKAKRMKEWMKRIK(T) (SEQ ID NO:7);
(iv) X2 is a peptide comprising the amino acid sequence having identity to the full length of peptide KDEAEKAKRMKEWMKRIK(T) (SEQ ID NO:7) of at least 65%; X1 is a peptide comprising the amino acid sequence having identity to the full length of peptide PKKKIQLHAEHALYDALMILNI (SEQ ID NO: 4) or QLHAEHALYDALMILNI (SEQ ID NO:320) of at least 65°4, X3 is a peptide comprising the amino acid sequence having identity to the full length of peptide LEDYAFNFELILEEIARLFESG (SEQ ID NO:5) or LEDYAFNFELILEEIARLFES (SEQ ID NO:321) of at least 65%; and X4 is a peptide comprising the amino acid sequence having identity to the full length of peptide EDEQEEMANAIITILQSWIF(S) (SEQ ID NO:6) or DEQEEMANAIITILQSWIFS (SEQ ID NO:322) of at least 65%;
(v) X2 is a peptide comprising the amino acid sequence having identity to the full length of peptide KDEAEKAKRMKEWMKRIK(T) (SEQ ID NO:7) of at least 75%; X1 is a peptide comprising the amino acid sequence having identity to the full length of peptide PKKKIQLHAEHALYDALMILNI (SEQ ID NO: 4) or QLHAEHALYDALMILNI (SEQ ID NO:320) of at least 75%; X3 is a peptide comprising the amino acid sequence having identity to the full length of peptide LEDYAFNFELILEEIARLFESG (SEQ ID NO:5) or LEDYAFNFELILEEIARLFES (SEQ ID NO:321) of at least 75%; and X4 is a peptide comprising the amino acid sequence having identity to the full length of peptide EDEQEEMANAIITILQSWIF(S) (SEQ ID NO:6) or DEQEEMANAIITILQSWIFS (SEQ ID NO:322) of at least 75%;

(vi) X2 is a peptide comprising the amino acid sequence having identity to the full length of peptide KDEAEKAKRMKEWMKRIK(T) (SEQ ID NO:7) of at least 80%; X1 is a peptide comprising the amino acid sequence having identity to the full length of peptide PKKKIQLHAEHALYDALMILNI (SEQ ID NO: 4) or QLHAEHALYDALMILNI (SEQ ID NO:320) of at least 80%; X3 is a peptide comprising the amino acid sequence having identity to the full length of peptide LEDYAFNFELILEEIARLFESG (SEQ ID NO:5) or LEDYAFNFELILEEIARLFES (SEQ ID NO:321) of at least 80%; and X4 is a peptide comprising the amino acid sequence having identity to the full length of peptide EDEQEEMANAIITILQSWIF(S) (SEQ ID NO:6) or DEQEEMANAIITILQSWIFS (SEQ ID NO:322) of at least 80%;

(vii) X2 is a peptide comprising the amino acid sequence having identity to the full length of peptide KDEAEKAKRMKEWMKRIK(T) (SEQ ID NO:7) of at least 90%; X1 is a peptide comprising the amino acid sequence having identity to the full length of peptide PKKKIQLHAEHALYDALMILNI (SEQ ID NO: 4) or QLHAEHALYDALMILNI (SEQ ID NO:320) of at least 90%; X3 is a peptide comprising the amino acid sequence having identity to the full length of peptide LEDYAFNFELILEEIARLFESG (SEQ ID NO:5) or LEDYAFNFELILEEIARLFES (SEQ ID NO:321) of at least 90%; and X4 is a peptide comprising the amino acid sequence having identity to the full length of peptide EDEQEEMANAIITILQSWIF(S) (SEQ ID NO:6) or DEQEEMANAIITILQSWIFS (SEQ ID NO:322) of at least 90%; or (viii) X2 is a peptide comprising the amino acid sequence having 100% identity to the full length of peptide KDEAEKAKRMKEWMKRIK(T) (SEQ ID NO:7); X1 is a peptide comprising the amino acid sequence having 100% identity to the full length of peptide PKKKIQLHAEHALYDALMILNI (SEQ ID NO: 4) or QLHAEHALYDALMILNI (SEQ ID NO:320); X3 is a peptide comprising the amino acid sequence having 100% identity to the full length of peptide LEDYAFNFELILEEIARLFESG (SEQ ID NO:5) or LEDYAFNFELILEEIARLFES (SEQ ID NO:321); and X4 is a peptide comprising the amino acid sequence having 100% identity to the full length of peptide EDEQEEMANAIITILQSWIF(S) (SEQ ID NO:6) or DEQEEMANAIITILQSWIFS (SEQ ID NO:322).

In exemplary embodiments of (i) through (viii) above, the listed optional amino acid residues in SEQ ID NO:7 are present. In exemplary embodiments of (i) through (viii) above, the peptides for X1, X3, and X4 are shown in SEQ ID Nos. 4, 5, and 6. In exemplary embodiments of (i) through (viii) above, the peptides for X1, X3, and X4 are shown in SEQ ID Nos. 320, 321, and 322.

In various embodiments:
(i) the first polypeptide component includes one of X1, X2, X3, and X4, and the second polypeptide component includes the three of X1, X2, X3, and X4 that are not present in the first polypeptide component; or
(ii) the first polypeptide component includes two of X1, X2, X3, and X4, and the second polypeptide component includes the two of X1, X2, X3, and X4 that are not present in the first polypeptide component.

In further embodiments;
(a) the first polypeptide comprises X1 and excludes X2, X3, and X4; and the second polypeptide is a fusion protein comprising X3-Z1-X2-Z2-X4 and excluding X1;
(b) the first polypeptide comprises X4 and excludes X1, X2, and X3; and the second polypeptide is a fusion protein comprising X1-Z1-X3-Z2-X2 and excluding X4; or
(c) the first polypeptide is a fusion protein comprising X1-Z1-X3 and excluding X2 and X4; and the second polypeptide is a fusion protein comprising X2-Z1-X4 and excluding X1 and X3;

wherein each of Z1 and Z2 independently are an optional amino acid linker. Z1 and/or Z2 may comprise any number of amino acid residues to separate domains within the first and/or second polypeptide as deemed appropriate for an intended use. The 1 and/or Z2 linker may be of any suitable length and amino acid composition. In one embodiment, Z1 and Z2 are both absent; in another embodiment, 1 and 2 are both present; in a further embodiment, one of Z1 sand Z2 is present and the other is absent.

In other embodiments, X1, X2, X3, and X4, respectively comprise a peptide at least 25%, 27%, 30%, 35%, 40%, 45%, 50%, 55%, 60%, 65%, 70%, 75%, 80%, 85%, 90%, 95%, 98%, or 100% identical, respectively, to the full length of X1, X2, X3, and X4 domains shown below (SEQ ID NOS: 4-7), where residues in parentheses may be present or absent:

```
X1:
                                  (SEQ ID NO: 4)
PKKKIQLHAEHALYDALMILNI

X2:
                                  (SEQ ID NO: 7)
(K)DEAEKAKRMKEWMKRIKT

X3:
                                  (SEQ ID NO: 5)
(LE)DYAFNFELILEEIARLF(ESG)

X4:
                                  (SEQ ID NO: 6)
(E)DFQEEMANAIITILQSWIFS
```

In other embodiments, X1, X2, X3, and X4 are peptides comprising amino acid sequences at least 80% identical, respectively, to the full length of X1, X2, X3, and X4 domains shown below (SEQ ID NOS: 4-7), where residues in parentheses may be present or absent:

```
X1:
                                  (SEQ ID NO: 4)
PEKKIQLHAEHALYDALMILNI

X2:
                                  (SEQ ID NO: 7)
(K)DEAEKAKRMKEWMKRIKT
```

X3:

(SEQ ID NO: 5)
(LE)DYAFNFELILEEIARLF(ESG)

X4:

(SEQ ID NO: 6)
(E)DEQEEMANAIITILQSWIFS

In other embodiments, X1, X2, X3, and X4 are peptides comprising amino acid sequences at least 90% identical, respectively, to the full length of X1, X2, X3, and X4 domains shown below (SEQ ID NOS: 4-7), where residues in parentheses may be present or absent:

X1:

(SEQ ID NO: 4)
PKKYIQLHAEHALYDALMILNI

X2:

(SEQ ID NO: 7)
(K)DEAEKAKRMKEWMKRIKT

X3:

(SEQ ID NO: 5)
(LE)DYAFNFELILEEIARLF(ESG)

X4:

(SEQ ID NO: 6)
(E)DEQEEMANAIITILQSWIFS.

In other embodiments, X1, X2, X3, and X4, respectively are 25%, 27%, 30%, 35%, 40%, 45%, 50%, 55%, 60%, 65%, 70%, 75%, 80%, 85%, 90%, 95%, 98%, or 100% identical, respectively, to the full length of X1, X2, X3, and X4 domains shown below, where residues in parentheses may be present or absent:

X1:

(SEQ ID NO: 320)
QLHAEHALYDALMILNI

X2:

(SEQ ID NO: 7)
(K)DEAEKAKRMKEWMKRIKT

X3:

(SEQ ID NO: 321)
LEDYAFNFELILEEIARLFES

X4:

(SEQ ID NO: 322)
DEQEEMANAIITILQSWIFS.

In other embodiments, X1, X2, X3, and X4, respectively are peptides comprising amino acid sequences at least 80% identical, respectively, to the full length of X1, X2, X3, and X4 domains shown below, where residues in parentheses may be present or absent:

X1:

(SEQ ID NO: 320)
QLHAEHALYDALMILNI

X2:

(SEQ ID NO: 7)
(K)DEAEKAKRMKEWMKRIKT

X3:

(SEQ ID NO: 321)
LEDYAFNFELILEEIARLFES

X4:

(SEQ ID NO: 322)
DEQEEMANAIITILQSWIFS.

In other embodiments, X1, X2, X3, and X4, respectively are peptides comprising amino acid sequences at least 90% identical, respectively, to the full length of X1, X2, X3, and X4 domains shown below, where residues in parentheses may be present or absent:

X1:

(SEQ ID NO: 320)
QLHAEHALYDALMILNI

X2:

(SEQ ID NO: 7)
(K)DEAEKAKRMKEWMKRIKT

X3:

(SEQ ID NO: 321)
LEDYAFNFELILEEIARLFES

X4:

(SEQ ID NO: 322)
DEQEEMANAIITILQSWIFS.

In one embodiment, one or more or all of the optional amino acids are present; in another embodiment, one or more or all of the optional amino acids are absent. In other embodiments:

(i) X1 is a peptide comprising the amino acid sequence having identity to the full length of the amino acid sequence of SEQ ID NO:4 or SEQ ID NO:320 of at least 55%; X2 is a peptide comprising the amino acid sequence having identity to the full length of the amino acid sequence of SEQ ID NO:7 of at least 55%, X3 is a peptide comprising the amino acid sequence having identity to the full length of the amino acid sequence of SEQ ID NO:5 or SEQ ID NO:321 of at least 55%; and X4 is a peptide comprising the amino acid sequence having identity to the full length of the amino acid sequence of SEQ ID NO:6 or SEQ ID NO:322 of at least 55%;

(ii) X1 is a peptide comprising the amino acid sequence having identity to the full length of the amino acid sequence of SEQ ID NO:4 or SEQ ID NO:320 of at least 75%; X2 is a peptide comprising the amino acid sequence having identity to the full length of the amino acid sequence of SEQ ID NO:7 of at least 75%, X3 is a peptide comprising the amino acid sequence having identity to the full length of the amino acid sequence of SEQ ID NO:5 or SEQ ID NO:321 of at least 75%; and X4 is a peptide comprising the amino acid sequence having identity to the full length of the amino acid sequence of SEQ ID NO:6 or SEQ ID NO:322 of at least 75%;

(iii) X1 is a peptide comprising the amino acid sequence having identity to the full length of the amino acid sequence of SEQ ID NO:4 or SEQ ID NO:320 of at least 80%; X2 is a peptide comprising the amino acid sequence having identity to the full length of the amino acid sequence of SEQ ID NO:7 of at least 80%, X3 is a peptide comprising the amino acid sequence having identity to the full length of the amino acid sequence of SEQ ID NO:5 or SEQ ID NO:321 of at least 80%; and X4 is a peptide comprising the amino acid sequence having identity to the full length of the amino acid sequence of SEQ ID NO:6 or SEQ ID NO:322 of at least 80%;

(iv) X1 is a peptide comprising the amino acid sequence having identity to the full length of the amino acid sequence of SEQ ID NO:4 or SEQ ID NO:320 of at least 90%; X2 is a peptide comprising the amino acid sequence having identity to the full length of the amino acid sequence of SEQ ID NO:7 of at least 90%, X3 is a peptide comprising the amino acid sequence having identity to the full length of the amino acid sequence of SEQ ID NO:5 or SEQ ID NO:321 of at least 90%; and X4 is a peptide comprising the amino acid sequence having identity to the full length of the amino acid sequence of SEQ ID NO:6 or SEQ ID NO:322 of at least 90%; or (vi) X1 is a peptide comprising the amino acid sequence having 100% identity to the full length of the amino acid sequence of SEQ ID NO:4 or SEQ ID NO:320; X2 is a peptide comprising the amino acid sequence having 100% identity to the full length of the amino acid sequence of SEQ ID NO:7; X3 is a peptide comprising the amino acid sequence having 100% identity to the full length of the amino acid sequence of SEQ ID NO:5 or SEQ ID NO:321: and X4 is a peptide comprising the amino acid sequence having 100% identity to the full length of the amino acid sequence of SEQ ID NO:6 or SEQ ID NO:322.

In exemplary embodiments of (i) through (vi) above, the peptides for X1, X3, and X4 are shown in SEQ ID NOs. 4, 5, and 6. In exemplary embodiments of (i) through (vi) above, the peptides for X1, X3, and X4 are shown in SEQ ID NOs. 320, 321, and 322.

In another embodiment, the first polypeptide and the second polypeptide, am at least 25%, 27%, 30%, 35%, 40%, 45%, 50%, 55%, 60%, 65%, 70%, 75%, 80%, 85%, 90%, 95%, 98%, or 100% identical to a pair of first and second polypeptides shown below (underlined residues or "X" residues" are optional and each residue of the optional domain, when present, may comprise any amino acid):

```
(i)
First polypeptide X1 (Neo2A)
                                                            (SEQ ID NO: 256)
PKKKIQLHAEHALYDALMILNIVKTNS
and Second polypeptide: X3-X2'-X4 (Neo2B)
                                                            (SEQ ID NO: 257)
TNSPPAEEKLEDYAFNFELILEEIARLFESGDQKDEAEKAKRMKEWMKRIKTTASEDEQEEMANAIIT

ILQWIFS (ii)
First polypeptide X1-X3-X2'
                                                            (SEQ ID NO: 258)
PKKKIQLHAEHALYDALMILNIVKTNSPPAEEKLEDYAFNFELILEEIARLFESGDQKDEAEKAKRMK EWMKRIKTTAS
and Second polypeptide X4
                                                            (SEQ ID NO: 259)
TTASEDEQEEMANAIITILQSWIFS;

(iii)
First polypeptide X1-X3
                                                            (SEQ ID NO: 260)
PKKKIQLHAEHALYDALMILNIVKTNSPPAEEKLEDYAFNFELILEEIARLFESGD
and Second polypepLide X2-X4
                                                            (SEQ ID NO: 261)
DQKDEAEKAKRMKEWMKRIKTTASEDEQEEMANAIITILQSWIFS (iv)
First polypeptide X1 (Neo4A)
                                                            (SEQ ID NO: 262)
PKKKIQIMAEEALKDALSILNIVKTNS Second polypeptide X3-X2'-X4 (Neo4B)
                                                            (SEQ ID NO: 263)
TNSPPAEEQLERFAKRFERNLWGIARLFESGDQKDEAEKAKRMIEWMKRIKTTASEDEQEEMANAIIT ILQSWFFS
(v)
First polypeptide X1 (Neo2A)
                                                            (SEQ ID NO: 311)
PKKKIQLHAEHALYDALMILNIXXXXX
and Second polypeptide: X3-X2'-X4 (Neo2B)
                                                            (SEQ ID NO: 264)
XXXXXXXXXLEDYAFNFELILEEIARLFESGXXKDEAEKAKRMKEWMKRIKTXXXEDEQEEMANAIIT

ILQSWIFS
```

-continued (vi)
First polypeptide X1-X3-X2'
(SEQ ID NO: 265)
PKKKIQLHAEHALYDALMILNIXXXXXXXXXXXLEDYAFNFELILEEIARLFESGXXKDEAEKAKRMK EWMKRIKTTAS
and Second polypeptide X4
(SEQ ID NO: 266)
XXXXXDEQFFMANAIITILQSWIFS;

First polypeptide X1-X3
(SEQ ID NO: 267)
PKKKIQLHAEHALYDALMILNIXXXXXXXXXXXLEDYAFNFELILEEIARLFESXXGD
and Second polypeptlde X2-X4
(SEQ ID NO: 268)
DQKDEAFKAKRMKEWMKRIKTXXXEDEQEEMANAIITILQSWIFS (viii)
First polypeptide X1 (Neo4A)
(SEQ ID NO: 269)
PKKKIQIMAEEALKDALSILNIXXXXX Second polypeptide X3-X2'-X4 (Neo4B)
(SEQ ID NO: 270)
XXXXXXXXQLERFAKRFERNLWGIARLFESGXXKDEAEKAKRMIEWMKRIKTXXXEDEQEEMANAIIT

ILQSWFFS (ix)
First polypeptide >Neo4_H1-H3'
(SEQ ID NO: 312)
PKKKIQIMAEEALKDALSILNIVKTNSPPAEEQLERFAKRFERNLWGIARLFESGD Second polypeptide >Neo4_H2-H4
(SEQ ID NO: 313)
DQKDEAEKAKRMIEWMKRIKTTASEDEQEEMANAIITILQSWFFS (x)
First polypeptide >Neo4_H1-H3'
(SEQ ID NO: 314)
PKKKIQIMAEEALKDALSILNIXXXXXXXXXXQLERFAKRFERNLWGIARLFESXX Second polypeptide >Neo4_H2-H4
(SEQ ID NO: 315)
XXKDEAEKAKRMIEWMKRIKXXXXEDEQEEMANAIITILQSWFFS (xi)
First polypeptide Neo4_H1-H3'-H2
(SEQ ID NO: 316)
PKKKIQIMAEEALKDALSILNIVKTNSPPAEEQLERFAKRFERNLWGIARLFESGDQKDEAEKAKRMI

EWMKRIKTTA

Second polypeptide Neo4_H4
(SEQ ID NO: 317)
TTASEDEQEEMANAIITILQSWFFS (xii)
First polypeptide Neo4_H1-H3'-H2
(SEQ ID NO: 318)
PKKKIQIMAEEALKDALSILNIXXXXXXXXXXXLERFAKRFERNLWGIARLFESXXXKDEAEKAKRMI

EWMKRIKXXX

Second polypeptide Neo4_H4
(SEQ ID NO: 319)
XXXXXDEQEEMANAIITILQSWFFS (xiii)
First polypeptide (X1)
(SEQ ID NO: 323)
PKKKIQLHAEHALYDALMILNIVGGSS,
or (SEQ ID NO: 324)
SKEAIQLHAEHALYDALMILNIVKTNS,
or -continued (SEQ ID NO: 325)
PIQLHAEHALYDALMILNIV Second polypeptide (X3-X2'-X4)
(SEQ ID NO: 326)
PKLEDYAFNFELILEEIARLFESGDQKDEAEKAKRMKEWMKRIKTTASEDEQEEMANAIITILQSWI FS;
or (SEQ ID NO: 327)
GGSSGGLEDYAFNFELILEEIARLFESGGSSGGKDEAEKAKRMKEWMKRITGGSSGGDEQEEMANAI ITILQSWIFS;
or (SEQ ID NO: 328)
GGSSGGLEDYAFNFELILEEIARLFESGGSSGGGGEAEKAKRMKEWMKRIGGSSGGDEQEEMANAIIT

ILQSWIFS

In exemplary embodiments, the first polypeptide and the second polypeptide are peptides comprising an amino acid sequence at least 80% identical to a pair of first and second polypeptides shown in embodiments (i)-(viii) above (underlined residues or "X" residues" are optional and each residue of the optional domain, when present, may comprise any amino acid).

In exemplary embodiments, the first polypeptide and the second polypeptide are peptides comprising an amino acid sequence at least 90% identical to a pair of first and second polypeptides shown in embodiments (i)-(viii) above (underlined residues or "X" residues" are optional and each residue of the optional domain, when present, may comprise any amino acid).

In exemplary embodiments, the first polypeptide and the second polypeptide are peptides comprising an amino acid sequence 100% identical to a pair of first and second polypeptides shown in embodiments (i)-(viii) above (underlined residues or "X" residues" are optional and each residue of the optional domain, when present, may comprise any amino acid).

In various further embodiments. X1, X2, X3, and X4, respectively, comprise a peptide at least 25%, 27%, 30%, 35%, 40%, 45%, 50%, 55%, 60%, 65%, 70%, 75%, 80%, 85%, 90%, 95%, 98%, or 100% identical to, respectively, X1, X2, X3, and X4 domains (as defined in Table 1 (though listed as H1, H2, H3. and H4 domains) present within the amino acid sequence of SEQ ID NO:11-94, 190-216, 247, and SEQ ID NOS:275-300.

Table 1 provides two SEQ ID NOs for many of the variants: a first SEQ ID NO: that lists the linker positions as optional and variable (shown by underlining in the table), and a second SEQ ID NO: that includes the linker positions as required. Table 1 shows the domain arrangement for the polypeptide of SEQ ID NOS:11-94, 190-216, 247, and SEQ ID NOS: 275-300 (see the second column), while the sequence shows underlined amino acid linkers separating domains. See, for example, SEQ ID NO:11, having the domain arrangement H1->H4≥H2'≥H3 (corresponding to an X1-X4-X2-X3 arrangement):

(SEQ ID NO: 11)
STKKWQLQAEHALLDWQMALNKSPEPNENLNRAITAAQSWISTGKIDLDK

AEDIRRNSDQARREAEKRGIDVRDLISNAQVILLEAR

As will be apparent to those of skill in the art based on this arrangement, in SEQ ID NO:11 the X1 domain is STKKWQLQAEHALLDWQMALNK (SEQ ID NO:271), the X4 domain is ENLNRAITAAQSWIS (SEQ ID NO:272), the X2 domain is LDKAEDIRRNSDQARRE-AEK (SEQ ID NO:273), and the X3 domain is RDLIS-NAQVILLEAR (SEQ ID NO:274). Similarly, the amino acid sequence of each X1, X2, X3, and X4 domains SEQ ID NOS:11-94, 190-216, 247, and SEQ ID NOS: 275-300 will be clear to those of skill in the art based on the teachings herein. As will be understood by those of skill in the art, the X1, X2, X3, and/or X4 amino acids may include additional (1, 2, 3, 4, 5, or more) amino acids at the N-terminus and/or the C-terminus relative to the X1, X2, X3, and X4 domains shown in SEQ ID NOS: 11-94, 190-216, 247, and SEQ ID NOS: 275 300.

TABLE 1

| Name | Domain arrangement | Sequence |
| --- | --- | --- |
| G1_neo2_33 | H1->H4->  H2'->  H3 | STKKWQLQAEHALLDWQMALNKSPEPNENLNRAITAAQSWISTGKIDLDKAEDIRRNSDQARR  EAEKRGIDVRDLISNAQVILLEAR (SEQ ID NO: 11)  STKKWQLQAEHAILDWQMALNKSPEPNENLNRAITAAQSWISTGKIDLDKAEDIRRNSDQARR  EAEKRGIDVRDLISNAQVILLEAR (SEQ ID NO: 103) |
| G1_neo2_34 | H1->H4->  H2'->  H3 | STKKWQLQAEHALLDWQMALNKSPEPNENLNRAITAAQSCISTGKCDLDKAEDIRRNSDQARR  EAEKRGIDVRDLISNAQVILLEAR (SEQ ID NO: 12)  STKKWQLQAEHALLDWQMALNKSPEPNENLNRAITAAQSCISTGKCDLDKAEDIRRNSDQARR  EAEKRGIDVRDLISNAQVILLEAR (SEQ ID NO: 104) |

TABLE 1-continued

| Name | Domain arrangement | Sequence |
|---|---|---|
| G1_neo2_35 | H1->H4-><br>H2'-><br>H3 | STKKWQLQAEHALLDWQMALNKSPEPNENLNRAITAAQSWISTGKIDCDKAEDIRRNSDQARR<br>EAEKRGIDVRDLISNAQVILLEAC (SEQ ID NO: 13)<br>STKKWQLQAEHALLDWQMALNKSPEPNENLNRAITAAQSWISTGKIDCDKAEDIRRNSDQARR<br>EAEKRGIDVRDLISNAQVILLEAC (SEQ ID NO: 105) |
| G1_neo2_36 | H1->H4-><br>H2'-><br>H3 | STKKLQLQAEHFLLDVQMILNESPEPNEELNRAITDAQSWISTGKIDLDRAEELARNLEKVRD<br>EALKRGIDVRDLVSNAKVIALELK (SEQ ID NO: 14)<br>STKKLQLQAEHFLLDVQMILNESPEPNEELNRAITDAQSWISTGKIDLDRAEELARNLEKVRD<br>EALKRGIDVRDLVSNAKVIALELK (SEQ ID NO: 106) |
| G1_neo2_37 | H1->H4-><br>H2'-><br>H3 | STKKLQLQAEHFLLDVQMILNESPEPNEELNRCITDAQSWISTGKIDLDRAEECARNLEKVRD<br>EALKRGIDVRDLVSNAKVIALELK (SEQ ID NO: 15)<br>STKKLQLQAEHFLLDVQMILNESPEPNEELNRCITDAQSWISTGKIDLDRAEECARNLEKVRD<br>EALKRGIDVRDLVSNAKVIALELK (SEQ ID NO: 107) |
| G1_neo2_38 | H1->H4-><br>H2'-><br>H3 | STKKLQLQAEHFLLDVQMILNESPEPNEELNRAITDAQSCISTGKCDLDRAEELAPNLEKVRD<br>EALKRGIDVRDLVSNAKVIALELK (SEQ ID NO: 16)<br>STKKLQLQAEHFLLDVQMILNESPEPNEELNRAITDAQSCISTGKCDLDRAEELARNLEKVRD<br>EALKRGIDVRDLVSNAKVIALELK (SEQ ID NO: 108) |
| G1_neo2_39 | H1->H4-><br>H2'-><br>H3 | STKKLQLQAEHELLDVQMILNESPEPNEELNRAITDAQSWISTGKIDLDRAEELCRNLEKVRD<br>EALKRGIDVRDLVSNACVIALELK (SEQ ID NO: 17)<br>STKKLQLQAEHFLLDVQMILNESPEPNEELNRAITDAQSWISTGKIDLDRAEELCRNLEKVRD<br>EALKRGIDVRDLVSNACVIALELK (SEQ ID NO: 109) |
| G1_neo2_40 | H1->H4-><br>H2'-><br>H3 | STKKLQLQAEHALLDAQMMLNRSPEPNEKLNRIITTMQSWISTGKIDLDGAKELAKEVEELRQ<br>EAEKRGIDVRDLASNLKVILLELA (SEQ ID NO: 18)<br>STKKLQLQAEHALLDAQMMLNRSPEPNEKLNRIITTMQSWISTGKIDLDGAKELAKEVEELPQ<br>EAEKRGIDVRDLASNLKVILLELA (SEQ ID NO: 110) |
| G1_neo2_41 | H1->H4-><br>H2'-><br>H3 | STKKLQLQAEHALLDAQMMLNRSPEPNEKLNRIITTMQSCISTGKCDLDGAKELAKEVEELRQ<br>EAEKRGIDVRDLASNLKVILLELA (SEQ ID NO: 19)<br>STKKLQLQAEHALLDAQMMLNRSPEPNEKLNRIITTMQSCISTGKCDLDGAKELAKEVEELRQ<br>EAEKRGIDVRDLASNLKVILLELA (SEQ ID NO: 111) |
| G1 neo2_42 | H1->H4-><br>H2'-><br>H3 | STKKIQLQLEHALLDVQMALNRSPEPNESLNRMITWLQSWISTGKIDLDNAQEMAKEAEKIRK<br>EMEKRGIDVPDLISNIIVILLELS (SEQ ID NO: 20)<br>STKKIQLQLEHALLDVQMALNRSPEPNESLNRMITWLQSWISTGKIDLDNAQEMANEAEKIRK<br>EMEKRGIDVRDLISNIIVILLELS (SEQ ID NO: 112) |
| G1_neo2_43 | H1->H4-><br>H2'-><br>H3 | STKKIQLQLEHALLDVQMALNRSPEPNESLNRMITWLQSCISTGKCDLDNAQEMAKEAEKIRK<br>EMEKRGIDVRDLISNIIVILLELS (SEQ ID NO: 21)<br>STKKIQLQLEHALLDVQMALNRSPEPNESLNRMITWLQSCISTGKCDLDNAQEMAKEAEKIRK<br>EMEKRGIDVRDLISNIIVILLELS (SEQ ID NO: 113) |
| G1_neo2_44 | H1->H4-><br>H2'-><br>H3 | STKKIQLQLEHALLDVQMALNRSPEPNESLNRMITWLQSWISTGKIDLDNAQEMCKEAEKIRK<br>EMEKRGIDVRDLISNICVILLELS (SEQ ID NO: 22)<br>STKKIQLQLEHALLDVQMALNRSPEPNESLNRMITWLQSWISTGKIDLDNAQEMCKEAEKIRK<br>EMEKRGIDVRDLISNICVILLELS (SEQ ID NO: 114) |
| G1_neo2_40_1A | H1->H4-><br>H2'-><br>H3 | STKKTQLLAEHALLDAFMMLNVVPEPNEKLNRIITTMQSWIYTGKIDADGAKELAKEVEELEQE<br>YEKRGIDVEDDASNLKVILLELA (SEQ ID NO: 23)<br>STKKTQLLAERALLDAFMMLNVVPEPNEKLNRIITTMQSWIYTGKIDADGAKELAKEVEELEQE<br>YEKRGIDVEDDASNLKVILLELA (SEQ ID NO: 115) |
| G1_neo2_40_1B | H1->H4-><br>H2'-><br>H3 | STKKTQLLAEHALLDAHMMLNMLPEPNEKLNRIITTMQSWIHTGKIDGDGAQELAKEVEELEQE<br>YEKRGIDVEDEASNLKVILLELA (SEQ ID NO: 24)<br>STKKTQLLAEHALLDAHMMLMMLPEPNEKLNRIITTMQSWIHTGKIDGDGAQELAKEVEELEQE<br>YEKRGIDVEDEASNLKVILLELA (SEQ ID NO: 116) |
| G1_neo2_40_1C | H1->H4-><br>H2'-><br>H3 | STKKTQLLAERALLDAFMMLNMVPEPNEKLNRIITTMQSWIFTGKIDGDGAKELAKEVEELEQE<br>FEKRGIDVEDEASNLKVILLELA (SEQ ID NO: 25)<br>STKKTQLLAERALLDAFMMLNMVPEPNEKLNRIITTMQSWIFTGKIDGDGAKELAKEVEELEQE<br>FEKRGIDVEDEASNLKVILLELA (SEQ ID NO: 117) |
| G1_neo2_40_1D | H1->H-4-><br>H2'-><br>H3 | STKKTQLLAEHALLDALMMLNMVPEPNEKLNRIITTMQSWIFTGKIDGDGAQELAKEVEELEQE<br>LEKRGIDVEDYASNLKVILLELA (SEO ID NO: 26)<br>STKKTQLLAEHALLDALMMLNMVPEPNEKLNRIITTMQSWIFTGKIDGDGAQELAKEVEELEQE<br>LEKRGIDVEDYASNLKVILLELA (SEQ ID NO: 118) |
| G1_neo2_40_1E | H->H4-><br>H2'-><br>H3 | STKKTQLLAEHALLDALMMLNMVPEPNEKLNRIITTMQSWIFTGKIDGDGAQELAKEVEELEQE<br>LEKRGIDVEDYASNLKVILLELA (SEQ ID NO: 27)<br>STKKTQLLAEHALLDAHMMLNVVPEPNEKLNRIITTMQSWIYTGKIDRDGAQELAKEVEELEQE<br>LEKRGIDVDDDASNLKVILLELA (SEQ ID NO: 119) |

TABLE 1-continued

| Name | Domain arrangement | Sequence |
|---|---|---|
| G1_neo2_40_1F | H1->H4->H2'->H3 | STKKTQLLAEHALLDALMMLNLLPEPNEKLNRIITTMQSWIFTGKIDGDAQELAKEVEELEQE HEKRGIDVEDYASNLKVILLELA (SEQ ID NO: 28) STKKTQLLAEHALLDALMMLNLLPEPNEKLNRIITTMQSWIFTGKIDGDAQELAKEVEELEQE HEKRGIDVEDYASNLKVILLELA (SEQ ID NO: 120) |
| G1_neo2_40_1G | H1->H4->H2'->H3 | STKKTQLLAEHALLDAYMMLNMVPEPNEKLNRIITTMQSWILTGKIDSDGAQELAKEVEELEQE LEKRGIDVDDDASNLKVILLELA (SEQ ID NO: 29) STKKTQLLAEHALLDAYMMLNNVPEPNEKLNRIITTMQSWILTGKIDSDGAQELAKEVEELEQE LEKRGIDVDDDASNLKVILLELA (SEQ ID NO: 121) |
| G1_neo2_40_1H | H1->H4->H2'->H3 | STKKTHLLAEHALLDAYMMLNVMPEPNEKLNRIITTMQSWIFTGKIDGDGAKELAKEVEELEQE FEKRGIDVDDDASNLKVILLELA (SEQ ID NO: 30) STKKTHLLAEHALLDAYMMLNVMPEPNEKLNRIITTMQSWIFTGKIDGDGAKELAKEVEELEQE FEKRGIDVDDDASNLKVILLELA (SEQ ID NO: 122) |
| G1_neo2_40_1I | H1->H4->H2'->H3 | STKKTQLLAEHALLDAYMMLNLVPEPNEKLNRIITTMQSWIFTGKIDADGAQELAIEVEELEQE YEKRGIDVDDYASNLKVILLELA (SEQ ID NO: 31) STKKTQLLAEHALLDAYMMLNLVPEPNEKLNRIITTMQSWIFTGKIDADGAQELAIEVEELEQE YEKRGIDVDDYASNLKVILLELA (SEQ ID NO: 123) |
| G1_neo2_40_1J | H1->H4->H2'->H3 | STKKTQLMAEHALLDAFMMLNVLPEPNEKLNRIITTMQSWIFTGKIDGDDAQELAKEVEELEQE LEKRGIDVDDDASNLKVILLELA (SEQ ID NO: 32) STKKTQLMAEHALLDAFMMLNVLPEPNEKLNRIITTMQSWIFTGKIDGDDAQELAKEVEELEQE LEKRGIDVDDDASNLKVILLELA (SEQ ID NO: 124) |
| G1_neo2_40_1F_H1 | H1->H4->H2'->H3 | STKKTQLLIEHALLDALDMSRNLPEPNEKLSRIITTMQSWIFTGKIDGDGAQQLAKEVEELEQE HEKRGEDVEDEASNLKVILLELA (SEQ ID NO: 33) STKKTQLLIEHALLDALDMSRNLPEPNEKLSRIITTMQSWIFTGKIDGDGAQQLAKEVEELEQE HEKRGEDVEDEASNLKVILLELA (SEQ ID NO: 125) |
| G1_neo2_40_1F_H2 | H1->H4->H2'->H3 | STKKTQLLLEHALLDALHMRRNLPEPNEKLSRIITTMQSWIFTGKIDGDGAQELAKEVEELEQE HEKRGRDVEDDASNLKVILLELA (SEQ ID NO: 34) STKKTQLLLEHALLDALHMRRNLPEPNEKLSRIITTMQSWIFTGKIDGDGAQELAKEVEELEQE HEKRGRDVEDDASNLKVILLELA (SEQ ID NO: 126) |
| G1_neo2_40_1FH3 | H1->H4->H2'->H3 | STKKTQLLIEHALLDALNMRKKLPEPNEKLSRIITDMQSWIFTGKIDGDGAQQLAKEVEELEQE HEKRGGDVEDYASNLKVILLELA (SEQ ID NO: 35) STKKTQLLIEHALLDALNMRKKLPEPNEKLSRIITDMQSWIFTGKIDGDGAQQLAKEVEELEQE HEKRGGDVEDYASNLKVILLELA (SEQ ID NO: 127) |
| G1_neo2_40_1F_H4 | H1->H4->H2'->H3 | STKKTQLLLEHALLDALHMSRELPEPNEKLNRIITDMQSWIFTGKIDGDGAQDLAKEVEELEQE HEKRGGDVEDYASNLKVILLELA (SEQ ID NO: 36) STKKTQLLLEHALLDALHMSRELPEPNEKLNRIITDMQSWIFTGKIDGDGAQDLAKEVEELEQE HEKRGGDVEDYASNLKVILLELA (SEQ ID NO: 128) |
| G1_neo2_40_1F_H5 | H1->H4->H2'->H3 | STKKTQLLIEHALLDALHMSRKLPEPNEKLSRIITTMQSWIFTGKIDGDGAQHLAKEVEELEQE HEKRGGEVEDEASNLKVILLELA (SEQ ID NO: 37) STKKTQLLIEHALLDALHMSRKLPEPNEKLSRIITTMQSWIFTGKIDGDGAQHLAKEVEELEQE HEKRGGEVEDEASNLKVILLELA (SEQ ID NO: 129) |
| G1_neo2_40_1F_H6 | H1->H4->H2'->H3 | STKKTQLLIEHALLDALHMKRKLPEPNEKLNRIITNMQSWIFTEKIDGDGAQDLAKEVEELEQE HEKRGQDVEDYASNLKVILLELA (SEQ ID NO: 38) STKKTQLLIEHALLDALHMKRKLPEPNEKLNRIITNMQSWIFTEKIDGDGAQDLAKEVEELEQE HEKRGQDVEDYASNLKVILLELA (SEQ ID NO: 130) |
| G1_neo2_40_1F_M1 | H1->H4->H2'->H3 | STEKTQLAAEHALRDALMLKHLLNEPNEKLARIITTMQSWQFTGKIDGDGAQELAKEVEELQQE HEVRGIDVEDYASNLKVILLHLA (SEQ ID NO: 39) STEKTQLAAEHALRDALMLKHLLNEPNEKLARIITTMQSWQFTGKIDGDGAQELAKEVEELQQE HEVRGIDVEDYASNIKVILLHLA (SEQ ID NO: 131) |
| G1_neo2_40_1F_M2 | H1->H4->H2'->H3 | STKNTQLAAEDALLDALMLRNLLNEPNEKLARIITTMQSWQFTEKIDGDGAQELAKEVEELQQE HEERGIDVEDYASNLKVILLQLA (SEQ ID NO: 40) STKNTQLAAEDALLDALMLRNLLNEPNEKLARIITTMQSWQFTEKIDGDGAQELAKEVEELQQE HEERGIDVEDYASNLKVILLQLA (SEQ ID NO: 132) |
| G1_neo2_40_1FM3 | H1->H4->H2'->H3 | STEKTQHAAEDALRDALMLRNLLNEPNEKLARIITTMQSWQFTEKIDGDGAQELAKEVEELQQE HEVRGIDVEDYASNLKVILLQLA (SEQ ID NO: 41) STEKTQHAAEDALRDALMLRNLLNEPNEKLARIITTMQSWQFTEKIDGDGAQELAKEVEELQQE HEVRGIDVEDYASNLKVILLQLA (SEQ ID NO: 133) |
| G1_neo2_40_1F_seq02 | H1->H4->H2'->H3 | TQKKQQLLAEHALLDALMILNMLKTSSEAVNRMITIAQSWIFTGTSNPEEAKEMIKMAEQAEEE ARPEGVDTEDYVSNLNVILKEIA (SEQ ID NO: 42) TQKKQQLLAEHALLDALMILNMLKTSSEAVNRMITIAQSWIFTGTSNPEEAKEMIKMAEQAEEE ARREGVDTEDYVSNLKVILKEIA (SEQ ID NO: 134) |

TABLE 1-continued

| Name | Domain arrangement | Sequence |
|---|---|---|
| G2_neo2_40_1F_seq03 | H1->H4->H2'->H3 | TTKKYQLLVEHALLDALMMLNLSSESNEKMNRIITTMQSWIFTGTFDPDQAEELAKLVEELREE FRKRGIDTEDYASNLKVILKELS (SEQ ID NO: 43) <br> TTKKYQLLVEHALLDALMMLNLSSESNEKMNPIITTMQSWIFTGTFDPDQAEELAKLVEELREE FRKRGIDTEDYASNLKVILKELS (SEQ ID NO: 135) |
| G2_neo2_40_1F_seq04 | H1->H4->H2'->H3 | TTKKIQLLVEHALLDALMILNLSSESNEKLNRIITTLQSWIFRGEIDPDRAPELAKILELIKEE MRKRGIDTEDYVSNMIVIIRELA (SEQ ID NO: 44) <br> TTKKIQLLVEHALLDALMILNLSSESNEKLNRIITTLQSWIFRGEIDPDRARELAKLLEEIREE MRKRGIDTEDYVSNMIVIIRELA SEQ ID NO: 136) |
| G2_neo2_40_1F_seq05 | H1->H4->H2'->H3 | TKKKIQLLAEHVLLDLEMMLNLSSESNEKMNPLITIVQSWIFTGTIDPDQAEEMAKWVEELREE FRKRGIDTEDYASNVKVILKELS (SEQ ID NO: 45) <br> TKKKIQLLAEHVLLDLLMMLNLSSESNEKMNRLITIVQSWIFTGTIDPDQAEEMAKWVEELREE FRKRGIDTEDYASNVKVILKELS (SEQ ID NO: 137) |
| G2_neo2_40_1E_seq06 | H1->H4->H2'->H3 | TKKWYQLLIEHLLLDALMVLNMSSESNEKLNRIITILQSWIFTGTWDPDLAEEMEKLMQEIEEE LRPRGIDTEDYMSNMRVIIKELS (SEQ ID NO: 46) <br> TKKKYQLLIEHLLLDALMVLNRIITILQSWIKTGTWDPDLAEEMEKLMQEIEEE LRRRGIDTEDYMSNMRVIIKELS (SEQ ID NO: 138) |
| G2_neo2_40_1F_seq07 | H1->H4->H2'->H3 | TKKKLQLLVEHLLLDMLMILNMSSESNEKLNRLITELQSWIFRGEIDPDKAEEMWKIMEEIEKE LRERGIDTEDYMSNAKVIIKELS (SEQ ID NO: 47) <br> TKKKLQLLVEHLLLDMLMILNMSSESNEKLNRLITELQSWIFRGEIDPDKAEEMWKIMEEIEKE LRERGIDTEDYMSNAKVIIKELS (SEQ ID NO: 139) |
| G2_neo2_40_1F_seq08 | H1->H4->H2'->H3 | TSKKQQLLAEHALLDALMILNISSESSEAVNRAITWLQSWIFKGTVNPDQAEEMRKLAEQIREE MRKRGIDTEDYVSNLEVIAKELS (SEQ ID NO: 48) <br> TSKKQQLLAEHALLDALMILNISSESSEAVNRAITWLQSWIFKGTVNPDQAEEMRKLAEQIREE MRKRGIDTEDYVSNLEVIAKELS (SEQ ID NO: 140) |
| G2_neo2_40_1F_seq09 | H1->H4->H2'->H3 | TKKKYQLLIEHLLLDLLMVINMSSESNEKINRLITWLQSWIFTGTYDPDLAEEMYKILEELREE MRERGIDTEDYMSNMRVIVKELS (SEQ ID NO: 49) <br> TKKKYQLLIEHLLLDLLMVLNMSSESNEKINRLITWLQSWIFTGTYDPDLAEEMYKILEELREE MRERGIDTEDYMSNMRVIVKELS (SEQ ID NO: 141) |
| G2_neo2_40_1E_seq10 | H1->H4->H2'->H3 | TKKKWQLLIEHLLLDLLMILNLSSESNEKLNRLITWLQSWIFTGTYDPDLAEEMKKMMDEIEDE LRERGIDTEDYMSNAKVIIKELS (SEQ ID NO: 50) <br> TKKKWQLLIEHLLLDLLMILNLSSESNEKLNRLITWLQSWIFTGTYDPDLAEEMKKMMDEIEDE LRERGIDTEDYMSNAKVIIKELS (SEQ ID NO: 142) |
| G2_neo2_40_1F_seq11 | H1->H4->H2'->H3 | TKKKIQLLVEHALLDALMILNLSSESNEKLNRIITTMQSWIFTGTIDPDQAEELSKLVEEIREE MRKRGIDTEDYVSNLKVILDELS (SEQ ID NO: 51) <br> TKKKIQLLVEHALLDALMILNLSSESNEKLNRIITTMQSWIFTGTIDPDQAEELSKLVEEIREE HPKRGIDTEDYVSNLKVILDELS (SEQ ID NO: 143) |
| G2_neo2_40_1E_seq12 | H1->H4->H2'->H3 | TEKKLQLLVEHALLDALMILNLWSESNEKLNRIITTMQSWIFTGRIDPDKAEELAKLVEELREE ARERGIDTEDYVSNDKVILKEDS (SEQ ID NO: 52) <br> TEKKLQLLVEHALLDALMILNLWSESNEKLNPIITTMQSWIFTGRIDPDKAEELAKLVEELREE ARERGIDTEDYVSNLKVILKELS (SEQ ID NO: 144) |
| G2_neo2_40_1F_seq13 | H1->H4->H2'->H3 | TKKKYQLLMEHLLLDLLMVLNMSSESNEKLNRLITIIQSWIFTGTWDPDKAKEEMAMLKEIEDE LRERGIDTEDYMSNMIVIMKELS (SEQ ID NO: 53) <br> TKKKYQLLMEHLLLDLLMVLNMSSESNEKLNRLITIIQSWIFTGTWDPDKAEEMAKMLNEIEDE LRERGIDTEDYMSNMIVIMKELS (SEQ ID NO: 145) |
| G2_neo2_40_1F_seq14 | H1->H4->H2'->H3 | TTKKIQLLVEHALLDALMLLNLSSESNEKMNRIITTMQSWIFEGRIDPDQAQELAKLVEELREE FRKRGIDTEDYVSNLKVILEELS (SEQ ID NO: 54) <br> TTKKIQLLVEHALLDALMLLNESSESNEKMNRIITTMQSWIFEGRIDPDQAQELAKLVEELREE FRKRGIDTEDYVSNLKVILEELS (SEQ ID NO: 146) |
| G2_neo20_40-1F_seq15 | H1->H4->H2'->H3 | TKKKIQLLVEHALLDALMMLNLSSESNEKLNRIITTMQSWIFTGTIDPDQAEELAKLVRELREE FRKRGIDTEDYASNLEVILRELS (SEQ ID NO: 55) <br> TKKKIQLLVEHALLDALMMLNLSSESNEKLNRIITTMQSWIFTGTIDPDQAEELAKLVRELREE FRKRGIDTEDYASNLEVILRELS (SEQ ID NO: 147) |
| G2_neo2_40_1F_seq16 | H1->H4->H2'->H3 | TKKKIQLLVEHALLDALMILNLSSKSNEKLNRIITTMQSWIFNGTIDPDRARELAKLVEEIRDE MEKNGIDTEDYVSNLKVILEELA (SEQ ID NO: 56) <br> TKKKIQLLVEHALLDALMILNLSSKSNEKLNRIITTMQSWIFNGTIDPDRARELAKLVEEIRDE MEKNGIDTEDYVSNLKVILEELA (SEQ ID NO: 148) |
| G2_neo2_40_1F_seq17 | H1->H4->H2'->H3 | TKKKYQLLIEHVLLDLLMLLNLSSESNEKMNRLITILQSWIFTGTYDPDKAEEMAKLLKELREE FRERGIDTEDYISNAIVILKELS (SEQ ID NO: 57) <br> TKKKYQLLIEHVLLDLLMLLNLSSESNEKMNRLITILQSWIFTGTYDPDRAEEMAKLLKELPEE FRERGIDTEDYISNAIVILKELS (SEQ ID NO: 149) |

TABLE 1-continued

| Name | Domain arrangement | Sequence |
|---|---|---|
| G2_neo2_40_1F_seq18 | H1->H4-><br>H2'-><br>H3 | TKKKIQLLVEHALLDALMMLNLSSESNEKLNRIITTMQSWIFTGTIDPDRAEELAKLVEELREE<br>FRKRGIDTEDYASNLKVILKELS (SEQ ID NO: 58)<br>TKKKIQLLVEHALLDALMMLNLSSESNEKLNRIITTMQSWIFTGTIDPDRAEELAKLVEELREE<br>FRKRGIDTEDYASNLKVILKELS (SEQ ID NO: 150) |
| G2_neo2_40_1F_seq19 | H1->H4-><br>H2'-><br>H3 | TKKKIQLLVEHALLDALMMLNLSSESNEKLNRIITTMQSWIFNGTIDPDQARELAKLVEELREE<br>FRKRGIDTEDYASNLKVILEELA (SEQ ID NO: 59)<br>TKKKIQLLVEHALLDALMMLNLSSESNEKLNRIITTMQSWIFNGTIDPDQARELAKLVEELREE<br>FRKRGIDTEDYASNLKVILEELA (SEQ ID NO: 151) |
| G2_neo2_40_1F_seq20 | H1->H4-><br>H2'-><br>H3 | TKKNLQLLVEHALLDALMLLNLSSESNEKLNRIITTMQSWIFTGTVDPDQAEELAKLVEEIREE<br>LRKRGIDTEDYVSNLKVILKELS (SEQ ID NO: 60)<br>TKKKLQLLVEHALLDALMLLNLSSESNEKLNRIITTMQSWIFTGTVDPDQAEELAKLVEEIREE<br>LRKRGIDTEDYVSNLKVILKELS (SEQ ID NO: 152) |
| G2_neo2_40_1F_seq21 | H1->H4-><br>H2'-><br>H3 | TTKKYQLLVEHALLDALMILNLSSESNEKLNRIITTMQSWIFTGTFDPDQAEELAKLVREIREE<br>MRKRGIDTEDYVSNLEVILRELS (SEQ ID NO: 61)<br>TTKKYQLLVEHALLDALMILNLSSESNEKLNRIITTMQSWIFTGTFDPDQAEELAKLVREIREE<br>MRKRGIDTEDYVSNLEVILRELS (SEQ ID NO: 153) |
| G2_neo2_40_1F_seq22 | H1->H4-><br>H2'-><br>H3 | TKKKIQLLVEHALLDALMILNLSSESNEKLNRIITTMQSWIFTGTIDPDRAEELAKLVREIREE<br>MRKRGIDTEDYVSNLEVILRELS (SEQ ID NO: 62)<br>TKKKIQLLVEHALLDALMILNLSSESNEKLNRIITTMQSWIFTGTIDPDRAEELAKLVREIREE<br>MRKAGIDTEDYVSNLEVILRELS (SEQ ID NO: 154) |
| G2_neo2_40_1F_seq23 | H1->H4-><br>H2'-><br>H3 | TKKKYQLLIEHLLLDLLMILNLSSESNEKLNALITWLQSWIFRGEWDPDKAEEWAKILKEIREE<br>LRERGIDTEDYMSNAIVIMKELS (SEQ ID NO: 63)<br>TKKKYQLLIEHLLLDLLMILNLSSESNEKLNRLITWLQSWIFRGEWDPDKAEEWAKILKEIREE<br>LRERGIDTEDYMSNAIVIMKELS (SEQ ID NO: 155) |
| G2_neo2_40_1F_seq24 | H1->H4-><br>H2'-><br>H3 | TDKKLQLLVEHLLLDLLMMLNLSSKSNEKMNRLITIAQSWIFTGKVDPDLAREMIKLLEETEDE<br>NRKNGIDTEDYVSNARVIAKELE (SEQ ID NO: 64)<br>TDKNLQLLVEHLLLDLLMMLNLSSKSNEKMNRLITIAQSWIFTGKVDPDLAREMIKLLEETEDE<br>NRKNGIDTEDYVSNARVIAKELE (SEQ ID NO: 156) |
| G2_neo2_40_1F_seq25 | H1->H4-><br>H2'-><br>H3 | TKKKIQLLVEHALLDALMLLNLSSESNEKMNRIITTMQSWIFTGTIDPDQAEELAKLVEELKEE<br>FKKRGIDTEDYVSNLKVILKELS (SEQ ID NO: 65)<br>TKKKIQLLVEHALLDALMLLNLSSESNEKMNRIITTMQSWIFTGTIDPDQAEELAKLVEELKEE<br>FKKRGIDTEDYVSNLKVILKELS (SEQ ID NO: 157) |
| G2_neo2_40_1F_seq26 | H1->H4-><br>H2'-><br>H3 | TKKNYQLLIEHALLDALMILNLWSESNEKLNRIITTMQSWIFTGTYDPDKAEELEKLAKEIEDE<br>ARERGIDTEDYMSNLRVILKELS (SEQ ID NO: 66)<br>TKKKYQLLIEHALLDALMILNLWSESNEKLNPIITTMQSWIFIGTYDPDKAEELEKLAKEIEDE<br>ARERGIDTEDYMSNLRVILKELS (SEQ ID NO: 158) |
| G2_neo2_40_1F_seq27 | H1->H4-><br>H2'-><br>H3 | TKKKAQLLAEHALLDALMLLNLSSESNERLNRIITWLQSIIFTGTYDPDMVKEAVKLADEIEDE<br>MRKRGIDTEDYVSNLRVILQELA (SEQ ID NO: 67)<br>TKKKAQLLAEHALLDALMLLNLSSESNERLNRIITWLQSIIFTGTYDPDMVKEAVKLADEIEDE<br>MRKRGIDTEDYVSNLRVILQELA (SEQ ID NO: 159) |
| G2_neo2_40_1F_seq28 | H1->H4-><br>H2'-><br>H3 | TQKKNQLLAEHLLLDALMVLNQSSESSEVANRIITWAQSWIFEGRVDPNKAEEAKKLAKKLEEE<br>MRKRGIDMEDYISNMKVIAEEMS (SEQ ID NO: 68)<br>TQKKNQLLAEHLLLDALMVLNQSSESSEVANRIITWAQSWIFEGRVDPNKAEEAKKLAKKLEEE<br>MRKRGIDMEDYISNMKVIAEEMS (SEQ ID NO: 160) |
| G2_neo2_40_1F_seq29 | H3-><br>H2'-><br>H4->H1 | EDYYSNLKVILEELREAMERNGLSDKAEEWRQWKKIVERIRQIRSNNSDLNEAKELLNRLITYI<br>QSQIFEISERIRETDQEKKEESWKKWQLLLEHALLDVLMLLND (SEQ ID NO: 69)<br>EDYYSNLKVILEELAREMERNGLSDKAEEWRQWKKIVERIRQIRSNNSDLNEAKELLNRLITYI<br>QSQIFEISERIRETDQEKKEESWKKWQLLLEHALLDVLMLLND (SEQ ID NO: 161) |
| G2_neo2_40_1F_seq30 | H1->H3-><br>H2'-><br>H4 | PEKKRQLLLEHILLDALMLLNLXXXXXXXNTESKFEDYISNAEVIAEELAKLMESXXLSDEAEKK<br>KKIKQWLREVWRIWXXXXWSTLEDKAPELLNRIITTIQSQIFY (SEQ ID NO: 70)<br>PEKKRQLLLEHILLDALMLLNLLETNPQNTESKFEDYISNAEVIAEELAKLMESLGLSDEAEKK<br>KKIKQWLREVWRIWSSTNWSTLEDKARELLNRIITTIQSQIFY (SEQ ID NO: 162) |
| G2_neo2_40_1F_seq31 | H1->H3-><br>H2'-><br>H4 | PEKKRQLLLEHILLDLLMILNMXXXXXXXNTESEMEDYWSNVRVILRELARLMEEXXXKELSELM<br>ERMRKIVEKIRQIVTXXXXLDTAREWLNRLITWIQSLIFR (SEQ ID NO: 71)<br>PEKKRQLLLEHILLDLLMILNMIETNRENTESEMEDYQSNVRVILRELARLMEELNYKELSELM<br>ERMRKIVEKIRQIVTNNSSLDTAREWLNRLITWIQSLIFR (SEQ ID NO: 163) |
| G2_neo2_40_1F_seq32 | H1->H3-><br>H2'-><br>H4 | PEKKRQLLAEHALLDALMLLNIIETNSKNTESKMEDYVSNLEVILTEFKKLAEKLNFSEEAERA<br>ERMKRWARKAYQMMTLDLSLDKAKEMLNRIITILQSIIFN (SEQ ID NO: 72)<br>PEKKRQLLAEHALLDALMLLNIIETNSKNTESKMEDYVSNLEVILTEFKKLAEKLNFSEEAERA<br>ERMKRWARNAYQMMTLDLSLDKAKEMLNRIITILQSIIFN (SEQ ID NO: 164) |

TABLE 1-continued

| Name | Domain arrangement | Sequence |
|---|---|---|
| G2_neo2_40_1F_seq33 | H1->H3-><br>H2'-><br>H4 | PEKKRQLLAEHLLLDVLMMLNGNASLKDYASNAQVIADEFRELARELGLTDEAKKAEKIIEALE<br>RAREWLLNNKDKEKAKEALNRAITIAQSWIKN (SEQ ID NO: 73)<br>PEKKRQLLAEHLLLDVLMMLNGNASLKDYASNAQVIADEFRELARELGLTDEAKKAEKIIEALE<br>RAREWLLNNKDKEKAKEALNRAITIAQSWIFN (SEQ ID NO: 165) |
| G2_neo2_40_1F_seq34 | H1->H3-><br>H2'-><br>H4 | PEKKRQLLLEHLLLDLLMILNMLRTNPKNIESDWEDYMSNIEVIIEELRKIMESLGRSEKAKEW<br>KRMKQWVRRILEIVKNNSDLEEAKEWLNRLITIVQSEIFE (SEQ ID NO: 74)<br>PEEKRQLLLEHLLLDLLMILNMLRTNPKNIESDWEDYMSNIEVIIEELRKIMESLGRSEKAKEW<br>KRMKQWVRRILEIVKNNSDLEEAKEWLNRLITIVQSEIFE (SEQ ID NO: 166) |
| G2_neo2_40_1F_seq35 | H1->H3><br>H2'-><br>H4 | WEKKRQLLLEHLLLDLLMILNMWRTNPQNTESLMEDYMSNAKVIVEELAPMMRSQGLEDKAREW<br>EEMKKRIEEIRQIIQNNSSKERAKEELNRLITYVQSEIFR (SEQ ID NO: 75)<br>WEKKRQLLLEHLLLDLLMILNMWRTNPQNTESLMEDYMSNAKVIVEELARMMRSQGLEDKAREW<br>EEMKKRIEEIRQIIQNNSSKERKEELNRLITYVQSEIFR (SEQ ID NO: 167) |
| G2_neo2_40_1F_seq36 | H1->H3-><br>H2'-><br>H4 | PKKKIQLLAEHALLDALMILNIVKTNSQNAEEKLEDYASNVEVILEEIARLMESGDQKDEAEKA<br>KRMKEWMKRIKTTASEDEQEEMANRIITLLQSWIFS (SEQ ID NO: 76)<br>PKKKIQLLAEHALLDALMILNIVKTNSQNAEEKLEDYASNVEVILEEIARLMESGDQKDEAEKA<br>KRMKEWMKRIKTTASEDEQEEMANRIITLLQSWIFS (SEQ ID NO: 168) |
| G2_neo2_40_1F_seq37 | H1->H3-><br>H2'-><br>H4 | PEKKRQKLLAEHALLDALMILNXXXXXXQNAEEKLEDYMSNVEVIMEEFARMMRXXXXEEAENA<br>ERIKKWVRKASSXXXSEEQREMMNRAITLMQSWIFE (SEQ ID NO: 77)<br>PEKKRQLLAEHALLDALMILNILQTNPQNAEEKLEDYMSNVEVIM*EEFARMMR*NGDRSEEAENA<br>ERIKKWVRKASSTASSEEQREMMNRAITLMQSWIFE (SEQ ID NO: 169) |
| G2_neo2_40_1F_seq38 | H1->H3-><br>H2'-><br>H4 | PEKKRQLLAEHLLLDALMVLNMXXXXXXXNTEEKLEDYISNMKVIIKEMIELMRSLXXXEEAEKW<br>KEALKAVEKIXXXXDSETARELANRIITLAQSAIFY (SEQ ID NO: 78)<br>PEKKRQLLAEHLLLDALMVLNMLTTNSKNTEEKLEDYISNMKVIIKEMIELMRSLGRLEEAEKW<br>KEALKAVEKIGSRMDSETARELANRIITLAQSAIFY (SEQ ID NO: 170) |
| G2_neo2_40_1F_seq39 | H1->H3-><br>H2'-><br>H4 | PEKKRQLLAEHALLDALMFLNLXXXXXXQAEEKIEDYASNLRVIAEELARLFENLXXXDEAQKA<br>KDIKELAERARSXXSSEKRKEAMNRAITILQSMIFR (SEQ ID NO: 79)<br>PEKKRQLLAEHALLDALMFLNLVETNPDQAEEKIEDYASNLRVIAEELARLFENLGRLDEAQKA<br>KDIKELAEPARSRVSSEKRKEAMNRAITILQSMIFR (SEQ ID NO: 171) |
| G2_neo2_40_1F_seq40 | H1->H3-><br>H2'-><br>H4 | PEKKRQLLAEHALLDALMILNIIRTNSDNTESKLEDYISNLKVILEEIARLMESLGLSDEAEKA<br>KEAMRLADKAGSTASEEEKKEAMNRVITWAOQWIFN (SEQ ID NO: 80)<br>PEKKRQLLAEHALLDALMILNIIRTNSDNTESKLEDYISNLKVILEEIARLMESLGLSDEAEKA<br>KEAMRLADKAGSTASEEEKKEAMNRVITWAQSWIFN (SEQ ID NO: 172) |
| G2_neo2_40_1F_seq41 | H1->H3-><br>H2'-><br>H4 | PEKKRQLLAEHALLDALMMLNILRTNPDNAEEKLEDYWSNLIVILREIAKLMESLGLTDEAEKA<br>KEAARWAEEARTTASKDQRRELANRIITLLQSWIFS (SEQ ID NO: 81)<br>PEKKRQLLAEHALLDALMMLNILRTNPDNAEEKLEDYWSNLIVILREIAKLMESLGLTDEAEKA<br>KEAARWAEEARTTASKDQRRELANRIITLLQSWIFS (SEQ ID NO: 173) |
| G2_neo2_40_1F_seq42 | H1->H3-><br>H2'-><br>H4 | PEKKRQLLAEHLLLDALMILNIIETNEQNAESKLEDYISNAKVILDEFREMARDLGLLDEAKKA<br>EKMKRWLEKMRSNASSDERREWANRMITTAQSWIFN (SEQ ID NO: 82)<br>PEKKRQLLAEHLLLDALMILNIIETNEQNAESKLEDYISNAKVILDEFREMARDLGLLDEAKKA<br>EKMKRWLEKMRSNASSDERREWANRMITTAQSWIFN (SEQ ID NO: 174) |
| G2_neo2_40_1F_seq27_S3 | H1->H4-><br>H2'-><br>H3 | TNKKAQLHAEFALHDALMLLNLSSESNERLNRIITWLQSIIFYGTYDPDMVKEAVKDADEIEDE<br>MRKRGIDTEDYVSNLRLILQELA (SEQ ID NO: 83)<br>TNKKAQLHAEFALHDALMLLNLSSESNERLNRIITWLQSIIFYGTYDPDMVKEAVKDADEIEDE<br>MRKRGIDTEDYVSNLRLILQELA (SEQ ID NO: 245) |
| G2_neo2_40_1F_seq27_S18 | H1->H4-><br>H2'-><br>H3 | TNKEAQLHAEFALYDALMLLNLSSESNERLNRIITWLQSIIFYETYDPDMVKEAVKLADEIEDE<br>MRKRKIDTEDYVVNLRLILQELA (SEQ ID NO: 84)<br>TNKEAQLHAEFALYDALMLLNLSSESNERLNRIITWLQSIIFYETYDPDMVKEAVKLADEIEDE<br>MRKRKIDTEDYVVNLRLILQELA (SEQ ID NO: 175) |
| G2-neo2_40_1F_seq27_S22 | H1->H4-><br>H2'-><br>H3 | TKKDAELLAEFALYDALMILNLSSESNERLNEIITWLQSIIFYGTYDPDMVKEAVKLADEIEDE<br>MRKRGIDTEDYVSNLRLILQELA (SEQ ID NO: 85)<br>TKEDAELLAEFALYDALMLLNLSSESNERLNEIITWLQSIIFYGTYDPDMVKEAVKLADEIEDE<br>MRKRGIDTEDYVSNLRLILQELA (SEQ ID NO: 176) |
| G2_neo2_40_1F_seq27_S24 | H1->H4-><br>H2'-><br>H3 | TNKKAQLHAEFALYDALMLLNLSSESNERLNDIITWLQSIIFTGTYDPDMVKEAVKLADEIEDE<br>MRKRKIDTEDYVVNLRYILQELA (SEQ ID NO: 86)<br>TNKKAQLHAEFALYDALMLLNLSSESNERLNDIITWLQSIIFTGTYDPDMVKEAVKLADEIEDE<br>MRKPRIDTEDYVVNLRYILQELA (SEQ ID NO: 177) |
| G2_neo2_40_1F_seq29_S6 | H3-><br>H2'-><br>H4->H1 | EDYYSNLKLILEELAREMERNGLSDKAEEWRQWKKIVERIRQIRSNNSDLNEAKELLNRLITYI<br>QSQIFEVLHGVGETDQEKKEESWKKWDLLLEHALLDVLMLLND (SEQ ID NO: 87)<br>EDYYSNLKLILEELAREMERNGLSDKAEEWRQWKKIVERIRQIRSNNSDLNEAKELLNRLITYI<br>QSQIFEVLHGVGETDQEKKEESWKKWDLLLEHALLDVLMLLND (SEQ ID NO: 178) |

TABLE 1-continued

| Name | Domain arrangement | Sequence |
|---|---|---|
| G2_neo2_40_1F_seq29_S7 | H3-><br>H2'-><br>H4->H1 | EDYYSNLKVILEELAREMERNGLSDKAEEWRQWKKIVERIRQIRSNNSDLNEAKELLNELITYI<br>QSQIFEVIEPEGETDQEKKEESWKKWELHLEHALLDVLMLLND (SEQ ID NO: 138)<br>EDYYSNLKVILEELAREMERNGLSDKAEEWRQWKKIVERIRQIRSNNSDLNEAKELLNELITYI<br>QSQIFEVIEREGETDQEKKEESWKKWELHLEHALLDVLMLLND (SEQ ID NO: 179) |
| G2_neo2_40_1F_seq29_S8 | H3-><br>H2'-><br>H4->H1 | EDYYSNLKLILEELAREMERNGLSDKAEEWRQWKKIVERIRQIRSNNSDLNEAKELLNRLITYI<br>QSQIFEVLEGVGETDQEKKEESWKKWELHLEHALLDVLMLLND (SEQ ID NO: 89)<br>EDYYSNLKLILEELAREMERNGLSDKAEEWRQWKKIVERIRQIRSNNSDLNEAKELLNRLITYI<br>QSQIFEVLEGVGETDQEKKEESWKKWELHLEHALLDVLMLLND (SEQ ID NO: 130) |
| Neoleukin-2/15 (i.e. G2_neo2_40_1F_seq36_S11) | H1-'H3-><br>H2'-><br>H4 | PKKKIQLHAEHALYDALMILNIVKTNSPPAEEKLEDYAFNFELILEEIARLFESGDQKDEAEKA<br>KRMKEWMKRIKTTASEDEQEEMANAIITILQSWIFS (SEQ ID NO: 90, version 1)<br>PEKKKIQLHAEHALYEALMILNIVKTNSPPAEEKLEDYAFNFELILEEIARLFESGDQKDEAEKA<br>KRMKEWMKRIKTTASEDEQEEMANAIITILQSWIFS (SEQ ID NO: 90, version 2)<br>PKKKIQLHAEHALYDALMILNIVKTNSPPAEEKLEDYAFNFELILEEIARLFESGDQKDEAEKA<br>KRMKEWMKRIKTTASEDEQEEMANAIITILQSWIFS (SEQ ID NO: 181) |
| G2_neo2_40_1F_seq36_S12 | H1->H3-><br>H2'-><br>H4 | PKKKIQLLAEHALFDLLMILNIVKTNSQNAEEKLEDYAYNAGVILEEIARLFESGDQKDEAEKA<br>KRMKEWMKRIKDTASEDEQEEMANEIITILQSWNFS (SEQ ID NO: 91)<br>PKKKIQLLAEHALFDLLMILNIVKTNSQNAEEKLEDYAYNAGVILEEIARLFESGDQKDEAEKA<br>KRMKEWMKRIKDTASEDEQEEMANEIITILQSWNFS (SEQ ID NO: 182) |
| Neoleukin-2/15-H8Y-K33E | H1->H3-><br>H2'-><br>H4 | PKKKIQLYAEHALYDALMILNIVKTNSPPAEETLEDYAFNFELILEEIARLFESGDQKDRAEKA<br>KRMKEWMKRIKTTASEDEQEEMANAIITILQSWIFS (SEQ ID NO: 94)<br>PKKKIQLYAEHALYDALMILNIVKTNSPPAEEELEDYAFNFELILEEIARLFESGDQKDEAEKA<br>KRMKEWMKRIKTTASEDEQEEMANAIITILQSWIFS (SEQ ID NO: 246) |
| Neoleukin-2/15 (K32 is considered to be a residue of the optional linker in this depicted sequence) | H1->H3->H2'->H4 | PKKKIQLHAEHALYDALMILNIVKTNSPPAEEKLEDYAFNFELILEEIARLFESGDQKDEAEKA<br>KRMKEWMKRIKTTASEDEQEEMANAIITILQSWIFS (SEQ ID NO: 247) |
| IL4_G2_neo2_40_1F_seq36_S11 | | PKKKIQITAEEEALKDALSILNIVKTNSPPAEEQLERFAKRFERNLWGIARLFESGDQKDEAEKAKRMKE<br>WMKRIKTTASEDEQEEMANAIITILQSWIFS (SEQ ID NO: 92)<br>PKKKIQITAEEEALKDALSILNIVKTNSPPAEEQLERFAKRFERNLWGIARLFESGDQKDEAEKAKRMKE<br>WMKRIKTTASEDEQEEMANAIITILQSWIFS (SEQ ID NO: 183) |
| Neoleukin-4 (i.e. IL4_G2_neo2_40_1F_seq36_S11_MIF) | | PKKKIQIMAEEEALKDAISILNIVKTNSPPAEEQLERFAERFERNLWGIARLFESGDQKDEAEKAKRMIE<br>WMKRIKTTASEDEQEEMANAIITILQSWFFS (SEQ ID NO: 93)<br>PKKKIQIMAEEEALKDALSILNIVKTNSPPAEEQLERFAKRFERNLWGIARLFESGDQKDEAEKAKRMIE<br>WMKRIKTTASEDEQEEMANAIITILQSWFFS (SEQ ID NO: 184) |
| Neoleukin-2/15_R50C | | PKKKIQLHAEHALYDALMILNIXXXXXXXXXXXLEDYAFNFELILEEIACLFESGXXKDEAEK<br>AKRMKEWMKRIKTXXXEDEQEEMANAIITILQSWIFS* (SEQ ID NO: 275) |
| Neoleukin-2/15_E53C | | PKKKIQLHAEHALYDALMILNIXXXXXXXXXXXLEDYAFNFELILEEIARLFCSGXXKDEAEK<br>AKRMKEWMKRIKTXXXEDEQEEMANAIITILQSWIFS* (SEQ ID NO: 276) |
| Neoleukin-2/15_D56C | | PKKKIQLHAEHALYDALMILNIXXXXXXXXXXXLEDYAFNFELILEEIARLFESGCQKDEAEK<br>AKRMKEWMKRIKTXXXEDEQEEMANAIITILQSWIFS* (SEQ ID NO: 277) |
| Neoleukin-2/15_K58C | | PKKKIQLHAEHALYDALMILNIXXXXXXXXXXXLEDYAFNFELILEEIARLFESGXXCDEAEK<br>ARRMKEWMKRIKTXXXEDEQEEMANAIITILQSWIFS* (SEQ ID NO: 278) |
| Neoleukin-2/15_D59C | | PKKKIQLHAEHALYDALMILNIXXXXXXXXXXXLEDYAFNFELTLEEIARLFESGXXKCEAEK<br>AKRMKEWMKRIKTXXXEDEQEEMANAIITILQSWIFS* (SEQ ID NO: 279) |
| Neoleukin-2/15_E62C | | PKKKIQLHAEHALYDALMILNIXXXXXXXXXXXLEDYAFNFELILEEIARLFESGXXKDEACK<br>AKRMKEWMKRIKTXXXEDEQEEMANAIITILQSWIFS* (SEQ ID NO: 280) |
| Neoleukin-2/15_R66C | | PKKKIQLHAEHALYDALMILNIXXXXXXXXXXXLEDYAFNFELILEEIARLFESGXXKDEAEK<br>AKCMKEWMKRIKTXXXEDEQEEMANAIITILQSWIFS* (SEQ ID NO: 281) |
| Neoleukin-2/15_E69C | | PKKKIQLHAEHALYDALMILNIXXXXXXXXXXXLEDYAFNFELILEEIARLFESGXXKDEAEK<br>AKRMKCWMKRIKTXXXEDEQEEMANAIITILQSWIFS* (SEQ ID NO: 282) |
| Neoleukin-2/15_R73C | | PKKKIQLHAEHALYDALMILNIXXXXXXXXXXXLEDYAFNFEL1LEEIARLFESGXXKDEAEK<br>AKRMKEWMKCIKTXXXEDEQEEMANAIITILQSWIFS* (SEQ ID NO: 283) |

TABLE 1-continued

| Name | Domain arrangement | Sequence |
|---|---|---|
| Neoleukin-2/15_777C | | PKKKIQLHAEHALYDALMILNIXXXXXXXXXXXXLEDYAFNFELILEEIARLFESGXXKDEAEK AKRMKEWMKRIKTCASEDEQEEMANAIITILQSWIFS* (SEQ ID NO: 284) |
| Neoleukin-2/15_E82C | | PKKKIQLHAEHALYDALMILNIXXXXXXXXXXXXLEDYAFNFELILEEIARLFESGXXKDEAEK AKRMKEWMKRIKTXXXEDCQEEMANAIITILQSWIFS* (SEQ ID NO: 285) |
| Neoleukin-2/15_E85C | | PKKKIQLHAEHALYDALMILNIXXXXXXXXXXXXLEDYAFNFELILEEIARLFESGXXKDEAEK AKRMKEWMKRIKTXXXEDEQECMANAIITILQSWIFS* (SEQ ID NO: 286) |
| Neoleukin-2/15_R50C_R73C | | PKKKIQLHAEHALYDALMILNIXXXXXXXXXXXXLEDYAFNFELILEEIACLFESGXXKDEAEK AKRMKEWMKCIKTXXXEDEQEEMANAIITILQSWIFS* (SEQ ID NO: 287) |
| Neoleukin-2/15_E53C_R73C | | PKKKIQLHAEHALYDALMILNIXXXXXXXXXXXXLEDYAFNFELILERIARLFCSGXXKDEAEK AKRMKEWMKCIKTXXXEDEQEEMANAIITILQSWIFS* (SEQ ID NO: 288) |
| Neoleukin-2/15_56C_R73C | | PKKKIQLHAEHALYDALMILNIXXXXXXXXXXXXLEDYAFNFELILEEIARLFESGCQKDEAEK AKRMKEWMKCIKTXXXEDEQEEMANAIITILQSWIFS* (SEQ ID NO: 289) |
| Neoleukin-2/15_K58C_R73C | | PKKKIQLHAEHALYDALMILNIXXXXXXXXXXXXLEDYAFNFELILERIARLFESGXXCDEAEK AKRMKEWMKCIKTXXXEDEQEEMANAIITILQSWIFS* (SEQ ID NO: 290) |
| Neoleukin-2/15_D59C_R73C | | PKKKIQLHAEHALYDALMILNIXXXXXXXXXXXXLEDYAFNFELILERIARLFESGXXKCEAEK AERMKEWMKCIKTXXXEDEQEEMANAIITILQSWIFS* (SEQ ID NO: 291) |
| Neoleukin-2/15_R66C_R73C | | PKKKIQLHAEHALYDALMILNIXXXXXXXXXXXXLEDYAFNFELILERIARLFESGXXKDEAEK AKCMKEWMKCIKTXXXEDEQEEMANAIITILQSWIFS* (SEQ ID NO: 292) |
| Neoleukin-2/15_R50C_E82C | | PKKKIQLHAEHALYDALMILNIXXXXXXXXXXXXLEDYAFNFELILEEIACLFESGXXKDEAEK AKRMKEWMKRIKTXXXEDCQEEMANAIITILQSWIFS* (SEQ ID NO: 293) |
| Neoleukin-2/15_E53C_E82C | | PKKKIQLHAEHALYDALMILNIXXXXXXXXXXXXLEDYAFNFELTLEEIARLFCSGXXKDEAEK AERMKEWMKRIKTXXXEDCQEEMANAIITILQSWIFS* (SEQ ID NO: 294) |
| Neoleukin-2/15_D56C_E82C | | PKKKIQLHAEHALYDALMILNIXXXXXXXXXXXXLEDYAFNFELILEEIARLFESGCQKDEAEK AKRMKEWMKRIKTXXXEDCQEEMANAIITILQSWIFS* (SEQ ID NO: 295) |
| Neoleukin-2/15_K58C_E82C | | PKKKIQLHAEHALYDALMILNIXXXXXXXXXXXXLEDYAFNFELILEEIARLFESGXXCDEAEK AKRMKEWMKRIKTXXXEDCQEEMANAIITILQSWIFS* (SEQ ID NO: 296) |
| Neoleukin-2/15_D59C_E82C | | PKKKIQLHAEHALYDALMILNIXXXXXXXXXXXXLEDYAFNFELILEEIARLFESGXXKCEAEK AFFMKEWMKPIKTXXXEDCQEEMANATITILQSWITS* (SEQ ID NO: 297) |
| Neoleukin-2/15_E62C_E82C | | PKKKIQLHAEHALYDALMILNIXXXXXXXXXXXXLEDYAFNFELTLEEIARLFESGXXKDEACK AKRMFEWMKRIFTXXXEDCQEEMANAIITTLQSWIFS* (SEQ ID NO: 298) |
| Neoleukin-2/15_R66C_E82C | | PKKKIQLHAEHALYDALMILNIXXXXXXXXXXXXLEDYAFNFELILEEIARLFESGXXKDEAEK AKCMKEWMKRIKTXXXEDCQEEMANALLTILQSWIFS* (SEQ ID NO: 299) |
| Neoleukin-2/15_E69C_E82C | | PKKKIQLHAEHALYDALMILNIXXXXXXXXXXXXLEDYAFNFELILEEIARLFESGXXKDEAEK AKRMKCWMKRIKTXXXEDCQEEMANAIITILQSWIFS* (SEQ ID NO: 300) |

In a specific embodiment, X1, X2, X3, and X4, respectively, are 25%, 27%, 30%, 35%, 40%, 45%, 50%, 55%, 60%, 65%, 70%, 75%, 80%, 85%, 90%, 95%, 98%, or 100% identical to, respectively, X1, X2, X3, and X4 domains (as defined in Table 1 (though listed as H1, H2, H3, and H4 domains) present within the amino acid sequence of SEQ ID NO:90 version 1 or 2. which have the same primary amino acid sequence but which differ slightly in optional/variable linker residues. In various embodiments, this embodiment may include variants of X1, X2, X3, and/or X4 domains present in SEQ ID NO:90 version 1 or 2 that incorporate the mutations relative to the SEQ ID NO:90 primary amino acid sequence shown in SEQ ID NOS:275-300.

In one embodiment of any embodiment or combination of embodiments disclosed herein, X1, X2, X3, and X4 are alpha-helical domains. In another embodiment, the amino acid length of each of X1, X2, X3 and X4 is independently at least about 8, 10, 12, 14, 16, 19, or more amino acids in length. In other embodiments, the amino acid length of each of X1, X2, X3 and X4 is independently no more than 1000, 500, 400, 300, 200, 100, or 50 amino acids in length. In various further embodiments, the amino acid length of each of X1, X2, X3 and X4 is independently between about 8-1000, 8-500, 8-400, 8-300, 8-200, 8-100, 8-50, 10-1000, 10-500, 10-400, 10-300, 10-200, 10-100, 10-50, 12-1000, 12-500, 12-400, 12-300, 12-200, 12-100, 12-50, 14-1000, 14-500, 14-400, 14-300, 14-200, 14-100, 14-50, 16-1000, 16-500, 16-400, 16-300, 16-200, 16-100, 16-50, 19-1000, 19-500, 19-400, 19-300, 19-200, 19-100, or about 19-50 amino acids in length.

In one embodiment, the first polypeptide component and/or the second polypeptide component includes at least one disulfide bond.

In another embodiment, the first polypeptide component and the second polypeptide component are non-covalently associated. As noted herein, the first polypeptide component and the second polypeptide component are not active receptor agonists individually, and wherein the first polypeptide component and the second polypeptide interact to form an active agonist of IL-2 receptor β$γ_c$ heterodimer (IL-2Rβ $γ_c$),IL-4 receptor α$γ_c$heterodimer (IL-4Rα$γ_c$), IL-13 alpha, or IL-4Ralpha/IL13Ralpha heterodimer. Thus, in this embodiment the first polypeptide and the second polypeptide may interact to form an active agonist. This interaction may be any suitable interaction, such as a non-covalent interaction. The interaction may comprise direct non-covalent binding of the first and second polypeptides, or an indirect interaction In one embodiment, the first polypeptide component and the second polypeptide component are indirectly bound to each other through a receptor, such as an IL-2 receptor β$γ_c$, heterodimer (IL-2Rβ$γ_c$), an IL-4 receptor α$γ_c$heterodimer (IL-4Rα$γ_c$), IL-13 alpha, or an IL-4Ralpha/IL13Ralpha heterodimer.

Methods of determining binding to receptors are known in the art and described herein, e.g., bio-Layer Interferometry binding assays. In some embodiments when the first polypeptide component and the second polypeptide interact at their intended receptor, they co-localize to bind to that receptor with a binding affinity of 1000 nm or less, 200 nm or less, 100 nm or less, 50 nM or less, or 25 nM or less. For example, a split IL-2 mimetic of the present invention will co-localize to bind to the IL-2 receptor βY, heterodimer (IL-2Rβ$γ_c$) with a binding affinity of 1000 nm or less, 200 nm or less, 100 nm or less, 50 nM or less, or 25 nM or less. Similarly, as an example, a split IL-4 mimetic of the present invention will co-localize to bind to the IL-4 receptor α $γ_c$heterodimer (IL-4Rα$γ_c$) with a binding affinity of 1000 nm or less, 200 nm or less, 100 nm or less, 50 nM or less, or 25 nM or less. In some aspects, agonism of the receptor to which the split mimetics co-localize and bind is measured by STAT5 phosphorylation.

In another aspect, the disclosure provides polypeptides comprising 1, 2, or 3, but not all 4 domains X1, X2, X3, and X4, wherein:
(a) X1, when present, is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (PKKKIQ)LHAEHALYDAL(MILNI); (SEQ ID NO: 4);
(b) X2, when present, is any helical peptide domain;
(c) X3, when present, is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to the full length of peptide (LE)DYAFNFELILEE((IARLFESG) (SEQ ID NO:5); and
(d) X4, when present, is a peptide comprising the amino acid sequence at least 25%, 27%, 30%, 35%, 40%, 45%, 50%, 55%, 60%, 65%, 70%, 75%, 80%, 85%, 90%, 95%, 98%, OR 100% IDENTICAL TO THE FULL LENGTH OF PEPTIDE (EDEQEEMANAI) ITILQSWIF(S) (SEQ ID NO:6); and
amino acid residues in parentheses may be present or absent.

The polypeptides of this aspect can be used, for example, to generate the conditionally active receptor agonists of any embodiment or combination of embodiments disclosed herein (i.e.: the polypeptides of this aspect are either the first polypeptide or the second polypeptide of the conditionally active receptor agonists of the disclosure). Thus, as will be clear to those of skill in the art, all embodiments and combinations of embodiments of the first and second polypeptides disclosed above, all embodiments and combinations of embodiments of the X1, X2, X3, and X4 domains described above are equally applicable to the polypeptides of this aspect of the disclosure. In one embodiment, (a) amino acid (AA) substitutions in X1 relative to the AA sequence of SEQ ID NO:4 occur at no more than 3 AA residues marked in bold font, or occur at no more than 2 AA residues marked in bold font, or occur at no more than 1 AA residue marked in bold font, or do not occur at AA residues marked in bold font;

(b) AA substitutions in X3 relative to the AA sequence of SEQ ID NO:5 occur at no more than 3 AA residues marked in bold font, or occur at no more than 2 AA residues marked in bold font, or occur at no more than 1 AA residue marked in bold font, or do not occur at AA residues marked in bold font; and/or (c) AA substitutions in X4 relative to the AA sequence of SEQ ID NO:6 occur at no more than 2 AA residues marked in bold font, or occur at no more than 1 AA residue marked in bold font, or do not occur at AA residues marked in bold font.

In another embodiment, AA substitutions in X2 relative to the AA sequence of SEQ ID NO:7 do not occur at AA residues marked in bold font.

In various embodiments, the polypeptide may be selected from the group consisting of:

(i) a polypeptide comprising X1 and excluding X2, X3, and X4;

(ii) a polypeptide comprising X2 and excluding X1, X3, and X4;

(iii) a polypeptide comprising X3 and excluding X1, X2, and X4;

(iv) a polypeptide comprising X4 and excluding X1, X2, and X3;

(v) a polypeptide comprising X1 and X2, and excluding X3 and X4;

(vi) a polypeptide comprising X1 and X3, and excluding X2 and X4;

(vii) a polypeptide comprising X1 and X4, and excluding X2 and X3;

(viii) a polypeptide comprising X2 and X3, and excluding X1 and X4;

(ix) a polypeptide comprising X2 and X4, and excluding X1 and X3;

(x) a polypeptide comprising X3 and X4, and excluding X1 and X2;

(xi) a polypeptide comprising X1, X2, and X3 and excluding X4;

(xii) a polypeptide comprising X1, X2, and X4 and excluding X3;

(xiii) a polypeptide comprising X1, X3, and X4 and excluding X2: and (xiv) a polypeptide comprising X2, X3, and X4 and excluding X1.

In one embodiment, the polypeptide comprise the amino acid sequence at least 25%, 27%, 30%, 35%, 40%, 45%, 50%, 55%, 60%, 65%, 70%, 75%, 80%, 85%, 90%, 95%, 98%, or 100% identical to, a first polypeptide or a second polypeptide listed below (underlined residues are optional and each optional residue, when present, may comprise any amino acid):

(i)
First polypeptide X1 (Neo2A)
(SEQ ID NO: 256)
PKKKIQLHAEHALYDALMILNIVKTNS
and Second polypeptide: X3-X2'-X4 (Neo2B)
(SEQ ID NO: 257)
TNSPPAEEKLEDYAFNFELILEEIARLFESGDQKDEAEAKRMKEWMKRIKTTASEDEQEEMANAIIT

ILQSWIFS (ii)
First polypeptide X1-X3-X2'
(SEQ ID NO: 258)
PKKKIQLHAEHALYDALMILNIVKTNSPPAEEKLEADYAFNFELILEEIARLFESGDQKDEAEKAKRMK EWMKRIKTTAS
and Second polypeptide X4
(SEQ ID NO: 259)
TTASEDEQEEMANAIITILQSWIFS;

(iii)
First polypeptide X1-X3
(SEQ ID NO: 260)
PKKKIQLHAEHALYDALMILNIVKTNSPPAEKLEDYAFNFELILEEIARLFESGD
and Second polypeptide X2-X4
(SEQ ID NO: 261)
DQKDEAEKAKRMKEWMKRIKTTASEDEQEEMANAIITILQSWIFS (iv)
First polypeptide X1 (Neo4A)
(SEQ ID NO: 262)
PKKKIQIMAEELKDALSILNIVKTNS Second polypeptide X3-X2'-X4 (Neo4B)
(SEQ ID NO: 263)
TNSPPAEEQLERFAKRFERNLWGIARLEESGDQKDEAEKAKRMIEWMKRIKTTASEDEQEEMANAIIT

ILQSWFFS (v)
First polypeptide X1 (Neo2A)
(SEQ ID NO: 311)
PKKKIQLHAEHALYDALMILNIXXXXX
and Second polypeptide: X3-X2'-X4 (Neo2B)
(SEQ ID NO: 264)
XXXXXXXXXLEDYAFNFELILEEIARLFESGXXKDEAEKAKPREEWMKRIKTXXXEDEQEEMANAIIT

ILQSWIFS (vi)
First polypeptide X1-X3-X2'
(SEQ ID NO: 265)
PKKKIQLHAEHALYDALMILNIXXXXXXXXXXLEDYAFNFELILEEIARLFESGXXKDEAEKAKRMK EWMKRIKTTTAS
and Second polypeptide X4
(SEQ ID NO: 266)
XXXXXDEQEEMANIITTILQSWIFS;

(vii)
First polypeptide X1-X3
(SEQ ID NO: 267)
PKEKIQLHAEHALYDADMILNIXXXXXXXXXXXLEDYAFNFELILEEIARLFESXXGD
and Second polypeptide X2-X4
(SEQ ID NO: 268)
DQKDEAEKAKRMKEWNKRIKTXXXEDEQEEMANAIITILQSWIFS (viii)
First polypeptide X1 (Neo4A)

(SEQ ID NO: 269)
PKKKIQIMAEEALKDAISILNIXXXXX

Second polypeptide X3-X2'-X4 (Neo4B)

(SEQ ID NO: 270)
XXXXXXXXQLERFAKRFERNLWGIARLFESGXXKDEAEKAKRMIEWMKRIKTXXXEDEQEEMANAIIT

ILQSWFFS (ix)
First polypeptide >Neo4_H1-H3'

(SEQ ID NO: 312)
PKKKIQIMAEEALKDALSILNIVKTNSPPAEEQLERFAKRFERNLWGIARLFESGD

Second polypeptide >Neo4_H2-H4

(SEQ ID NO: 313)
DQKDEAEKAKRMIEWMKRIKTTASEDEQEEMANAIITILQSWFFS (x)
First polypeptide >Neo4_H1-H3'

(SEQ ID NO: 314)
PKKKIQIMAEEALKDALSILNIXXXXXXXXXXQLERFAKRFERNLWGIARLFESXX

Second polypeptide >Neo4_H2-H4

(SEQ ID NO: 315)
XXKDEAEKAKRMIEWMKRIKXXXXEDEQEEMANAIITILQSWFFS (xi)
First polypeptide Neo4_H1-H3'-H2

(SEQ ID NO: 316)
PKKKIQIMAEEALKDALSILNIVKTNSPPAEEQLERFAKRFERNLWGIARLFESGDQKDEAEKAKRMI

EWMKRIKTTA

Second polypeptide Neo4_H4

(SEQ ID NO: 317)
TTASEDEQEEMANAIITILQSWFFS (xii)
First polypeptide Neo4_H1-H3'-H2

(SEQ ID NO: 318)
PKKKIQIMAEEALKDALSILNIXXXXXXXXXXXLERFAKRFERNLWGIARLFESXXXXKDEAEKAKRMI

EWMKRIKXXX

Second polypeptide Neo4_H4

(SEQ ID NO: 319)
XXXXXDEQEEMANAIITILQSWFFS;

(xiii)
First polypeptide (X1)

(SEQ ID NO: 323)
PKKKIQLHAEHALYDALMILNIVGGSS,
or (SEQ ID NO: 324)
SKEAIQLHAEHALYDALMILNIVKTNS,
or (SEQ ID NO: 325)
PIQLHAEHALYDALMILNIV

Second polypeptide (X3-X2'-X4)

(SEQ ID NO: 326)
PKLEDYAFNFELILEEIARLFESGDQKDEAEKAKRMKEWMKRIKTTASEDEQEEMANAIITILQ

SWIFS;
or (SEQ ID NO: 327)
GSGSSGGLEDYAFNFELILEEIARLFESGGSSGGKDEAEKAKRMKEWMKRITGGSSGGDEQEEMANAI

ITILQSWIFS;
or (SEQ ID NO: 328)
GGSSGGLEDYAFNFELILEEIARLFESGGSSGGGGEAEKAKRMKEWMKRIGGSSGGDEQEEMANAIIT

ILQSWIFS.

In exemplary embodiments, the polypeptide comprises an amino acid sequence at least 80% identical to a first or second polypeptides shown in embodiments (i)-(viii) above (underlined residues or "X" residues" are optional and each residue of the optional domain, when present, may comprise any amino acid).

In exemplary embodiments, the polypeptide comprises an amino acid sequence at least 90% identical to a first or second polypeptides shown in embodiments (i)-(viii) above (underlined residues or "X" residues" are optional and each residue of the optional domain, when present, may comprise any amino acid).

In exemplary embodiments, the polypeptide comprises an amino acid sequence at least 100% identical to a first or second polypeptides shown in embodiments (i)-(viii) above (underlined residues or "X" residues" are optional and each residue of the optional domain, when present, may comprise any amino acid).

In another embodiment, X1, X2, X3, and X4, when present, comprise the amino acid sequence at least 25%, 27%, 30%, 35%, 40%, 45%, 50%, 55%, 60%, 65%, 70%, 75%, 80%, 85%, 90%, 95%, 98%, or 100% identical to, respectively, X1, X2, X3, and X4 domains (as defined in Table 1) present within the amino acid sequence selected from the group consisting of SEQ ID NO:11-94, 190-216, 247, and SEQ ID NOS275-300. In a specific embodiment, X1, X2, X3, and X4, when present, comprise the amino acid sequence at least 25%, 27%, 30%, 35%, 40%, 45%, 50%, 55%, 60%, 65%, 70%, 75%, 80%, 85%, 90%, 95%, 98%, or 100% identical to, respectively, X1, X2, X3, and X4 domains (as defined in Table 1 (though listed as H1, H2, H3, and H4 domains) present within the amino acid sequence of SEQ ID NO:90 versions 1 or 2, which have the same primary amino acid sequence but which differ slightly in optional/variable linker residues. In various embodiments, this embodiment may include variants of X1, X2, X3, and/or X4 domains present SEQ ID NO:90 version 1 or 2 that incorporate the mutations relative to the SEQ ID NO:90 primary amino acid sequence shown SEQ ID NOS:275-300.

The first polypeptides, second polypeptides, and polypeptides described herein may be chemically synthesized or recombinantly expressed (when the polypeptide is genetically encodable). The polypeptides may be linked to other compounds, such as stabilization compounds to promote an increased half-life in vivo, including but not limited to albumin, PEGylation (attachment of one or more polyethylene glycol chains), HESylation, PASylation, glycosylation, or may be produced as an Fc-fusion or in deimmunized variants. Such linkage can be covalent or non-covalent. For example, addition of polyethylene glycol ("PEG") containing moieties may comprise attachment of a PEG group linked to maleimide group ("PEG-MAL") to a cysteine residue of the polypeptide. Suitable examples of PEG-MAL are methoxy PEG-MAL 5 kD; methoxy PEG-MAL 20 kD; methoxy (PEG)2-MAL 40 kD; methoxy PEG (MAL)2 5 kD; methoxy PEG(MAL)2 20 kD; methoxy PEG(MAL)2 40 kD; or any combination thereof. See also U.S. Pat. No. 8,148,109. In other embodiments, the PEG may comprise branched chain PEGS and/or multiple PEG chains.

In one embodiment, the stabilization compound, including but not limited to a PEG-containing moiety, is linked at a cysteine residue in the polypeptide. In another embodiment, the cysteine residue is present in the X2 domain. In some embodiments, the cysteine residue is present, for example, in any one of a number of positions in the X2 domain. In some such embodiments, the X2 domain is at least 19 amino acids in length and the cysteine residue is at positions 1, 2, 5, 9 or 16 relative to those 19 amino acids. In a further embodiment, the stabilization compound, including but not limited to a PEG-containing moiety, is linked to the cysteine residue via a maleimide group.

In a further embodiment, the first polypeptides, second polypeptides, and polypeptides may further comprise a targeting domain. In this embodiment, the conditionally receptor agonist can be directed to a target of interest. The targeting domain may be covalently or non-covalently bound to the first polypeptide, second polypeptide, and/or polypeptide. In embodiments where the targeting domain is non-covalently bound, any suitable means for such non-covalent binding may be used, including but not limited to streptavidin-biotin linkers.

In another embodiment, the targeting domain, when present, is a translational fusion with the polypeptide. In this embodiment, the polypeptide and the targeting domain may directly abut each other in the translational fusion or may be linked by a polypeptide linker suitable for an intended purpose. Exemplary such linkers include, but are not limited, to those disclosed in WO2016178905, WO2018153865 (in particular, at page 13), and WO 2018170179 (in particular, at paragraphs [0316]-[0317]). In other embodiments, suitable linkers include, but are not limited to peptide linkers, such as GGGGG (SEQ ID NO: 95), GSGGG (SEQ ID NO: 96), GGGGGG (SEQ ID NO: 97), GGSGGG (SEQ ID NO: 98), GGSGGSGGGSGGSGSG (SEQ ID NO: 99), GSGGSGGGSGGSGSG (SEQ ID NO: 100), GGSGGSGGGSGGSGGGGSGGSGGGSGGGGS (SEQ ID NO: 101), and [GGGGX]$_n$ (SEQ ID NO: 102), where X is Q, E or S and n is 2-5.

The targeting domains are polypeptide domains or small molecules that bind to a target of interest. In one non-limiting embodiment, the targeting domain binds to a cell surface protein; in this embodiment, the cell may be any cell type of interest that includes a surface protein that can be bound by a suitable targeting domain. In one embodiment, the cell surface proteins are present on the surface of cells selected from the group consisting of tumor cells, tumor vascular component cells, tumor microenvironment cells (e.g. fibroblasts, infiltrating immune cells, or stromal elements), other cancer cells and immune cells (including but not limited to CD8+ T cells, T-regulatory cells, dendritic cells, NK cells, or macrophages). When the cell surface protein is on the surface of a tumor cell, vascular component cell, or tumor microenvironment cell (e.g. fibroblasts, infiltrating immune cells, or stromal elements), any suitable tumor cell, vascular component cell, or tumor microenvironment cell surface marker may be targeted, including but not limited to EGFR, EGFRvIII, Her2, HER3, EpCAM, MSLN, MUC16, PSMA, TROP2, ROR1, RON, PD-L1, CD47, CTLA-4, CD5, CD19, CD20, CD25, CD37, CD30, CD33, CD40, CD45, CAMPATH-1, BCMA, CS-1, PD-L1, B7-H3, B7-DC, HLD-DR, carcinoembryonic antigen (CEA), TAG-72, EpCAM, MUC1, folate-binding protein, A33, G250, prostate-specific membrane antigen (PSMA), ferritin, GD2, GD3, GM2, Le$^v$, CA-125, CA19-9, epidermal growth factor, p185HER2, IL-2 receptor. EGFRvIII (de2-7 EGFR), fibroblast activation protein, tenascin, a metalloproteinase, endosialin, vascular endothelial growth factor, avB3, WT1, LMP2, HPV E6, HPV E7, Her-2/neu, MAGE A3, p53 nonmutant, NY-ESO-1, MelanA/MART1, Ras mutant, gp100, p53 mutant, PRI, bcr-abl, tyrosinase, survivin, PSA, hTERT, a Sarcoma translocation breakpoint protein, EphA2, PAP, ML-IAP, AFP, ERG, NA17, PAX3, ALK, androgen receptor, cyclin B 1, polysialic acid, MYCN, RhoC, TRP-2, fucosyl GM1, mesothelin (MSLN), PSCA, MAGE A1, sLe(animal), CYP1B1, PLAV1, GM3, BORIS, Tn, GloboH, ETV6-AML, NY-BR-1, ROSS, SART3, STn, Carbonic anhydrase IX, PAX5, OY-TESL Sperm protein 17, LCK, HMWMAA, AKAP-4, SSX2, XAGE 1, Legumain, Tie 3, VEGFR2, MAD-CT-1, PDGFR-B, MAD-CT-2, ROR2, TRAIL1, MUC16, MAGE A4, MAGE C2, GAGE, EGFR, CMET, HER3, MUC15, CA6, NAPI2B, TROP2, CLDN6, CLDN16, CLDN18.2. CLorf186, RON, LY6E, FRA, DLL3, PTK7, STRA6, TMPRSS3, TMPRSS4, TMEM238, UPK1B, VTCN1, LIV1, ROR1, Fos-related antigen I, BMPR1B (bone morphogenetic protein receptor-type IB, Genbank accession no. NM. 001203); E6 (LAT1. SLC7A5, Genbank accession no. NM-003486); STEAP1 (six transmembrane epithelial antigen of prostate, Genbank accession no. NM 012449); 0772P (CA125, MUC16, Genbank accession no. AF361486): MPF (MPF, MSLN, SMR, megakaryocyte potentiating factor, mesothelin, Genbank accession no. NM 005823); Napi3b (NAPI-3B, NPTIIb, SLC34A2, solute carrier family 34 (sodium phosphate), member 2, type II sodium-dependent phosphate transporter 3b, Genbank accession no. NM 006424); Sema 5b (FLJ10372, KIAA1445, Mm. 42015, SEMA5B, SEMAG, Semaphorin 5b Flog. sema domain, seven thrombospondin repeats (type 1 and type 1-like), transmembrane domain (TM) and short cytoplasmic domain, (semaphorin) 5B, Genbank accession no. AB040878); PSCA hlg (2700050C12Rik, C530008O16Rik, RIKEN cDNA 2700050C12, RIKEN cDNA 2700050C12 gene, Genbank accession no. AY358628); ETBR (Endothelin type B receptor, Genbank accession no. AY275463); MSG783 (RNF124, hypothetical protein FLJ20315, Genbank accession no. NM 017763); STEAP2 (HGNC.sub.-8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); TrpM4 (BR22450, FLJ20041, TRPM4, TRPM4B, transient receptor potential cation channel, subfamily M, member 4, Genbank accession no. NM 017636); CRIPTO (CR, CR1, CRGF, CRIPTO, TDGF1, teratocarcinoma-derived growth factor, Genbank accession no. NP003203 or NM003212); CD21 (CR2 (Complement receptor 2) or C3DR(C3d/Epstein Barr virus receptor) or Hs. 73792, Genbank accession no. M26004); CD79b (IGb (immunoglobulin-associated beta), B29. Genbank accession no. NM 000626); FcRH2 (IFGP4, IRTA4, SPAP1A (SH2 domain containing phosphatase anchor protein 1a), SPAP1B, SPAP1C, Genbank accession no. NM030764); HER2 (Genbank accession no. M11730); NCA (Genbank accession no. M18728); MDP (Genbank accession no. BC017023); IL20R.alpha. (Genbank accession no. AF18497); Brevican (Genbank accession no. AF229053); Ephb2R (Genbank accession no. NM004442); ASLG659 (Genbank accession no. AX092328); PSCA (Genbank accession no. AJ297436); GEDA (Genbank accession no. AY260763); BAFF-R (Genbank accession no. NP443177.); CD22 (Genbank accession no. NP-001762.1); CD79a (CD79A, CD79.alpha., immunoglobulin-associated alpha, a B cell-specific protein that covalently interacts with Ig beta (CD79B) and forms a complex on the surface with Ig M molecules, transduces a signal involved in B-cell differentiation, Genbank accession No. NP001774.1); CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP001707.1); HLA-DOB (Beta subunit of MI-1C class II molecule (Ia antigen) that binds peptides and presents them to CD4+ T lymphocytes. Genbank accession No. NP002111.1); P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP002552.2); CD72 (B-cell differentiation antigen CD72, Lyb-2, Genbank accession No. NP001773.1); LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank accession No. NP005573.1); FCRH1 (Fc receptor-like protein 1, a putative receptor for the immunoglobulin Fc domain that contains C2 type Ig-like and ITAM domains, may have a role in B-lymphocyte differentiation, Genbank accession No. NP443170.1); or IRTA2 (Immunoglobulin superfamily receptor translocation associated 2, a putative immunoreceptor with possible roles in B cell development and lymphomagenesis; deregulation of the gene by translocation occurs in some B cell malignancies, Genbank accession No. NP112571.1).

In another embodiment, the targeting domain binds to immune cell surface markers. In this embodiment, the target may be cell surface proteins on any suitable immune cell, including but not limited to CD8+ T cells, T-regulatory cells, dendritic cells, NK cells or macrophages. The targeting domain may target any suitable immune cell surface marker (whether an endogenous or an engineered immune cell, including but not limited to engineered CAR-T cells), including but not limited to CD3, CD4, CD8, CD19, CD20, CD21, CD25, CD37, CD30, CD33, CD40, CD68, CD123, CD254, PD-1, B7-H3, and CTLA-4. In another embodiment, the targeting domain binds to PD-1, PDL-1, CTLA-4, TROP2, B7-H3, CD33, CD22, carbonic anhydrase IX, CD123, Nectin-4, tissue factor antigen, CD154, B7-H3, B7-H4, FAP (fibroblast activation protein) or MUC16, and/or wherein the targeting domain binds to PD-1, PDL-1, CTLA-4, TROP2, B7-H3, CD33, CD22, carbonic anhydrase IX, CD123, Nectin-4, tissue factor antigen, CD154, B7-H3, B7-H4. FAP (fibroblast activation protein) or MUC16.

In all these embodiments, the targeting domains can be any suitable polypeptides that bind to targets of interest and can be incorporated into the polypeptide of the disclosure. In non-limiting embodiments, the targeting domain may include but is not limited to an scFv, a F(ab), a F(ab')$_2$, a B cell receptor (BCR), a DARPin, an affibody, a monobody, a nanobody, diabody, an antibody (including a monospecific or bispecific antibody); a cell-targeting oligopeptide including but not limited to RGD integrin-binding peptides, de novo designed binders, aptamers, a bicycle peptide, conotoxins, small molecules such as folic acid, and a virus that binds to the cell surface.

The first polypeptides, second polypeptides, and polypeptides of the disclosure may include additional residues at the N-terminus, C-terminus, or both that are not present in the first polypeptides, second polypeptides, and polypeptides of the disclosure; these additional residues are not included in determining the percent identity of the polypeptides or peptide domains of the disclosure relative to the reference polypeptide. Such residues may be any residues suitable for an intended use, including but not limited to detection tags (i.e.: fluorescent proteins, antibody epitope tags, etc.), adaptors, ligands suitable for purposes of purification (His tags, etc.), other peptide domains that add functionality to the polypeptides, etc. Residues suitable for attachment of such groups may include cysteine, lysine or p-acetylphenylalanine residues or can be tags, such as amino acid tags suitable for reaction with transglutaminases as disclosed in U.S. Pat. Nos. 9,676,871 and 9,777,070.

In a further aspect, the present invention provides nucleic acids, including isolated nucleic acids, encoding the first polypeptides, second polypeptides, and polypeptides of the present disclosure that can be genetically encoded. The isolated nucleic acid sequence may comprise RNA or DNA. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In another aspect, the present disclosure provides expression vectors comprising the nucleic acid of any aspect of the invention operatively linked to a suitable control sequence. "Expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors include but are not limited to, plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector (including but not limited to a retroviral vector or oncolytic virus), or any other suitable expression vector. In some embodiments, the expression vector can be administered in the methods of the disclosure to express the polypeptides in vivo for therapeutic benefit. In non-limiting embodiments, the expression vectors can be used to transfect or transduce cell therapeutic targets (including but not limited to CAR-T cells or tumor cells) to effect the therapeutic methods disclosed herein.

In a further aspect, the present disclosure provides host cells that comprise the expression vectors and/or nucleic acids disclosed herein, wherein the host cells can be either prokaryotic or eukaryotic. The cells can be transiently or stably engineered to incorporate the expression vector of the invention, using techniques including but not limited to bacterial transformations, calcium phosphate co-precipitation, electroporation, or liposome mediated-. DEAE dextran mediated-, polycationic mediated-, or viral mediated transfection. (See, for example, *Molecular Cloning: A Laboratory Manual* (Sambrook, et al., 1989, Cold Spring Harbor Laboratory Press); *Culture of Animal Cells: A Manual of Basic Technique, 2$^{nd}$ Ed.* (R. I. Freshney. 1987. Liss, Inc. New York, NY)). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium.

In another aspect, the present disclosure provides pharmaceutical compositions, comprising one or more conditionally active receptor agonist, polypeptide, nucleic acids, expression vectors, and/or host cells of any aspect or embodiment of the disclosure and a pharmaceutically acceptable carrier. The pharmaceutical compositions of the disclosure can be used, for example, in the methods of the disclosure described below. The pharmaceutical composition may comprise in addition to the polypeptide of the disclosure (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The conditionally active receptor agonists, polypeptides, nucleic acids, expression vectors, and/or host cells may be the sole active agent in the pharmaceutical composition, or the composition may further comprise one or more other active agents suitable for an intended use.

In a further aspect, the present disclosure provides methods for treating cancer, comprising administering to a subject in need thereof a therapeutically effective amount of the conditionally active receptor agonist, polypeptide, nucleic acids, expression vectors, and/or host cells of any embodiment or combination of embodiments disclosed herein under conditions wherein the first polypeptide component and the second polypeptide component interact at cells of the tumor to treat the cancer. In embodiments for administering the conditionally active receptor agonists, the first and second polypeptide may be administered together, or may be administered in separate pharmaceutical formulations.

As used herein, "treat" or "treating" means accomplishing one or more of the following: (a) reducing the size or volume of tumors and/or metastases in the subject: (b) limiting any increase in the size or volume of tumors and/or metastases in the subject: (c) increasing survival: (d) reducing the severity of symptoms associated with cancer; (e) limiting or preventing development of symptoms associated with cancer: and (f) inhibiting worsening of symptoms associated with cancer.

The methods can be used to treat any suitable cancer, including but not limited to colon cancer, melanoma, renal cell cancer, head and neck squamous cell cancer, gastric cancer, urothelial carcinoma. Hodgkin lymphoma, non-small cell lung cancer, small cell lung cancer, hepatocellular carcinoma, pancreatic cancer, Merkel cell carcinoma colorectal cancer, acute myeloid leukemia, acute lymphoblastic leukemia, chronic lymphocyte leukemia, non-Hodgkin lymphoma, multiple myeloma, ovarian cancer, cervical cancer, and any tumor types selected by a diagnostic test, such as microsatellite instability, tumor mutational burden, PD-L 1 expression level, or the immunoscore assay (as developed by the Society for Immunotherapy of Cancer).

The subject may be any subject that has cancer. In one embodiment, the subject is a mammal, including but not limited to humans, dogs, cats, horses, cattle, etc.

In one embodiment, the first targeting domain binds to a cell marker and the second targeting domain binds to a second and distinct cell marker, and wherein co-expression of these two markers on the same or nearby cells occurs more commonly in the tumor than in other tissues, and wherein the first polypeptide and the second polypeptide interact only after binding of the first targeting domain to the first cell marker and binding of the second targeting domain to the second cell marker. This embodiment, for example, employs two targeting domains that bind to separate markers that aren't themselves enriched on tumor cells, but for which the co-expression is enriched in the tumor.

In another embodiment, the first polypeptide component comprises a first targeting domain and the second polypeptide component comprises a second targeting domain, wherein the first targeting domain binds to a first tumor cell marker and the second targeting domain binds to a second tumor cell marker which may be the same or different than the first tumor cell marker, and wherein the first polypeptide and the second polypeptide interact only after binding of the first targeting domain to the first tumor cell marker and binding of the second targeting domain to the second tumor cell marker.

In another embodiment, the first polypeptide component comprises a first targeting domain and the second polypeptide component comprises a second targeting domain, wherein the first targeting domain binds to a tumor cell marker and the second targeting domain binds to an immune cell marker (including but not limited to CD8+ T cells, T-regulatory cells, dendritic cells, or macrophages), and wherein the first polypeptide and the second polypeptide interact only after binding of the first targeting domain to the tumor cell marker and binding of the second targeting domain to the immune cell marker.

In one embodiment, the first targeting domain binds to a cell marker and the second targeting domain binds to a second and distinct cell marker, and wherein co-expression of these two markers occur more commonly on tumor cells than on some other types of cells, and wherein the first polypeptide and the second polypeptide interact only after binding of the first targeting domain to the first cell marker and binding of the second targeting domain to the second cell marker on the same cell. This embodiment, for example, employs two targeting domains that bind to separate markers that aren't themselves enriched on tumor cells, but for which the co-expression is enriched in the tumor In a further embodiment, the first polypeptide component comprises a first targeting domain and the second polypeptide component comprises a second targeting domain, wherein the first targeting domain binds to a first immune cell marker (including but not limited to CD8+ T cells, T-regulatory cells, dendritic cells, or macrophages) and the second targeting domain binds to a second immune cell marker (including but not limited to CD8+ T cells. T-regulatory cells, dendritic cells, or macrophages) which may be the same or different than the first immune cell marker, and wherein the first polypeptide and the second polypeptide interact only after binding of the first targeting domain to the first immune cell marker and binding of the second targeting domain to the second immune cell marker.

In a further aspect, the present disclosure provides methods for modulating an immune response in a subject by administering to a subject a conditionally active receptor agonist, polypeptide, nucleic acid, expression vector, host cell, or the pharmaceutical composition of the present disclosure. In one embodiment, the method comprises administering to a subject a conditionally active receptor agonist under conditions wherein the first polypeptide component and the second polypeptide component interact at immune cells to modulate an immune response.

As used herein, an "immune response" being modulated refers to a response by a cell of the immune system, such as a B cell, T cell (CD4 or CD8), regulatory T cell, antigen-presenting cell, dendritic cell, monocyte, macrophage, NKT cell. NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response. In some embodiments of the compositions and methods described herein, an immune response being modulated is T-cell mediated.

In some aspects, the immune response is an anti-cancer immune response. In some such aspects, a conditionally active IL-2 mimetic described herein is administered to a subject having cancer to modulate an anti-cancer immune response in the subject.

In some aspects, the immune response is a tissue reparative immune response. In some such aspects, a conditionally active IL-4 mimetic described here is administered to a subject in need thereof to modulate a tissue reparative immune response in the subject.

In some aspects, the immune response is a wound healing immune response. In some such aspects, a conditionally active IL-4 mimetic described here is administered to a subject in need thereof to modulate a wound healing immune response in the subject.

In some aspects, methods are provided for modulating an immune response to a second therapeutic agent in a subject. In some such aspects, the method comprises administering a polypeptide of the present disclosure in combination with an effective amount of the second therapeutic agent to the subject. The second therapeutic agent can be, for example, a chemotherapeutic agent or an antigen-specific immunotherapeutic agent. In some aspects, the antigen-specific immunotherapeutic agent comprises chimeric antigen receptor T cells (CAR-T cells). In some aspects, the polypeptide of the present disclosure enhances the immune response of the subject to the therapeutic agent. The immune response can be enhanced, for example, by improving the T cell response (including CAR-T cell response), augmenting the innate T cell immune response, decreasing inflammation, inhibiting T regulatory cell activity, or combinations thereof.

In some aspects, a conditionally active cytokine mimetic of the present invention, e.g., a conditionally active IL-4 mimetic as described herein, will be impregnated to or otherwise associated with a biomaterial and the biomaterial will be introduced to a subject. In some aspects, the biomaterial will be a component of an implantable medical device and the device will be, for example, coated with the biomaterial. Such medical devices include, for example, vascular and arterial grafts. Conditionally active IL-4 and/or IL-4 associated biomaterials can be used, for example, to promote wound healing and/or tissue repair and regeneration.

In another aspect, the disclosure provides methods for agonizing the IL-2 receptor or the IL-4 receptor, comprising administering to a subject the conditionally active receptor agonist of any embodiment or combination of embodiments disclosed herein, under conditions wherein the first polypeptide component and the second polypeptide component interact at the receptor.

As used herein, a "therapeutically effective amount" refers to an amount of the conditionally active receptor agonist, polypeptide, nucleic acids, expression vectors, and/or host cells that is effective for treating and/or limiting the disease to be treated (e.g., cancer). The conditionally active receptor agonist, polypeptides, nucleic acids, expression vectors, and/or host cells are typically formulated as a pharmaceutical composition, such as those disclosed above, and can be administered via any suitable route, including but not limited to orally, by inhalation spray, ocularly, intravenously, subcutaneously, intraperitoneally, and intravascularly in dosage unit formulations containing conventional pharmaceutically acceptable carriers, adjuvants, and vehicles. In one particular embodiment, the polypeptides, nucleic acids, expression vectors, and/or host cells are administered mucosally, including but not limited to intraocular, inhaled, or intranasal administration. In another particular embodiment, the polypeptides, nucleic acids, expression vectors, and/or host cells are administered orally. Such particular embodiments can be administered via droplets, nebulizers, sprays, or other suitable formulations.

Any suitable dosage range may be used as determined by attending medical personnel. Dosage regimens can be adjusted to provide the optimum desired response (e.g., a therapeutic or prophylactic response). A suitable dosage range for the conditionally active receptor agonists or polypeptides may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. In some embodiments, the recommended dose could be lower than 0.1 mcg/kg, especially if administered locally. In other embodiments, the recommended dose could be based on weight/m$^2$ (i.e. body surface area), and/or it could be administered at a fixed dose (e.g., 0.05-100 mg). The conditionally active receptor agonists, polypeptides, nucleic acids, expression vectors, and/or host cells can be delivered in a single bolus, or may be administered more than once (e.g., 2, 3, 4, 5, or more times) as determined by an attending physician.

The conditionally active receptor agonists, polypeptides, nucleic acids, expression vectors, and/or host cells made be administered as the sole prophylactic or therapeutic agent, or may be administered together with (i.e.: combined or separately) one or more other prophylactic or therapeutic agents, including but not limited to tumor resection, chemotherapy, radiation therapy, immunotherapy, etc.

Numerous modifications and variations of the present disclosure are possible in light of the above teachings.

EXAMPLES

Example 1

A computational approach for designing de novo cytokine mimetics is described that recapitulate the functional sites of the natural cytokines, but otherwise are unrelated in topology or amino acid sequence. This strategy was used to design de novo non-split mimetics of IL-2 and interleukin-15 (IL-15) that bind to the IL-2 receptor $\beta \gamma_c$ heterodimer (IL-2R$\beta \gamma_c$), but have no binding site for IL-2R$\alpha$ or IL-15R$\alpha$. The designs are hyper-stable, bind to human and mouse IL-2R$\beta \gamma_c$ with higher affinity than the natural cytokines, and elicit downstream cell signaling independent of IL-2R$\alpha$ and IL-15R$\alpha$. Crystal structures of an experimentally optimized mimetic, neoleukin-2/15, are very close to the design model and provide the first structural information on the murine IL-2R$\beta \gamma_c$, complex. Neoleukin-2/15 has highly efficacious therapeutic activity compared to IL-2 in murine models of melanoma and colon cancer, with reduced toxicity and no signs of immunogenicity.

Figure 1A:
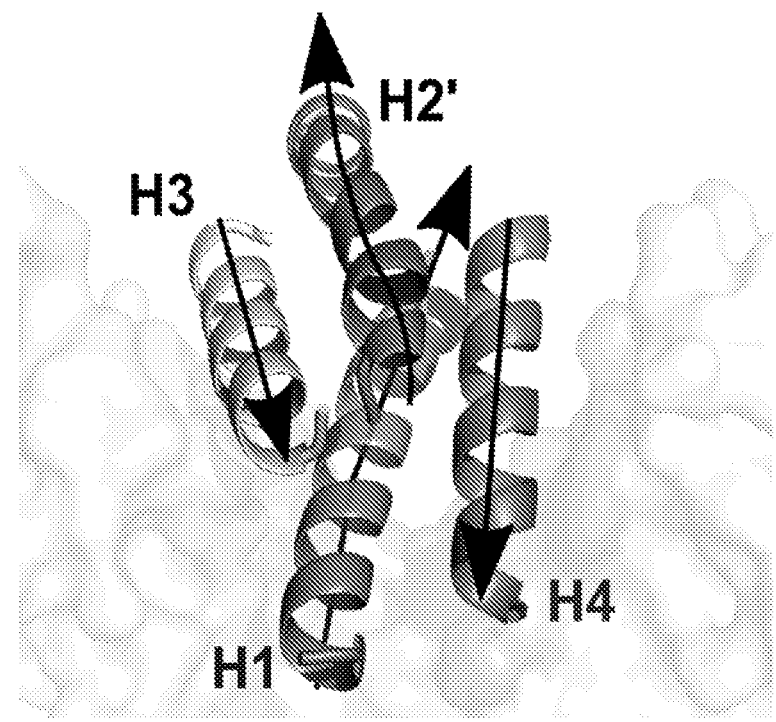
FIG. 1A-1C. Computational design of de novo cytokine mimetics.
Figure 1A:
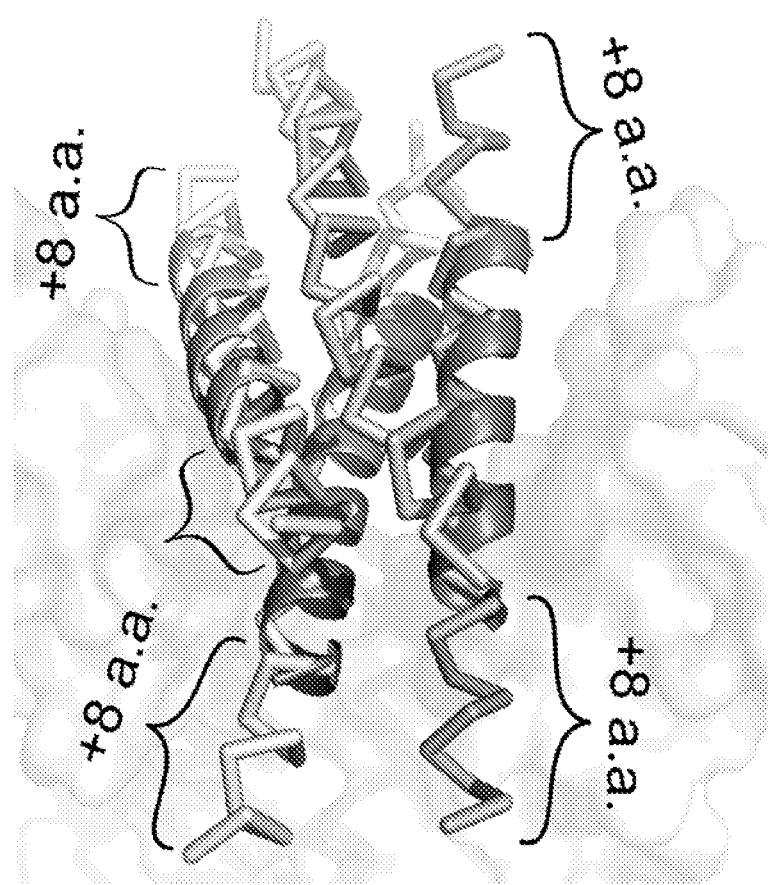
Figure 1B:
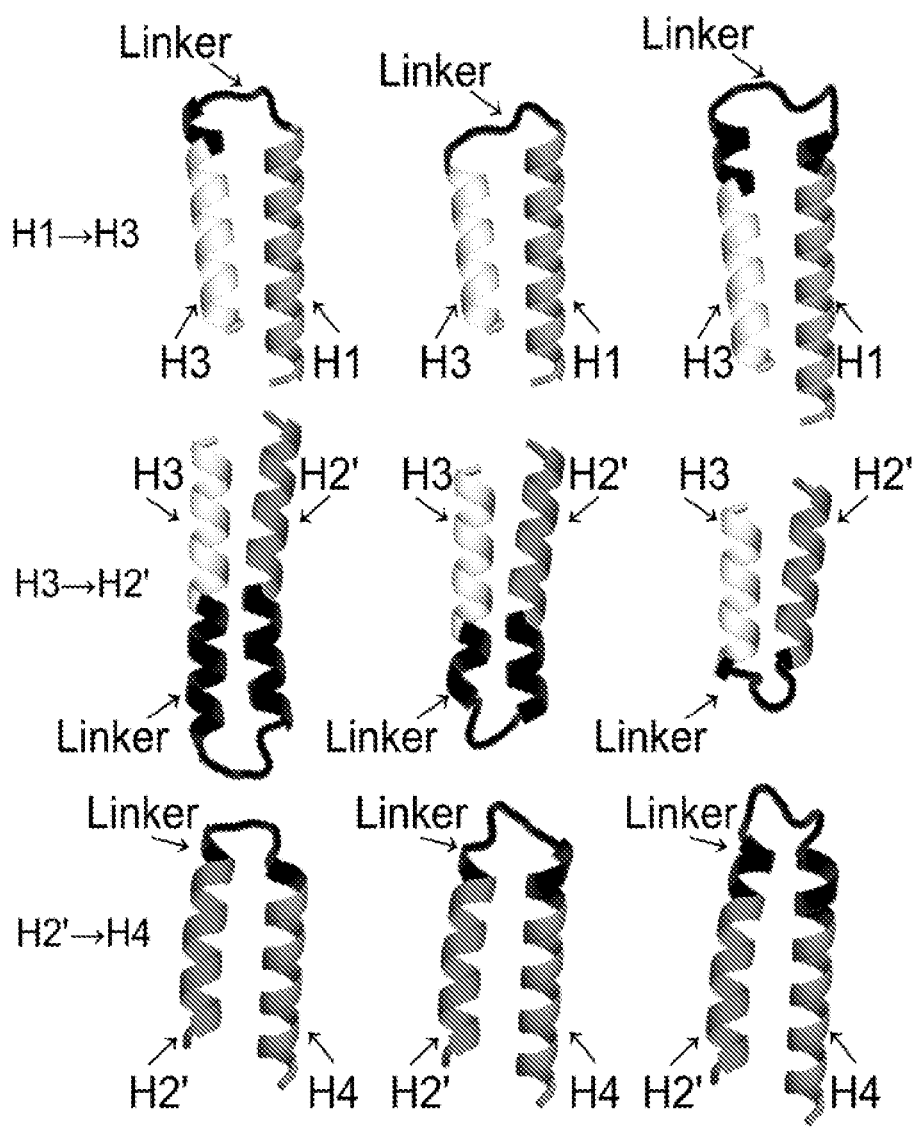

Many cytokines interact with multiple different receptor subunits, and like most naturally occurring proteins, contain non-ideal structural features that compromise stability but are important for function. A computational protocol was developed in which the structural elements interacting with the desired receptor subunit(s) are fixed in space, and an idealized globular protein structure is built to support these elements. Combinatorial fragment assembly was used to support short linear epitopes with parametric construction of disembodied helices coupled with knowledge-based loop closure (FIG. 1a-b). The approach was tested by attempting to de novo design stable idealized proteins with interaction surfaces mimicking those of human IL-2 (hIL-2) and human IL-15 (hIL-15) for the human IL-2R$\beta \gamma_c$ (hIL-2R$\beta \gamma_c$), but entirely lacking the IL-2 receptor alpha (IL-2R$\alpha$) interaction surface.

Figure 1C:
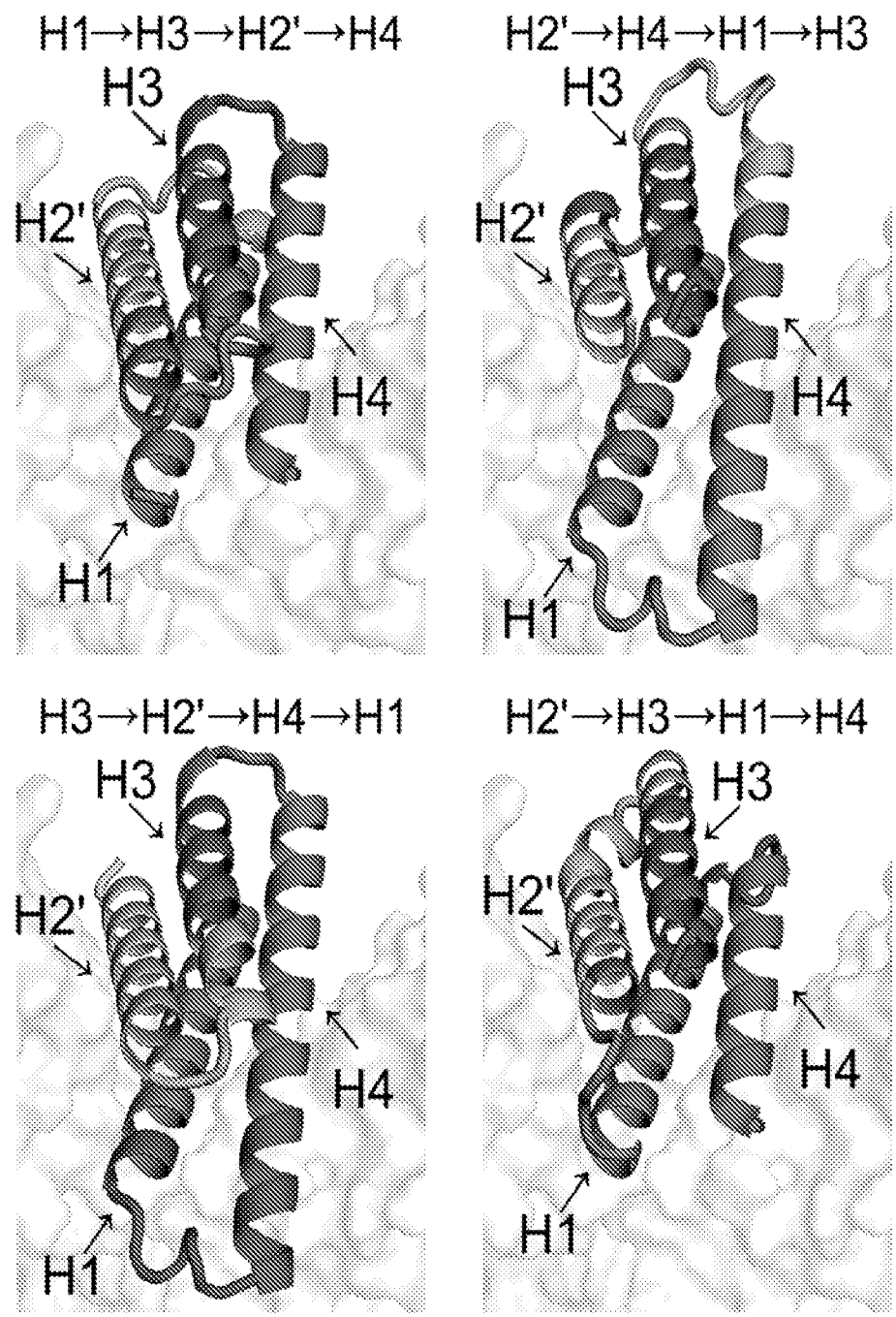

Computational design of non-split IL-2/IL-15 mimetics that bind and activate IL-2R$\beta \gamma_c$: Native hIL-2 comprises four helices connected by long irregular loops. The N-terminal helix (H1) interacts with both the beta and gamma subunits of the IL-2 receptor, the third helix (H3) interacts with the beta subunit, and the C-terminal helix (H4) with the gamma subunit the alpha subunit interacting surface is formed by the irregular second helix (H2) and two long loops, one connecting H1 to H2 and the other connecting H3 and H4. An idealized protein was designed that recapitulates the interface formed by H1, H3 and H4 with beta and gamma and to replace H2 with a regular helix that offers better packing. The helices H1, H3 and H4 (see FIG. 1a) were used as a template for the binding site, while helix H2 was reconstructed (H2') using a database off highly-represented clustered-fragments (see Methods). Pairs of helices were connected with loops extracted from the same database (see FIG. 1b), the resulting helical hairpins combined into fully connected backbones (see FIG. 1c), and Rosetta™ combinatorial flexible backbone sequence design calculations were carried out in the presence of hIL-2Rβ$\gamma_c$, (see Methods). The top four computational designs and eight single-disulfide stapled variations (see Table 2) were selected for experimental characterization by yeast display (see Methods). Eight designs were found to bind fluorescently-tagged beta-gamma chimeric IL-2 receptor at low-nanomolar concentrations. The best non-disulfide design (G1_neo2_40) was subjected to site saturation mutagenesis followed by selection and combination of affinity-increasing substitutions for the murine IL-2Rβ$\gamma_c$ (mIL-2Rβ$\gamma_c$, see FIG. 5). Optimized designs (were expressed recombinantly in E. coli and found to elicit pSTAT5 signaling in vitro on IL-2-responsive murine cells at low-nanomolar or even picomolar concentrations (Table 3, see Silva et al., Nature 565, pg. 186, Jan. 10, 2019), but had relatively low thermal stability (Tm~<45° C., see FIGS. 9 and 10). To improve stability, the computational design protocol was repeated starting from the backbone of the highest affinity first round design (G1_neo2_40_1F, topology: H1->H4->H2'->H3), coupling the loop building process with parametric variation in helix length (+/− 8 amino acids, see FIG. 1a bottom panel). This second approach improved the quality of the models by enabling the exploration of substantially more combinations of loops connecting each pair of helices. The fourteen best designs of the second generation, along with twenty-seven Rosetta™ sequence redesigns of G1_neo2_40_1F (see Table 4), were experimentally characterized and all but one were found to bind IL-2 receptor at low-nanomolar concentrations. The three highest affinity and stability designs (one sequence redesign and two new mimetics) were subjected to site saturation mutagenesis for mIL-2Rβ$\gamma_c$ binding (FIGS. 6-8), followed by selection and combination of affinity-increasing substitutions for both human and mouse IL-2Rβ$\gamma_c$. The matured designs (see Table 5) showed enhanced binding while retaining hyper-stability ((see Silva et al., Nature 565, pg. 186. Jan. 10, 2019)). The top design, neoleukin-2/15 (also referred to herein as Neo-2/15), is a 100 residue protein with a new topology and sequence quite different from human or murine IL-2 (29% sequence identity to hIL-2 over 89 residues, and 16% sequence identity to mIL-2 over 76 aligned residues, in structural topology-agnostic based alignment).

Figure 2C:
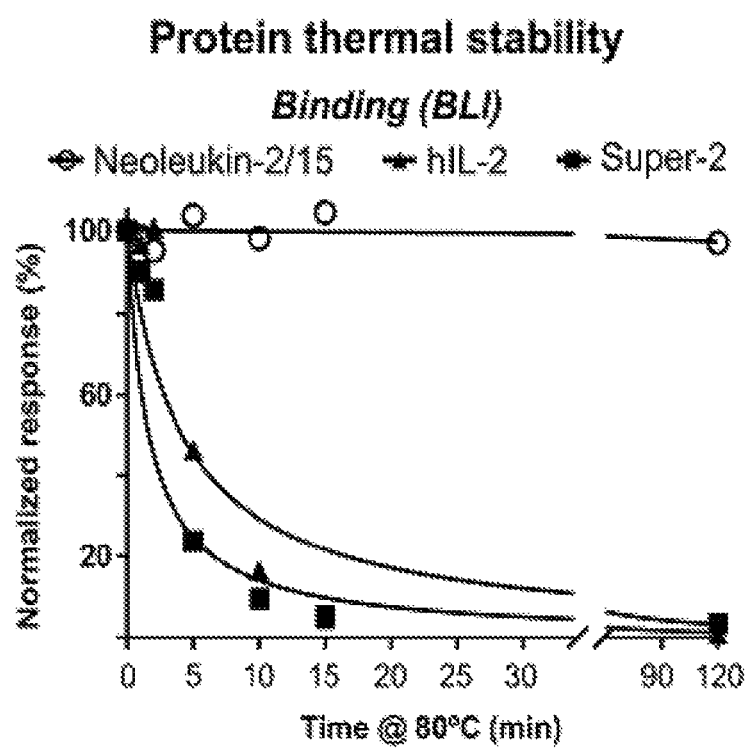
FIG. 2C. Characterization of neoleukin-2/15. Binding experiments (Biolayer Interferometry) show that neoleukin-2/15 can be incubated for 2 hours at 80° C. without any noticeable loss of binding, whereas human and murine IL-2 quickly lose activity.
Figure 12A:
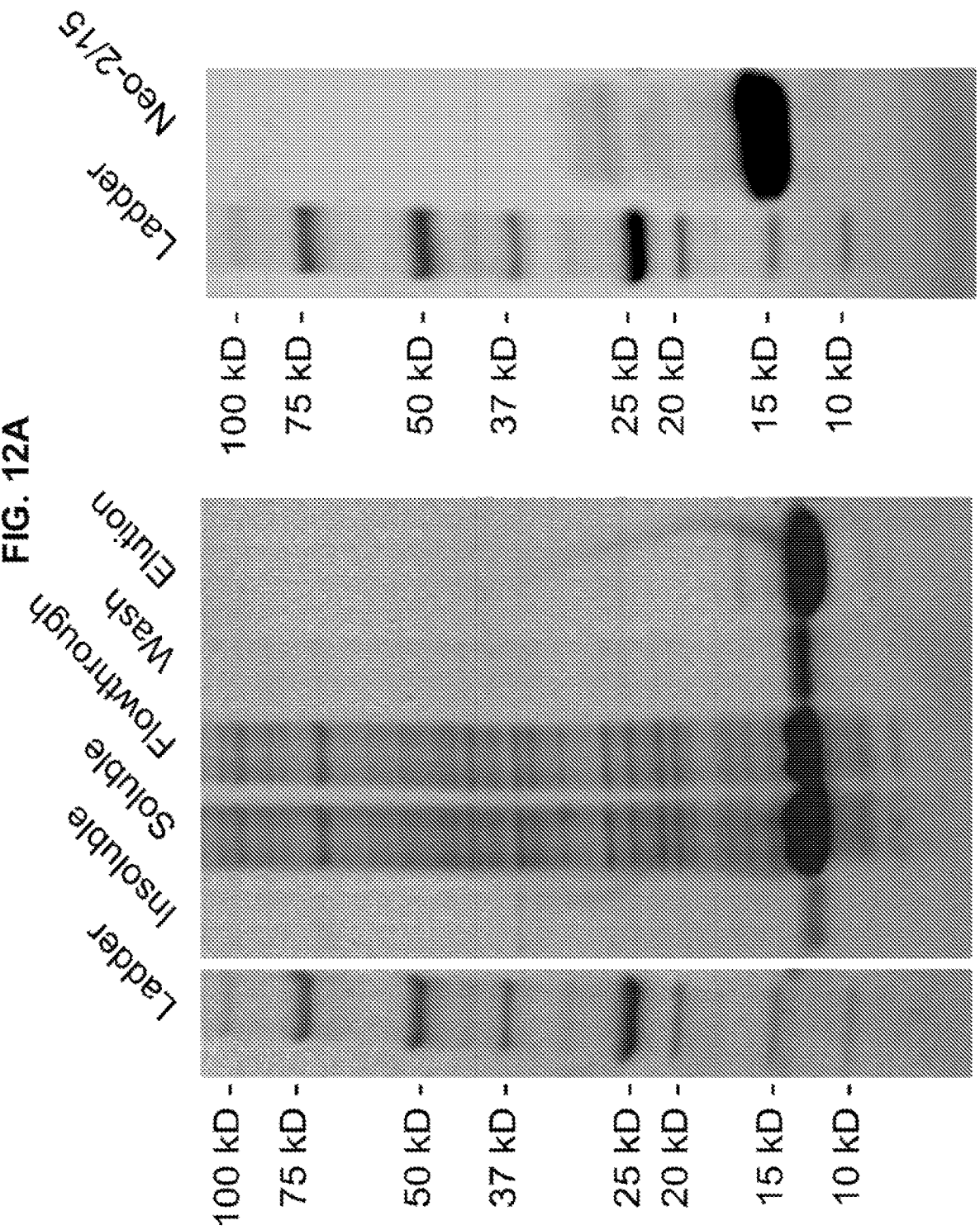
FIG. 12A-12C. Expression, purification, and thermal denaturation characterization of neoleukin-2/15.
Figure 12B:
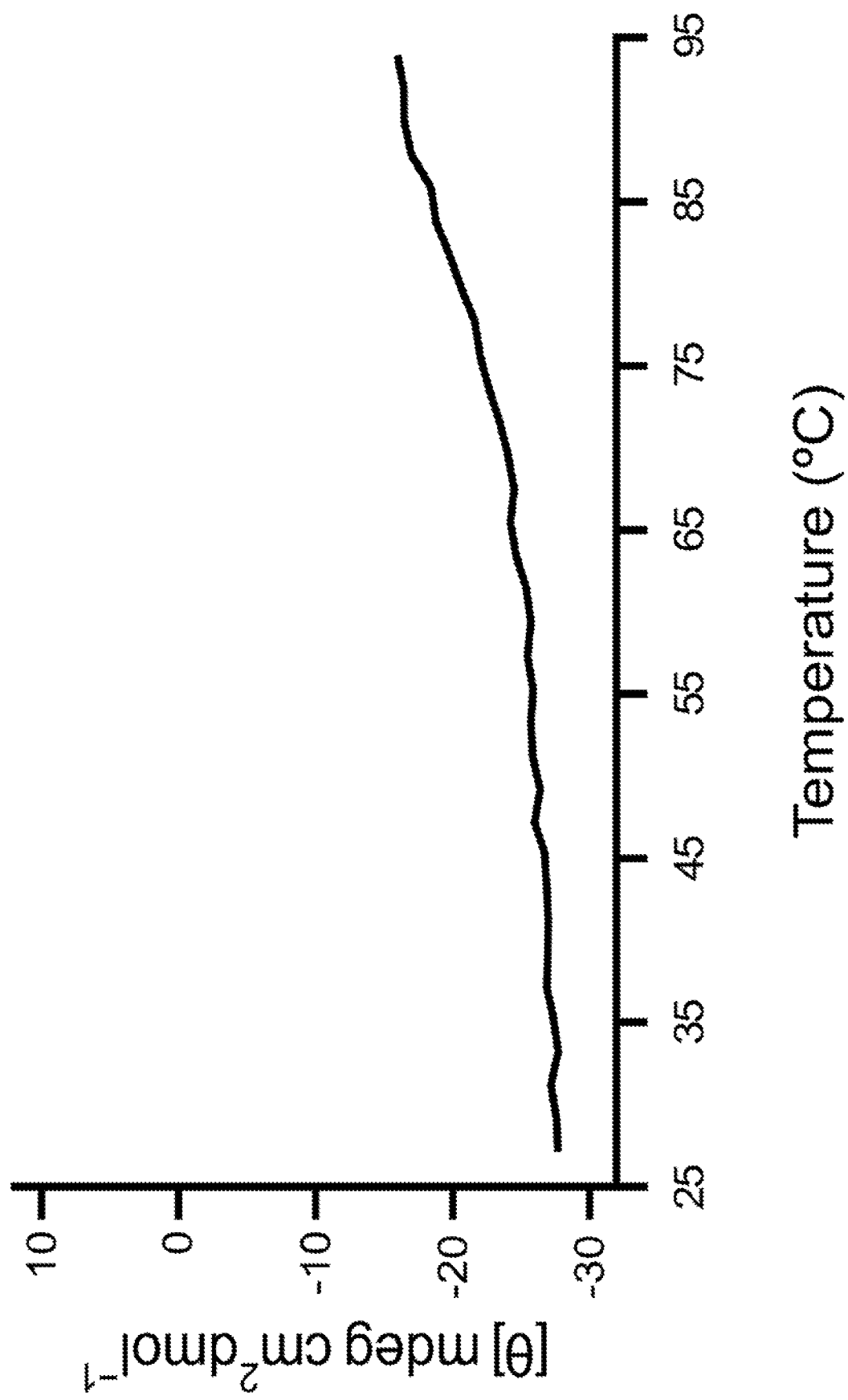
Figure 12C:
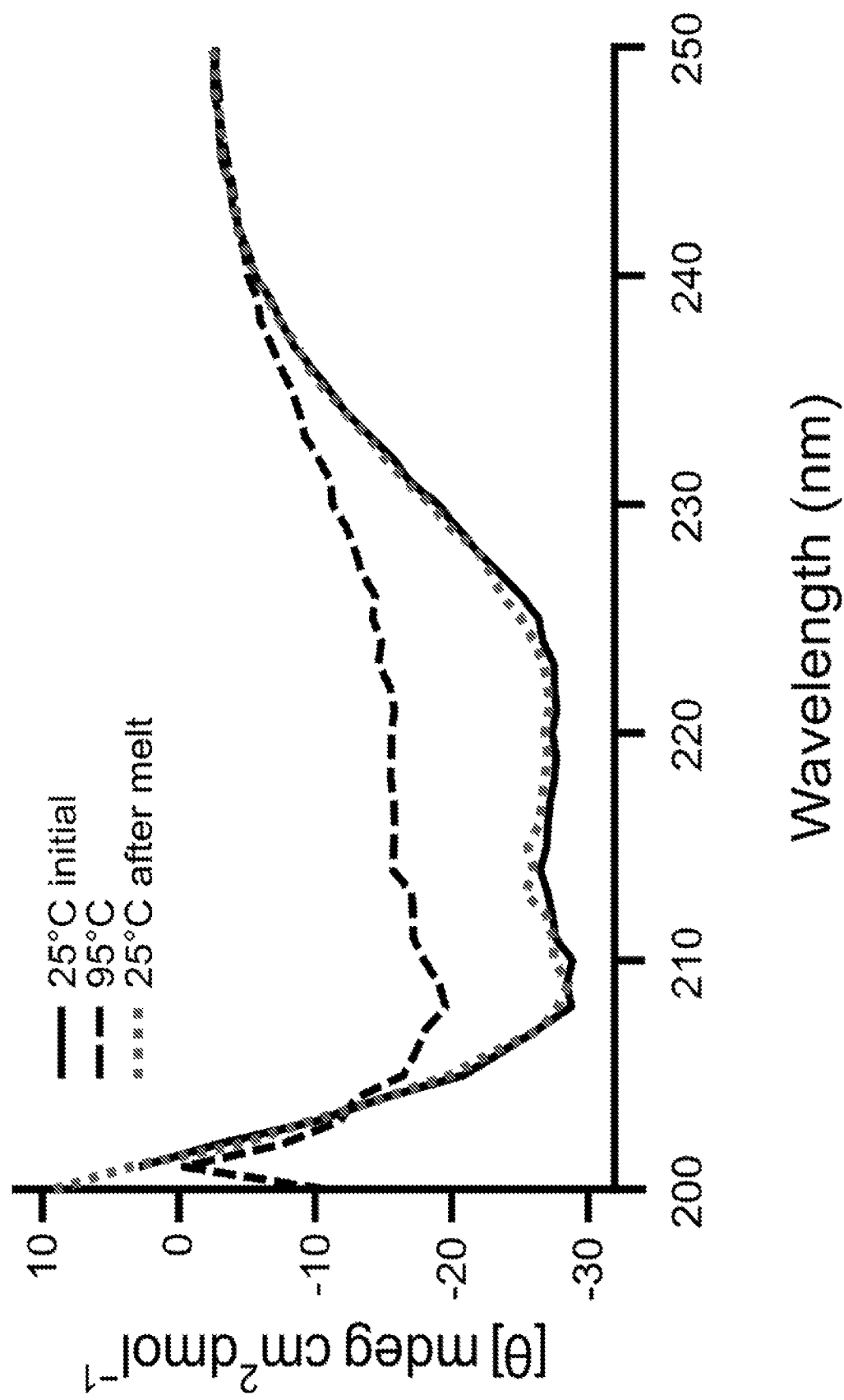
Figure 13A:
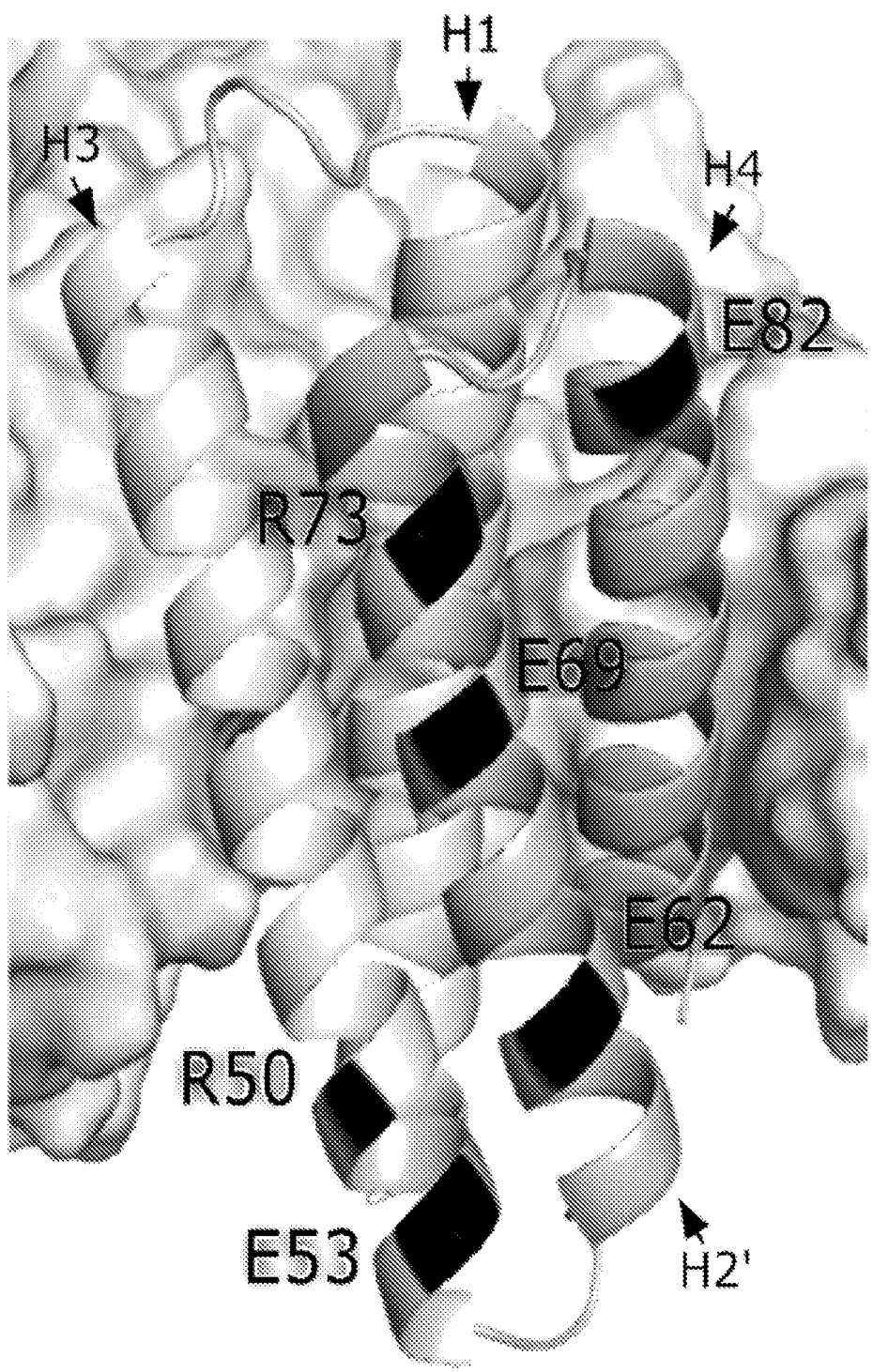
FIG. 13A-13B. Robustness of neoleukin-2/15 to single-point cysteine mutants on non-binding interface positions.
Figure 13B:
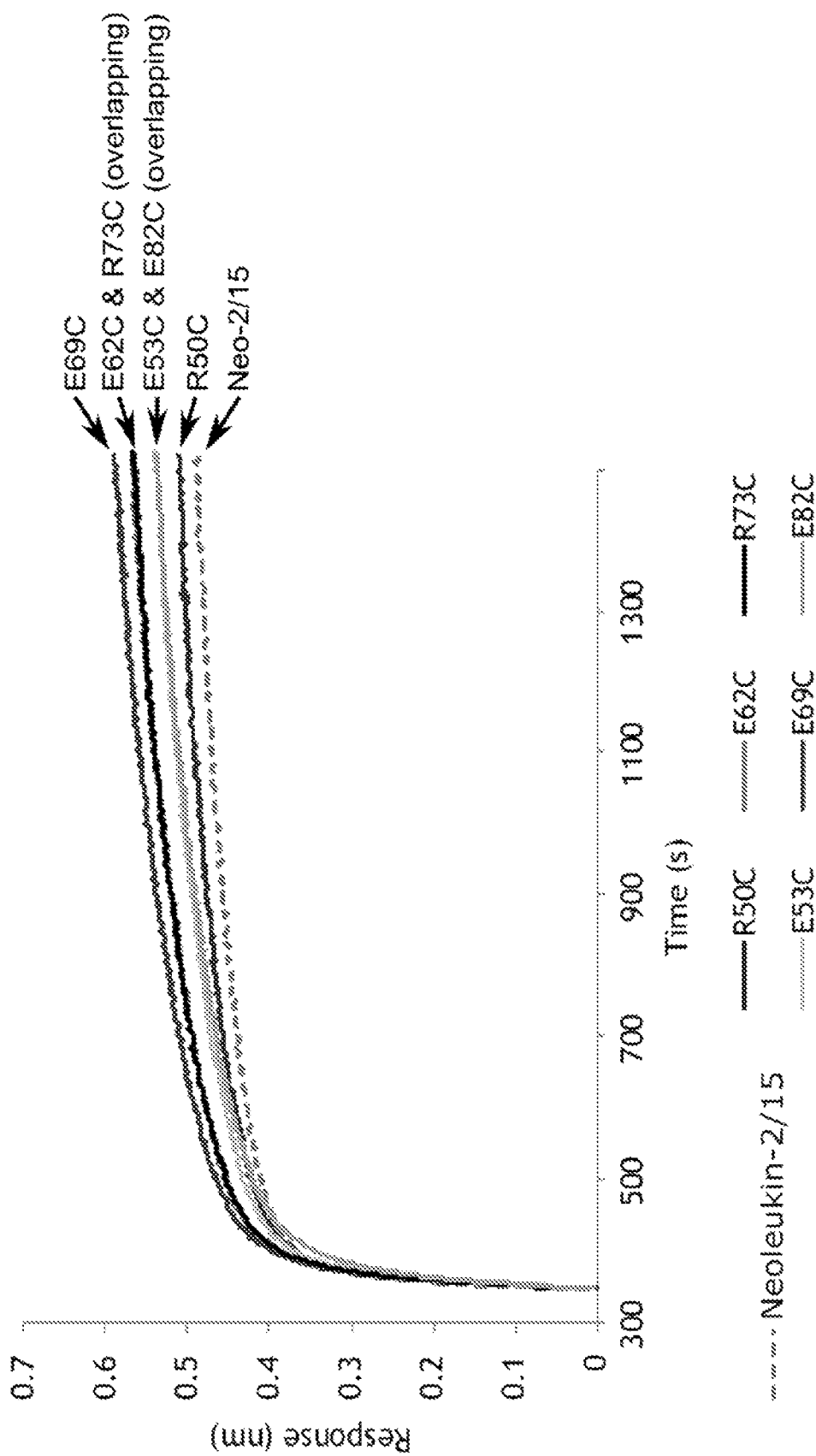

Functional characterization of neoleukin-2/15: Neoleukin-2/15 binds with high affinity to human and mouse IL-2Rβ$\gamma_c$, but does not interact with IL-2Rα (see Silva et al., Nature 565, pg. 186, Jan. 10, 2019). The affinities of Neoleukin-2/15 for the human and mouse IL-2 receptors (IL-2Rβ and IL-2Rβ$\gamma_c$) are significantly higher than those of the corresponding native IL-2 cytokines. In contrast with native IL-2, Neoleukin-2/15 elicits IL-2Rα-independent signaling in both human and murine IL-2-responsive cells, and in murine primary T cells (sec Silva et al., Nature 565, pg. 186, Jan. 10, 2019). Neoleukin-2/15 activates IL-2Rα− cells more potently than native human or murine IL-2 in accordance with its higher binding affinity. In primary cells, neoleukin-2/15 is more active on IL-2Rα− cells and less active on IL-2Rα+ compared to Super-2, presumably due to its complete lack of IL-2Rα binding. Neoleukin-2/15 is hyper-stable (see FIG. 12) and does not lose binding affinity for hIL-2Rβ$\gamma_c$, following incubation at 80° C. for 2 hours, while hIL-2 and Super-2 are completely inactivated after 10 minutes (half-inactivation time=~4.2 min and ~2.6 min, respectively, FIG. 2). Similarly, in ex vivo primary cell cultures, neoleukin-2/15 drove T cell survival effectively after being boiled for 60 minutes at 95° C., while these conditions inactivated both IL-2 and Super-2 (see Silva et al., Nature 565, pg. 186, Jan. 10, 2019). Thermal denaturation studies were carried out on many other of the designed mimetics, demonstrating their thermal stability as well (see FIG. 11). This unprecedented stability for a cytokine-like molecule, beyond eliminating the requirement for cold chain storage, suggests a robustness to mutations (see FIGS. 8 and 13), genetic fusions and chemical modification greatly exceeding that of native IL-2 (see FIG. 3).

Therapeutic applications of neoleukin-2/15: The clinical use of IL-2 has been mainly limited by toxicity. Although the interactions responsible for IL-2 toxicity in humans are incompletely understood, in murine models toxicity is T cell independent and ameliorated in animals deficient in the IL-2Rα chain (CD25+). Thus, many efforts have been directed to reengineer IL-2 to weaken interactions with IL-2Rα, but mutations in the CD25 binding site can be highly destabilizing. The inherent low stability of IL-2 and its tightly evolved dependence on CD25 have been barriers to the translation of reengineered IL-2 compounds. Other efforts have focused on IL-15, since it elicits similar signaling to IL-2 by dimerizing the IL-2Rβ$\gamma_c$, but has no affinity for CD25. However, IL-15 is dependent on trans presentation by the IL-15a (CD215) receptor that is displayed primarily on antigen-presenting cells and natural killer cells. The low stability of native IL-15 and its dependence on trans presentation have also been substantial barriers to reengineering efforts.

Dose escalation studies on naive mice show that mIL-2 preferentially expands regulatory T cells, consistent with preferential binding to CD25+ cells, while neoleukin-2/15 primarily drives expansion of CD8$^+$ T cells and does not induce or minimally induces expansion of regulatory T cells only at the highest dose tested. Similarly, in a murine model of airway inflammation, which normally induces a small percentage of tissue resident CD8+ T cells, neoleukin-2/15 produces an increase in Thy1.2$^-$ CD44$^+$ CD8$^+$ T cells without increasing CD4$^-$ Foxp3$^+$ antigen-specific Tregs in the lymphoid organs (data not shown; see Silva et al., Nature 565, pg. 186, Jan. 10, 2019).

The therapeutic efficacy of neoleukin-2/15 was tested in the poorly immunogenic B16F10 melanoma and the more immunogenic CT26 colon cancer mouse models. Single agent treatment with neoleukin-2/15 led to dose-dependent delays in tumour growth in both cancer models. In CT26 colon cancer, single agent treatment showed improved efficacy to that observed for recombinant mIL-2 (see Silva et al., Nature 565, pg. 186, Jan. 10, 2019). In B16F10 melanoma, co-treatment with the anti-melanoma antibody TA99 (anti-TRP 1) led to significant tumour growth delays, while TA99 treatment alone had little effect (see Silva et al., Nature 565, pg. 186, Jan. 10, 2019). In long term survival experiments (8 weeks), neoleukin-2/15 in combination with TA99 showed substantially reduced toxicity and an overall superior therapeutic effect compared to mIL-2 (see Silva et al., Nature 565, pg. 186, Jan. 10, 2019). Mice treated with the combination mIL-2 and TA99 steadily lost weight and their overall health declined to the point of requiring euthanasia, whereas little decline was observed with the combination of neoleukin-2/15 and TA99 (see Silva et al., Nature 565, pg. 186, Jan. 10, 2019). Consistent with a therapeutic benefit, neoleukin-2/15 treatment led to a significant increase in intratumoral CD8:$T_{reg}$ ratios (sec Silva et al., Nature 565, pg. 186, Jan. 10, 2019), which has been previously correlated with effective antitumor immune responses[58]. The increases of CD8:$T_{reg}$ ratios by neoleukin-2/15 are dose and antigen dependent (see Silva et al., Nature 565, pg. 186, Jan. 10, 2019); optimum therapeutic effects were obtained at higher doses and in combination with other immunotherapies (see Silva et al., Nature 565, pg. 186, Jan. 10, 2019). Altogether, these data show that neoleukin-2/15 exhibits the predicted homeostatic benefit derived from its IL-2 like immunopotentiator activity, but without the adverse effects associated with CD25+ preferential binding. The therapeutic efficacy of neoleukin-2/15 was tested in a CAR-T model. NSG mice inoculated with $0.5\times10^6$ RAJI tumor cells were left untreated, were treated with $0.8\times10^6$ anti-CD19 CAR-T cells (infused 7 days after inoculation of tumor cells), or were similarly treated with anti-CD19 CAR-T cells plus 20 μg/day of either human IL-2 or neoleukin-2/15 on days 8-14 after tumor inoculation. As expected, Neoleukin-2/15 was shown to significantly enhance the anti-tumor effect of CAR-T cell therapy, slowing growth of the tumor and extending the survival of the mouse ((see Silva et al., Nature 565, pg. 186, Jan. 10, 2019)).

De novo design of protein mimetics has the potential to transform the field of protein-based therapeutics, enabling the development of biosuperior molecules with enhanced therapeutic properties and reduced side-effects, Unlike recombinant IL-2 and engineered variants of hIL-2, neoleukin-2/15 can be solubly expressed in *E. coli* (see FIG. 17), retains activity at high temperature, does not interact with IL-2Rα and is robust to substantial sequence changes that allow the engineering of new functions (FIG. 7).

Figure 3A:
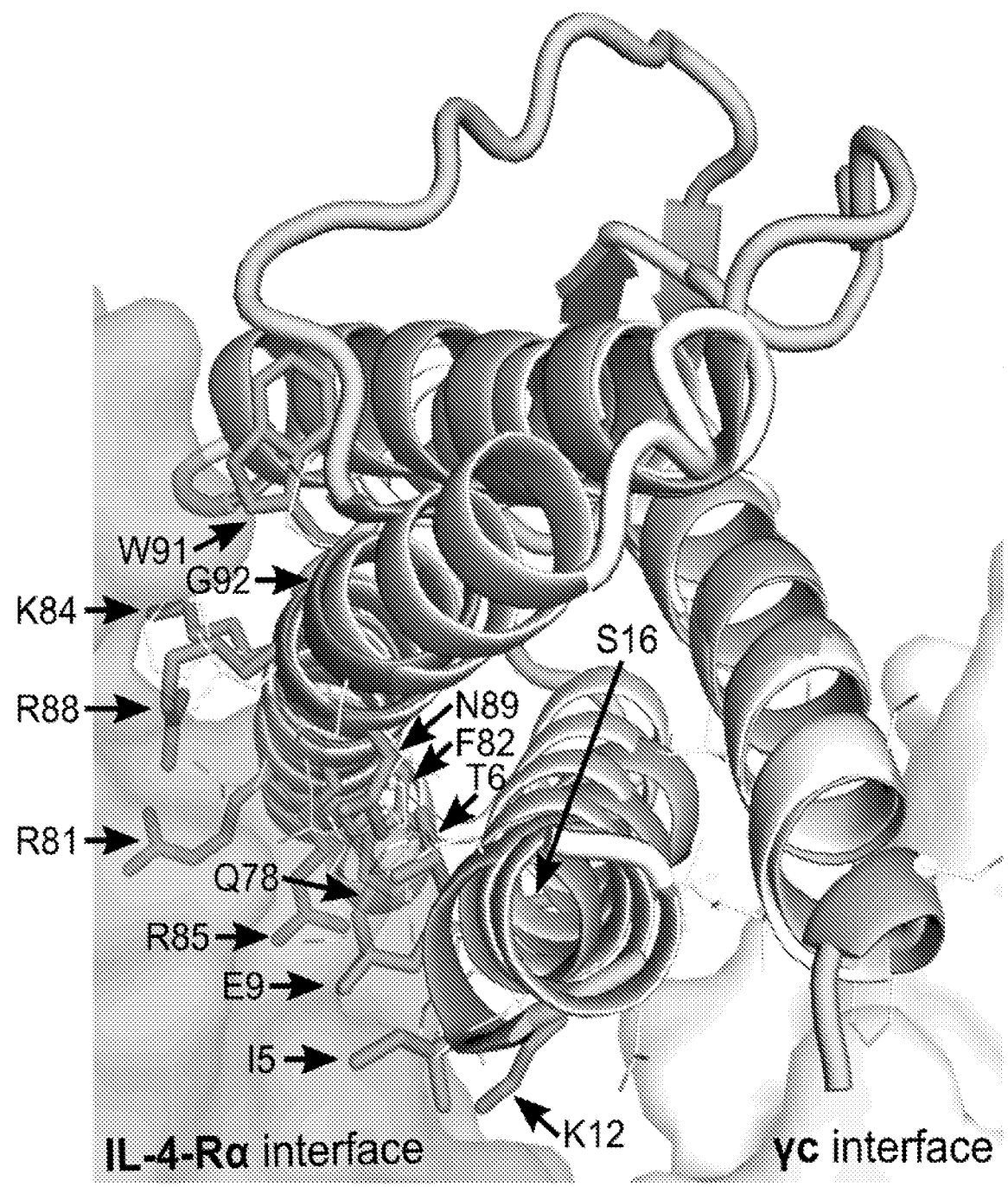
FIG. 3A-3C. Reengineering of neoleukin-2/15 into a human interleukin-4 (hIL-4) mimetic (neoleukin-4).
Figure 3B:
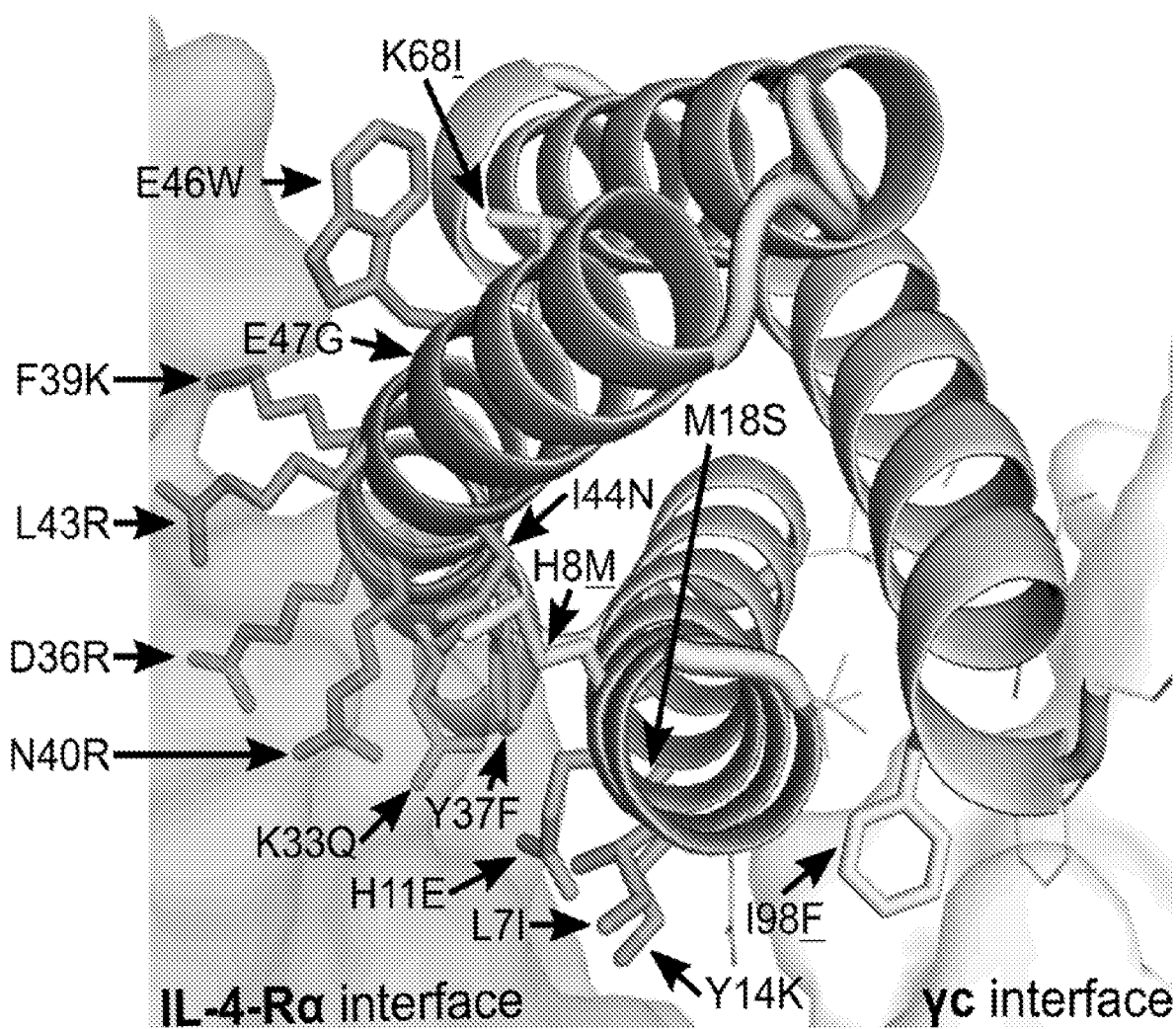
Figure 3C:
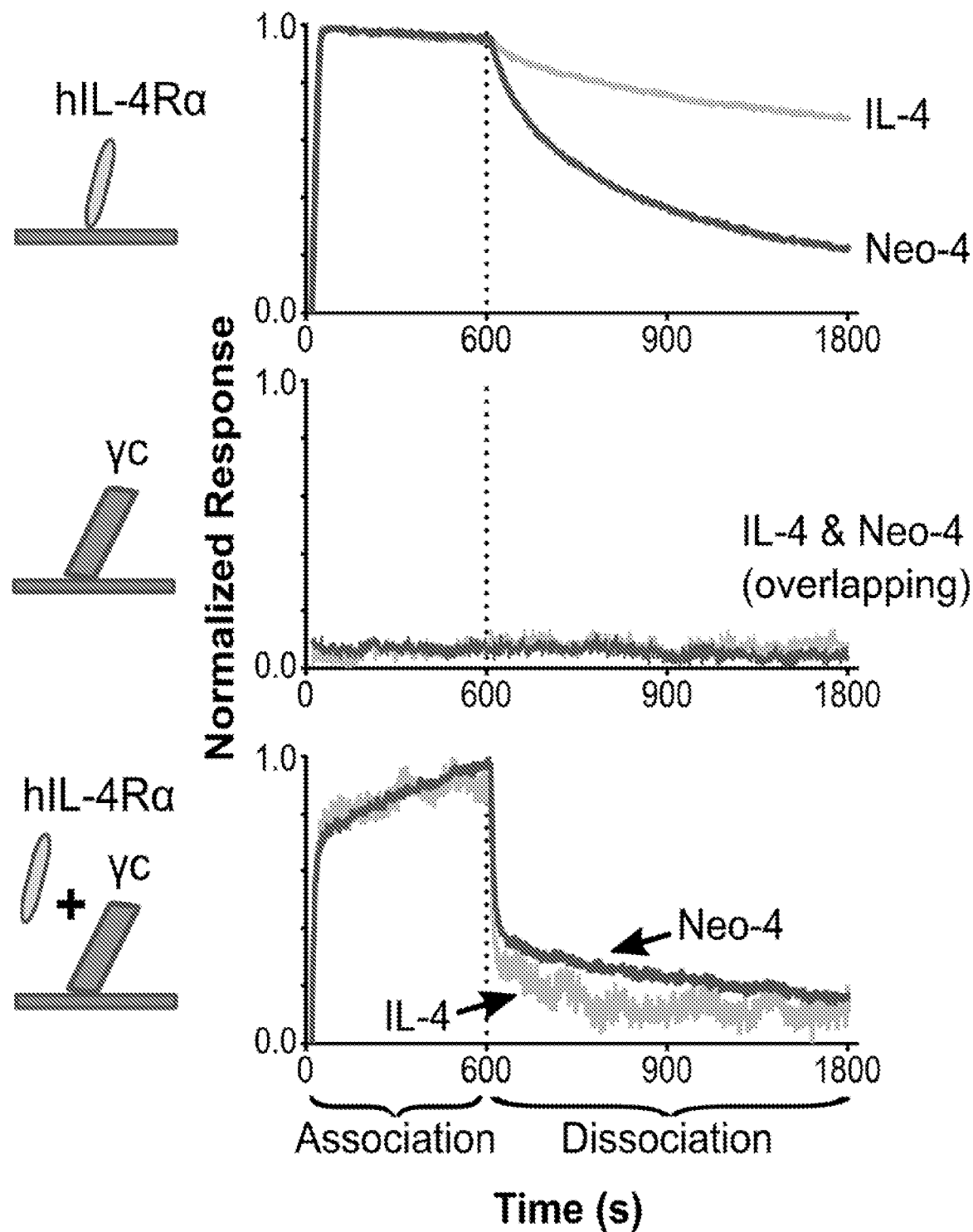
Figure 4A:
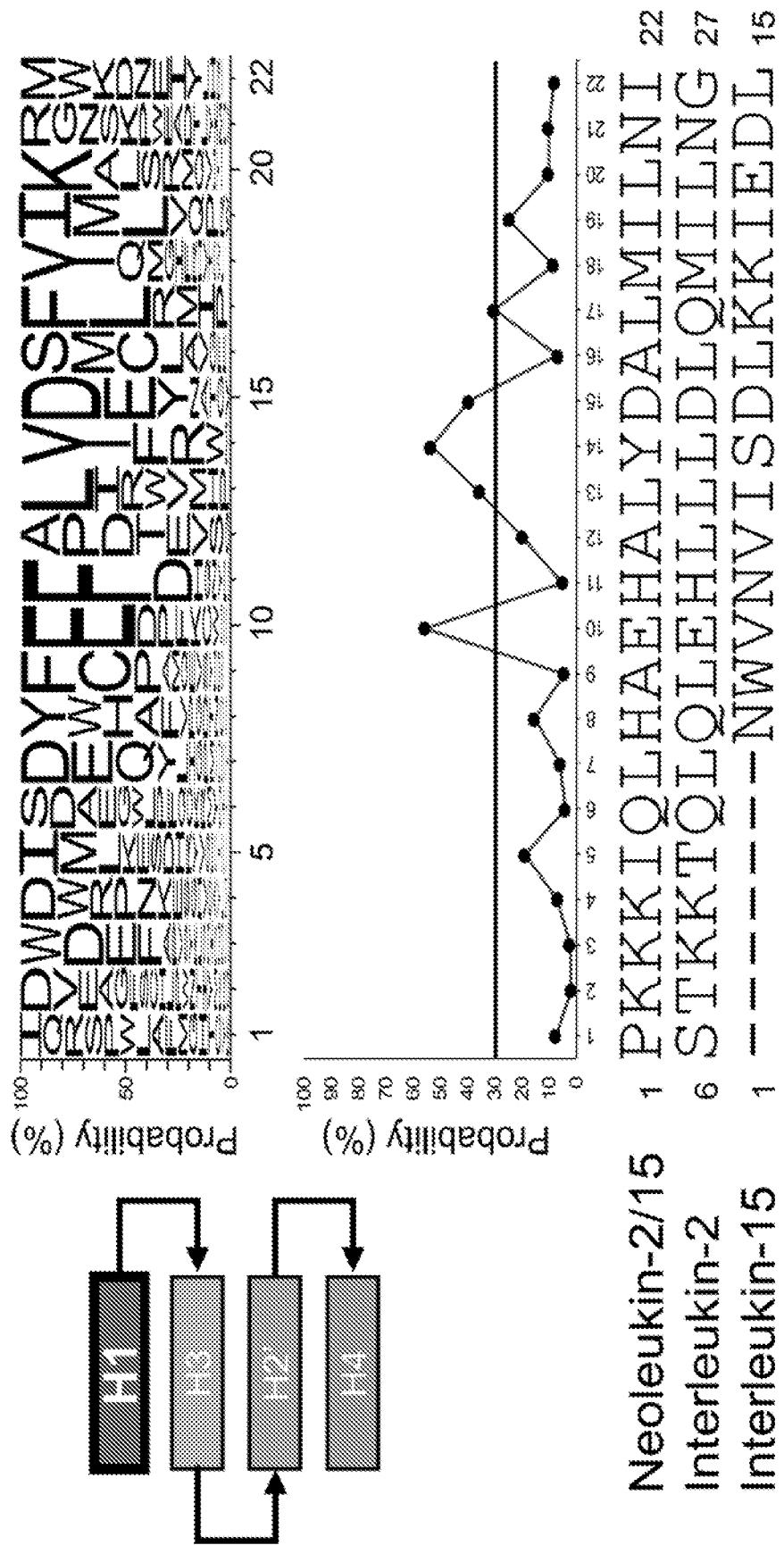
FIG. 4A-4D. Overall sequence conservation in binding residues for each of the four common helices, combining information from three different de novo-designed IL-2 mimics. Sequence logos were generated using combined data from binding experiments (using the heterodimeric mouse IL-2Rβγc) from three independent SSM mutagenesis libraries for G2_neo2_40_1F_seq27, G2_neo2_40_1F_seq29 and G2 neo2_40_1F_seq36 (FIGS. 11-13). All of these proteins are functional high-affinity de novo mimetics of mouse and human IL-2, some having topologies that differ from that of Neo-2/15, but all containing the four Helices H1 (FIG. 4A; Neo-2/15 1-22 is SEQ ID NO:04, IL-2 6-27 is SEQ ID NO:248, IL-15 1-15 is SEQ ID NO:249), H3 (FIG. 4B; Neo-2/15 34-55 is SEQ ID NO:05, IL-2 82-103 is SEQ ID NO:250, IL-15 59-80 is SEQ ID NO:251), H2' (FIG. 4C; Neo-2/15 58-76 is SEQ ID NO:07, IL-2 50-68 is SEQ ID NO:252, IL-15 34-52 is SEQ ID NO:253) and H4 (FIG. 4D; Neo-2/15 80-100 is SEQ ID NO:06, IL-2 111-131 is SEQ ID NO:254. IL-15 93-113 is SEQ ID NO:255). The logos show the combined information for each helix independently. Below each logo, a line graph shows the probability score (higher means more conserved) for each amino acid in the Neo-2/15 sequence. The solid horizontal line highlights positions where the Neo-2/15 amino acid has a probability score ≥30% (that is, these amino acids contribute more generally to receptor binding as they are globally enriched in the binding populations across all of the de novo IL-2 mimics tested). The topology of each helix in Neo-2/15 is shown left of each logo. The sequences of the Neo-2/15 helices and those of the corresponding helices (structurally aligned) in human IL-2 and IL-15 are shown below the graphs, highlighting the distinctiveness of the Neo-2/15 helices and binding interfaces.
Figure 4B:
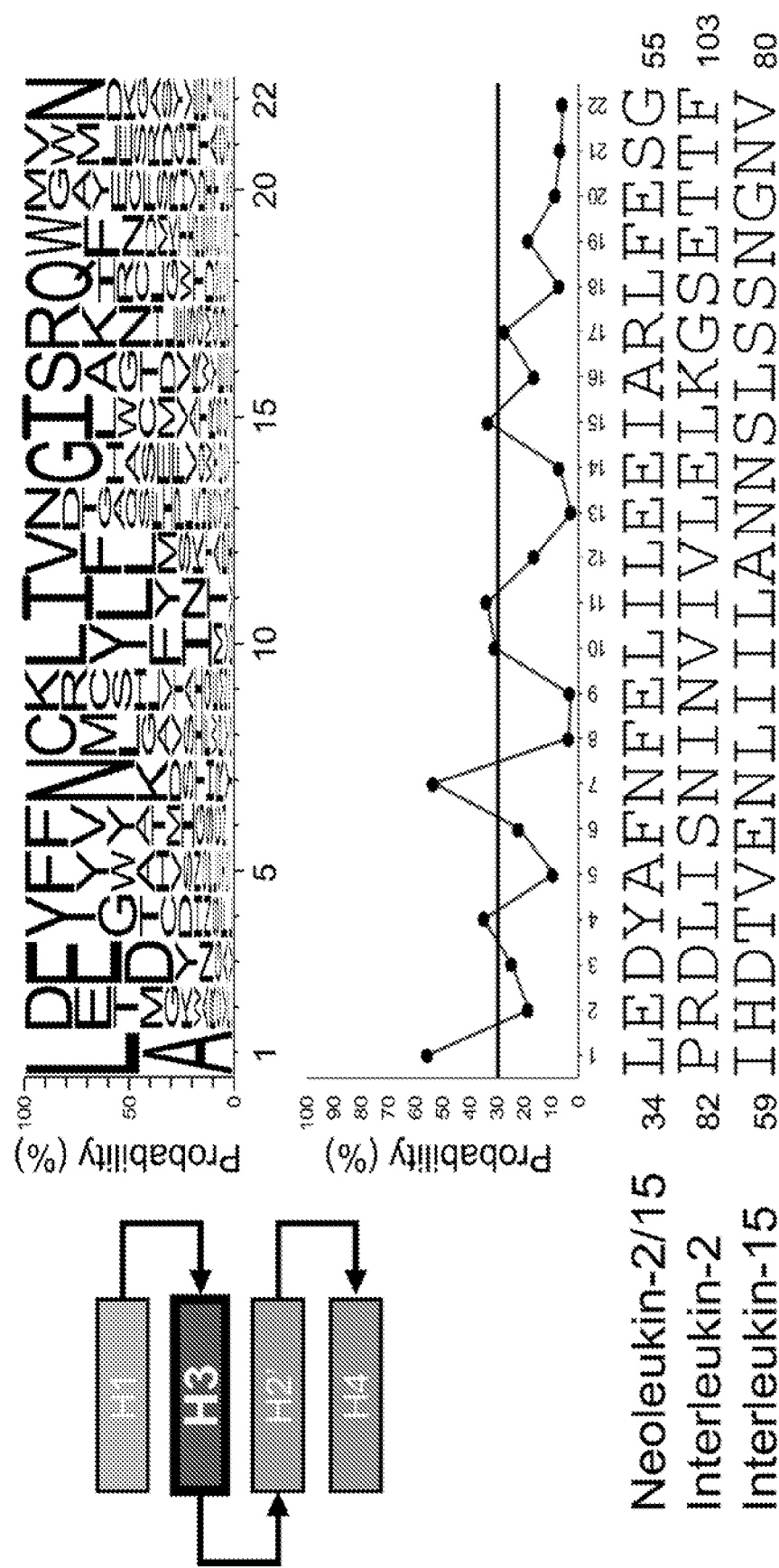
Figure 4C:
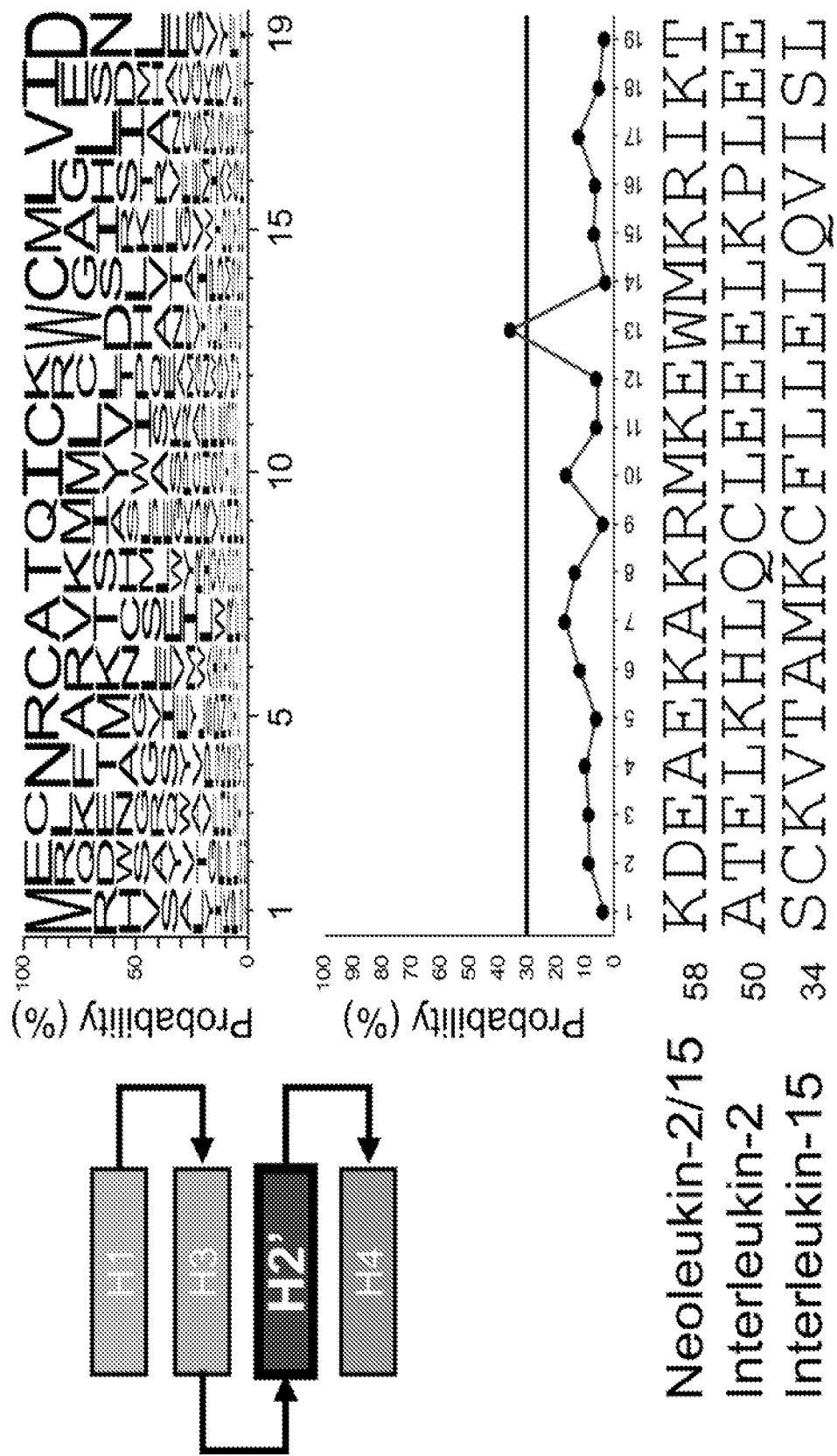
Figure 4D:
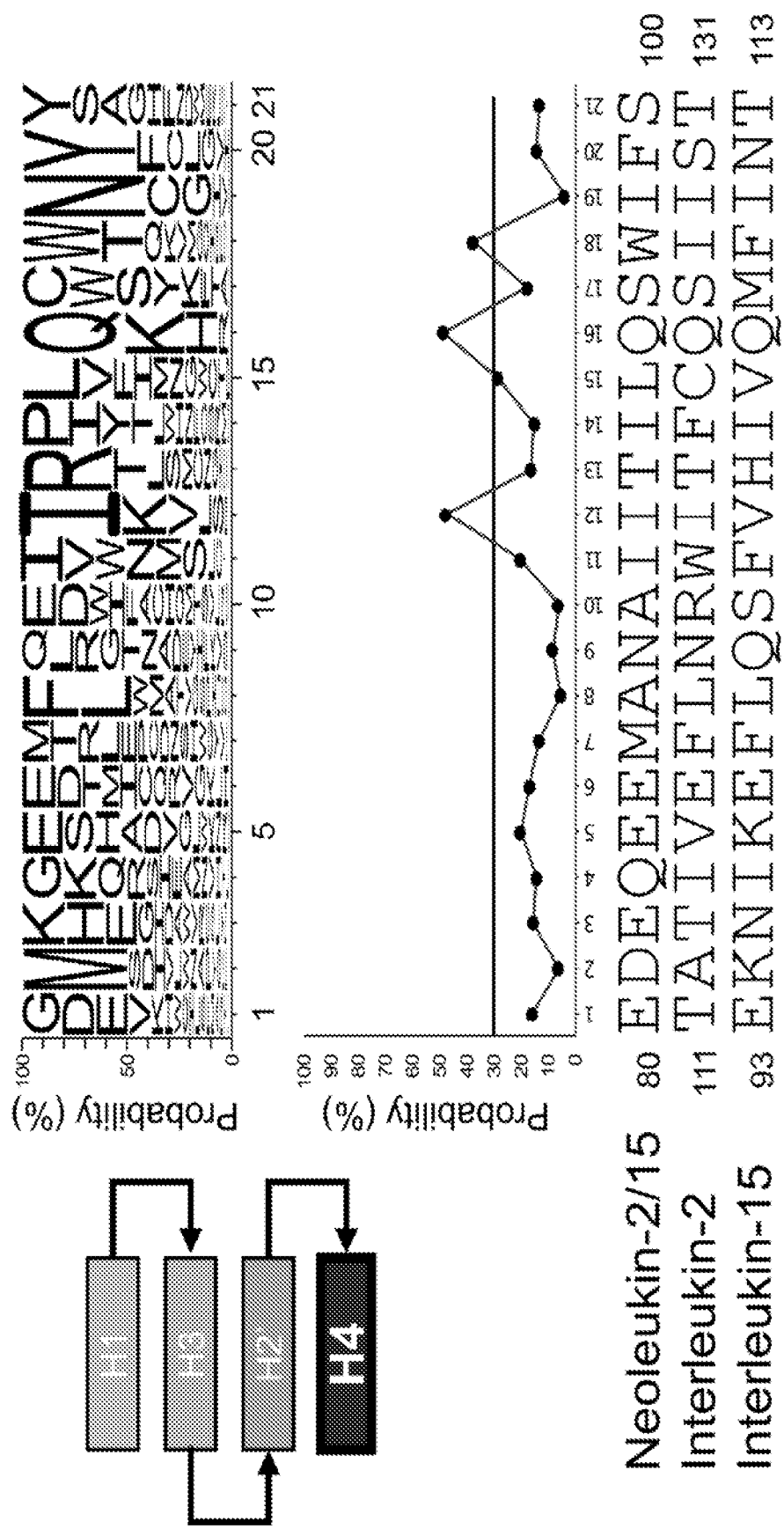
Figure 5A:
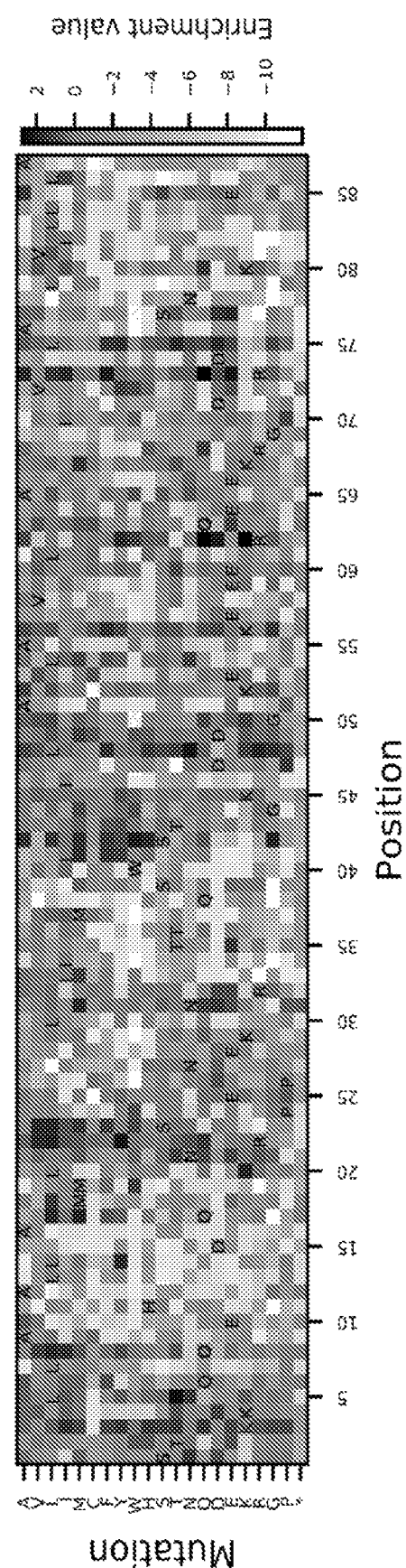
FIG. 5A-5D. Experimental optimization of G1_neo2_40.
Figure 5B:
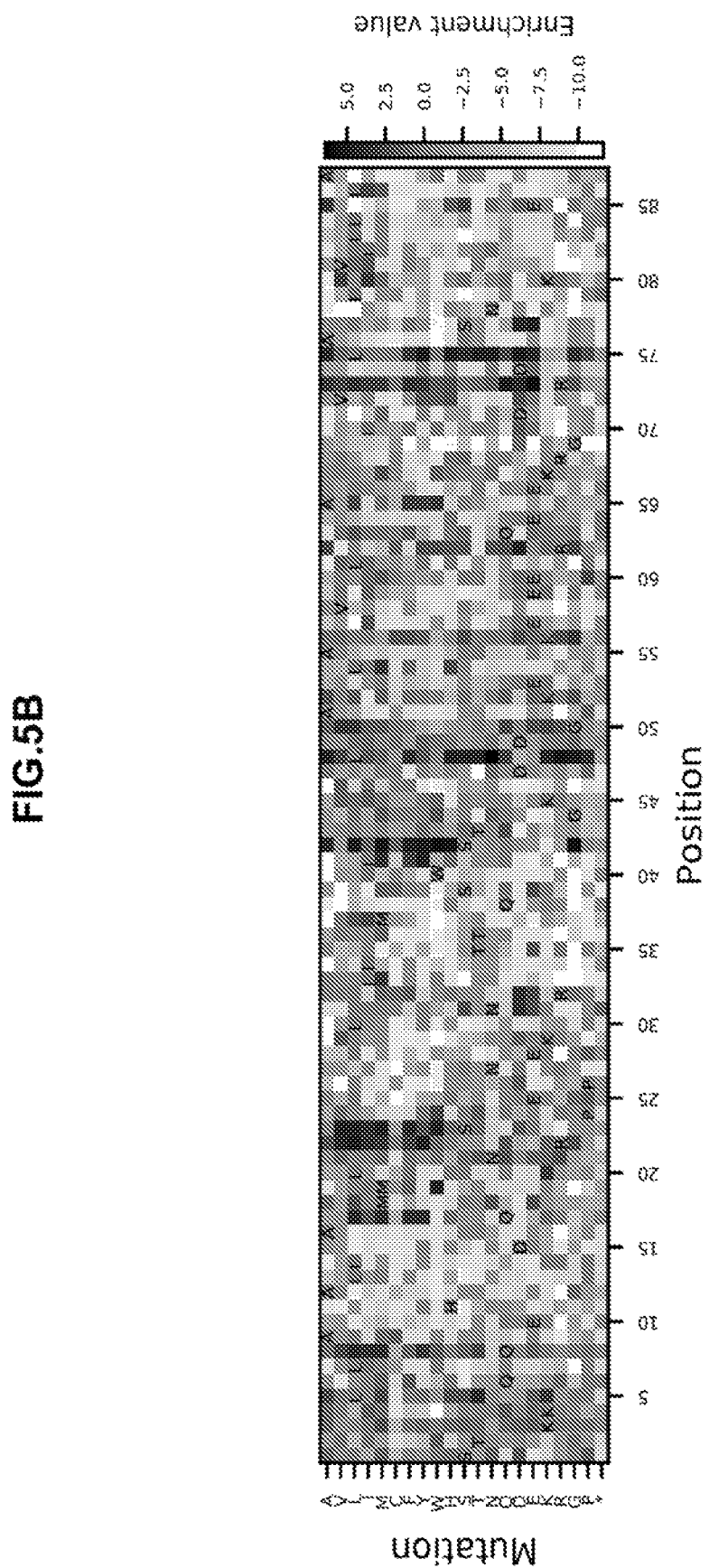
Figure 5C:
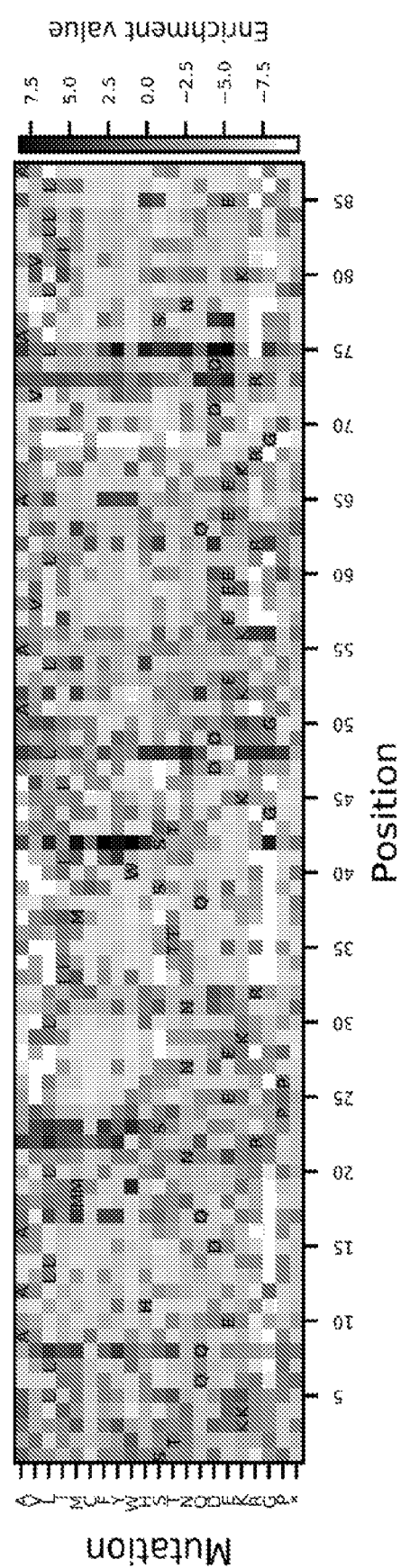
Figure 5D:
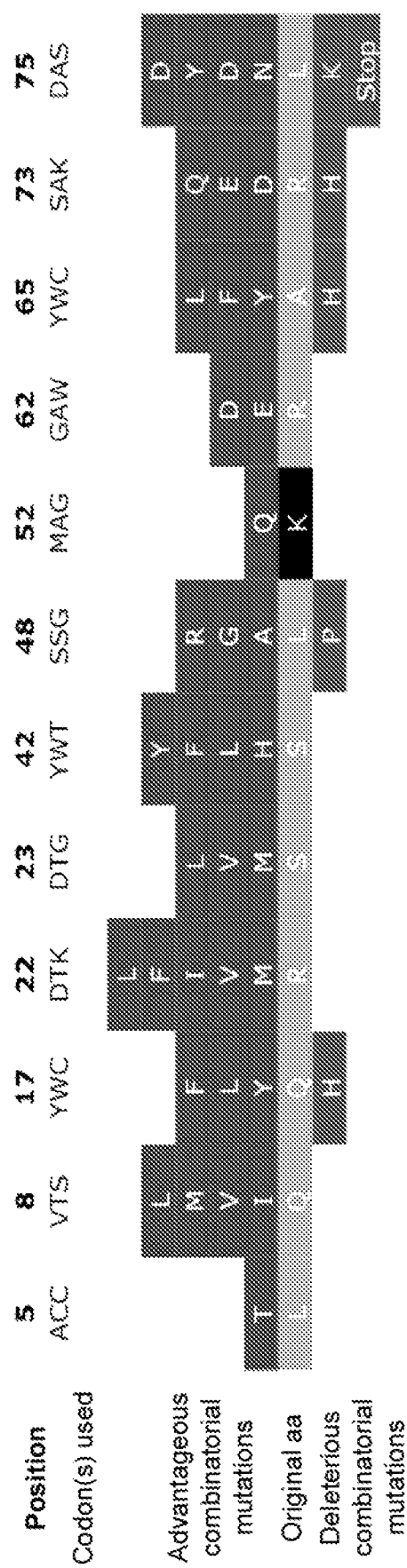
Figure 6A:
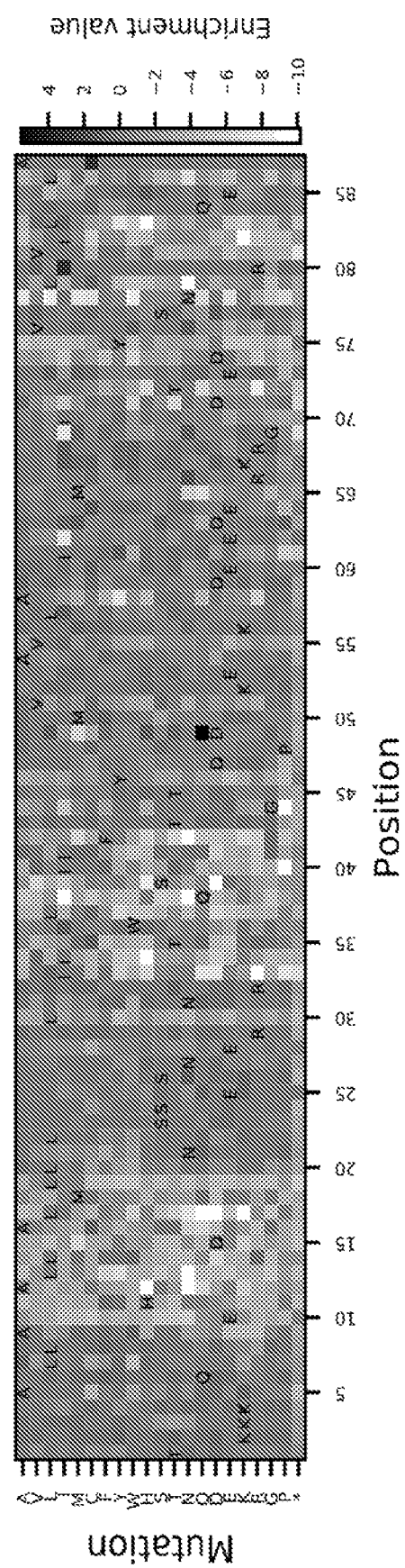
FIG. 6A-6E. Experimental optimization of G2 neo2_40_1F_seq27. Heatmaps for G2 neo2_40_1F_seq27 single-site mutagenesis library showing enrichment at specific positions after consecutive rounds of increasing selection with FIG. 6A) 10 nM, FIG. 6B) 1 nM.
Figure 6B:
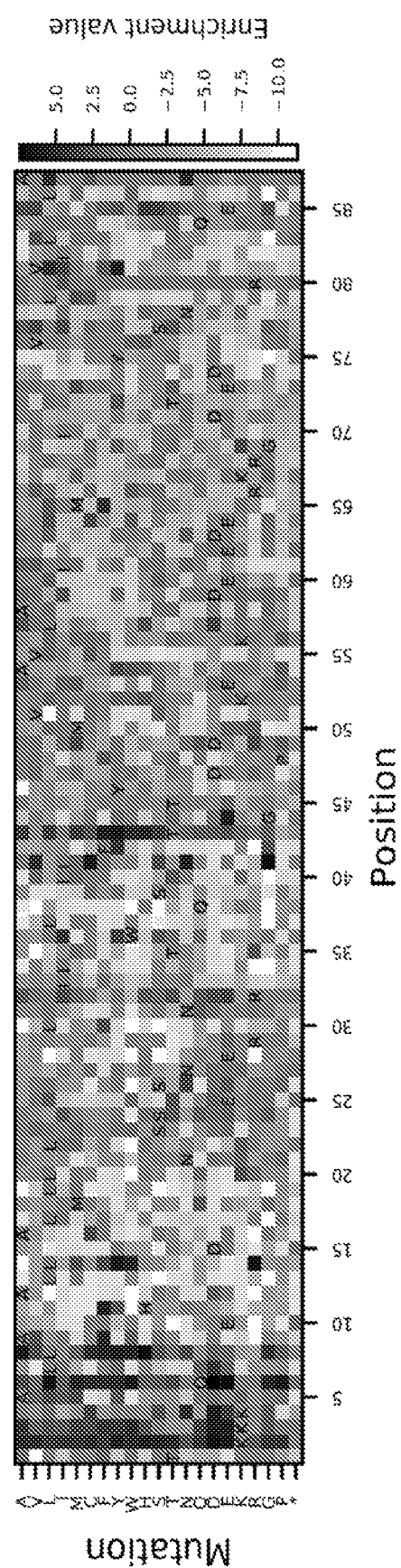
Figure 6C:
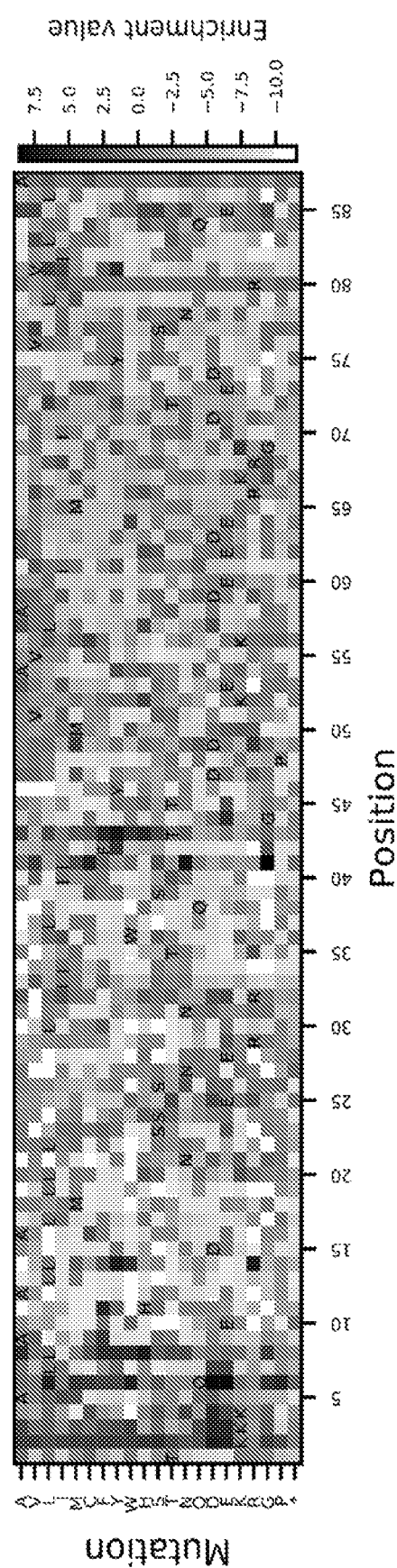
Figure 6D:
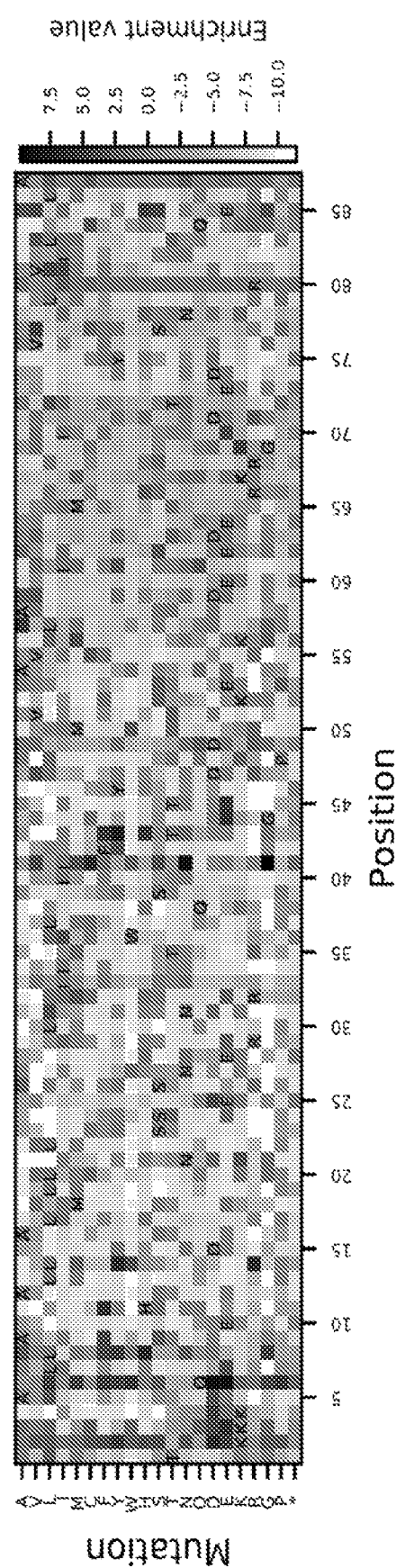
Figure 6E:
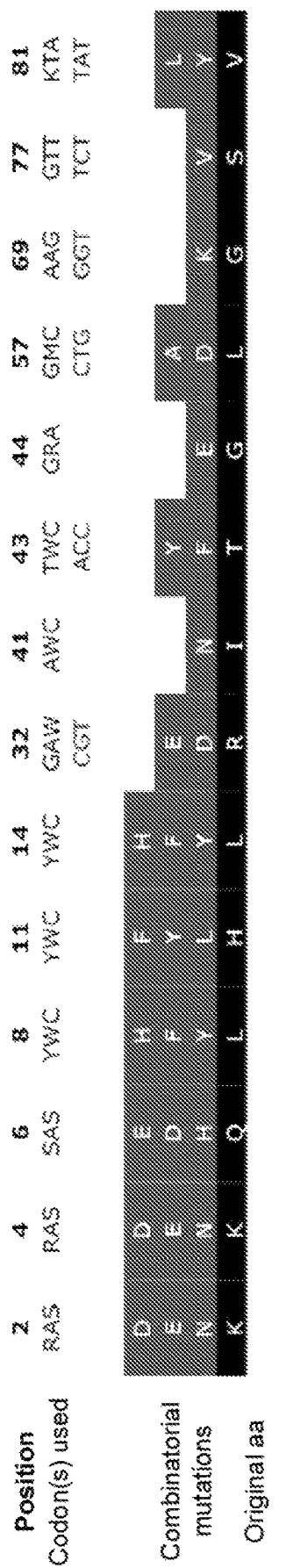
Figure 7A:
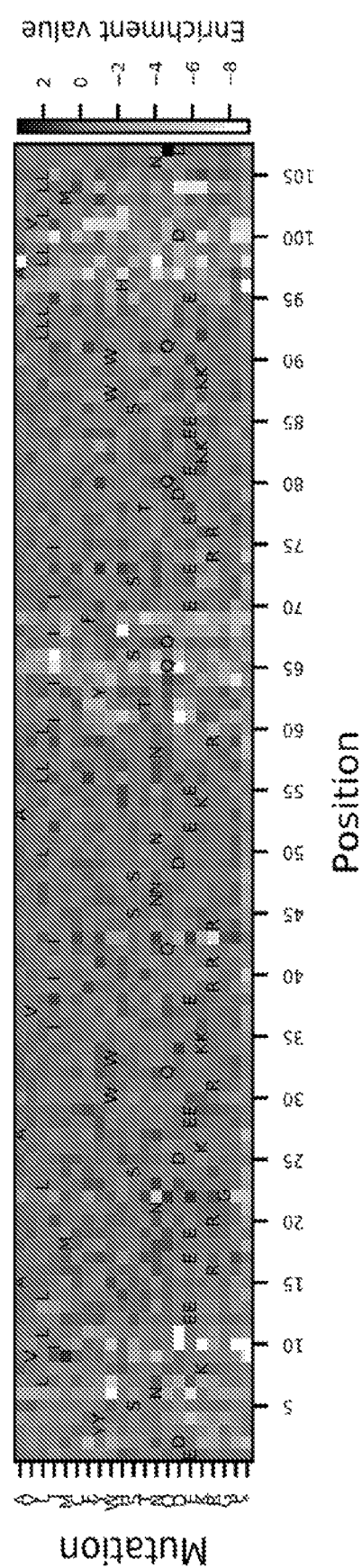
FIG. 7A-7E. Experimental optimization of G2 neo2_40_1F_seq29. Heatmaps for G2 neo2_40_1F_seq29 single-site mutagenesis library showing enrichment at specific positions after consecutive rounds of increasing selection with FIG. 7A) 10 nM, FIG. 7B) 1 nM.
Figure 7B:
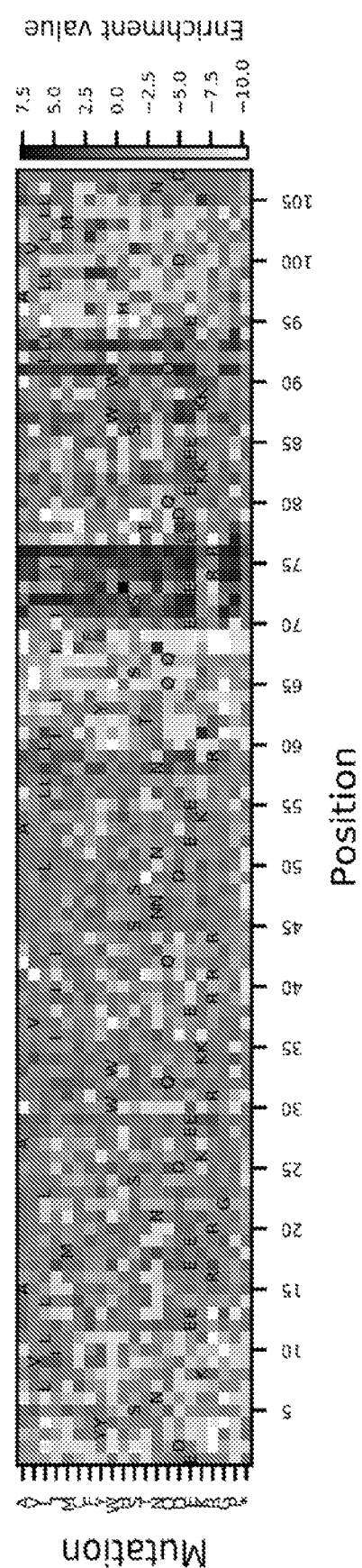
Figure 7C:
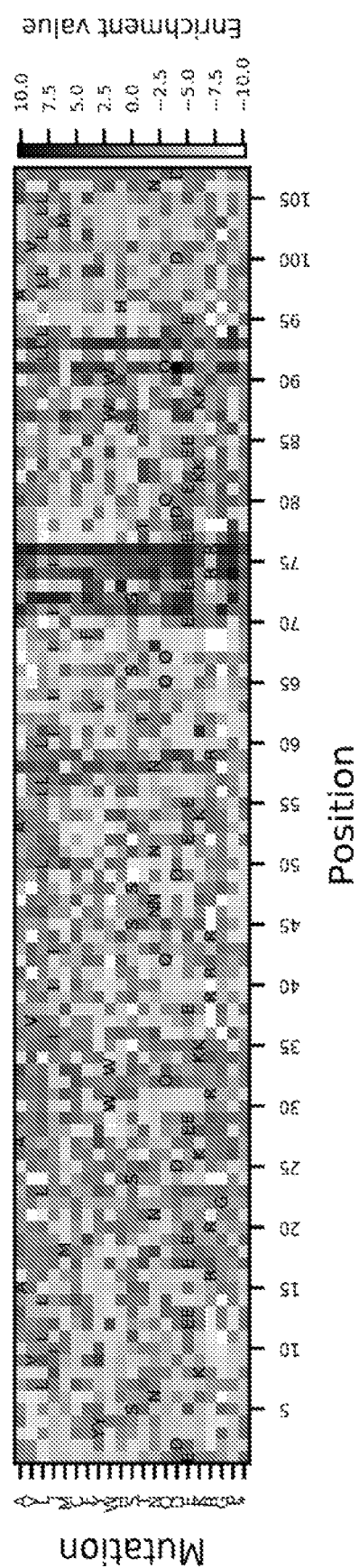
Figure 7D:
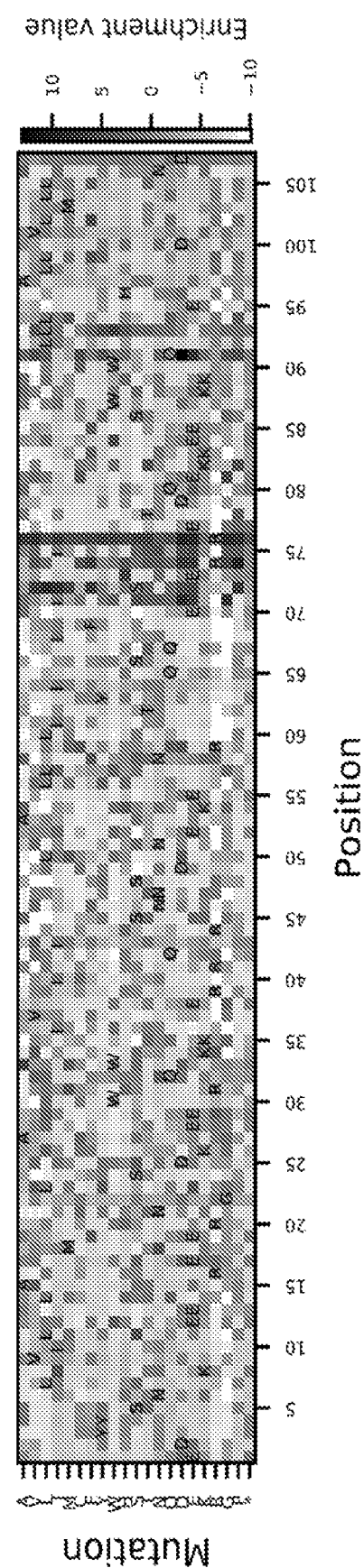
Figure 7E:
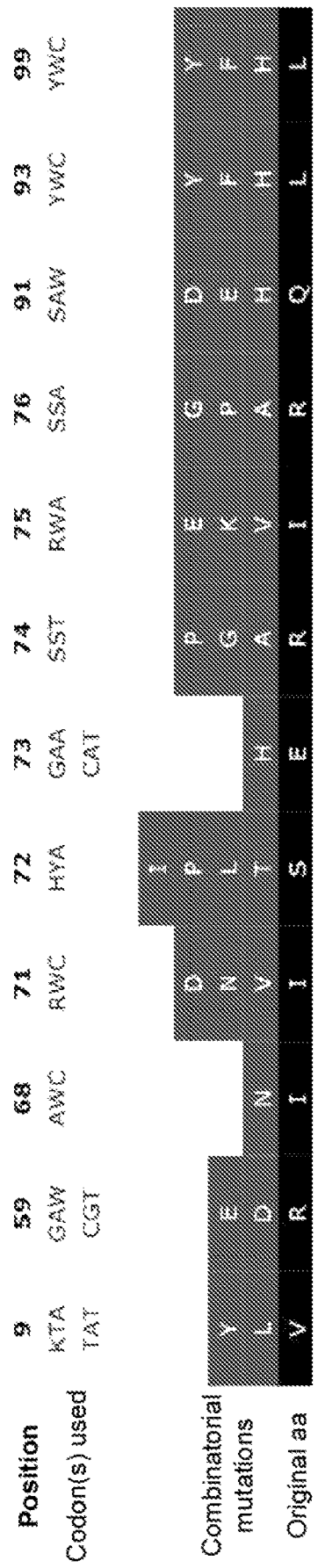
Figure 8A:
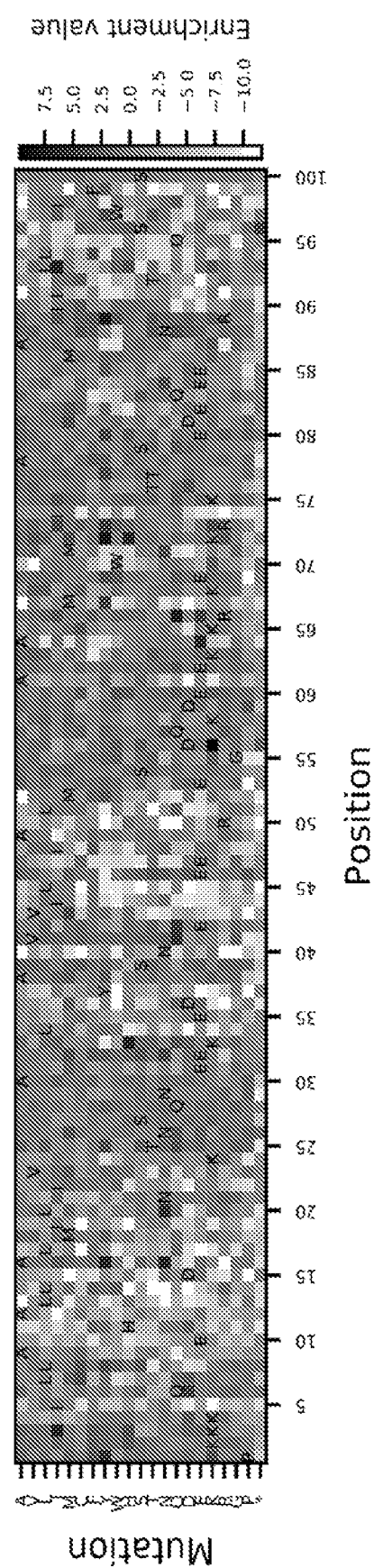
Figure 8B:
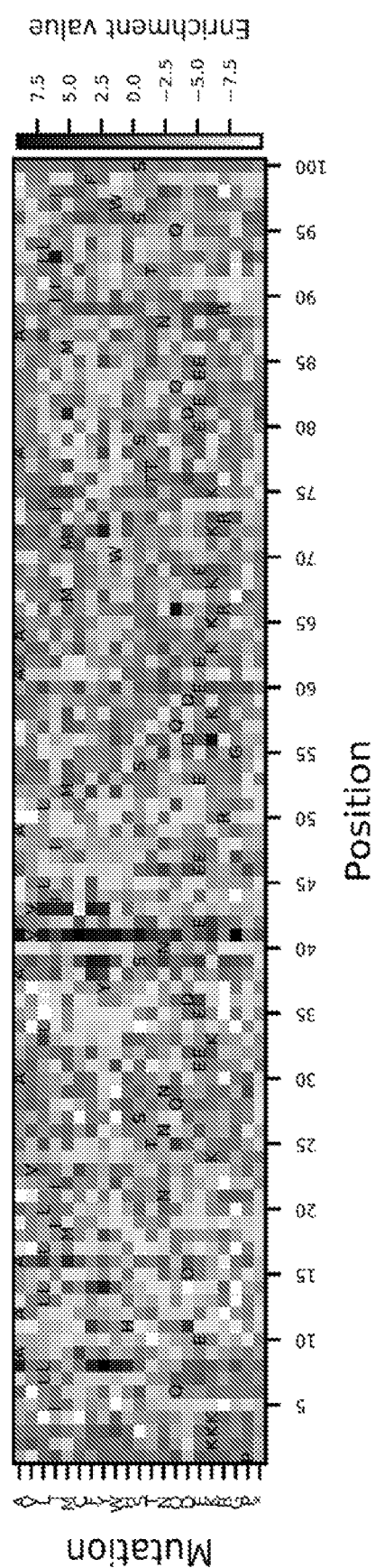
Figure 8C:
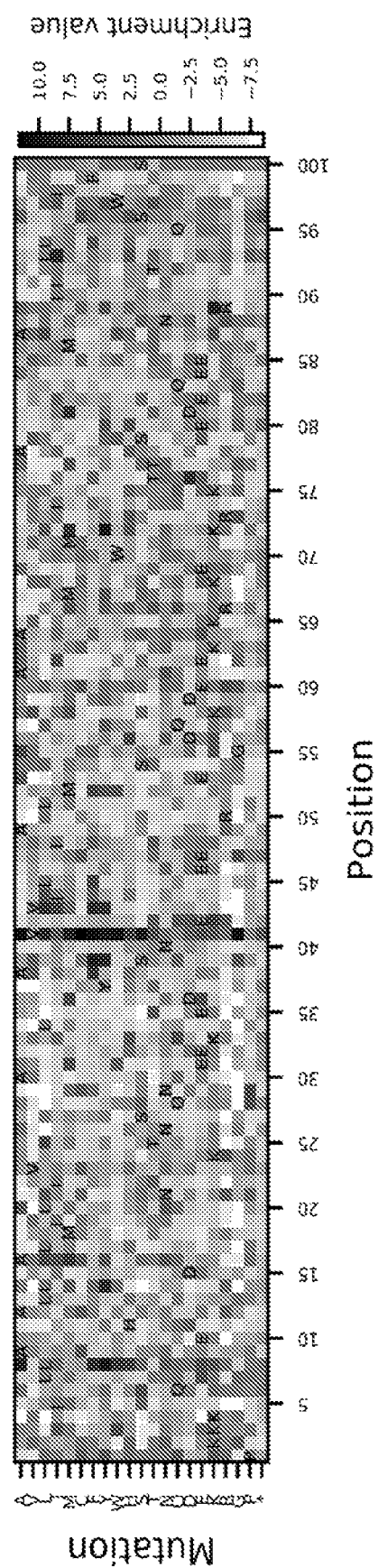
Figure 8D:
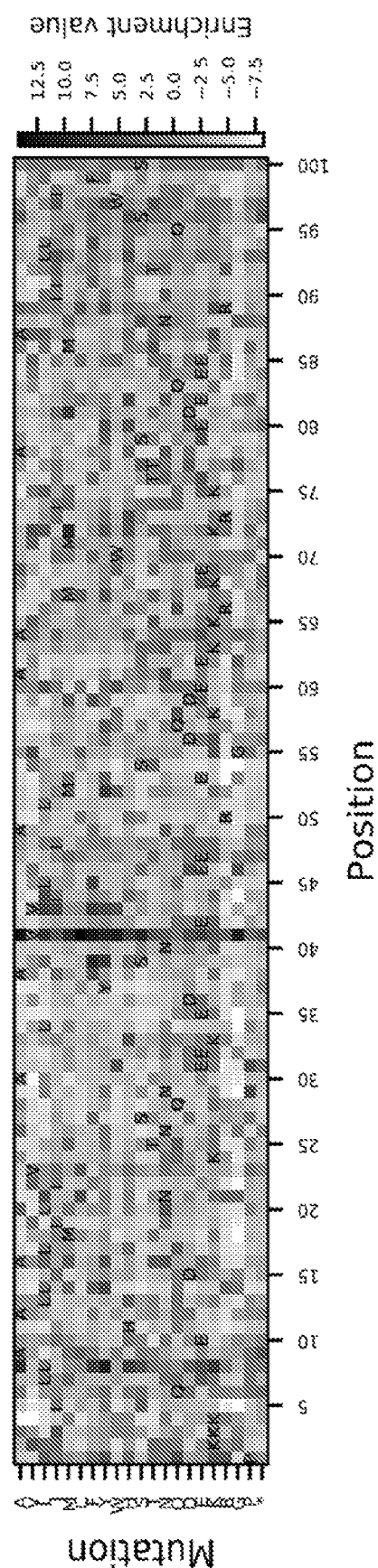
Figure 11A:
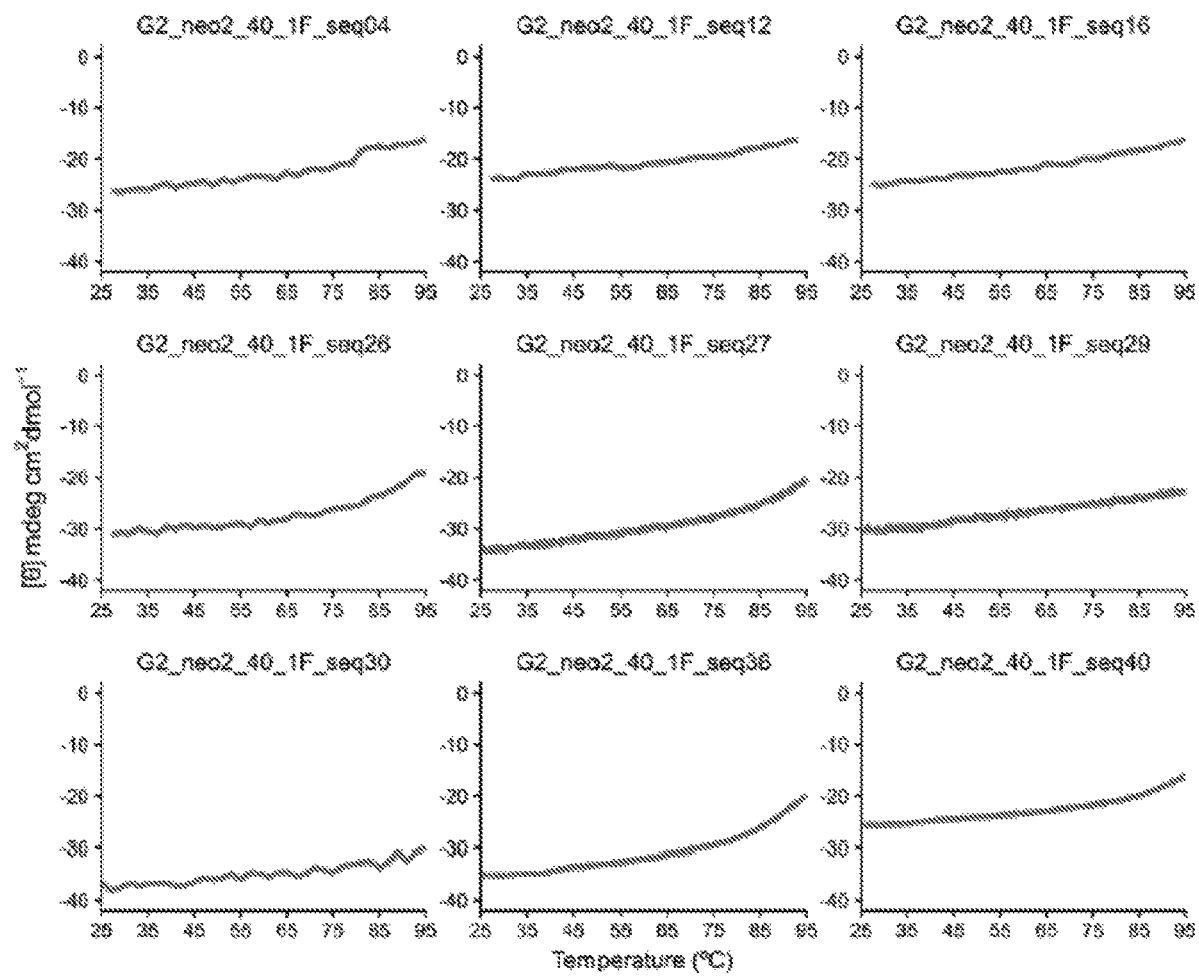
FIG. 11A-11D. Circular dichroism thermal melts for IL-2/IL-15 mimetic designs generation-2.
Figure 11B:
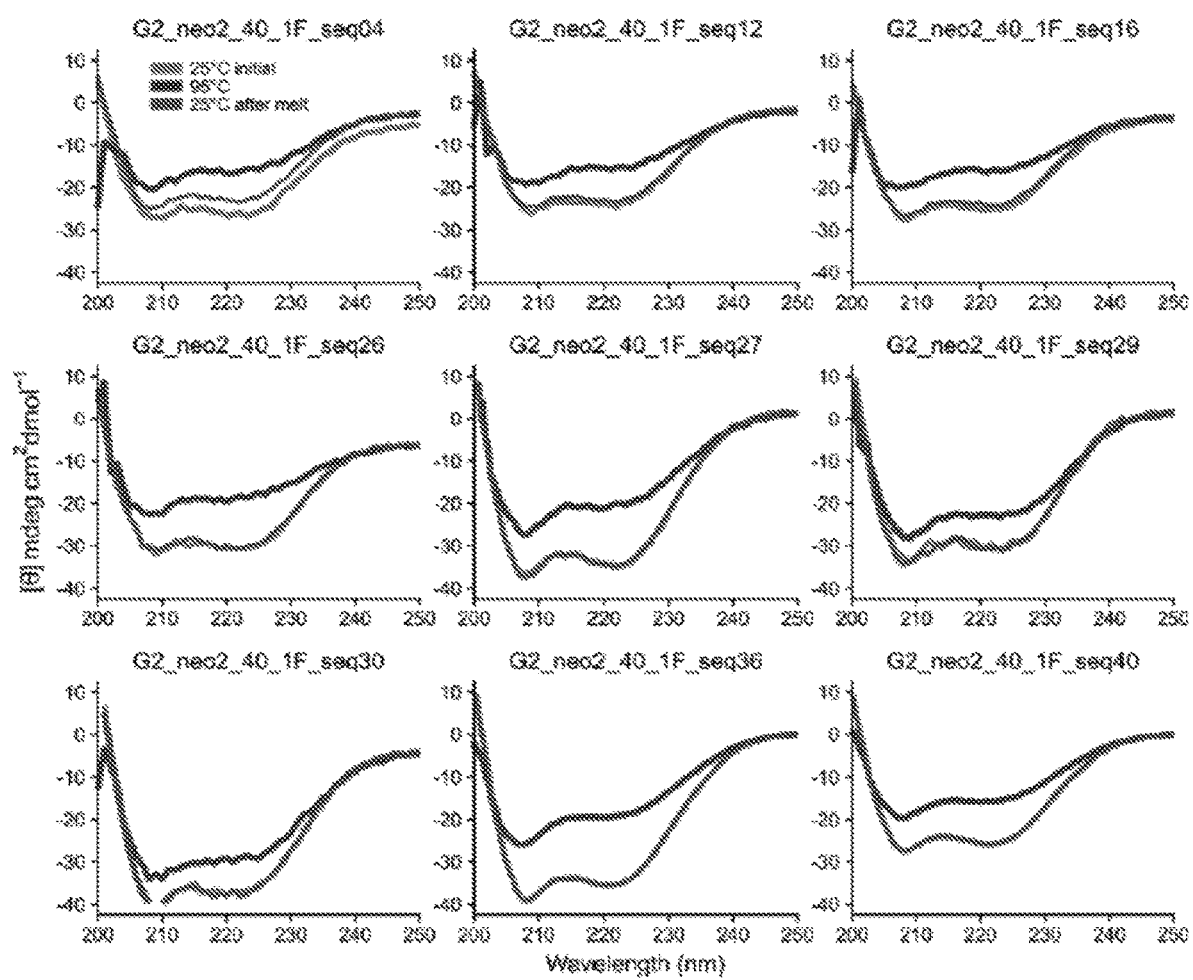
Figure 11C:
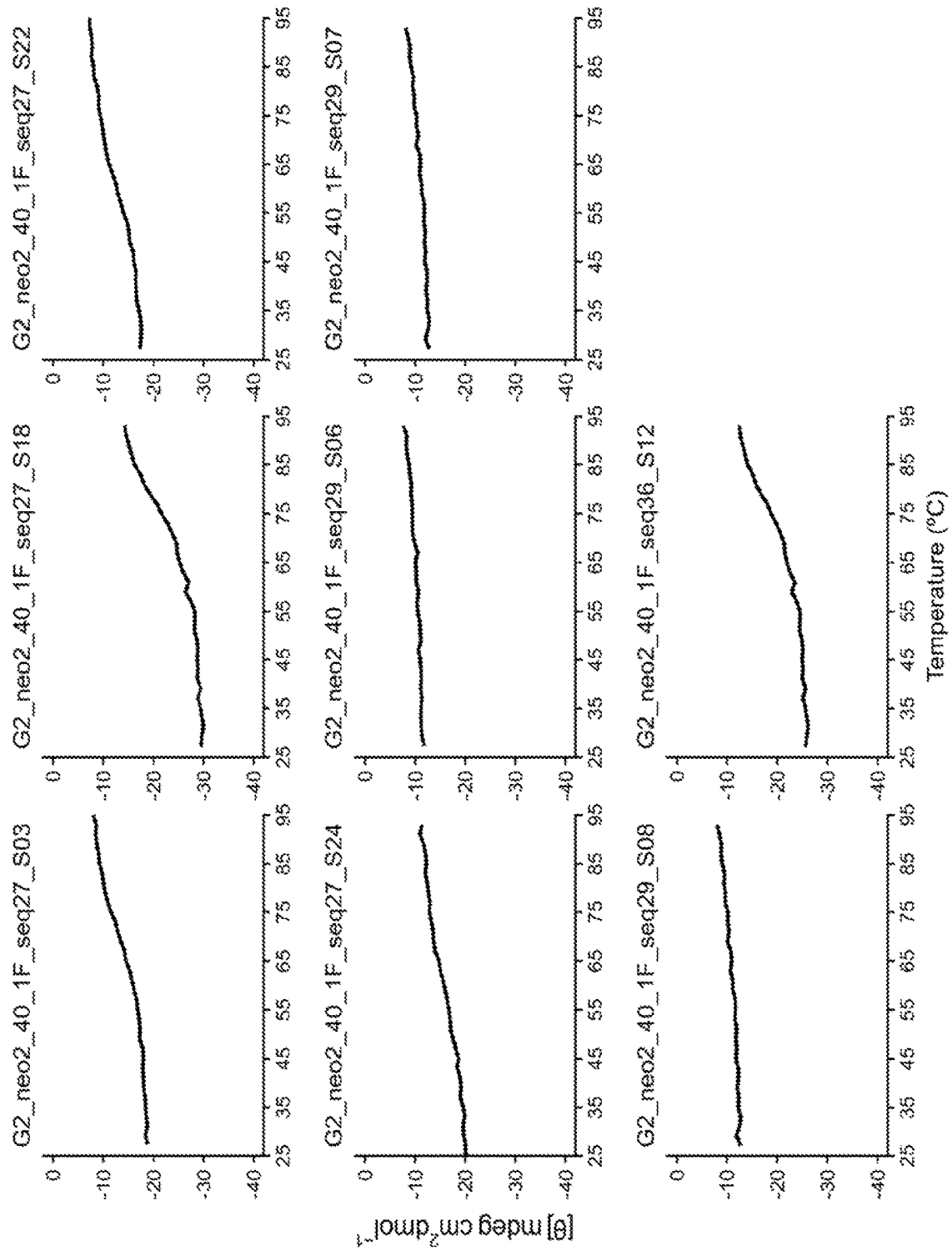
Figure 11D:
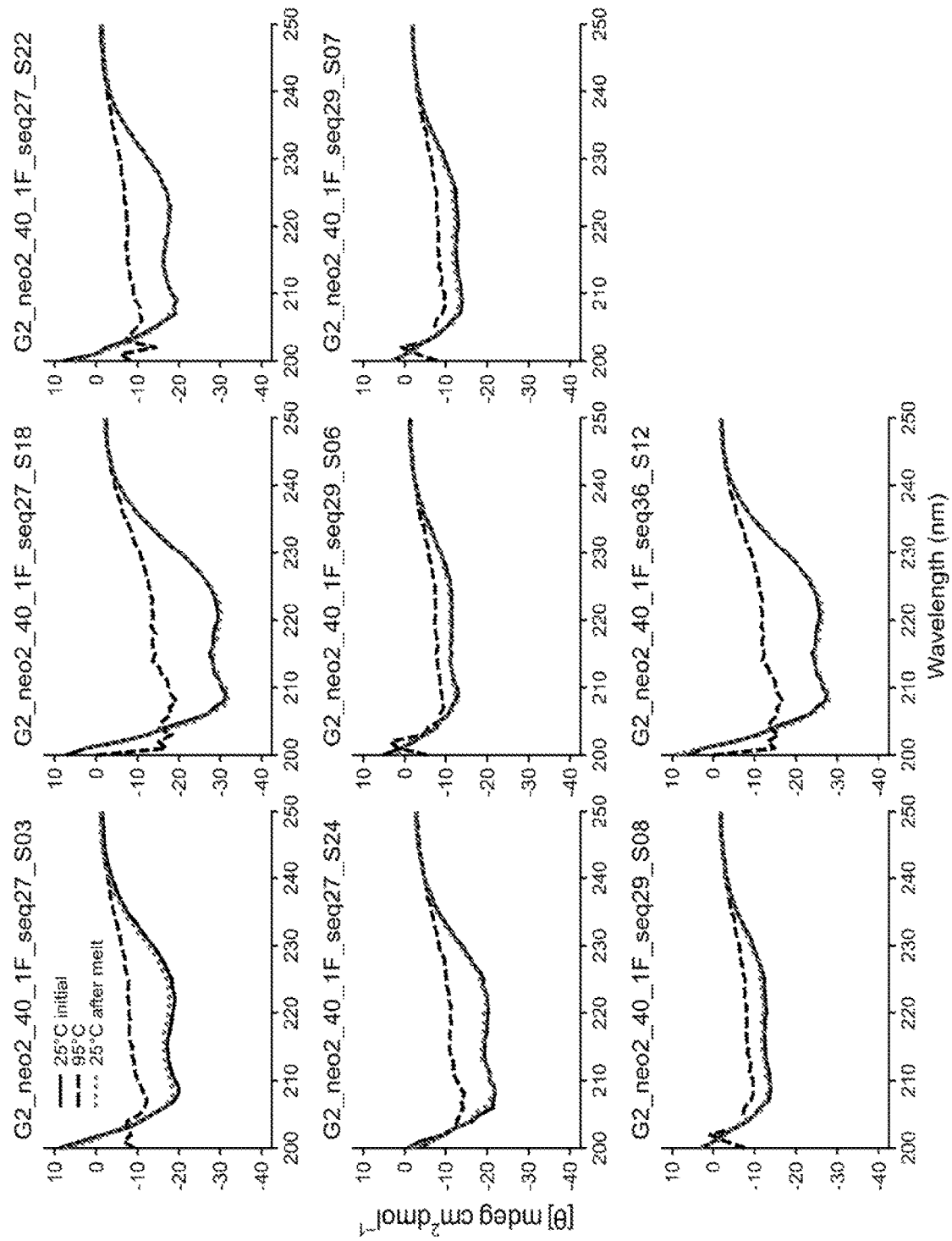
Figure 14A:
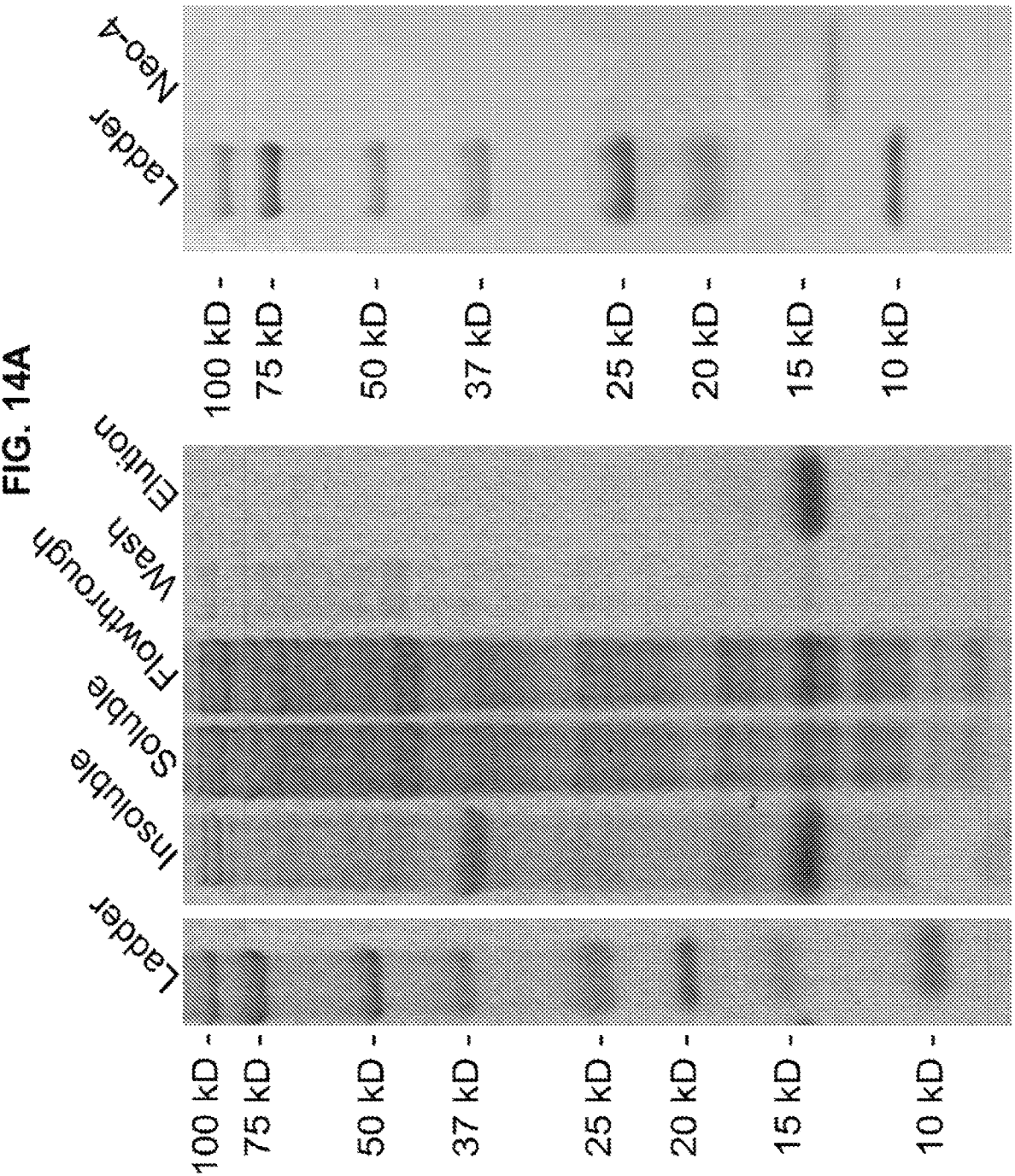
FIG. 14A-14C. Expression, purification, and thermal denaturation characterization of neoleukin-4.
Figure 14B:
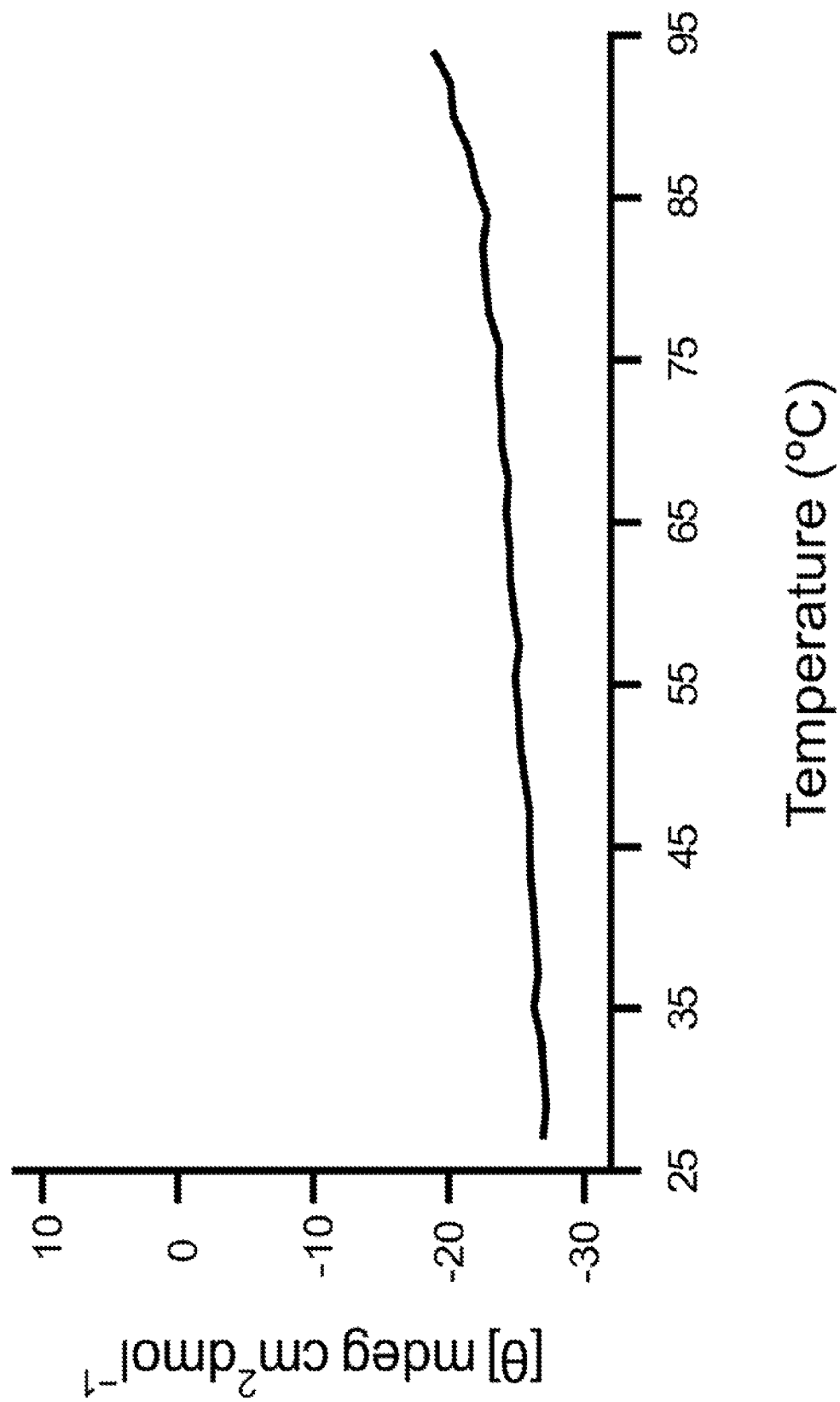
Figure 14C:
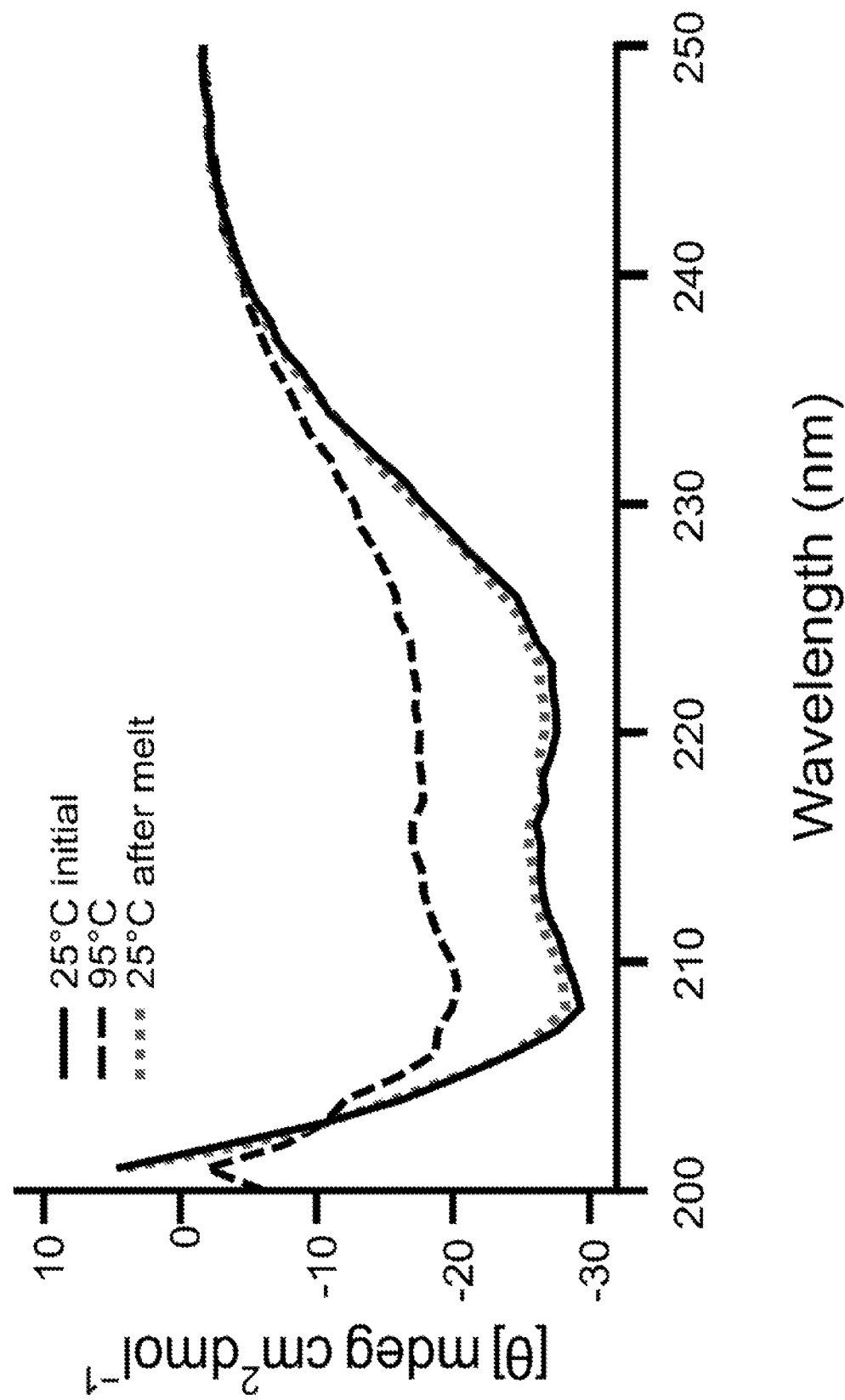

Robust modularity of neoleukin-2/15. Disulfide-stapling and reengineering into an IL-4 mimetic: Neoleukin-2/15 is highly modular, allowing to easily tune its properties, such as increasing its stability or modify its binding preference. This modularity and robustness was taken advantage of by introducing, by computational design, stability enhancing single-disulfide staples that preserve the function of neoleukin-2/15. In one example, a disulfide bridge was introduced by searching pairs of positions with favorable geometrical arrangements followed by flexible backbone minimization. The final design introduced a single disulfide between residues 38 and 75, which stabilizes helices H3 and H2. This strategy increased the stability of neoleukin-2/15 (Tm>95° C.), while retaining its sequence and function mostly unaffected (see Silva et al., Nature 565, pg. 186, Jan. 10, 2019). The modularity properties of neoleukin-2/15 were used to modify its binding preference. All cytokines in the interleukin-2 family interact with the $\gamma_c$ and share a common architecture. Therefore, it was hypothesized that neoleukin-2/15 could be transformed into another cytokine mimetic of the IL-2 family by changing only amino acids in the half of the binding-site that interacts with IL-2Rβ (helices H1 and H3). As proof of a concept, human interleukin-4 (hIL-4) was chosen as target, since it shares extensive structural homology with IL-2 and has potential applications in regenerative medicine. Neo-2/15 was modified to bind to the human IL-4 receptor (comprising IL-4Rα and $\gamma_c$) and not to the human IL-2 receptor (comprising IL-2Rβ and Yo by aligning the Neo-2/15 model into the structure of human IL-4 bound to its IL-4 receptor, and mutating 14 residues in Neo-2/15 to match the amino-acids of IL-4 at those structural positions that mediate interactions between IL-4 and IL4r (FIG. 3). Binding was further optimized by directed evolution using random mutagenesis and screening for high binding affinity variants, which introduced two additional amino acid substitutions and modified one of the fourteen original residues grafted from the IL-4 protein, thereby creating a new protein Neoleukin-4 with a total of sixteen mutations from Neoleukin-2/15. The resulting optimized design, neoleukin-4 (see Table 6), was recombinantly expressed and purified from *E. coli* and tested for binding. Neoleukin-4 binds with high affinity to IL-4Rα receptor, binds cooperatively to IL-4Rα$\gamma$ , (see FIG. 3), and does not bind with any affinity to the IL-2 receptor (data not shown) Neoleukin-4 retains the superior thermostable properties of neoleukin-2/15 (see FIG. 14*b,c*), and binds to the IL-13 receptor as expected given the natural cross-reactivity of IL-4 to IL-13 receptor (data not shown).

Methods

Computational design of de novo cytokine mimetics: The design of de novo cytokine mimetics began by defining a the structure of hIL-2 in the quaternary complex with the IL-2Rβ$\gamma_c$, receptor as template for the design. After inspection, the residues composing the binding-site were defined as hotspots using Rosetta™ metadata (PDBInfoLabels). The structure was feed into the new mimetic design protocol that is programmed in PyRosetta™, and which can automatically detect the core-secondary structure elements that compose the target-template and produce the resulting de novo mimetic backbones with full RosettaScripts™ compatible information for design. Briefly, the mimetic building algorithm works as follows. For the first generation of designs, each of the core-elements was idealized by reconstruction using loops from a clustered database of highly-ideal fragments (fragment-size 4 amino acids). After idealization, the mimetic building protocol aims to reconnect the idealized elements by pairs in all possible combinations. To do this it uses combinatorial fragment assembly of sequence-agnostic fragments from the database, followed by cartesian-constrained backbone minimization for potential solutions (i.e. where the N- and C-ends of the built fragment are close enough to link the two secondary structures). After minimization, the solutions are verified to contain highly ideal fragments (i.e. that every overlapping fragment that composes the two connected elements is also contained within the database) and no backbone clashes with the target (context) receptor. Passing backbone solutions were then profiled using the same database of fragments in order to determine the most probable amino acids at each position (this information was encoded in metadata on the design). Next, solutions for pairs of connected secondary structures were combinatorially recombined to produce fully connected backbones by using graph theory connected components. Since the number of solutions grows exponentially with each pair of elements, at each fragment combination step we ranked the designs to favor those with shorter interconnections between pairs of core elements, and kept only the top solutions to proceed to the next step. Fully connected solutions were then profiled by layer (interface, core, non-core-surface, surface), in order to restrict the identities of the possible amino acids to be layer-compatible. Finally, all the information on hotspots, compatible built-fragment amino acids and layers were combined (hotspot has precedence to amino acid probability, and amino acid probability took precedence to layer). These fully profiled backbones were then passed to RosettaScripts™ for flexible backbone design and filtering. For the second generation of designs, two approaches were followed. In the first approach, sequence redesigns of the best first generation optimized design were executed (G1_neo2_40_1F,). In the second approach new mimetics were engineered using G1_neo2_40_1F as the target template. The mimetic design protocol in this second generation was similar to the one described for the first generation, but with two key differences. Firstly, the core-fragments were no longer built from fragments, but instead by discovering parametric equations of repetitive phi and psi angles (omega fixed to 180°) that result in repetitive secondary structures that recapitulated each of the target helices as close as possible, a "pitch" on the phi and psi angles was allowed every X-amino acids in order to allow the helices the possibility to have curvature (final parameters: H1:, H2:, H3, H4), the sue of these parametric equations allowed to change the size of each of the core-elements in the target structure at will (either increase or decrease the size), which was coupled (max/min 8.a.a.) with the loop building process, and reductions in the size of the core elements were not allowed to remove hotspots from the binding site. The second difference in the second generation designs, is that instead of reconnecting the secondary structure core-elements we used a fragment-size of 7 amino acids, and no combinatorial assembly of more than one fragment was allowed (i.e. a single fragment has to be able to close a pair of secondary structures). The rest of the design algorithm was in essence similar to the one followed in the generation one. The Rosetta energy functions used were "talaris2013" and "talaris2014", for the first and second generation of designs, respectively.

The databases of highly ideal fragments used for the design of the backbones for the de novo mimetics were constructed with the new Rosetta™ application "kcenters_clustering_of_fragments" using an extensive database of non-redundant publicly available protein structures from the RCSB protein data bank, which was comprised of 16767 PDBs for the 4-mer database used for the first generation designs, and 7062 PDBs for the 7-mer database used for the second generation designs.

Yeast display: Yeast were transformed with genes encoding the proteins to be displayed together with linearized pETcon3 vector. The vector was linearized by 100 fold overdigestion by NdeI and XhoI (New England Biolabs) and then purified by gel extraction (Qiagen). The genes included 50 bases of overlap with the vector on both the 5' and 3' ends such that homologous recombination would place the genes in frame between the AGA2 gene and the myc tag on the vector. Yeast were grown in C-Trp-Ura media prior to induction in SGCAA media as previously described. 12-18 hours after induction, cells were washed in chilled display buffer (50 mM NaPO$_4$ pH 8, 20 mM NaCl, 0.5% BSA) and incubated with varying concentrations of biotinylated receptor (either human or murine IL-2Rα, IL-2Rβ, IL-2Rγ, or human IL-4Rα) while being agitated at 4° C. After approximately 30 minutes, cells were washed again in chilled buffer, and then incubated on ice for 5 minutes with FITC-conjugated anti-c-Myc antibody (1 uL per 3×10$^6$ cells) and streptavidin-phycoerythrin (1 uL per 100 uL volume of yeast). Yeast were then washed and counted by flow cytometry (Accuri C6) or sorted by FACS (Sony SH800). For experiments in which the initial receptor incubation was conducted with a combination of biotinylated IL-2Rγ and non-biotinylated IL-4Rα, the non-biotinylated receptor was provided in molar excess.

Mutagenesis and affinity maturation: For error-prone PCR based mutagenesis, the design to be mutated was cloned into pETcon3 vector and amplified using the MutaGene™ II mutagenesis kit (Invitrogen) per manufacturer's instructions to yield a mutation frequency of approximately 1% per nucleotide. 1 µg of this mutated gene was electroporated into EBY100 yeast together with 1 µg of linearized pETcon3 vector, with a transformation efficiency on the order of 10$^8$. The yeast were induced and sorted multiple times in succession with progressively decreasing concentrations of receptor until convergence of the population. The yeast were regrown in C-Trp-Ura media between each sort.

Site-saturation mutagenesis (SSM) libraries were constructed from synthetic DNA from Genscript. For each amino acid on each design template, forward primers and reverse primers were designed such that PCR amplification would result in a 5' PCR product with a degenerate NNK codon and a 3' PCR product, respectively. Amplification of "left" and "right" products by COF and COR primers yielded a series of template products each consisting of a degenerate NNK codon at a different residue position. For each design, these products were pooled to yield the SSM library. SSM libraries were transformed by electroporation into conditioned *Saccharomyccs cerevisiae* strain EBY100 cells, along with linearized pETCON3 vector, using the protocol previously described by Benatuil et al.

Combinatorial libraries were constructed from synthetic DNA from Genscript containing ambiguous nucleotides and similarly transformed into linearized pETCON3 vector.

Protein expression: Genes encoding the designed protein sequences were synthesized and cloned into pET-28b(+) *E. coli* plasmid expression vectors (GenScript. N-terminal 6×His tag and thrombin cleavage site). Plasmids were then transformed into chemically competent *E. coli* Lemo21 cells (NEB). Protein expression was performed using Terrific Broth™ and M salts, cultures were grown at 37° C. until OD$^{600}$ reached approximately 0.8, then expression was induced with 1 mM of isopropyl β-D-thiogalactopyranoside (IPTG), and temperature was lowered to 18° C. After expression for approximately 18 hours, cells were harvested and lysed with a Microfluidics M110P microfluidizer at 18,000 psi, then the soluble fraction was clarified by centrifugation at 24,000 g for 20 minutes. The soluble fraction was purified by Immobilized Metal Affinity Chromatograpy (Qiagen) followed by FPLC size-exclusion chromatography (Superdex™ 75 10/300 GL, GE Healthcare). The purified neoleukin-2/15 was characterized by Mass Spectrum (MS) verification of the molecular weight of the species in solution (Thermo Scientific), Size Exclusion-MultiAngle Laser Light Scattering (SEC-MALLS) in order to verify monomeric state and molecular weight (Agilent, Wyatt), SDS-PAGE, and endotoxin levels (Charles River).

Human and mouse IL-2 complex components including hIL-2 (a.a. 1-133), hIL-2Rα (a.a. 1-217), hIL-2Rβ (a.a. 1-214) hIL-2Rγ (a.a. 1-232), mIL-2 (a.a. 1-149), mIL-2Rα ectodomain (a.a. 1-213), mIL-2Rβ ectodomain (a.a. 1-215), and mγ$_c$ ectodomain (a.a. 1-233) were secreted and purified using a baculovirus expression system, as previously described [17,49]. All proteins were purified to >98% homogeneity with a Superdex™ 200 sizing column (GE Healthcare) equilibrated in HBS. Purity was verified by SDS-PAGE analysis. For expression of biotinylated human IL-2 and mouse IL-2 receptor subunits, proteins containing a C-terminal biotin acceptor peptide (BAP)-LNDIFEAQK-IEWHE (SEQ ID NO:303) were expressed and purified as described via Ni-NTA affinity chromatography and then biotinylated with the soluble BirA ligase enzyme in 0.5 mM Bicine pH 8.3, 100 mM ATP, 100 mM magnesium acetate, and 500 mM biotin (Sigma). Excess biotin was removed by size exclusion chromatography on a Superdex 200 column equilibrated in HBS.

Circular dichroism (CD): Far-ultraviolet CD measurements were carried out with an AVIV spectrometer model 420 in PBS buffer (pH 7.4) in a 1 mm path-length cuvette with protein concentration of ~0.20 mg/ml (unless otherwise mentioned in the text). Temperature melts where from 25 to 95° C. and monitored absorption signal at 222 nm (steps of 2° C./min, 30 s of equilibration by step). Wavelength scans (195-260 nm) were collected at 25° C. and 95° C., and again at 25° C. after fast refolding (~5 min).

STAT5 phosphorylation studies: In vitro studies: Approximately 2×10' YT-1, IL-2Rα+ YT-1, or CTLL-2 cells are plated in each well of a 96-well plate and re-suspended in RPM complete medium containing serial dilutions of hIL-2, mIL-2, Super-2, or engineered IL-2 mimetics. Cells are stimulated for 15 min at 37° C. and immediately fixed by addition of formaldehyde to 1.5% and 10 min incubation at room temperature. Permeabilization of cells is achieved by resuspension in ice-cold 100% methanol for 30 min at 4° C. Fixed and permeabilized cells are washed twice with FACS buffer (phosphate-buffered saline [PBS] pH 7.2 containing 0.1% bovine serum albumin) and incubated with Alexa Fluor® 647-conjugated anti-STAT5 pY694 (BD Biosciences) diluted in FACS buffer for 2 hours at room temperature. Cells are then washed twice in FACS buffer and MFI was determined on a CytoFLEX™ flow cytometer (Beckman-Coulter). Dose-response curves are fitted to a logistic model and half-maximal effective concentration ($EC_{50}$ values) are calculated using GraphPad Prism data analysis software after subtraction of the mean fluorescence intensity (MFI) of unstimulated cells and normalization to the maximum signal intensity. Experiments are conducted in triplicate and performed three times with similar results. Ex vivo studies: Spleens and lymph nodes are harvested from wild-type C57BL/6J or B6; 129S4-Il2ra$^{tm1Dw}$ (CD25KO) mice and made into a single cell suspension in sort buffer (2% Fetal Calf Serum in pH 7.2 phosphate-buffered saline). CD4+ T cells are enriched through negative selection by staining the cell suspension with biotin-conjugated anti-B220, CD8, NK 1.1, CD11b, CD11c, Ter119, and CD19 antibodies at 1:100 for 30 min on ice. Following a wash with sort buffer, anti-biotin Microbeads™ (Miltenyi Biotec) is added to the cell suspension at 20 μL per $10^7$ total cells and incubated on ice for 20 minutes. Cells are washed, resuspended and negative selection is then performed using EasySep™ Magnets (STEMCELL Technologies). Approximately 1×10$^5$ enriched cells are added to each well of a 96-well plate in RPMI complete medium with 5% FCS with 10-fold serial dilutions of mIL-2, Super-2, or Neoleukin-2/15. Cells are stimulated for 20 minutes at 37° C. in 5% $CO_2$, fixed with 4% PFA and incubated for 30 minutes at 4° C. Following fixation, cells are harvested and washed twice with sort buffer and again fixed in 500 μL 90% ice-cold methanol in $dH_2O$ for 30 minutes on ice for permeabilization. Cells are washed twice with Perm/Wash Buffer (BD Biosciences) and stained with anti-CD4-PerCP in Perm/Wash buffer (1:300), anti-CD44-Alexa Fluor 700 (1:200), anti-CD25-PE-Cy7 (1.200), and 5 μL per sample of anti-pSTAT5-PE pY694 for 45 min at room temperature in the dark. Cells are washed with Perm/Wash and re-suspended in sort buffer for analysis on a BD LSR II flow cytometer (BD Biosciences).

Data Tables

TABLE 2

Amino acid sequences for the best twelve first-round designs. Ten of the designs were (G1_neo2_35-44) were experimentally characterized by yeast display and all but two (G1_neo2_35 and G1_neo2_44) were found to bind fluorescently labeled chimeric ILRβγ$_c$ at low nanomolar concentrations via flow cytometry screening of designed first-round protein binders. Designs indicated were expressed on yeast and incubated with 2 nM hIL-2Rβγ$_c$ or 0 nM IL-2Rβγ$_c$ (data not shown).

| Design | Sequence |
| --- | --- |
| G1_neo2_33 | STKKWQLQAEHALLDWQMALNKSPEPNENLNRAITAAQSWISTGKIDLDKAEDIRRN-SDQARREAEKRGIDVRDLISNAQVILLEAR (SEQ ID NO: 103) |
| G1_neo2_34 | STKKWQLQAEHALLDWQMALNKSPEPNENLNRAITAAQSCISTGKCDLDKAEDIRRN-SDQARREAEKRGIDVRDLISNAQVILLEAR (SEQ ID NO: 104) |
| G1_neo2_35 | STKKWQLQAEHALLDWQMALNKSPEPNENLNRAITAAQSWISTGKIDCDKAEDIRRN-SDQARREAEKRGIDVRDLISNAQVILLEAC (SEQ ID NO: 105) |
| G1_neo2_36 | STKKLQLQAEHFLLDVQMILNESPEPNEELNRAITDAQSWISTGKIDLDRAEELARN-LEKVRDEALKRGIDVRDLVSNAKVIALELK (SEQ ID NO: 106) |
| G1_neo2_37 | STKKLQLQAEHFLLDVQMILNESPEPNEELNRCITDAQSWISTGKIDLDRAEECARN-LEKVRDEALKRGIDVRDLVSNAKVIALELK (SEQ ID NO: 107) |
| G1_neo2_38 | STKKLQLQAEHFLLDVQMILNESPEPNEELNRAITDAQSCISTGKCDLDRAEELARN-LEKVRDEALKRGIDVRDLVSNAKVIALELK (SEQ ID NO: 108) |

TABLE 2-continued

Amino acid sequences for the best twelve first-round designs. Ten of the designs were (G1_neo2_35-44) were experimentally characterized by yeast display and all but two (G1_neo2_35 and G1_neo2_44) were found to bind fluorescently labeled chimeric ILRβγ$_c$ at low nanomolar concentrations via flow cytometry screening of designed first-round protein binders. Designs indicated were expressed on yeast and incubated with 2 nM hIL-2Rβγ$_c$ or 0 nM IL-2Rβγ$_c$ (data not shown).

| Design | Sequence |
|---|---|
| G1_neo2_39 | STKKLQLQAEHFLLDVQMILNESPEPNEELNRAITDAQSWISTGKIDLDRAEELCRN-<br>LEKVRDEALKRGIDV<br>RDLVSNACVIALELK<br>(SEQ ID NO: 109) |
| G1_neo2_40 | STKKLQLQAEHALLDAQMMLNRSPEPNEKLNRIITTMQSWISTGKIDLDGAKELAKEV-<br>EELRQEAEKRGIDV<br>RDLASNLKVILLELA<br>(SEQ ID NO: 110) |
| G1_neo2_41 | STKKLQLQAEHALLDAQMMLNRSPEPNEKLNRIITTMQSCISTGKCDLDGAKELAKEV-<br>EELRQEAEKRGIDV<br>RDLASNLKVILLELA<br>(SEQ ID NO: 111) |
| G1_neo2_42 | STKKIQLQLEHALLDVQMALNRSPEPNESLNRMITWLQSWISTGKIDLDNAQEMAKE-<br>AEKIRKEMEKRGIDV<br>RDLISNIIVILLELS<br>(SEQ ID NO: 112) |
| G1_neo2_43 | STKKIQLQLEHALLDVQMALNRSPEPNESLNRMITWLQSCISTGKCDLDNAQEMAKE-<br>AEKIRKEMEKRGIDV<br>RDLISNIIVILLELS<br>(SEQ ID NO: 113) |
| G1_neo2_44 | STKKIQLQLEHALLDVQMALNRSPEPNESLNRMITWLQSWISTGKIDLDNAQEMCKE-<br>AEKIRKEMEKRGIDV<br>RDLISNICVILLELS<br>(SEQ ID NO: 114) |

TABLE 3

Amino acid sequences for the experimentally optimized first-round designs.

| Design | Sequence |
|---|---|
| G1_neo2_40_1A | STKKTQLLAEHALLDAFMMLNVVPEPNEKLNRIITTMQSWIYTGKIDADGAKELAKEVEELEQEYEKRGIDVEDD<br>ASNLKVILLELA<br>(SEQ ID NO: 115) |
| G1_neo2_40_1B | STKKTQLLAEHALLDAHMMLNMLPEPNEKLNRIITTMQSWIHTGKIDGDGAQELAKEVEELEQEYEKRGIDVEDE<br>ASNLKVILLELA<br>(SEQ ID NO: 116) |
| G1_neo2_40_1C | STKKTQLLAEHALLDAFMMLNMVPEPNEKLNRIITTMQSWIFTGKIDGDGAKELAKEVEELEQEFEKRGIDVEDE<br>ASNLKVILLELA<br>(SEQ ID NO: 117) |
| G1_neo2_40_1D | STKKTQLLAEHALLDALMMLNMVPEPNEKLNRIITTMQSWIFTGKIDGDGAQELAKEVEELEQELEKRGIDVEDY<br>ASNLKVILLELA<br>(SEQ ID NO: 118) |
| G1_neo2_40_1E | STKKTQLLAEHALLDAHMMLNVVPEPNEKLNRIITTMQSWIYTGKIDRDGAQELAKEVEELEQELEKRGIDVDDD<br>ASNLKVILLELA<br>(SEQ ID NO: 119) |
| G1_neo2_40_1F | STKKTQLLAEHALLDALMMLNLLPEPNEKLNRIITTMQSWIFTGKIDGDGAQELAKEVEELEQEHEKRGIDVEDY<br>ASNLKVILLELA<br>(SEQ ID NO: 120) |
| G1_neo2_40_1G | STKKTQLLAEHALLDAYMMLNMVPEPNEKLNRIITTMQSWILTGKIDSDGAQELAKEVEELEQELEKRGIDVDDD<br>ASNLKVILLELA<br>(SEQ ID NO: 121) |
| G1_neo2_40_1H | STKKTHLLAEHALLDAYMMLNVMPEPNEKLNRIITTMQSWIFTGKIDGDGAKELAKEVEELEQEFEKRGIDVDDD<br>ASNLKVILLELA<br>(SEQ ID NO: 122) |

TABLE 3-continued

Amino acid sequences for the experimentally optimized first-round designs.

| Design | Sequence |
|---|---|
| G1_neo2_40_1I | STKKTQLLAEHALLDAYMMLNLVPEPNEKLNRIITTMQSWIFTGKIDADGAQELAIEVEELEQEYEKRGIDVDDY<br>ASNLKVILLELA<br>(SEQ ID NO: 123) |
| G1_neo2_40_1J | STKKTQLMAEHALLDAFMMLNVLPEPNEKLNRIITTMQSWIFTGKIDGDDAQELAKEVEELEQELEKRGIDVDDD<br>ASNLKVILLELA<br>(SEQ ID NO: 124) |
| G1_neo2_40_1F_H1 | STKKTQLLIEHALLDALDMSRNLPEPNEKLSRIITTMQSWIFTGKIDGDGAQQLAKEVEELEQEHEKRGEDVEDE<br>ASNLKVILLELA<br>(SEQ ID NO: 125) |
| G1_neo2_40_1F_H2 | STKKTQLLLEHALLDALHMRRNLPEPNEKLSRIITTMQSWIFTGKIDGDGAQELAKEVEELEQEHEKRGRDVEDD<br>ASNLKVILLELA<br>(SEQ ID NO: 126) |
| G1_neo2_40_1F_H3 | STKKTQLLIEHALLDALNMRKKLPEPNEKLSRIITDMQSWIFTGKIDGDGAQQLAKEVEELEQEHEKRGGDVEDY<br>ASNLKVILLELA<br>(SEQ ID NO: 127) |
| G1_neo2_40_1F_H4 | STKKTQLLLEHALLDALHMSRELPEPNEKLNRIITDMQSWIFTGKIDGDGAQDLAKEVEELEQEHEKRGGDVEDY<br>ASNLKVILLELA<br>(SEQ ID NO: 128) |
| G1_neo2_40_1F_H5 | STKKTQLLIEHALLDALHMSRKLPEPNEKLSRIITTMQSWIFTGKIDGDGAQHLAKEVEELEQEHEKRGGEVEDE<br>ASNLKVILLELA<br>(SEQ ID NO: 129) |
| G1_neo2_40_1F_H6 | STKKTQLLIEHALLDALHMKRKLPEPNEKLNRIITNMQSWIFTEKIDGDGAQDLAKEVEELEQEHEKRGQDVEDY<br>ASNLKVILLELA<br>(SEQ ID NO: 130) |
| G1_neo2_40_1F_M1 | STEKTQLAAEHALRDALMLKHLLNEPNEKLARIITTMQSWQFTGKIDGDGAQELAKEVEELQQEHEVRGIDVEDY<br>ASNLKVILLHLA<br>(SEQ ID NO: 131) |
| G1_neo2_40_1F_M2 | STKNTQLAAEDALLDALMLRNLLNEPNEKLARIITTMQSWQFTEKIDGDGAQELAKEVEELQQEHEERGIDVEDY<br>ASNLKVILLQLA<br>(SEQ ID NO: 132) |
| G1_neo2_40_1F_M3 | STEKTQHAAEDALRDALMLRNLLNEPNEKLARIITTMQSWQFTEKIDGDGAQELAKEVEELQQEHEVRGIDVEDY<br>ASNLKVILLQLA<br>(SEQ ID NO: 133) |

TABLE 4

Amino acid sequences for second-round designs. G2_neo2_40_1F_seq02
to G2_neo2_40_1F_seq28 correspond to the 27 Rosetta™ sequence redesigns of
G1_neo2_40_1F; G2_neo2_40_1F_seq29 to G2_neo2_40_1F_seq42 represent the 14 new
de novo mimetic designs.

| Design | Sequence |
|---|---|
| G2_neo2_40_1F_seq02 | TQKKQQLLAEHALLDALMILNMLKTSSEAVNRMITIAQSWIFTGTSNPEEAKEMIKMAEQAEEEARREGV<br>DTEDYVSNLKVILKEIA<br>(SEQ ID NO: 134) |
| G2_neo2_40_1F_seq03 | TTKKYQLLVEHALLDALMMLNLSSESNEKMNRIITTMQSWIFTGTFDPDQAEELAKLVEELREEFRKRGI<br>DTEDYASNLKVILKELS<br>(SEQ ID NO: 135) |
| G2_neo2_40_1F_seq04 | TTKKIQLLVEHALLDALMILNLSSESNEKLNRIITTLQSWIFRGEIDPDRARELAKLLEEIREEMRKRGI<br>DTEDYVSNMIVIIRELA<br>(SEQ ID NO: 136) |
| G2_neo2_40_1F_seq05 | TKKKIQLLAEHVLLDLLMMLNLSSESNEKMNRLITIVQSWIFTGTIDPDQAEEMAKWVEELREEFRKRGI<br>DTEDYASNVKVILKELS<br>(SEQ ID NO: 137) |
| G2_neo2_40_1F_seq06 | TKKKYQLLIEHLLLDALMVLNMSSESNEKLNRIITILQSWIFTGTWDPDLAEEMEKLMQEIEEELRRRGI<br>DTEDYMSNMRVIIKELS<br>(SEQ ID NO: 138) |

TABLE 4 -continued

Amino acid sequences for second-round designs. G2_neo2_40_1F_seq02 to G2_neo2_40_1F_seq28 correspond to the 27 Rosetta™ sequence redesigns of G1_neo2_40_1F; G2_neo2_40_1F_seq29 to G2_neo2_40_1F_seq42 represent the 14 new de novo mimetic designs.

| Design | Sequence |
|---|---|
| G2_neo2_40_1F_seq07 | TKKKLQLLVEHLLLDMLMILNMSSESNEKLNRLITELQSWIFRGEIDPDKAEEMWKIMEEIEKELRERGI DTEDYMSNAKVIIKELS (SEQ ID NO: 139) |
| G2_neo2_40_1F_seq08 | TSKKQQLLAEHALLDALMILNISSESSEAVNRAITWLQSWIFKGTVNPDQAEEMRKLAEQIREEMRKRGI DTEDYVSNLEVIAKELS (SEQ ID NO: 140) |
| G2_neo2_40_1F_seq09 | TKKKYQLLIEHLLLDLLMVLNMSSESNEKINRLITWLQSWIFTGTYDPDLAEEMYKILEELREEMRERGI DTEDYMSNMRVIVKELS (SEQ ID NO: 141) |
| G2_neo2_40_1F_seq10 | TKKKWQLLIEHLLLDLLMILNLSSESNEKLNRLITWLQSWIFTGTYDPDLAEEMKKMMDEIEDELRERGI DTEDYMSNAKVIIKELS (SEQ ID NO: 142) |
| G2_neo2_40_1F_seq11 | TKKKIQLLVEHALLDALMILNLSSESNEKLNRIITTMQSWIFTGTIDPDQAEELSKLVEEIREEMRKRGI DTEDYVSNLKVILDELS (SEQ ID NO: 143) |
| G2_neo2_40_1F_seq12 | TEKKLQLLVEHALLDALMILNLWSESNEKLNRIITTMQSWIFTGRIDPDKAEELAKLVEELREEARERGI DTEDYVSNLKVILKELS (SEQ ID NO: 144) |
| G2_neo2_40_1F_seq13 | TKKKYQLLMEHLLLDLLMVLNMSSESNEKLNRLITIIQSWIFTGTWDPDKAEEMAKMLKEIEDELRERGI DTEDYMSNMIVINKELS (SEQ ID NO: 145) |
| G2_neo2_40_1F_seq14 | TTKKIQLLVEHALLDALMLLNLSSESNEKMNRIITTMQSWIFEGRIDPDQAQELAKLVEELREEFRKRGI DTEDYVSNLKVILEELS (SEQ ID NO: 146) |
| G2_neo2_40_1F_seq15 | TKKKIQLLVEHALLDALMMLNLSSESNEKLNRIITTMQSWIFTGTIDPDQAEELAKLVRELREEFRNRGI DTEDYASNLEVILRELS (SEQ ID NO: 147) |
| G2_neo2_40_1F_seq16 | TKKKIQLLVEHALLDALMILNLSSKSNEKLNRIITTMQSWIFNGTIDPDRARELAKLVEEIRDEMEKNGI DTEDYVSNLKVILEELA (SEQ ID NO: 148) |
| G2_neo2_40_1F_seq17 | TKKKYQLLIEHVLLDLLMLLNLSSESNEKMNRLITILQSWIFTGTYDPDKAEEMAKLLKELREEFRERGI DTEDYISNAIVILKELS (SEQ ID NO: 149) |
| G2_neo2_40_1F_seq18 | TKKKIQLLVEHALLDALMMLNLSSESNEKLNRIITTMQSWIFTGTIDPDRAEELAKLVEELREEFRKRGI DTEDYASNLKVILKELS (SEQ ID NO: 150) |
| G2_neo2_40_1F_seq19 | TKKKIQLLVEHALLDALMMLNLSSESNEKLNRIITTMQSWIFNGTIDPDQARELAKLVEELREEFRKRGI DTEDYASNLKVILEELA (SEQ ID NO: 151) |
| G2_neo2_40_1F_seq20 | TKKKLQLLVEHALLDALMLLNLSSESNEKLNRIITTMQSWIFTGTVDPDQAEELAKLVEEIREELRKRGI DTEDYVSNLKVILKELS (SEQ ID NO: 152) |
| G2_neo2_40_1F_seq21 | TTKKYQLLVEHALLDALMILNLSSESNEKLNRIITTMQSWIFTGTFDPDQAEELAKLVREIREEMRKRGI DTEDYVSNLEVILRELS (SEQ ID NO: 153) |
| G2_neo2_40_1F_seq22 | TKKKIQLLVEHALLDALMILNLSSESNEKLNRIITTMQSWIFTGTIDPDRAEELAKLVREIREEMRKRGI DTEDYVSNLEVILRELS (SEQ ID NO: 154) |
| G2_neo2_40_1F_seq23 | TKKKYQLLIEHLLLDLLMILNLSSESNEKLNRLITWLQSWIFRGEWDPDKAEEWAKILKEIREELRERGI DTEDYMSNAIVIMKELS (SEQ ID NO: 155) |
| G2_neo2_40_1F_seq24 | TDKKLQLLVEHLLLDLLMMLNLSSKSNEKMNRLITIAQSWIFTGKVDPDLAREMIKLLEETEDENRKNGI DTEDYVSNARVIAKELE (SEQ ID NO: 156) |

TABLE 4 -continued

Amino acid sequences for second-round designs. G2_neo2_40_1F_seq02
to G2_neo2_40_1F_seq28 correspond to the 27 Rosetta™ sequence redesigns of
G1_neo2_40_1F; G2_neo2_40_1F_seq29 to G2_neo2_40_1F_seq42 represent the 14 new
de novo mimetic designs.

| Design | Sequence |
| --- | --- |
| G2_neo2_40_1F_seq25 | TKKKIQLLVEHALLDALMLLNLSSESNEKMNRIITTMQSWIFTGTIDPDQAEELAKLVEELKEEFKKRGI<br>DTEDYVSNLKVILKELS<br>(SEQ ID NO: 157) |
| G2_neo2_40_1F_seq26 | TKKKYQLLIEHALLDALMILNLWSESNEKLNRIITTMQSWIFTGTYDPDKAEELEKLAKEIEDEARERGI<br>DTEDYMSNLRVILKELS<br>(SEQ ID NO: 158) |
| G2_neo2_40_1F_seq27 | TKKKAQLLAEHALLDALMLLNLSSESNERLNRIITWLQSIIFTGTYDPDMVKEAVKLADEIEDEMRKRGI<br>DTEDYVSNLRVILQELA<br>(SEQ ID NO: 159) |
| G2_neo2_40_1F_seq28 | TQKKNQLLAEHLLLDALMVLNQSSESSEVANRIITWAQSWIFEGRVDPNKAEEEAKKLAKKLEEEMRKRGI<br>DMEDYISNMKVIAEEMS<br>(SEQ ID NO: 160) |
| G2_neo2_40_1F_seq29 | EDYYSNLKVILEELAREMERNGLSDKAEEWRQWKKIVERIRQIRSNNSDLNEAKELLNRLITYIQSQIFE<br>ISERIRETDQEKKEESWKKWQLLLEHALLDVLMLLND<br>(SEQ ID NO: 161) |
| G2_neo2_40_1F_seq30 | PEKKRQLLLEHILLDALMLLNLLETNPQNTESKFEDYISNAEVIAEELAKLMESLGLSDEAEKFKKIKQW<br>LREVWRIWSSTNWSTLEDKARELLNRIITTIQSQIFY<br>(SEQ ID NO: 162) |
| G2_neo2_40_1F_seq31 | PEKKRQLLLEHILLDLLMILNMIETNRENTESEMEDYWSNVRVILRELARLMEELNYKELSELMERMRKI<br>VEKIRQIVTNNSSLDTAREWLNRLITWIQSLIFR<br>(SEQ ID NO: 163) |
| G2_neo2_40_1F_seq32 | PEKKRQLLAEHALLDALMLLNIIETNSKNTESKMEDYVSNLEVILTEFKKLAEKLNFSEEAERAERMKRW<br>ARKAYQMMTLDLSLDKAKEMLNRIITILQSIIFN<br>(SEQ ID NO: 164) |
| G2_neo2_40_1F_seq33 | PEKKRQLLAEHLLLDVLMMLNGNASLKDYASNAQVIADEFRELARELGLTDEAKKAEKIIEALERAREWL<br>LNNKDKEKAKEALNRAITIAQSWIFN<br>(SEQ ID NO: 165) |
| G2_neo2_40_1F_seq34 | PEKKRQLLLEHLLLDLLMILNMLRTNPKNIESDWEDYMSNIEVIIEELRKIMESLGRSEKAKEWKRMKQW<br>VRRILEIVKNNSDLEEAKEWLNRLITIVQSEIFE<br>(SEQ ID NO: 166) |
| G2_neo2_40_1F_seq35 | WEKKRQLLLEHLLLDLLMILNMWRTNPQNTESLMEDYMSNAKVIVEELARMMRSQGLEDKAREWEEMKKR<br>IEEIRQIIQNNSSKERAKEELNRLITYVQSEIFR<br>(SEQ ID NO: 167) |
| G2_neo2_40_1F_seq36 | PKKKIQLLAEHALLDALMILNIVKTNSQNAEEKLEDYASNVEVILEEIARLMESGDQKDEAEKAKRMKEW<br>MKRIKTTASEDEQEEMANRIITLLQSWIFS<br>(SEQ ID NO: 168) |
| G2_neo2_40_1F_seq37 | PEKKRQLLAEHALLDALMILNILQTNPQNAEEKLEDYMSNVEVIMEEFARMMRNGDRSEEAENAERIKKW<br>VRKASSTASSEEQREMMNRAITLMQSWIFE<br>(SEQ ID NO: 169) |
| G2_neo2_40_1F_seq38 | PEKKRQLLAEHLLLDALMVLNMLTTNSKNTEEKLEDYISNMKVIIKEMIELMRSLGRLEEAEKWKEALKA<br>VEKIGSRMDSETARELANRIITLAQSAIFY<br>(SEQ ID NO: 170) |
| G2_neo2_40_1F_seq39 | PEKKRQLLAEHALLDALMFLNLVETNPDQAEEKIEDYASNLRVIAEELARLFENLGRLDEAQKAKDIKEL<br>AERARSRVSSEKRKEAMNRAITILQSMIFR<br>(SEQ ID NO: 171) |
| G2_neo2_40_1F_seq40 | PEKKRQLLAEHALLDALMILNIIRTNSDNTESKLEDYISNLKVILEEIARLMESLGLSDEAEKAKEAMRL<br>ADKAGSTASEEEKKEAMNRVITWAQSWIFN<br>(SEQ ID NO: 172) |
| G2_neo2_40_1F_seq41 | PEKKRQLLAEHALLDALMMLNILRTNPDNAEEKLEDYWSNLIVILREIAKLMESLGLTDEAEKAKEAARW<br>AEEARTTASKDQRRELANRIITLLQSWIFS<br>(SEQ ID NO: 173) |
| G2_neo2_40_1F_seq42 | PEKKRQLLAEKLLLDALMILNIIETNEQNAESKLEDYISNAKVILDEFREMARDLGLLDEAKKAEKMKRW<br>LEKMRSNASSDERREWANRMITTAQSWIFN<br>(SEQ ID NO: 174) |

TABLE 5

Amino acid sequences for the experimentally optimized second-round designs.

| Design | Sequence |
|---|---|
| G2_neo2_40_1F_seq27_S18 | TNKEAQLHAEFALYDALMLLNLSSESNERLNRIITWLQSIIFYETYDPDMVKEAVKLADEIEDEMR KRKIDTEDYVVNLRLILQELA (SEQ ID NO: 175) |
| G2_neo2_40_1F_seq27_S22 | TKKDAELLAEFALYDALMLLNLSSESNERLNEIITWLQSIIFYGTYDPDMVKEAVKLADEIEDEMR KRGIDTEDYVSNLRLILQELA (SEQ ID NO: 176) |
| G2_neo2_40_1F_seq27_S24 | TNKKAQLHAEFALYDALMLLNLSSESNERLNDIITWLQSIIFTGTYDPDMVKEAVKLADEIEDEMR KRKIDTEDYVVNLRYILQELA (SEQ ID NO: 177) |
| G2_neo2_40_1F_seq29_S6 | EDYYSNLKLILEELAREMERNGLSDKAEEWRQWKKIVERIRQIRSNNSDLNEAKELLNRLITYIQS QIFEVLHGVGETDQEKKEESWKKWDLLLEHALLDVLMLLND (SEQ ID NO: 178) |
| G2_neo2_40_1F_seq29_S7 | EDYYSNLKVILEELAREMERNGLSDKAEEWRQWKKIVERIRQIRSNNSDLNEAKELLNELITYIQS QIFEVIEREGETDQEKKEESWKKWELHLEHALLDVLMLLND (SEQ ID NO: 179) |
| G2_neo2_40_1F_seq29_S8 | EDYYSNLKLILEELAREMERNGLSDKAEEWRQWKKIVERIRQIRSNNSDLNEARELLNRLITYIQS QIFEVLEGVGETDQEKKEESWKKWELHLEHALLDVLMLLND (SEQ ID NO: 180) |
| Neoleukin-2/15 (i.e. G2_neo2_40_1F_seq36_S11) | PKKKIQLHAEHALYDALMILNIVKTNSPPAEEKLEDYAFNFELILEEIARLFESGDQKDEAEKAKR MKEWMKRIKTTASEDEQEEMANAIITILQSWIFS (SEQ ID NO: 181) |
| G2_neo2_40_1F_seq36_S12 | PKKKIQLLAEHALFDLLMILNIVKTNSQNAEEKLEDYAYNAGVILEEIARLFESGDQKDEAEKAKR MKEWMKRIKDTASEDEQEEMANEIITILQSWNFS (SEQ ID NO: 182) |

Neoleukin-2/15-H8Y-K33E: H1->H3->H2'->H4
PKKKIQLYAEHALYDALMILNIVKTNSPPAEEELEDYAFNFELILEEIARLFESGDQKDEAEKAKRMKEWMKRIKTTASEDEQEEMANAIITILQSWIFS (SEQ ID NO: 94)

Binding of Neoleukin-2/15-H8Y-K33E to the IL2 receptor was measured by biolayer interferometry, and it was found to have higher binding affinity than Neoleukin-2 for IL2-Rbeta, both when tested against IL2Rbeta alone and when tested against the IL2Rbeta-gamma complex. This increased affinity was attributable mostly to an improved off rate from IL2-Rbeta.

designed IL-2 mimetic protein, Neoleukin-2/15. This system enables the delivery of conditionally active therapeutic proteins that reconstitute their activity by colocalization on the surface of target cells. We identified potential split sites and demonstrated successful reconstitution of Neoleukin-2/15 activity by binding to the IL-2 Receptors, cell signaling and colocalization-dependent activation on the surface of

TABLE 6

Amino acid sequences for the interleukin-4 mimetic designs based on reengineering of neolukin-2/15.

| Design | Sequence |
|---|---|
| IL4_G2_neo2_40_1F_seq36_S11 | PKKKIQITAEEALKDALSILNIVKTNSPPAEEQLERFAKRFERNLWGIARLFESGDQKDEAE KAKRMKEWMKRIKTTASEDEQEEMANAIITILQSWIFS (SEQ ID NO: 183) |
| Neoleukin-4 (i.e. IL4_G2_neo2_40_1F_seq36_S11_MIF) | PKKKIQIMAEEALKDALSILNIVKTNSPPAEEQLERFAKRFERNLWGIARLFESGDQKDEAE KAKRMIEWMKRIKTTASEDEQEEMANAIITILQSWFFS (SEQ ID NO: 184) |

Example 2: Split Cytokine Mimics for Targeted Immunotherapy

De novo proteins are designed following the rules of an ideal protein structure providing them with unusual biochemical properties, such as extreme thermostability and mutational robustness. Therefore, de novo designed proteins are ideal candidates to use for the development of conditionally active protein therapeutics. Here, we report the development of split cytokine mimetics for highly-targeted immunotherapy based on the recently developed de novo target tumor cells. We also demonstrate this application to another de novo designed cytokine mimic, Neoleukin-4.

Figure 15A:
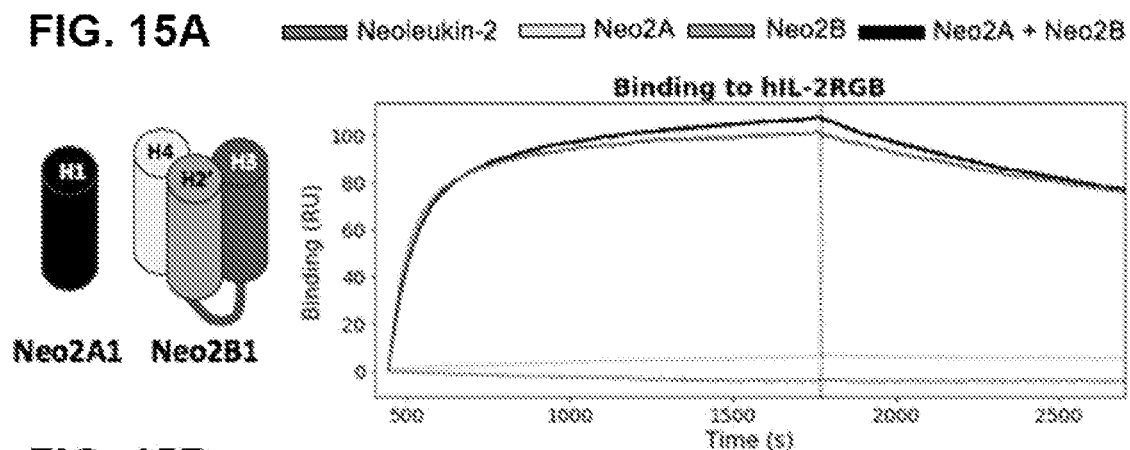
FIG. 15A-C. Split-Neo-2/15 variants can reconstitute Neoleukin-2/15 activity by binding to the human IL-2 receptor. a. Bio-Layer Interferometry binding assay of Neo-2/15 split between helices H1+H3-H2'-H4 (Neo2A1 and Neo2B1 respectively) to human IL-2 Receptor. Binding data were collected in an Octet RED96 (ForteBio) and processed using ForteBio™ Data Analysis Software version 9.0.0.10. Biotinylated target receptor human γc was immobilized on streptavidin-coated biosensors (SA ForteBio) at 1 µg/ml in binding buffer (10 mM HEPES (pH 7.4), 150 mM NaCl, 3 mM EDTA, 0.05% surfactant P20, 0.5% non-fat dry milk) for 300 seconds. After loading the γc target receptor onto the biosensor, baseline measurement was performed dipping the biosensors in binding buffer alone, then, the binding kinetics were monitored by dipping the biosensors in wells containing the target analyte protein (association step) and then dipping the sensors back into baseline/buffer (dissociation). For the association step, analyte proteins (i.e. Neoleukin-2/15. Neo2A1, Neo2B1, and an equimolar ratio of Neo2A1+Neo2B1) were diluted from concentrated stocks into binding buffer to a final concentration of 100 nM. Human IL-2Rβ was also added in solution at saturating concentration (250 nM). b. Bio-Layer interferometry binding assay of Neo-2/15 split into helixes H1-H3+H2'-H4 (Neo2A2 and Neo2B2 respectively), following the aforementioned experimental protocol. c. Bio-Layer Interferometry binding assay of Neo-2/15 split into helixes H1-H3-H2'+H4 (Neo2A3 and Neo2B3 respectively), following the aforementioned experimental protocol.
Figure 15B:
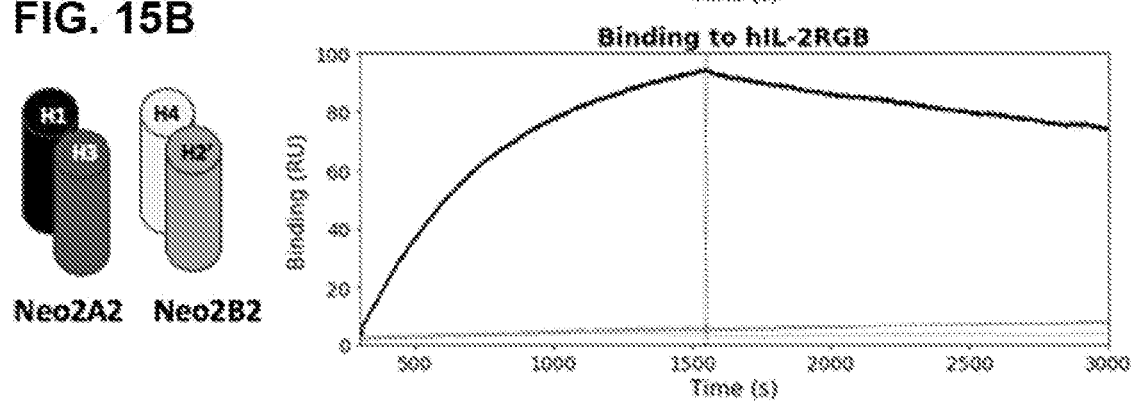
Figure 15C:
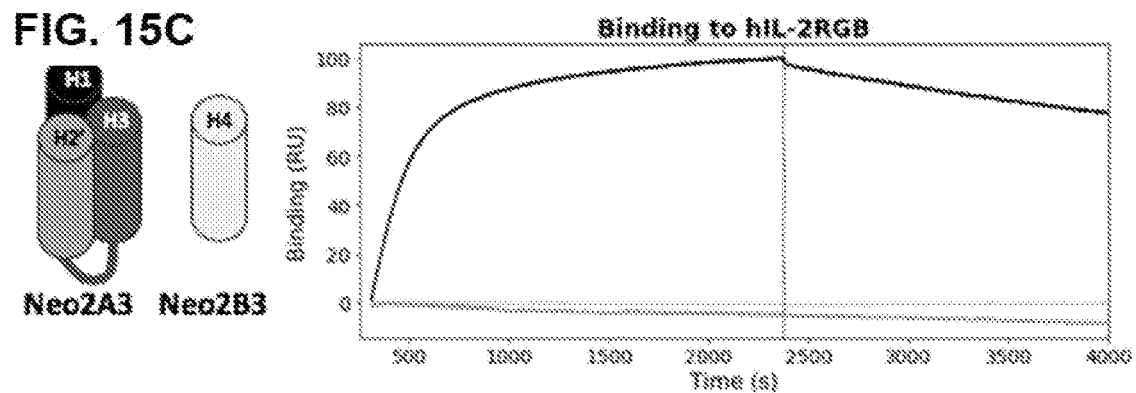

In order to identify potential split sites of Neoleukin-2/15 (Neo2), we evaluated the protein structure to find split positions that would minimize detrimental effects on the function of the protein. As a result, we defined three exemplary split positions: (i) between the helical elements H1 (Neo2A1) and H3'-H2-H4 (Neo2B1), (ii) between the helical elements H1-H3' (Neo2A2) and H2-H4 (Neo2B2), (iii) between the helical elements H1-H3' 1-12 (Neo2A3) and H4 (Neo2B3)(FIG. 15). The split-Neo2 fragments were characterized by analyzing their binding capacity to human IL-2 Receptor (FIG. 15) and signaling on IL-2 responsive CTTL-2 cells (FIG. 16). The individual split fragments were shown to have negligible binding to IL-2Rβγ and signaling capacity in most cases, but potent activity upon equimolar combination of the complementary split fragments.

The development of split-Neo2, enables co-localization-dependent reconstitution of the protein, and thus, conditional-activation of split-Neo2. In order to enable the colocalization of Neo2A and Neo2B fragments, we firstly performed genetic fusions to targeting domains (FIG. 17). Neo2A1, Neo2A2 and Neo2A3 were fused to the C-terminus of a Her2-targeted designed ankyrin repeat protein (DARPin) by a 15-residue flexible linker (GSGGSGGGSGGSGSG; SEQ ID NO:100). Neo2B1, Neo2B2 and Neo2B3 were fused to the N-terminus of an EGFR-targeted designed ankyrin repeat protein (DARPin) by a 15-residue flexible linker (GSGGSGGGSGGSGSG; SEQ ID NO:100). Then, we evaluated their ability to reconstitute binding to IL-2Rβγ after combination of the split fragments, demonstrating that the fusions did not interfere with their reconstitution capacity of splitNeo-2 (FIG. 17).

To evaluate the colocalization-dependent activation and targeting selectivity of the split-Neo2 system, we performed an in vitro assay with split Neo-2/15 targeted to EGFR and Her2 (FIG. 18*a*) on the surface of engineered K562 cell lines. We used four engineered cell lines: (i) no surface receptors, (ii) Her2+/eGFP+, (iii) EGFR+/iRFP+, (iv) Her2+/eGFP+ EGFR+/iRFP+ (FIG. 18*b*). The four cell lines were mixed in equivalent ratios and incubated with the targeted split-Neo2 fragments for 15 minutes. Subsequently, the cells were washed and incubated with a mixture of biotinylated IL-2Receptor and a fluorescent streptavidin-phycoerythrin conjugate (SAPE). Finally, the cells were analyzed by Fluorescence-activate cell sorting (FACS). Successful reconstitution of Neo-2 activity resulted in fluorescent labelling with PE on the surface of target cells (FIG. 18*c*). We observed strong IL-2 Receptor binding on the surface of Her2+ and Her2+/EGFR+ when full Neo2 was targeted with a single anti-Her2 targeting domain (aHer2-Neo2). Similar binding was observed when Neo2A1 and Neo2B1 split fragments were both targeted to Her2 (aHer2-Neo2A1+aHer2-Neo2B1), demonstrating that both fragments could be delivered to the same cell surface marker if desired. Additionally, we observed highly selective reconstitution on the surface of double positive Her2+/EGFR+ when each split fragment was targeted to either Her2 or EGFR (aHer2-Neo2A1+Neo2B1-aEGFR, aHer2-Neo2A2+Neo2B2-aEGFR, aHer2-Neo2A3+Neo2B3-aEGFR). Further studies demonstrated that for each combination of split-Neo2 fragments, the simultaneous presence of both fragments was necessary to enable IL-2Receptor recruitment on the surface of K562 cells (FIG. 19). These results demonstrate the high selectivity of the split cytokine mimetics to reconstitute the desired activity specifically on the surface of target cells.

The applications of the split cytokine mimic technology are not only limited to targeting tumor associated antigens. For given applications, targeting specific subsets of immune cells to be selectively stimulated would be beneficial to direct the immune response to treat disease. For instance, this application would be useful to specifically augment the expansion of CD8+ cytotoxic T cells, Natural Killer cells or engineered CAR T-cells to potentiate their anti-tumor response, but also, targeting to regulatory T-cells to suppress a strong immune response (FIG. 20*a*). Furthermore, in some scenarios, mixed targeting approaches can be deployed, i.e. target one split fragment to the tumor cells or tumor microenvironment, while the other fragment is delivered to immune cells (FIG. 20*b*)

Finally, to demonstrate the transferability of the methodology described here to other de novo designed interleukins, we created a new conditionally active IL-4 mimetic (FIG. 21). To achieve this, we successfully introduced specific mutations on splitNeo-2 that modify the binding interface to the hIL-2Beta receptor, to bind hIL-4alpha receptor.

Exemplary Split Neoleukin-2115 variants sequences used in Example 2

H1 (Neo2A1)
(SEQ ID NO: 256)
PKKKIQLHAEHALYDALMILNIVKTNS

H3-H2'-H4 Neo2B1)
(SEQ ID NO: 257)
TNSPPAEEKLEDYAFNFELILEEIARLFESGDQKDEAEKAKRMKEWMKRI
KTTASEDEQEEMANAIITILQSWIFS

H1-H3-H2' Neo2A3
(SEQ ID NO: 258)
PKKKIQLHAEHALYDALMILNIVKTNSPPAEEKLEDYAFNFELILEEIAR
LFESGDQKDEAEKAKRMKEWMKRIKTTAS

H4 (Neo2B3)
(SEQ ID NO: 259)
TTASEDEQEEMANAIITILQSWIFS

H1-H3 (Neo2A2)
(SEQ ID NO: 260)
PKKKIQLHAEHALYDALMILNIVKTNSPPAEEKLEDYAFNFELILEEIAR
LFESGD

H2'-H4 (Neo2B2)
(SEQ ID NO: 261)
DQKDEAEKAKRMKEWMKRIKTTASEDEQEEMANAIITILQSWIFS

Exemplary Split Neoleukin-4 sequences used in Example 2

H1 Neo4A1)
(SEQ ID NO: 262)
PKKKIQIMAEEALKDALSILNIVKTNS

H3-H2'-H4 (a.k.a. Neo4B1)
(SEQ ID NO: 263)
TNSPPAEEQLERFAKRFERNLWGIARLFESGDQKDEAEKAKRMIEWMKR
IKTTASEDEQEEMANAIITILQSWFFS

Exemplary constructs used in Example 2

X2-Z1-X3-Z2-X4-E01_EGER_DARPin
(SEQ ID NO: 304)
(MGSHHHHHHGSGSENLYFQGSGGG)TNSPPAEEKLEDYAFNFELILEE
IARLFESGDQKDEAEKAKRMKEWMKRIKTTASEDEQEEMANAIITILQS
WIFS(GSGGSGGGSGGSGSGGSGGG)DLGKKLLEAARAGQDDEVRILMA
NGADVNADDTWGWTPLHLAAYQGHLEIVEVLLKNGADVNAYDYIGWTPL
HLAADGHLEIVEVLLKNGADVNASDYIGDTPLHLAAHNGHLEIVEVLLK
HGADVNAQDKFGKTAFDISIDNGNEDLAEILQKLN

G3_Her2_DARPin_X1
(SEO ID NO: 305)
(MGSHHHHHHGSGSENLYFQGSGSG)DLGKKELEAARAGQDDEVRILMA
NGADVNAKDEYGLTPLYLATAHGHLEIVEVLLKNGADVNAVDAIGFTPL

HLAAFIGHLEIAEVLLKHGADVNAQDKFGKTAFDISIGNGNEDLAEILQ

KLN(GSGGSGGGSGGSGSG)PKKKIQLHAEHALYDALMILNIVKTNS

G3_Her2_DARPin_X2-Z1-X3-Z3-X4
(SEQ ID NO: 306)

(MGSHHHHHHGSGSENLYFQGSGSG)DLGKKLLEAARAGQDDEVRILMA

NGADVNAKDEYGLTPLYLATAHGHLEIVEVLLKNGADVNAVDATGFTPL

HLAAFIGHLEIAEVLLKHGADVNAQDKFGKTAFDISIGNGNEDLAEILQ

KLN(GSGGSGGGSGGSGSG)TNSPPAEFKLEDYAFNFELILEEIARLFE

SGDQKDEAEKAKRMKEWMKRIKTTASEDEQEEMANAIITILQSWIFS

X2-Z1-X3-Z2-X4-E01_EGFR_DARPin
(SEQ ID NO: 307)

(MGSHHHHHHGSGSENLYFQGSGGG)TNSPPAEEKLEDYAFNFELILEE

IARLFESGDQKDEAEKAKRMKEWMKRIKTTASEDEQEEMANAIITILQS

WIFS(GSGGSGGGSGGSGSGGSGGG)DLGKKLLEAARAGQDDEVRILMA

NGADVNADDTWGWTPLHLAAYQGHLEIVEVLLKNGADVNAYDIGWTPL

HLAADGHLEIVEVLLKNGADVNASDYIGDTPLHLAAHNGHLEIVEVLLK

HGADVNAQDKFGKTAFDISIDNGNEDLAEILQKLN

X2-Z2-X4-E01_EGFR_DARPin
(SEQ ID NO: 308)

(MGSHHHHHHGSGSENLYFQGSGGG)DQKDEAEKAKRMKEWMKRIKTTA

SEDEQEEMANAIITILQSWIFS(GSGGSGGGSGGSGSGGSGGG)DLGKK

LLEAARAGQDDEVRILMANGADVNADDTWGWTPLHLAAYQGHLEIVEVL

LKNGADVNAYDYIGWTPLHLAADGHLEIVEVLLKNGADVNASDYIGDTP

LHLAAHNGHLEIVEVLLKHGADVNAQDKFGKTAFDISIDNGNEDLAEIL

QKLN

X4-E01_EGFR_DARPin
(SEQ ID NO: 309)

(MGSHHHHHHGSGSENLYFQGSGGG)TTASEDEQEEMANAIITILQSWI

FS(GSGGSGGGSGGSGSGGSGGG)DLGKKLLEAARAGQDDEVRILMANG

ADVNADDTWGWTPLHLAAYQGHLEIVEVLLKNGADVNAYDIGWTPLHL

AADGHLEIVEVLLKNGADVNASDIYGDTPLHLAAHNGHLEIVEVLLKHG

ADVNAQDKFGKTAFDISIDNGNEDLAEILQKLN

G3_Her2_DARPin_X1-Z1-X3
SEQ ID NO: 310)

(MGSHHHHHHGSGSENLYFQGSGSG)DLGKKLLEAARAGQDDEVRILMA

NGADVNAKDEYGLTPLYLATAHGHLEIVEVLLKNGADVNAVDAIGFTPL

HLAAFIGHLEIAEVLLKHGADVNAQDKFGKTAFDISIGNGNEDLAEILQ

KLN(GSGGSGGGSGGSGSG)PKKKIQLHAEHALYDALMILNIVKTNSPP

AEEKLEDYAFNFELILEEIARLFESG

G3_Her2_DARPin_X1-Z1-X3-Z2-X2
(SEQ ID NO: 311)

(MGSHHHHHHGSGSENLYFQGSGSG)DLGKKLLEAARAGQDDEVRILMA

NGADVNAKDEYGITPLYLATAHGHLEIVEVLLKNGADVNAVDAIGFTPL

HLAAFIGHLEIAEVLLKHGADVNAQDKFGKTAFDISIGNGNEDLAEILQ

KLN(GSGGSGGGSGGSGSG)PKKKIQLHAEHALYDALMILNDTKTNSPP

AEEKLEDYAFNFELILEEIARLFESGDQKDEAEKAKRMKEWMKRIKTTA

---

We claim:

1. A non-naturally occurring conditionally active receptor agonist, comprising a first polypeptide component and a second polypeptide component, wherein the first polypeptide component and the second polypeptide component are not present in a fusion protein, wherein in total the first polypeptide component and the second polypeptide component comprise domains X1, X2, X3, and X4, wherein:
   (a) X1 is a peptide comprising an amino acid sequence at least 75% identical to the amino acid sequence (PKK-KIQ) LHAEHALYDAL(MILNI) (SEQ ID NO: 4);
   (b) X2 is any helical peptide domain;
   (c) X3 is a peptide comprising an amino acid sequence at least 75% identical to the amino acid sequence (LE) DYAFNFELILEE(IARLFESG) (SEQ ID NO:5); and
   (d) X4 is a peptide comprising an amino acid sequence at least 75% identical to the amino acid sequence (ED-EQEEMANAI)ITILQSWIF(S) (SEQ ID NO:6), wherein:
   (i) amino acid residues in parentheses may be present or absent;
   (ii) the first polypeptide component comprises at least one of X1, X2, X3, and X4 but does not comprise each of X1, X2, X3, and X4; and
   (iii) the second polypeptide component comprises each of X1, X2, X3, and X4 that is not present in the first polypeptide component;

wherein the first polypeptide component and the second polypeptide component are not active receptor agonists individually, and wherein the first polypeptide component and the second polypeptide interact to form an active agonist of IL-2 receptor $\beta\gamma_c$ heterodimer (IL-$2R\beta\gamma_c$), or IL-4 receptor $\alpha\gamma_c$ heterodimer (IL-$4R\alpha\gamma_c$).

2. The conditionally active receptor agonist of claim 1, wherein:
   (a) X1 is a peptide comprising an amino acid sequence at least 85% identical to the amino acid sequence PKK-KIQLHAEHALYDALMILNI (SEQ ID NO: 4) or QLHAEHALYDALMILNI (SEQ ID NO:320);
   (b) X3 is a peptide comprising an amino acid sequence at least 85% identical to the amino acid sequence LEDYAFNFELILEEIARLFESG (SEQ ID NO:5) or LEDYAFNFELILEEIARLFES (SEQ ID NO:321); and (c) X4 is a peptide comprising an amino acid sequence at least 85% identical to the amino acid sequence EDEQEEMANAIITILQSWIF(S) (SEQ ID NO:6) or DEQEEMANAIITILQSWIF(S) (SEQ ID NO:322).

3. The conditionally active receptor agonist of claim 1, wherein:
X2 is a peptide comprising an amino acid sequence at least 75% identical to the amino acid sequence KDEAEKAKRMKEWMKRIK(T) (SEQ ID NO:7), wherein amino acid residues in parentheses may be present or absent.

4. The conditionally active receptor agonist of claim 1, wherein:
(i) the first polypeptide component includes one of X1, X2, X3, and X4, and the second polypeptide component includes the three of X1, X2, X3, and X4 that are not present in the first polypeptide component; or
ii) the first polypeptide component includes two of X1, X2, X3, and X4, and the second polypeptide component includes the two of X1, X2, X3, and X4 that are not present in the first polypeptide component.

5. The conditionally active receptor agonist of claim 1, wherein
(i) the first polypeptide comprises X1 and the second polypeptide comprises X2, X3, and X4;
(ii) the first polypeptide comprises X2 and the second polypeptide comprises X1, X3, and X4;
(iii) the first polypeptide comprises X3 and the second polypeptide comprises X1, X2, and X4;
(iv) the first polypeptide comprises X4 and the second polypeptide comprises X1, X2, and X3;
(v) the first polypeptide comprises X1 and X2, and the second polypeptide comprises X3 and X4;
(vi) the first polypeptide comprises X1 and X3, and the second polypeptide comprises X2 and X4;
(vii) the first polypeptide comprises X1 and X4, and the second polypeptide comprises X2 and X3;
(viii) the first polypeptide comprises X2 and X3, and the second polypeptide comprises X1 and X4;
(ix) the first polypeptide comprises X2 and X4, and the second polypeptide comprises X1 and X3;
(x) the first polypeptide comprises X3 and X4, and the second polypeptide comprises X1 and X2;
(xi) the first polypeptide comprises X1, X2, and X3 and the second polypeptide comprises X4;
(xii) the first polypeptide comprises X1, X2, and X4 and the second polypeptide comprises X3;
(xiii) the first polypeptide comprises X1, X3, and X4 and the second polypeptide comprises X2; or
(xiv) the first polypeptide comprises X2, X3, and X4 and the second polypeptide comprises X1.

6. The conditionally active receptor agonist of claim 1, wherein:
(a) the first polypeptide comprises X1 and excludes X2, X3, and X4; and the second polypeptide is a fusion protein comprising X3-Z1-X2-Z2-X4 and excluding X1;
(b) the first polypeptide comprises X4 and excludes X1, X2, and X3; and the second polypeptide is a fusion protein comprising X1-Z1-X3-Z2-X2 and excluding X4; or
(c) the first polypeptide is a fusion protein comprising X1-Z1-X3 and excluding X2 and X4; and the second polypeptide is a fusion protein comprising X2-Z1-X4 and excluding X1 and X3;
wherein each of Z1 and Z2 independently are an optional amino acid linker.

7. The conditionally active receptor agonist of claim 1, wherein the first polypeptide and the second polypeptide comprise an amino acid sequence at least 75% identical to the amino acid sequence of a pair of first and second polypeptides selected from options (i)-(xiii), wherein (underlined residues or "X" residues" are optional and each optional residue, when present, may comprise any amino acid):

```
(i)
First polypeptide X1 (Neo2A)
                                          (SEQ ID NO: 256)
PKKKIQLHAEHALYDALMILNIVKTNS
and Second polypeptide: X3-X2'-X4 (Neo2B)
                                          (SEQ ID NO: 257)
TNSPPAEEKLEDYAFNFELILEEIARLFESGDQKDEAEKAKRMKEWMKRI

KTTASEDEQEEMANAIITILQSWIFS (ii)
First polypeptide X1-X3-X2'
                                          (SEQ ID NO: 258)
PKKKIQLHAEHALYDALMILNIVKTNSPPAEEKLEDYAFNFELILEEIAR LFESGDQKDEAEKAKRMKEWMKRIKTTAS
and Second polypeptide X4
                                          (SEQ ID NO: 259)
TTASEDEQEEMANAIITILQSWIFS;

(iii)
First polypeptide X1-X3
                                          (SEQ ID NO: 260)
PKKKIQLHAEHALYDALMILNIVKTNSPPAEEKLEDYAFNFELILEEIAR LFESGD
and Second polypeptide X2-X4
                                          (SEQ ID NO: 261)
DQKDEAEKAKRMKEWMKRIKTTASEDEQEEMANAIITILQSWIFS (iv)
First polypeptide X1 (Neo4A)
                                          (SEQ ID NO: 262)
PKKKIQIMAEEALKDALSILNIVKTNS Second polypeptide X3-X2'-X4 (Neo4B)
                                          (SEQ ID NO: 263)
TNSPPAEEQLERFAKRFERNLWGIARLFESGDQKDEAEKAKRMIEWMKRI

KTTASEDEQEEMANAIITILQSWFFS (v)
First polypeptide X1
                                          (SEQ ID NO: 311)
PKKKIQLHAEHALYDALMILNIXXXXX
and Second polypeptide: X3-X2'-X4
                                          (SEQ ID NO: 264)
XXXXXXXXXLEDYAFNFELILEEIARLFESGXXKDEAEKAKRMKEWMKRI

KTXXXEDEQEEMANAIITILQSWIFS (vi)
First polypeptide X1-X3-X2'
                                          (SEQ ID NO: 265)
PKKKIQLHAEHALYDALMILNIXXXXXXXXXXXLEDYAFNFELILEEIAR LFESGXXKDEAEKAKRMKEWMKRIKTTAS
and
```

-continued

Second polypeptide X4
(SEQ ID NO: 266)
XXXXXDEQEEMANAIITILQSWIFS;

(vii)
First polypeptide X1-X3
(SEQ ID NO: 267)
PKKKIQLHAEHALYDALMILNIXXXXXXXXXXXXLEDYAFNFELILEEIAR LFESXXGD
and Second polypeptide X2-X4
(SEQ ID NO: 268)
DQKDEAEKAKRMKEWMKRIKTXXXEDEQEEMANAIITILQSWIFS (viii)
First polypeptide X1
(SEQ ID NO: 269)
PKKKIQIMAEEALKDALSILNIXXXXX Second polypeptide X3-X2'-X4
(SEQ ID NO: 270)
XXXXXXXXQLERFAKRFERNLWGIARLFESGXXKDEAEKAKRMIEWMKRI

KTXXXEDEQEEMANAIITILQSWFFS (ix)
First polypeptide >Neo4_X1-X3'
(SEQ ID NO: 312)
PKKKIQIMAEEALKDALSILNIVKTNSPPAEEQLERFAKRFERNLWGIAR

LFESGD

Second polypeptide >Neo4_X2-X4
(SEQ ID NO: 313)
DQKDEAEKAKRMIEWMKRIKTTASEDEQEEMANAIITILQSWFFS (x)
First polypeptide > Neo4_X1-X3'
(SEQ ID NO: 314)
PKKKIQIMAEEALKDALSILNIXXXXXXXXXXQLERFAKRFERNLWGIAR

LFESXX

Second polypeptide >Neo4_X2-X4
(SEQ ID NO: 315)
XXKDEAEKAKRMIEWMKRIKXXXXEDEQEEMANAIITILQSWFFS (xi)
First polypeptide Neo4_X1-X3'-X2
(SEQ ID NO: 316)
PKKKIQIMAEEALKDALSILNIVKTNSPPAEEQLERFAKRFERNLWGIAR

LFESGDQKDEAEKAKRMIEWMKRIKTTA

Second polypeptide Neo4X4
(SEQ ID NO: 317)
TTASEDEQEEMANAIITILQSWFFS (xii)
First polypeptide Neo4_X1-X3'-X2
(SEQ ID NO: 318)
PKKKIQIMAEEALKDALSILNIXXXXXXXXXXXLERFAKRFERNLWGIAR

LFESXXXKDEAEKAKRMIEWMKRIKXXX

Second polypeptide Neo4_X4
(SEQ ID NO: 319)
XXXXXDEQEEMANAIITILQSWFFS;
or (xiii)
First polypeptide (X1)
(SEQ ID NO: 323)
PKKKIQLHAEHALYDALMILNIVGGSS,
or (SEQ ID NO: 324)
SKEAIQLHAEHALYDALMILNIVKTNS,
or (SEQ ID NO: 325)
PIQLHAEHALYDALMILNIV Second polypeptide (X3-X2'-X4)
(SEQ ID NO: 326)
PKLEDYAFNFELILEEIARLFESGDQKDEAEKAKRMKEWMKRIKTTASED EQEEMANAIITILQSWIFS;
or (SEQ ID NO: 327)
GGSSGGLEDYAFNFELILEEIARLFESGGSSGGKDEAEKAKRMKEWMKRI TGGSSGGDEQEEMANAIITILQSWIFS;
or (SEQ ID NO: 328)
GGSSGGLEDYAFNFELILEEIARLFESGGSSGGGGEAEKAKRMKEWMKRI

GGSSGGDEQEEMANAIITILQSWIFS.

8. The conditionally active receptor agonist of claim 1, wherein the first polypeptide component and the second polypeptide component are non-covalently associated.

9. The conditionally active receptor agonist of claim 1, wherein the first polypeptide component and the second polypeptide component are indirectly bound to each other through a receptor.

10. The conditionally active receptor agonist of claim 1, wherein the first polypeptide component further comprises a first targeting domain or the second polypeptide component further comprises a second targeting domain.

11. The conditionally active receptor agonist of claim 1, wherein the first polypeptide component further comprises a first targeting domain and the second polypeptide component further comprises a second targeting domain.

12. A polypeptide comprising 1, 2, or 3, but not all 4 domains X1, X2, X3, and X4, wherein:
 (a) X1, when present, is a peptide comprising an amino acid sequence at least 75% identical to the amino acid sequence (PKKKIQ)LHAEHALYDAL(MILNI); (SEQ ID NO: 4);
 (b) X2, when present, is any helical peptide domain comprising an amino acid sequence at least 75% identical to the amino acid sequence KDEAEKAKRMKEWMKRIKT (SEQ ID NO:7);
 (c) X3, when present, is a peptide comprising an amino acid sequence at least 75% identical to the amino acid sequence (LE)DYAFNFELILEE(IARLFESG) (SEQ ID NO:5); and
 (d) X4, when present, is a peptide comprising an amino acid sequence at least 75% identical to the amino acid sequence (EDEQEEMANAI)ITILQSWIF(S) (SEQ ID NO:6);
wherein amino acid residues in parentheses may be present or absent.

13. The polypeptide of claim 12, wherein
 (a) X1, when present, is a peptide comprising an amino acid sequence at least 85% identical to the amino acid sequence PKKKIQLHAEHALYDALMILNI (SEQ ID NO: 4) or QLHAEHALYDALMILNI (SEQ ID NO:320);
 (c) X3, when present, is a peptide comprising an amino acid sequence at least 85% 65% identical to the amino acid sequence LEDYAFNFELILEEIARLFESG (SEQ ID NO: 5) or LEDYAFNFELILEEIARLFES (SEQ ID NO:321); and
 (d) X4 is a peptide comprising an amino acid sequence at least at least 85% identical to the amino acid sequence EDEQEEMANAIITILQSWIF(S) (SEQ ID NO:6) or DEQEEMANAIITILQSWIF(S) (SEQ ID NO:322).

14. The polypeptide of claim 12, wherein the polypeptide comprises an amino acid sequence that is at least 75% identical to, a first polypeptide or a second polypeptide selected from options (i)-(xiii), wherein underlined residues are optional and each optional residue, when present, may comprise any amino acid:

(i)
First polypeptide X1 (Neo2A)
(SEQ ID NO: 256)
PKKKIQLHAEHALYDALMILNIVKTNS
and Second polypeptide: X3-X2'-X4 (Neo2B)
(SEQ ID NO: 257)
TNSPPAEEKLEDYAFNFELILEEIARLFESGDQKDEAEKAKRMKEWMKRI
KTTASEDEQEEMANAIITILQSWIFS (ii)
First polypeptide X1-X3-X2'
(SEQ ID NO: 258)
PKKKIQLHAEHALYDALMILNIVKTNSPPAEEKLEDYAFNFELILEEIAR
LFESGDQKDEAEKAKRMKEWMKRIKTTAS
and Second polypeptide X4
(SEQ ID NO: 259)
TTASEDEQEEMANAIITILQSWIFS;

(iii)
First polypeptide X1-X3
(SEQ ID NO: 260)
PKKKIQLHAEHALYDALMILNIVKTNSPPAEEKLEDYAFNFELILEEIAR
LFESGD
and Second polypeptide X2-X4
(SEQ ID NO: 261)
DQKDEAEKAKRMKEWMKRIKTTASEDEQEEMANAIITILQSWIFS (iv)
First polypeptide X1 (Neo4A)
(SEQ ID NO: 262)
PKKKIQIMAEEALKDALSILNIVKTNS Second polypeptide X3-X2'-X4 (Neo4B)
(SEQ ID NO: 263)
TNSPPAEEQLERFAKRFERNLWGIARLFESGDQKDEAEKAKRMIEWMKRI
KTTASEDEQEEMANAIITILQSWFFS (v)
First polypeptide X1 (Neo2A)
(SEQ ID NO: 311)
PKKKIQLHAEHALYDALMILNIXXXXX
and Second polypeptide: X3-X2'-X4 (Neo2B)
(SEQ ID NO: 264)
XXXXXXXXXLEDYAFNFELILEEIARLFESGXXKDEAEKAKRMKEWMKRI
KTXXXEDEQEEMANAIITILQSWIFS (vi)
First polypeptide X1-X3-X2'
(SEQ ID NO: 265)
PKKKIQLHAEHALYDALMILNIXXXXXXXXXXXLEDYAFNFELILEEIAR
LFESGXXKDEAEKAKRMKEWMKRIKTTAS
and Second polypeptide X4
(SEQ ID NO: 266)
XXXXXDEQEEMANAIITILQSWIFS;

(vii)
First polypeptide X1-X3
(SEQ ID NO: 267)
PKKKIQLHAEHALYDALMILNIXXXXXXXXXXXLEDYAFNFELILEEIAR
LFESXXGD
and Second polypeptide X2-X4
(SEQ ID NO: 268)
DQKDEAEKAKRMKEWMKRIKTXXXEDEQEEMANAIITILQSWIFS (viii)
First polypeptide X1 (Neo4A)
(SEQ ID NO: 269)
PKKKIQIMAEEALKDALSILNIXXXXX Second polypeptide X3-X2'-X4 (Neo4B)
(SEQ ID NO: 270)
XXXXXXXXQLERFAKRFERNLWGIARLFESGXXKDEAEKAKRMIEWMKRI
KTXXXEDEQEEMANAIITILQSWFFS (ix)
First polypeptide >Neo4_X1-X3'
(SEQ ID NO: 312)
PKKKIQIMAEEALKDALSILNIVKTNSPPAEEQLERFAKRFERNLWGIAR
LFESGD Second polypeptide >Neo4_X2-X4
(SEQ ID NO: 313)
DQKDEAEKAKRMIEWMKRIKTTASEDEQEEMANAIITILQSWFFS (x)
First polypeptide >Neo4_X1-X3'
(SEQ ID NO: 314)
PKKKIQIMAEEALKDALSILNIXXXXXXXXXXXQLERFAKRFERNLWGIAR
LFESXX Second polypeptide >Neo4_X2-X4
(SEQ ID NO: 315)
XXKDEAEKAKRMIEWMKRIKXXXXEDEQEEMANAIITILQSWFFS (xi)
First polypeptide Neo4_X1-X3'-X2
(SEQ ID NO: 316)
PKKKIQIMAEEALKDALSILNIVKTNSPPAEEQLERFAKRFERNLWGIAR
LFESGDQKDEAEKAKRMIEWMKRIKTTA Second polypeptide Neo4_X4
(SEQ ID NO: 317)
TTASEDEQEEMANAIITILQSWFFS (xii)
First polypeptide Neo4_X1-X3'-X2
(SEQ ID NO: 318)
PKKKIQIMAEEALKDALSILNIXXXXXXXXXXXLERFAKRFERNLWGIAR
LFESXXXKDEAEKAKRMIEWMKRIKXXX Second polypeptide Neo4_X4
(SEQ ID NO: 319)
XXXXXDEQEEMANAIITILQSWFFS;
or (xiii)
First polypeptide (X1)
(SEQ ID NO: 323)
PKKKIQLHAEHALYDALMILNIVGGSS,
or (SEQ ID NO: 324)
SKEAIQLHAEHALYDALMILNIVKTNS,
or (SEQ ID NO: 325)
PIQLHAEHALYDALMILNIV

```
Second polypeptide (X3-X2'-X4)
                                              (SEQ ID NO: 326)
PKLEDYAFNFELILEEIARLFESGDQKDEAEKAKRMKEWMKRIKTTASED EQEEMANAIITILQSWIFS;
or
                                              (SEQ ID NO: 327)
GGSSGGLEDYAFNFELILEEIARLFESGGSSGGKDEAEKAKRMKEWMKRI TGGSSGGDEQEEMANAIITILQSWIFS;
or
                                              (SEQ ID NO: 328)
GGSSGGLEDYAFNFELILEEIARLFESGGSSGGGGEAEKAKRMKEWMKRI

GGSSGGDEQEEMANAIITILQSWIFS.
```

15. The polypeptide of claim 12, wherein the polypeptide further comprises a targeting domain.

16. A pharmaceutical composition, (i) a first polypeptide component or a second polypeptide component of a non-naturally occurring conditionally active receptor agonist, wherein the first polypeptide component and the second polypeptide component are not present in a fusion protein, wherein in total the first polypeptide component and the second polypeptide component comprise domains X1, X2, X3, and X4, wherein the first polypeptide component comprises at least one of X1, X2, X3, and X4 but does not comprise each of X1, X2, X3, and X4; and the second polypeptide component comprises each of X1, X2, X3, and X4 that is not present in the first polypeptide component; wherein the first polypeptide component and the second polypeptide component are not active receptor agonists individually, and wherein the first polypeptide component and the second polypeptide interact to form an active agonist of IL-2 receptor $\beta\gamma_c$ heterodimer (IL-2R$\beta\gamma_c$) or IL-4 receptor $\alpha\gamma_c$ heterodimer (IL-4R$\alpha\gamma_c$ or (ii) one, two or three, but not all 4 domains X1, X2, X3, and X4; wherein:

(a) X1 is a peptide comprising an amino acid sequence at least 75% identical to the amino acid sequence (PKK-KIQ)LHAEHALYDAL(MILNI) (SEQ ID NO: 4);

(b) X2 is any helical peptide domain;

(c) X3 is a peptide comprising an amino acid sequence at least 75% identical to the amino acid sequence (LE)DYAFNFELILEE(IARLFESG) (SEQ ID NO:5); and (d) X4 is a peptide comprising an amino acid sequence at least 75% identical to the amino acid sequence (ED-EQEEMANAI)ITILQSWIF(S) (SEQ ID NO:6), wherein amino acid residues in parentheses may be present or absent, and a pharmaceutically acceptable carrier.

* * * * *